US009790468B2

United States Patent
Kerkis et al.

(10) Patent No.: US 9,790,468 B2
(45) Date of Patent: *Oct. 17, 2017

(54) MULTIFUNCTIONAL IMMATURE DENTAL PULP STEM CELLS AND THERAPEUTIC APPLICATIONS

(71) Applicant: AVITA INTERNATIONAL LTD., Tortola (VG)

(72) Inventors: Irina Kerkis, Sao Paulo (BR); Sabina Glozman, Naharya (IL)

(73) Assignees: AVITA IINTERNATIONAL LTD., Tortola (VG); FUNDAÇ CÃO BUTANTAN, São Paulo (BR)

( * ) Notice: Subject to any disclaimer, the term of this patent is extended or adjusted under 35 U.S.C. 154(b) by 0 days.

This patent is subject to a terminal disclaimer.

(21) Appl. No.: 14/214,016

(22) Filed: Mar. 14, 2014

(65) Prior Publication Data
US 2015/0050248 A1 Feb. 19, 2015

Related U.S. Application Data

(60) Provisional application No. 61/791,594, filed on Mar. 15, 2013, provisional application No. 61/800,245, filed on Mar. 15, 2013.

(51) Int. Cl.
| | |
|---|---|
| C12N 5/0775 | (2010.01) |
| A61K 35/30 | (2015.01) |
| A61K 35/32 | (2015.01) |
| C12N 5/0797 | (2010.01) |
| A61K 35/28 | (2015.01) |
| A61K 45/06 | (2006.01) |
| C12N 5/079 | (2010.01) |
| C12N 5/0793 | (2010.01) |
| C12N 5/071 | (2010.01) |

(52) U.S. Cl.
CPC ............ *C12N 5/0664* (2013.01); *A61K 35/28* (2013.01); *A61K 35/30* (2013.01); *A61K 35/32* (2013.01); *A61K 45/06* (2013.01); *C12N 5/0619* (2013.01); *C12N 5/0621* (2013.01); *C12N 5/0623* (2013.01); *C12N 5/0678* (2013.01); *C12N 2500/25* (2013.01); *C12N 2500/38* (2013.01); *C12N 2500/84* (2013.01); *C12N 2500/90* (2013.01); *C12N 2501/385* (2013.01); *C12N 2501/39* (2013.01); *C12N 2501/392* (2013.01); *C12N 2501/395* (2013.01); *C12N 2506/1361* (2013.01); *C12N 2533/76* (2013.01)

(58) Field of Classification Search
None
See application file for complete search history.

(56) References Cited

U.S. PATENT DOCUMENTS

| | | |
|---|---|---|
| 2005/0214344 A1 | 9/2005 | Barrows et al. |
| 2009/0324555 A1* | 12/2009 | Thie ............ C12N 5/0623 424/93.7 |
| 2010/0297094 A1 | 11/2010 | Harlan et al. |
| 2011/0002895 A1 | 1/2011 | Ueda et al. |
| 2011/0039338 A1 | 2/2011 | Yamanaka et al. |
| 2011/0059050 A1 | 3/2011 | Cetrulo et al. |
| 2011/0158962 A1 | 6/2011 | Ferro |
| 2012/0009601 A1 | 1/2012 | Moriguchi et al. |
| 2012/0219531 A1 | 8/2012 | Oh et al. |

FOREIGN PATENT DOCUMENTS

| | | |
|---|---|---|
| WO | 2007035843 A2 | 3/2007 |
| WO | 2008080200 A1 | 7/2008 |
| WO | 2012020687 A1 | 2/2012 |
| WO | 2015/024089 A1 | 2/2015 |

OTHER PUBLICATIONS

Blurton-Jones "Neural stem cells improve cognition via BDNF in a transgenic model of Alzheimer's disease." (2009) Proceedings of the National Academy of Science, vol. 106, No. 32: 13594-13599.*
Wang et al. "Stem Cells from Human-Exfoliated Deciduous Teeth Can Differentiate into Dopaminergic Neuron-Like Cells" (2010), Stem Cells and Development, vol. 19, No. 9: 1375-1383.*
Lindvall et al. "Stem cells in human neurodegenerative disorders—time for clinical translation?" (2010) Journal of Clinical Investigation: vol. 120, No. 1: 29-40.*
Johnson et al. "Neuroprotective Effects of Intravitreal Mesenchymal Stem Cell Transplantation in Experimental Glaucoma" (2010) Investigative Ophthalmology & Visual Science, vol. 51, No. 4: 2051-2059.*
McConnell et al. Mammalian Kruppe-Like Factors in Health and Disease (2010) Physiological Reviews, vol. 90: 1337-1381.*
Gomes et al., "Corneal Reconstruction with Tissue-Engineered Cell Sheets Composed of Human Immature Dental Pulp Stem Cells", Investigative Ophthalmology & Visual Science, 51(3):1408-1414 (Mar. 2010).
Kerkis et al., "Stem Cells in Dental Pulp of Deciduous Teeth", Tissue Engineering: Part B, 18(2):129-138 (2012).
Martins de Almeida et al., "Human Dental Pulp Cells: A New Source of Cell Therapy in a Mouse Model of Compressive Spinal Cord Injury", Journal of Neurotrauma, 28:1939-1949 (Sep. 2011).
Monteiro et al., "Human immature dental pulp stem cells share key characteristic features with limbal stem cells", Cell Prolif., 42:587-594 (2009).
Kerkis et al., "Isolation and Characterization of a Population of Immature Dental Pulp Stem Cells Expressing OCT-4 and Other Embryonic Stem Cell Markers", Cells Tissues Organs, 184:105-116 (2006).
Hayashi et al., "Long-Term Culture of Mouse Embryonic Stem Cell-Derived Adherent Neurospheres and Functional Neurons", Tissue Engineering: Part C, 16(6):1493-1502 (Jun. 16, 2010).

(Continued)

*Primary Examiner* — Robert Yamasaki
*Assistant Examiner* — Teresa E. Knight
(74) *Attorney, Agent, or Firm* — Rodney J. Fuller; Booth Udall Fuller, PLC

(57) ABSTRACT

The present invention is directed to therapeutic multifunctional immature dental pulp stem cells (IDPSCs), and IDPSCs multi-lineage compositions. The invention is further directed to the use of IDPSCs and compositions to reduce the risk of and/or treat degenerative diseases or for other medicinal and aesthetic purposes.

11 Claims, 100 Drawing Sheets

(56) References Cited

OTHER PUBLICATIONS

Lizier et al., "Scaling-Up of Dental Pulp Stem Cells Isolated from Multiple Niches", PLoS One, 7(6), e39885, pp. 1-12 (Jun. 2012).
Huschtscha et al., "Enhanced isolation of fibroblasts from human skin explants", BioTechniques, 53(4):239-244 (Oct. 1, 2012).
Karaoz et al., "Human dental pulp stem cells demonstrate better neural and epithelial stem cell properties than bone marrow-derived mesenchymal stem cells", Histochemistry and Cell Biology, 136(4):455-473 (Oct. 31, 2011).
Gronthos et al., "Stem Cell Properties of Human Dental Pulp Stem Cells", Journal of Dental Research, International Association for Dental Research, US, 81(8):531-535 (Aug. 1, 2002).
Janebodin et al., "Isolation and Characterization of Neural Crest-Derived Stem Cells from Dental Pulp of Neonatal Mice", PLOS ONE, 6(11):e27526 (Nov. 8, 2011).

\* cited by examiner

Engraftment of IDPSC into bone marrow of mice

C)

D)

A)

B)

C)

D)

A)

B)

C)

A)

B)

C)

D)

A)

B)

C)

D)

www.histology.leeds.ac.uk

SEQUENCE LISTING

```
<160> NUMBER OF SEQ ID NOS: 56

<210> SEQ ID NO 1
<211> LENGTH: 20
<212> TYPE: DNA
<213> ORGANISM: Artificial Sequence
<220> FEATURE:
<223> OTHER INFORMATION: primer sequences

<400> SEQUENCE: 1
ctctgacctg tcagaagaat                                              20
```

<210> SEQ ID NO 2
<211> LENGTH: 20
<212> TYPE: DNA
<213> ORGANISM: Artificial Sequence
<220> FEATURE:
<223> OTHER INFORMATION: primer sequence

<400> SEQUENCE: 2
gacgctgaca cttacagaat                                                    20

<210> SEQ ID NO 3
<211> LENGTH: 22
<212> TYPE: DNA
<213> ORGANISM: Artificial Sequence
<220> FEATURE:
<223> OTHER INFORMATION: primer sequence

<400> SEQUENCE: 3
aagcaggagt ccactgagta cc                                                 22

<210> SEQ ID NO 4
<211> LENGTH: 20
<212> TYPE: DNA
<213> ORGANISM: Artificial Sequence
<220> FEATURE:
<223> OTHER INFORMATION: primer sequence

<400> SEQUENCE: 4
gaaggtgacg agccatttcc                                                    20

<210> SEQ ID NO 5
<211> LENGTH: 21
<212> TYPE: DNA
<213> ORGANISM: Artificial Sequence
<220> FEATURE:
<223> OTHER INFORMATION: primer sequence

<400> SEQUENCE: 5
ggatcactta cggagaaaca g                                                  21

<210> SEQ ID NO 6
<211> LENGTH: 20
<212> TYPE: DNA
<213> ORGANISM: Artificial Sequence
<220> FEATURE:
<223> OTHER INFORMATION: primer sequence

<400> SEQUENCE: 6
gattgcatgc attgtgtcct                                                    20

<210> SEQ ID NO 7
<211> LENGTH: 20
<212> TYPE: DNA
<213> ORGANISM: Artificial Sequence
<220> FEATURE:
<223> OTHER INFORMATION: primer sequence

<400> SEQUENCE: 7
accacagtcc atgccatcac                                                    20

<210> SEQ ID NO 8
<211> LENGTH: 20
<212> TYPE: DNA
<213> ORGANISM: Artificial Sequence
<220> FEATURE:
<223> OTHER INFORMATION: primer sequence -continued

<400> SEQUENCE: 8
tccaccaccc tgttgctgta 20

<210> SEQ ID NO 9
<211> LENGTH: 20
<212> TYPE: DNA
<213> ORGANISM: Artificial Sequence
<220> FEATURE:
<223> OTHER INFORMATION: primer sequence

<400> SEQUENCE: 9
tctggaccac tggagaatac 20

<210> SEQ ID NO 10
<211> LENGTH: 20
<212> TYPE: DNA
<213> ORGANISM: Artificial Sequence
<220> FEATURE:
<223> OTHER INFORMATION: primer sequence

<400> SEQUENCE: 10
gaggcatgaa gtgagacaat 20

<210> SEQ ID NO 11
<211> LENGTH: 20
<212> TYPE: DNA
<213> ORGANISM: Artificial Sequence
<220> FEATURE:
<223> OTHER INFORMATION: primer sequence

<400> SEQUENCE: 11
acacggcatt agctgttatt 20

<210> SEQ ID NO 12
<211> LENGTH: 19
<212> TYPE: DNA
<213> ORGANISM: Artificial Sequence
<220> FEATURE:
<223> OTHER INFORMATION: primer sequence

<400> SEQUENCE: 12
agtatttgtt ctttgggca 19

<210> SEQ ID NO 13
<211> LENGTH: 19
<212> TYPE: DNA
<213> ORGANISM: Artificial Sequence
<220> FEATURE:
<223> OTHER INFORMATION: primer sequence

<400> SEQUENCE: 13
ccgacagcaa cgtggtctt 19

<210> SEQ ID NO 14
<211> LENGTH: 19
<212> TYPE: DNA
<213> ORGANISM: Artificial Sequence
<220> FEATURE:
<223> OTHER INFORMATION: primer sequence

<400> SEQUENCE: 14
caggttggcc cagatgatg 19

<210> SEQ ID NO 15

```
<210> SEQ ID NO 15
<211> LENGTH: 25
<212> TYPE: DNA
<213> ORGANISM: Artificial Sequence
<220> FEATURE:
<223> OTHER INFORMATION: primer sequence

<400> SEQUENCE: 15
tggcaccaca ccttctacaa tgagc                                              25

<210> SEQ ID NO 16
<211> LENGTH: 25
<212> TYPE: DNA
<213> ORGANISM: Artificial Sequence
<220> FEATURE:
<223> OTHER INFORMATION: primer sequence

<400> SEQUENCE: 16
gcacagcttc tccttaatgt cacgc                                              25

<210> SEQ ID NO 17
<211> LENGTH: 24
<212> TYPE: DNA
<213> ORGANISM: Artificial Sequence
<220> FEATURE:
<223> OTHER INFORMATION: primer sequence

<400> SEQUENCE: 17
gccgcctgag caaagtaaat gagg                                               24

<210> SEQ ID NO 18
<211> LENGTH: 22
<212> TYPE: DNA
<213> ORGANISM: Artificial Sequence
<220> FEATURE:
<223> OTHER INFORMATION: primer sequence

<400> SEQUENCE: 18
tagtccatca tgccgtcgga gc                                                 22

<210> SEQ ID NO 19
<211> LENGTH: 20
<212> TYPE: DNA
<213> ORGANISM: Artificial Sequence
<220> FEATURE:
<223> OTHER INFORMATION: primer sequence

<400> SEQUENCE: 19
accacagtcc atgccatcac                                                    20

<210> SEQ ID NO 20
<211> LENGTH: 20
<212> TYPE: DNA
<213> ORGANISM: Artificial Sequence
<220> FEATURE:
<223> OTHER INFORMATION: primer sequence

<400> SEQUENCE: 20
tccaccaccc tgttgctgta                                                    20

<210> SEQ ID NO 21
<211> LENGTH: 21
<212> TYPE: DNA
<213> ORGANISM: Artificial Sequence
<220> FEATURE:
<223> OTHER INFORMATION: primer sequence

<400> SEQUENCE: 21
```
agaggcttga catcattggc t                                              21

<210> SEQ ID NO 22
<211> LENGTH: 24
<212> TYPE: DNA
<213> ORGANISM: Artificial Sequence
<220> FEATURE:
<223> OTHER INFORMATION: primer sequence

<400> SEQUENCE: 22
caaaggcact tgactactga gcat                                           24

<210> SEQ ID NO 23
<211> LENGTH: 24
<212> TYPE: DNA
<213> ORGANISM: Artificial Sequence
<220> FEATURE:
<223> OTHER INFORMATION: primer sequence

<400> SEQUENCE: 23
caccagataa acaaatggca gtgc                                           24

<210> SEQ ID NO 24
<211> LENGTH: 22
<212> TYPE: DNA
<213> ORGANISM: Artificial Sequence
<220> FEATURE:
<223> OTHER INFORMATION: primer sequence

<400> SEQUENCE: 24
cgacaggtca tcatcaaagg cg                                             22

<210> SEQ ID NO 25
<211> LENGTH: 22
<212> TYPE: DNA
<213> ORGANISM: Artificial Sequence
<220> FEATURE:
<223> OTHER INFORMATION: primer sequence

<400> SEQUENCE: 25
atacaggcgg aaccacactc ag                                             22

<210> SEQ ID NO 26
<211> LENGTH: 22
<212> TYPE: DNA
<213> ORGANISM: Artificial Sequence
<220> FEATURE:
<223> OTHER INFORMATION: primer sequence

<400> SEQUENCE: 26
gtccacagta atgttgcggg tc                                             22

<210> SEQ ID NO 27
<211> LENGTH: 20
<212> TYPE: DNA
<213> ORGANISM: Artificial Sequence
<220> FEATURE:
<223> OTHER INFORMATION: primer sequence

<400> SEQUENCE: 27
tgggggagac tttgaatgac                                                20

<210> SEQ ID NO 28
<211> LENGTH: 20
<212> TYPE: DNA

```
<213> ORGANISM: Artificial Sequence
<220> FEATURE:
<223> OTHER INFORMATION: primer sequence

<400> SEQUENCE: 28
ctggcaaact cctttgatcc                                                      20

<210> SEQ ID NO 29
<211> LENGTH: 20
<212> TYPE: DNA
<213> ORGANISM: Artificial Sequence
<220> FEATURE:
<223> OTHER INFORMATION: primer sequence

<400> SEQUENCE: 29
aggaggcact gggtatctga                                                      20

<210> SEQ ID NO 30
<211> LENGTH: 20
<212> TYPE: DNA
<213> ORGANISM: Artificial Sequence
<220> FEATURE:
<223> OTHER INFORMATION: primer sequence

<400> SEQUENCE: 30
atccctgagg tctctcagca                                                      20

<210> SEQ ID NO 31
<211> LENGTH: 20
<212> TYPE: DNA
<213> ORGANISM: Artificial Sequence
<220> FEATURE:
<223> OTHER INFORMATION: primer sequence

<400> SEQUENCE: 31
tcgtggagag tctgtgcagt                                                      20

<210> SEQ ID NO 32
<211> LENGTH: 20
<212> TYPE: DNA
<213> ORGANISM: Artificial Sequence
<220> FEATURE:
<223> OTHER INFORMATION: primer sequence

<400> SEQUENCE: 32
tggacaggaa gtgtggtcag                                                      20

<210> SEQ ID NO 33
<211> LENGTH: 41
<212> TYPE: DNA
<213> ORGANISM: Artificial Sequence
<220> FEATURE:
<223> OTHER INFORMATION: primer sequence

<400> SEQUENCE: 33
agttccatgg cactggccat atcaggtagg caattgtgag g                              41

<210> SEQ ID NO 34
<211> LENGTH: 23
<212> TYPE: DNA
<213> ORGANISM: Artificial Sequence
<220> FEATURE:
<223> OTHER INFORMATION: primer sequence

<400> SEQUENCE: 34
ccttcttgct gatccagtgg tac                                                  23
```

<210> SEQ ID NO 35
<211> LENGTH: 20
<212> TYPE: DNA
<213> ORGANISM: Artificial Sequence
<220> FEATURE:
<223> OTHER INFORMATION: primer sequence

<400> SEQUENCE: 35
accaaggaca ccaccagcat                                              20

<210> SEQ ID NO 36
<211> LENGTH: 19
<212> TYPE: DNA
<213> ORGANISM: Artificial Sequence
<220> FEATURE:
<223> OTHER INFORMATION: primer sequence

<400> SEQUENCE: 36
ggcagagatc gagggtgtc                                               19

<210> SEQ ID NO 37
<211> LENGTH: 21
<212> TYPE: DNA
<213> ORGANISM: Artificial Sequence
<220> FEATURE:
<223> OTHER INFORMATION: primer sequence

<400> SEQUENCE: 37
gtcatccttc gcctgctgta g                                            21

<210> SEQ ID NO 38
<211> LENGTH: 44
<212> TYPE: DNA
<213> ORGANISM: Artificial Sequence
<220> FEATURE:
<223> OTHER INFORMATION: primer sequence

<400> SEQUENCE: 38
acatgaagaa gaaccacgag gatgtctgct cagcgatggt ttca                   44

<210> SEQ ID NO 39
<211> LENGTH: 15
<212> TYPE: DNA
<213> ORGANISM: Artificial Sequence
<220> FEATURE:
<223> OTHER INFORMATION: primer sequence

<400> SEQUENCE: 39
ggccacggct gcttc                                                   15

<210> SEQ ID NO 40
<211> LENGTH: 19
<212> TYPE: DNA
<213> ORGANISM: Artificial Sequence
<220> FEATURE:
<223> OTHER INFORMATION: primer sequence

<400> SEQUENCE: 40
gttggcgtac aggtctttg                                               19

<210> SEQ ID NO 41
<211> LENGTH: 24
<212> TYPE: DNA
<213> ORGANISM: Artificial Sequence
<220> FEATURE:

```
<223> OTHER INFORMATION: pimer sequence

<400> SEQUENCE: 41
gacaggggga ggggaggagc tagg                                            24

<210> SEQ ID NO 42
<211> LENGTH: 26
<212> TYPE: DNA
<213> ORGANISM: Artificial Sequence
<220> FEATURE:
<223> OTHER INFORMATION: primer sequence

<400> SEQUENCE: 42
cttccctcca accagttgcc ccaaac                                          26

<210> SEQ ID NO 43
<211> LENGTH: 26
<212> TYPE: DNA
<213> ORGANISM: Artificial Sequence
<220> FEATURE:
<223> OTHER INFORMATION: primer sequence

<400> SEQUENCE: 43
gggaaatggg aggggtgcaa aagagg                                          26

<210> SEQ ID NO 44
<211> LENGTH: 26
<212> TYPE: DNA
<213> ORGANISM: Artificial Sequence
<220> FEATURE:
<223> OTHER INFORMATION: pimer sequence

<400> SEQUENCE: 44
ttgcgtgagt gtggatggga ttggtg                                          26

<210> SEQ ID NO 45
<211> LENGTH: 25
<212> TYPE: DNA
<213> ORGANISM: Artificial Sequence
<220> FEATURE:
<223> OTHER INFORMATION: primer sequence

<400> SEQUENCE: 45
cagccccgat tcttccacca gtccc                                           25

<210> SEQ ID NO 46
<211> LENGTH: 25
<212> TYPE: DNA
<213> ORGANISM: Artificial Sequence
<220> FEATURE:
<223> OTHER INFORMATION: pimer sequence

<400> SEQUENCE: 46
cggaagattc ccagtcgggt tcacc                                           25

<210> SEQ ID NO 47
<211> LENGTH: 20
<212> TYPE: DNA
<213> ORGANISM: Artificial Sequence
<220> FEATURE:
<223> OTHER INFORMATION: primer sequence

<400> SEQUENCE: 47
gcaccgtcaa ggctgagaac                                                 20
```

```
<210> SEQ ID NO 48
<211> LENGTH: 19
<212> TYPE: DNA
<213> ORGANISM: Artificial Sequence
<220> FEATURE:
<223> OTHER INFORMATION: primer sequence

<400> SEQUENCE: 48
tggtgaagac gccagtgga                                                19

<210> SEQ ID NO 49
<211> LENGTH: 22
<212> TYPE: DNA
<213> ORGANISM: Artificial Sequence
<220> FEATURE:
<223> OTHER INFORMATION: primer sequence

<400> SEQUENCE: 49
aatgaaggga cacagaggtt tc                                            22

<210> SEQ ID NO 50
<211> LENGTH: 22
<212> TYPE: DNA
<213> ORGANISM: Artificial Sequence
<220> FEATURE:
<223> OTHER INFORMATION: primer sequence

<400> SEQUENCE: 50
ccagtagcac catcatttcc ac                                            22

<210> SEQ ID NO 51
<211> LENGTH: 22
<212> TYPE: DNA
<213> ORGANISM: Artificial Sequence
<220> FEATURE:
<223> OTHER INFORMATION: primer sequence

<400> SEQUENCE: 51
ggtcagtcct acaagattgg tg                                            22

<210> SEQ ID NO 52
<211> LENGTH: 22
<212> TYPE: DNA
<213> ORGANISM: Artificial Sequence
<220> FEATURE:
<223> OTHER INFORMATION: primer sequence

<400> SEQUENCE: 52
cttctcccag gcaagtacaa tc                                            22

<210> SEQ ID NO 53
<211> LENGTH: 22
<212> TYPE: DNA
<213> ORGANISM: Artificial Sequence
<220> FEATURE:
<223> OTHER INFORMATION: primer sequence

<400> SEQUENCE: 53
agaagaggtg tcctgctgac tg                                            22

<210> SEQ ID NO 54
<211> LENGTH: 22
<212> TYPE: DNA
<213> ORGANISM: Artificial Sequence
<220> FEATURE:
<223> OTHER INFORMATION: primer sequence
```

```
<400> SEQUENCE: 54
tcatgtcact gcagtcatag cc                                              22

<210> SEQ ID NO 55
<211> LENGTH: 22
<212> TYPE: DNA
<213> ORGANISM: Artificial Sequence
<220> FEATURE:
<223> OTHER INFORMATION: primer sequence

<400> SEQUENCE: 55
aatccaagtt tgctgacctc tc                                              22

<210> SEQ ID NO 56
<211> LENGTH: 22
<212> TYPE: DNA
<213> ORGANISM: Artificial Sequence
<220> FEATURE:
<223> OTHER INFORMATION: primer sequence

<400> SEQUENCE: 56
tgtaggtggc aatctcaatg tc                                              22
```

MULTIFUNCTIONAL IMMATURE DENTAL PULP STEM CELLS AND THERAPEUTIC APPLICATIONS

CROSS REFERENCE TO RELATED TO APPLICATIONS

This document claims the benefit of U.S. Provisional Patent Application 61/791,594, entitled "MULTIFUNCTIONAL IMMATURE DENTAL PULP STEM CELLS OBTAINED BY A ROBUST, LONG-TERM CULTURING SYSTEM" to Kerkis, which was filed on Mar. 15, 2013, and also the benefit of U.S. Provisional Patent Application 61/800,245, entitled "THERAPEUTIC APPLICATIONS OF MULTIFUNCTIONAL IMMATURE DENTAL PULP STEM CELLS" to Kerkis, which was filed on Mar. 15, 2013, the contents of each which are hereby incorporated by reference thereto for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 10,865 byte ASCII (text) file named "Seq_List" created on Mar. 14, 2014.

FIELD OF INVENTION

The present invention relates to compositions of multifunctional immature dental pulp stem cells (IDPSCs), methods for generating clinically useful amount of IDPSCs from the dental pulp (DP) of a patient or single donor at early passages with minimal risk of losing their "stemness" in order to use the stem cells thus obtained in stem cell therapy, and clinical and aesthetic use of IDPSC multi-lineage oriented therapeutic compositions to prevent and treat degenerative diseases and medicinal and aesthetic symptoms. By the methods presented herein a mixed population of multifunctional IDPSCs is obtained that is especially enriched with neuroepithelial markers. These cells originate mainly (preferentially) from a non-perivascular niche and are obtained only through prolonged culturing of non-enzymatically treated DP explants.

BACKGROUND OF INVENTION

In the last decades considerable attention has been directed by the scientific community to the derivation of cells, in particular stem cells (SCs) maintaining the ability to differentiate into specific tissue cells. This interest has been fueled by a strong need and desire to develop novel tissue and cell replacement approaches to heal the ailing body and reestablish cells and functions of afflicted and damaged tissues and parts of the body.

SCs are found in all multicellular organisms. They have the capacity to self-renew and to develop into different specialized cells. Mammalian stem cells are categorized into two general types, embryonic stem cells (ES cells) found during early embryonic development and adult stem cells (ASCs) found in tissues of the organism at later stages and throughout life.

ASCs, also called somatic stem cells; possess the same basic characteristics of all SCs. Namely they are capable of indefinite self-renewal, sometimes during an animal's entire life, and differentiation into specialized cell types. In mammals, the key tasks of ASCs are to sustain and heal the tissues in which where they are located. They remain as undifferentiated cells that may be activated upon tissue damage or other conditions to form multiple cell types and repair tissue damage (Friedenstein A et al. (1974). Precursors for fibroblasts in different populations of hematopoietic cells as detected by the in vitro colony assay method. Exp Hematol 2:83-92).

Additionally, ASCs secrete a large number of bioactive molecules within the tissue which act by modulating the inflammatory response of cells microenvironment, controlling angiogenesis and proliferation of cells involved in tissue repair process, and are therefore also known as pericytes (Caplan A I (2009). Why are MSCs therapeutic? New data: new insight. J Pathol. 217:318-324).

However ASCs have limited capacity for differentiation in comparison with pluripotent embryonic stem cells, and can usually differentiate to form only specific cell types of their tissue of origin. In contrast to embryonic stem cells, adult stem cells are not able to build a whole organism.

It is ES cells, existing during early stages of embryonic development (e.g. blastocyst stage), which possess truly high plasticity and pluripotency enabling them to differentiate to cells derived from all germ layers (Evans, M., and Kaufman, M. (1981) Establishment in culture of pluripotent cells from mouse embryos. Nature 292, 154-6). Upon reintroduction into a blastocyst, ES cells may recommence their regular development and may colonize the germinative tissues and additional embryo tissues.

Cultured ES cells may conserve an undifferentiated state over a long period and numerous cell divisions. On the other hand cultured ES cells can also be induced to differentiate. For instance, when cultivated in suspension, ES cells cultured in suspension form three-dimensional aggregates of pluripotent ES cells known as "embryoid bodies" (Ebs), which undergo cell specification to cells of all three germ lines (Ling, V., and Neben, S. (1997) In vitro differentiation of embryonic stem cells: immunophenotypic analysis of cultured embryoid bodies. J. Cell Physiol. 171, 104-5).

In view of their high pluripotency embryonic stem cells would theoretically be ideal cells to use in a large number of novel medical applications. However, the use of ES cells has generated a lot of controversy and significant ethical and legal concerns hinder their use in stem cell therapy. Treatment based on ASCs is much less controversial as it does not necessitate destruction of human embryos. Additionally ASCs do not produce teratomas and are of low immunogenicity.

For these reasons non-embryonic ASCs have become the focus of much research and work. After isolation and in vitro expansion, ASCs are known as mesenchymal stem cells (MSCs). MSCs are multipotent and preserve their in vivo ability to differentiate in vitro into several cell types such as bone, cartilage and muscle.

Regrettably, the challenges for practical use of adult stem cells in therapy are numerous. They are found only in infinitesimal numbers and it is extremely difficult to isolate them in useful amounts. Moreover their propagative capacity is relatively low and they may contain various DNA aberrations.

Another inherent difficulty and challenge for using MSCs in therapy is that their differentiation capacity is greatly dependent on suitable isolation and culture conditions. It is thus clear that in order for MSCs to fulfill their potential to treat a large number of devastating diseases it is necessary to achieve control over large scale production settings.

There are different methods of scaling up, but as a general rule, because of stem cells' inherent sensitivity to their environment, large-scale processes need to remain substantially similar to their original small-scale process for maintaining critical quality attributes. Davie, N. L. et al., (2012) Streamlining Cell Therapy Manufacture from Clinical to Commercial Scale. BioProcess International 10(3), 24-29. Thus, if cells grown for early clinical studies are cultured on planar surfaces (such as a T-flasks or trays), then on reaching larger-scale operations, those cells will need to be cultured similarly. But that may be difficult to implement and limit production capacity later on. Likewise, if a desired end point of a scaled-up process is to culture cells on microcarriers, then the product used in early studies ideally should have also been produced using suspension culture. If not, final product cells will probably not to be comparable to those later used in the clinic.

Even historically predictable scale-up strategies (e.g., from small to larger Nunc Cell Factory) can impart some unwanted cellular changes, such as the loss or gain of a certain marker or the halted or activated secretion of a particular cytokine. However, it is sometimes the case that such changes resulting from scaling methodologies are irrelevant to a product's clinical function. If it can be proven that the given changes do not affect the proposed mechanism of action or cause adverse side effects, then the new process is likely to be accepted by regulators. Agencies recognize this, which is why products need to be demonstrated as "comparable" and not "identical."

Indeed, improved methods for isolation and propagation of undifferentiated MSCs are considered vital for the development of novel adult stem cell therapy and regenerative medicine.

A number of processes are previously known for obtaining large numbers of MSCs from different tissues while preserving their capability for differentiation. (Kuehle, I., and Goodell, M. A. (2002). The therapeutic potential of stem cells from adults, B.M.J. 325, 372-376; Pittenger, M. F., and Martin, B J. (2004) and mesenchymal stem cells and their potential as cardiac therapeutics. Circ. Res. 95, 9-20).

Nevertheless, these methods result in isolation of MSCs having restricted differentiation ability, giving rise to only a limited variety of cell types. Moreover since the number of ASCs in tissues is very low these methods result in non-homogeneous cultures, containing large numbers of cells, which are not stem cells.

The main sources of MSCs currently used in medicine are the bone marrow and the umbilical cord. However, the isolation of pure populations of pluripotent SCs and in large amounts from these tissues is difficult. Alternative sources for the isolation of highly pluripotent and homogeneous stem cells are required, which will significantly increase the treatment efficacy of several diseases.

One such likely source includes MSCs derived from teeth and dental tissues. Teeth present a readily accessible source for obtaining MSCs useful for tissue regeneration and repair. Similar to other organs in the human body, the teeth and their surrounding tissues are composed by mixed populations of cells, which include multipotent MSCs/pericytes, progenitor and differentiated cells (Arthur et al. (2008). Adult human dental pulp stem cells differentiate toward functionally active neurons under appropriate environmental cues. Stem Cells 26: 1787-1795; Giordano G et al. (2011) Stem cells from oral niches: a review. Ann Stomatol (Roma) 2:3-8).

To conduct stem cell therapies significant in vitro expansion of stem cells is necessary in order to generate sufficient quantities of these cells to treat human disease. At the present time, there is no known reliable way to efficiently generate large numbers of relatively pure dental pulp stem cells populations in culture.

One of the reasons for this is that the regenerative potential diminishes with age and this has been ascribed to functional impairments of adult stem cells. Cells in culture undergo senescence after a certain number of cell divisions whereby the cells enlarge and finally stop proliferation (Wagner W et al. (2009). Aging and replicative senescence have related effects on human stem and progenitor cells. PLoS One 4:e5846).

Another important reason for the difficulty in large-scale production of dental pulp stem cells is that the expansion process itself induces senescence of stem cells and the loss of their stemness as shown by a decline in proliferative and differentiation capacity. Baxter et al. demonstrated the effect of in vitro expansion on the replicative capacity of MSCs by correlating their rate of telomere loss during in vitro expansion with their behavior in vivo. They showed that even protocols that involve minimal expansion induce a rapid aging of MSCs, with losses equivalent to about half their total replicative lifespan. (Baxter M A et al. (2004) Study of telomere length reveals rapid aging of human marrow stromal cells following in vitro expansion. Stem Cells 22, 675-682).

Moreover, prolonged culture of stem cells correlates with increased probability of genetic changes, which is detrimental to their safe use in clinical trials and in future therapies. For instance Wang et al. suggest that animals and cell culture differ in their ability to carry out genomic rearrangements as a means of maintaining telomere integrity when telomeres become critically shortened. (Wang Y et al. (2005). An increase in telomere sister chromatid exchange in murine embryonic stem cells possessing critically shortened telomeres. Proc Natl Acad Sci USA. July 19; 102(29):10256-60).

It is evident that the key to successful stem cell therapy is related to the process of harvesting of the cells and their expansion. This process must ideally allow for the production of very large amounts of a patient's own stem cells while at the same time maintaining their maximal capacity for differentiation. In this way patients who cryopreserve stem cells from their deciduous teeth as children or provide stem cells from their wisdom teeth or molars at later stages of life could benefit from the full therapeutic capacity of these precious cells.

It is very important to develop protocols for DSCs that will reduce the risk of tumorgenicity due to genetic abnormalities acquired during multiple passaging ASCs. It was shown in several preclinical studies that the success and efficiency of stem cells transplantation depends on the stem cells type, its proliferative and migration capacity and the site of injection.

Therefore, methods for the unlimited and consistent large scale production of highly potent ASCs of excellent quality and reduced risk of tumorgenicity at early passages derived from the same donor are desirable for the development of adult stem cell therapy.

SUMMARY OF THE INVENTION

An object of the present invention is to provide therapeutic compositions and methods of use of multilineage-oriented, multifunctionality of non-tumorogenic and non-immunogenic IDPSC s wherein said multilineage orientation and non-tumorogenecity is proven in vitro and in vivo. In vitro proof of multilineage orientation and is proven by multifunctional markers expression and multifunctionality towards various cell lineages and in vivo proven multilineage is based on in vivo grafting potential of IDPSCs into various tissue and characterized by tissue-specific functionalities. Strong proof in vivo multifunctionality is based on in utero transplantation of IDPSCs into multiple tissues without tumorogenicity and immunogenicity. Additional proof of non-tumorogenicity is p53, tumor suppressing gene, expression in LP-IDPSCs and need in low passage number following LP harvesting that prevent karyotype mutations and therefore also reduce risk of tumorogenicity. Additional advantage of disclosed methods of treatment by IDPSCs compositions are reduced immunogenicity potential is that said IDPSCs are negative for HLA-ABC and HLA-DR major histocompatibility (MHC) antigens, therefore allow allogenic transplantation.

Multifuctionality and strong neuroepithelial lineages orientation of IDPSCs of the invention offer multiple uses for regenerative medicine, especially in treatment and prevention of CNS diseases (including but not limited to neurodegenerative disorders), treat renal disorders, pancreatic disorders (diabetes), skin diseases (not limited by wound healing), hair loss symptoms, and assist reproductive functions in women (improve in utero functioning) and men (improve spermatogenesis). In utero proven multifunctionality of the IDPSC n provides a method for treating or alleviating the symptoms of various pathological or physiological conditions including, but not limited to, neurodegenerative diseases, heart failure, myocardial ischemia, limb ischemia, reproductive disorders, aesthetic symptoms, immune disorders, diabetes, stroke, and skin, liver and kidney diseases by administrating the therapeutic composition comprising IDPSCs concentrate, suspension, mixture as a single active biological ingredient or as an adjunct to additional therapeutic ingredients, such as, but not limited to, cells, active pharmaceutical or biological, or natural ingredients agents.

Aspects of the present disclosure are based on two approaches: the cultivation of organ and tissue explant, previously known and used for evaluation of the toxic effect of drugs, therapeutic substances and biological agents, for carcinogenic assays, and/or for susceptibility testing. However, both techniques in combination was used for the first in present invention for isolation of stem cells from dental pulp, which in combination cell culture conditions used for the cultivation of ES cells, allowed the discovery of a novel non-enzymatic method of isolating a population of IDPSC.

The advantages of some of the methods presented in this disclosure can be understood through the explanations below.

One objective for in vitro culture of parts of organ or an entire organ is to maintain organ culture tissue architecture. For example, the parenchyma and stroma are conserved both in terms of its structure and function, and thus the organ culture resembles the in vivo organ in question. Organ culture is widely used in ophthalmology as the method of choice for the preservation of human donor corneas. A second approach is to culture the explant used for isolation of cells. The tissue is isolated under aseptic conditions, chopped and the pieces are placed in a cell culture dish containing culture medium. Explant culture is a culture wherein the cells are left in their surrounding extracellular matrix that more accurately mimic the in vivo environment and over time, progenitor cells migrate out of the tissue and adhere to the surface of the culture dish.

Both approaches have similarities, since they preserve the environment and stem cell niches. However, the tissue is exposed during the cultivation time to a hypoxia that presents a great advantage to maintain the undifferentiated state of stem cells. Therefore the mechanical transfer of the dental pulp, which is a small organ, and pieces of DP, explant, is a strategy to continuously isolate MSC that maintain their primordial characteristics unchanged after isolation.

It is worth noting that the strategy chosen for the isolation of IDPSC (explant), which are cells of neural crest origin, was also used for isolation of migratory "genuine" neural crest stem cells from the neural tube. It is also worth noting that the strategy chosen for the isolation of CTIPD (explant), which are cells of neural crest origin, was also adopted for isolation of migratory trunk neural crest cells using the neural tube explant.

Epi-fluorescence. DAPI (blue) was used for nuclear visualization. (C) Negative control; mice injected with saline. Bars (A) 20 µm; (B, C) 100 µm.

Figure 28:
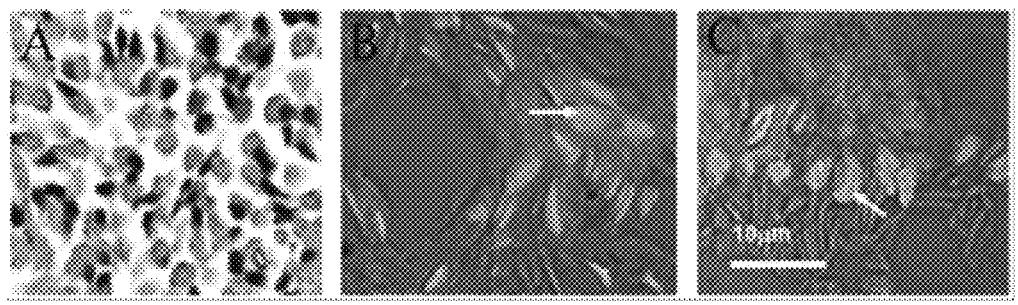

FIG. 28 depicts LP IDPSC transplantation into testes of a fertile mouse. (A, B) On day 9 these cells formed fluorescent groups containing cells with different morphologies observed in the central lumen (B). Sperm of mice are indicated by red arrows (B, C). Some of them exhibit morphology similar to human sperm (white arrows) (B, C). Bars (A-C) 20 µm.

Figure 29:
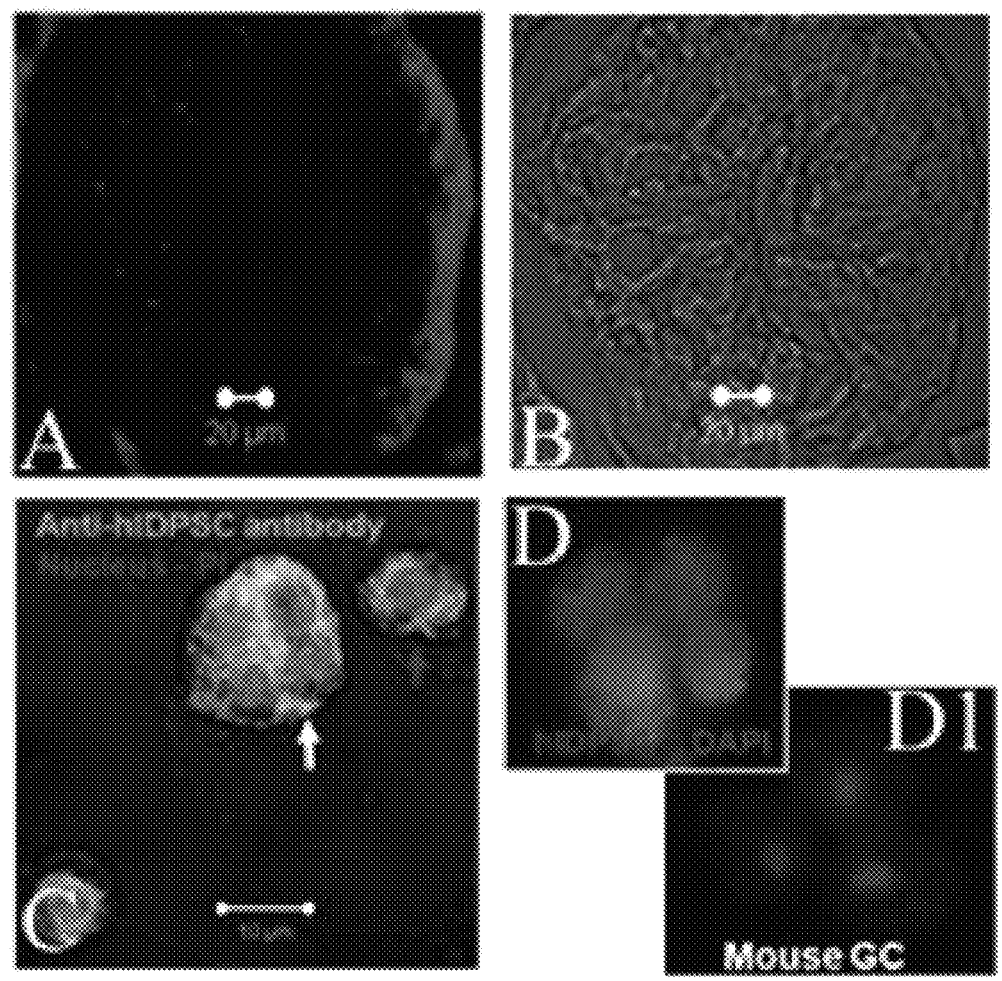

FIG. 29 depicts images of testes from infertile mice transplanted with LP IDPSC. Localization of IDPSC was observed in the periphery of the TS, which are grafted in the tunica albuginea (A, B). (C) The white arrow indicates probable round spermatids while the red arrow indicates the primordial germ cells. In (D) the presence of a tetrad a four spermatids is shown with Vibrant (IDPSC stained). In (D1) is shown another tetrad isolated from the same mouse testicle as a negative control. PI (red) (C) and DAPI (blue) (D, D1) used for nuclear visualization. Bars (A, B) 20 µm, (C) 10 µm.

Figure 30:
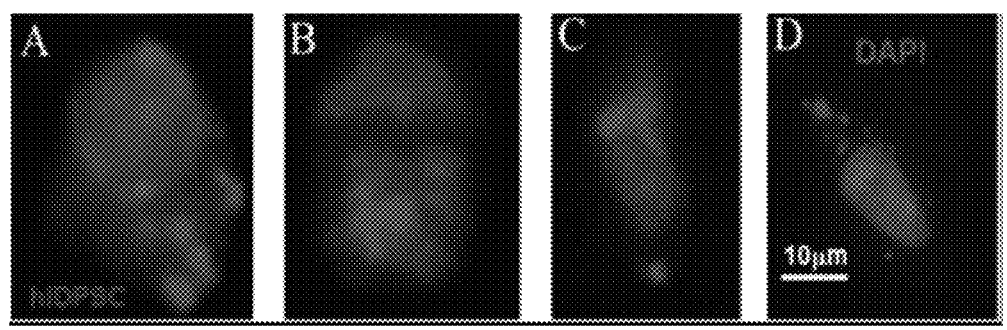

FIG. 30 depicts LP IDPSC derived spermatid-like cells shown in red at different stages of maturation in fertile mice (A-D). (A) Round spermatid. (B-C) elongated spermatids. Bars 10 µm.

Figure 31:
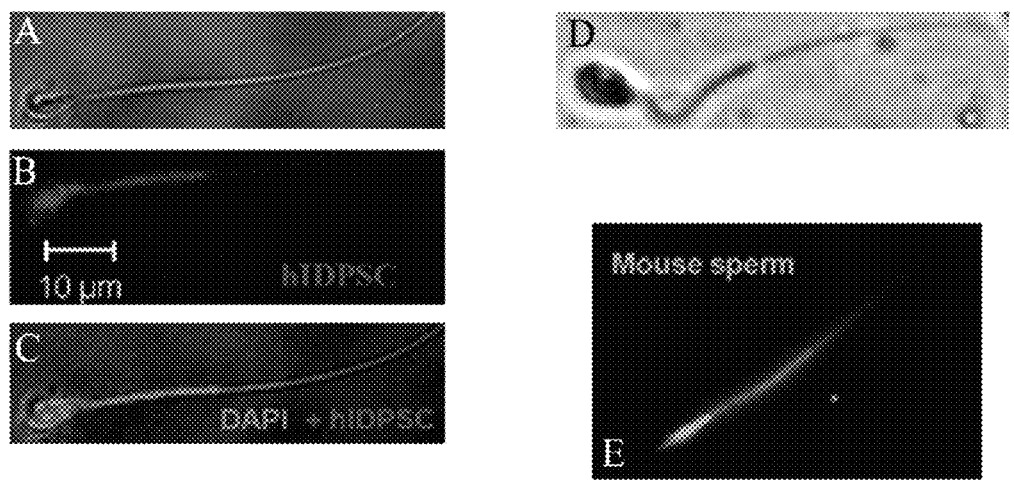

FIG. 31 depicts phenotype identification in human and mouse sperm. Some fluorescently labeled sperm cells (shown in red) with morphology quite similar to human sperm were detected (A-C). (D) A human sperm-like morphology. (E) Morphology of mouse sperm. Bars 10 µm.

Figure 32:
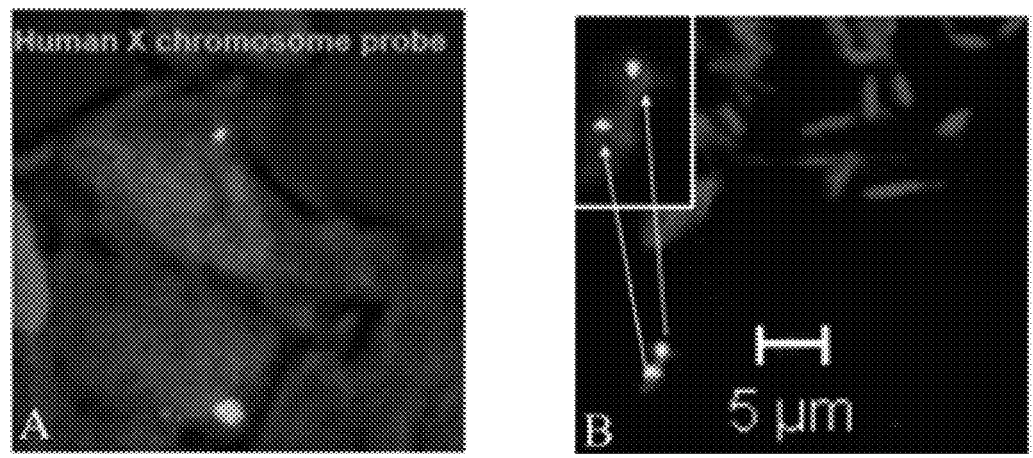

FIG. 32 depicts a cytogenetic analysis. FISH analysis using a probe specific for human X chromosome confirmed the presence of only one X signal within some cells suggesting a reduction of chromosomes, which occurs during meiosis. Note that the cells form pairs, which is consistent with the fact that if diploid cells divided the haploid cells would be situated close to each other. Scale Bars 5 µm.

Figure 33:
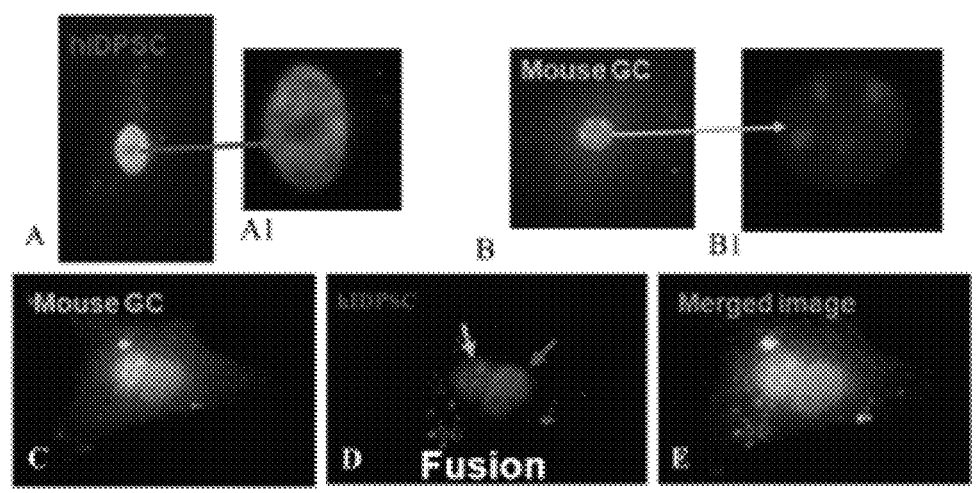

FIG. 33 depicts cell fusion. (A and A1) LP IDPSC cytoplasm stained with Vybrant in red; note the morphology of the nucleus (DAPI, blue) in (A1). Mouse germ cell cytoplasm is stained in green (B) with a greater increase in the nucleolus (B1). (C) Cell with two fused nuclei and green-stained cytoplasm. (D) A cell with two fused nucleus and red-stained cytoplasm. (E) Overlap between (C) and (D).

Figure 34:
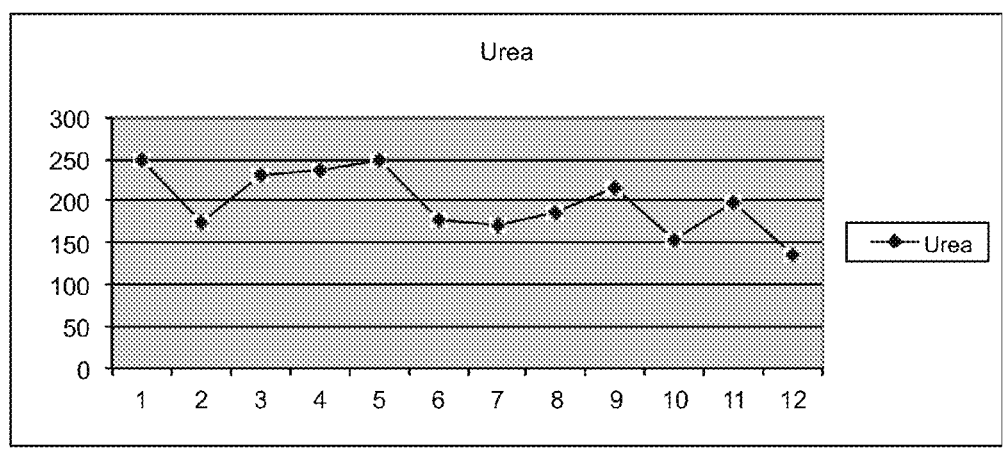

FIG. 34 depicts the fluctuations in urea levels during the course of LP IDPSC transplantation, which occurred at time points 4, 7, and 9.

Figure 35:
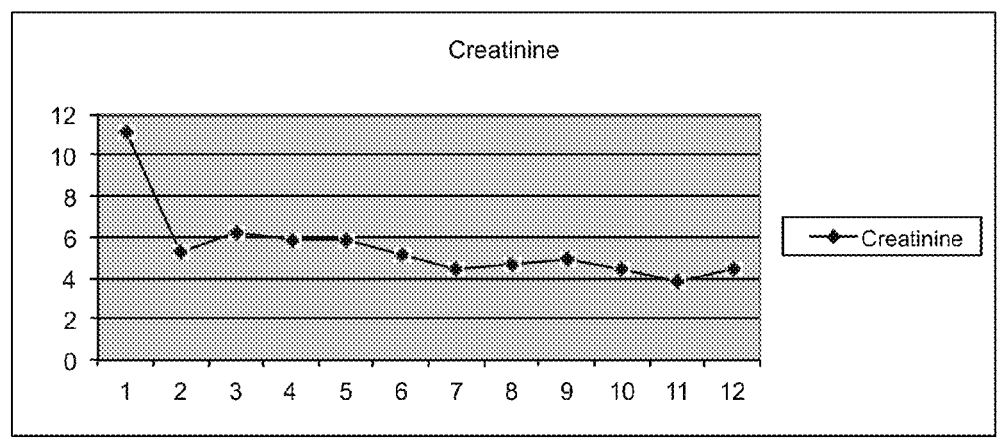

FIG. 35 depicts the fluctuations in creatinine levels during the course of LP IDPSC transplantation, which occurred at time points 4, 7, and 9.

Figure 36:
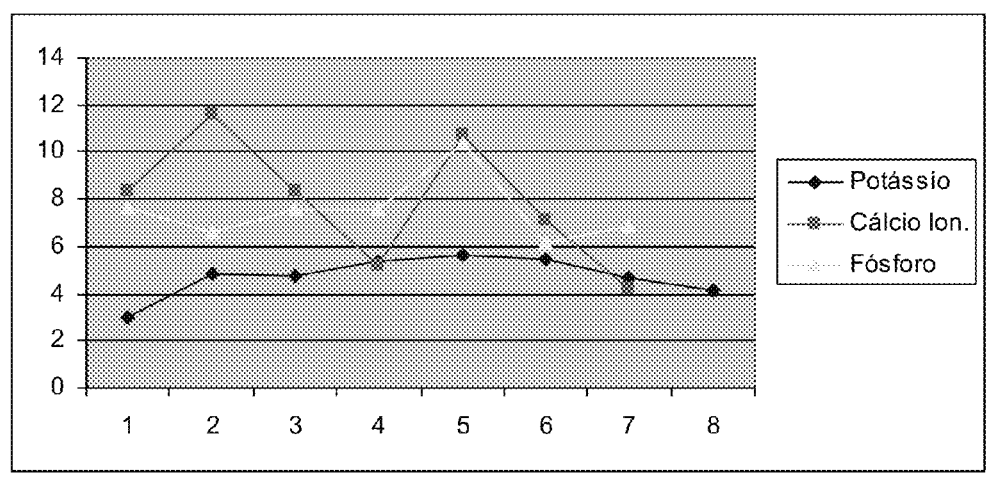

FIG. 36 depicts the fluctuations in electrolyte levels (potassium, calcium, and phosphorus) during the course of LP IDPSC transplantation, which occurred at time points 4, 7, and 9.

Figure 37:
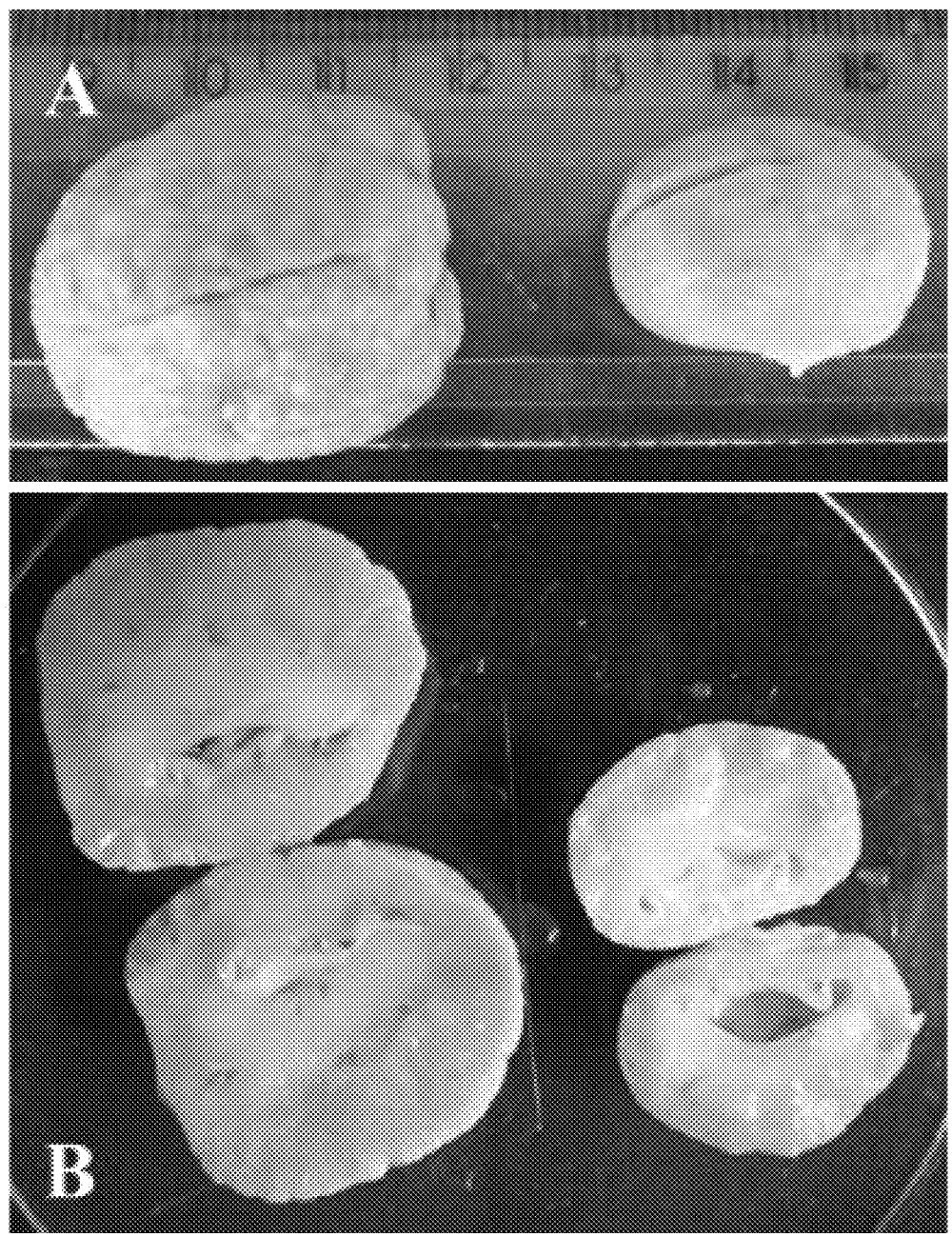

FIG. 37 depicts a macroscopical presentation of cat kidney that received human IDPSC therapy. A) Difference in size between left (major size)), received IDPSC, and right kidney. B) Neoformation of irregular appearance is evident in the left kidney.

Figure 38:
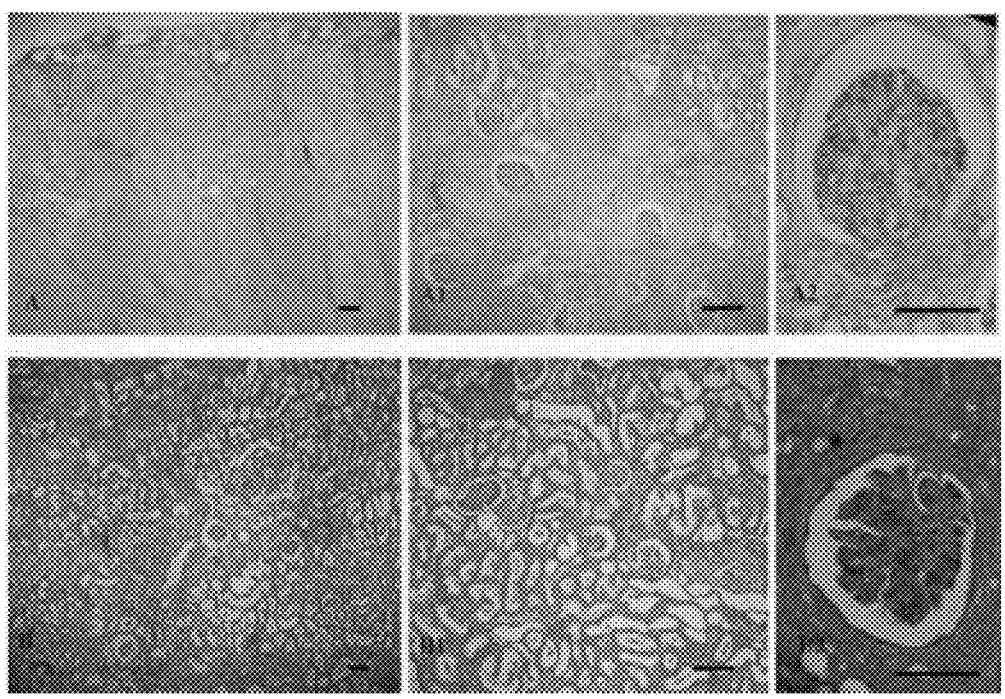

FIG. 38 depicts a histological presentation of left (A-A2) and right (B-B2) kidneys. Scale bars; A-B2=200 µm. Blood infiltration (red) can also be observed in B1 and B2. In B2 preservation of glomerular endothelial cell is visible.

Figure 39:
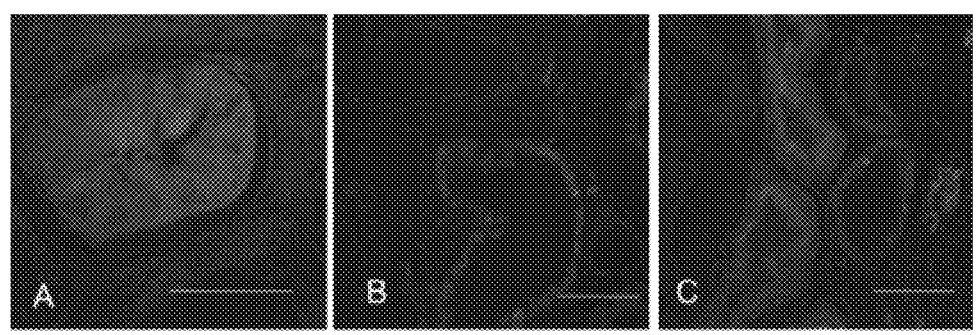

FIG. 39 depicts the presence of IDPSC in cat kidney. A) Glomerulus positive immunostaining with an anti-IDPSC antibody (red). B)-C) In renal tubules anti-IDPSC antibody reacts with renal tubular cells (red). Confocal microscopy merged images: digital interference contrast+fluorescent microscopy. Nucleus stained with DAPI (blue). Scale bars: A=200 µm, B and C=100 µm.

Figure 40:
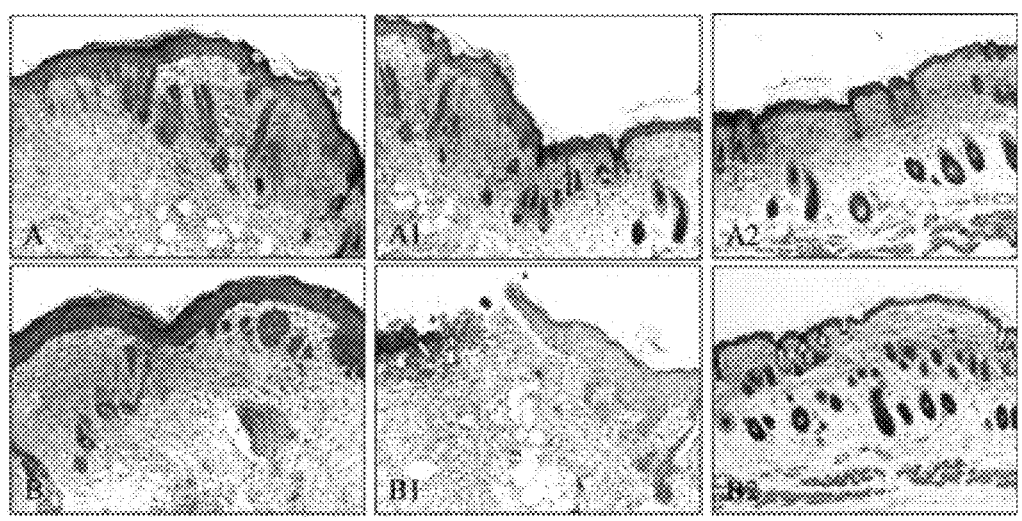

FIG. 40 depicts a histological presentation of skin remodeling demonstrated by Masson's Trichrome staining: A)-A2) Representative images from animals which received LP EGFP-IDPSC. B)-B2) Representative images from animals which received only PBS. Objective 20×.

Figure 41:
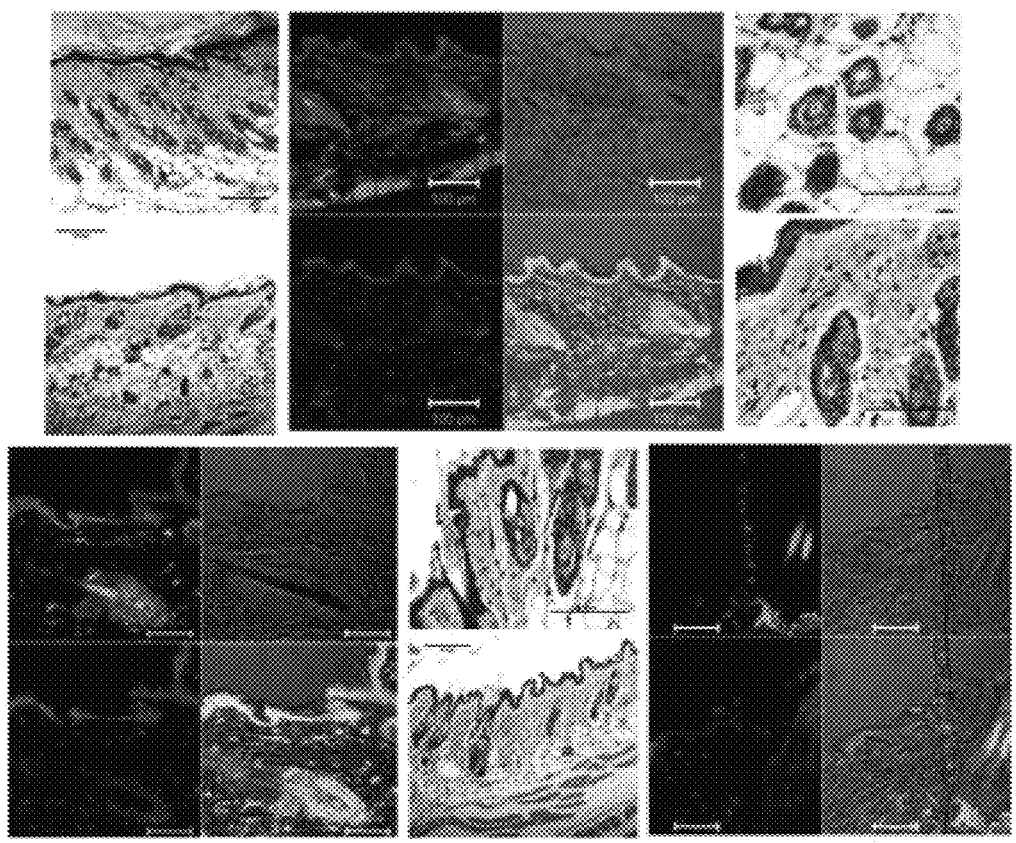

FIG. 41 depicts engraftment of LP EGFP-IDPSC (green) in injured skin. Nuclei were stained with propidium iodide (PI) (red). Confocal microscopy: Fluorescent microscopy (Fm), DIC and DIC+Fm. Histological presentation, H&E staining Scale bars=100 µm.

Figure 42:
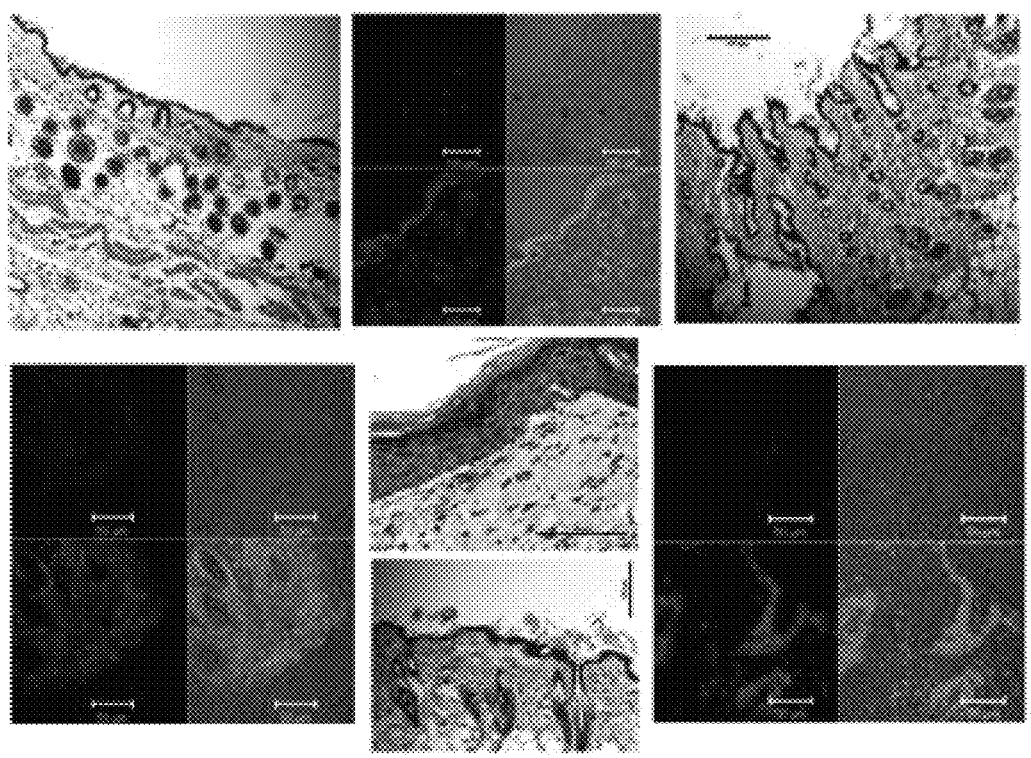

FIG. 42 depicts representative images from animals that received PBS only. Nuclei were stained with PI (red). Confocal microscopy: Fluorescent microscopy (Fm), DIC and DIC+Fm. Histological presentation, H&E staining. Scale bars=100 µm.

Figure 43:
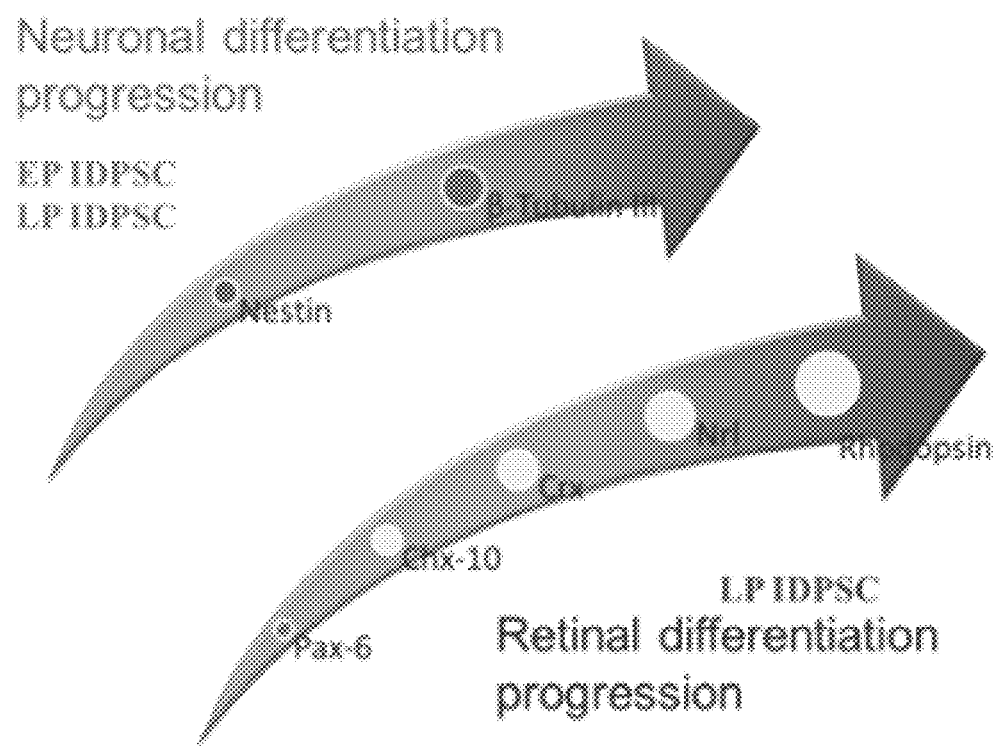

FIG. 43 depicts the neuronal and retinal potential of differentiation of EP and LP IDPSC. EP IDPSC are only able to follow neuronal, but not retinal differentiation expressing the early markers of neuronal differentiation nestin and beta-tubulin III. LP IDPSC express early markers of both neuronal and retinal differentiation (Pax 6 and Chx-10). Crx, Nrl, and Rhodopsin are late retinal neuronal markers, which are expressed by differentiated LP IDPSC but not by EP IDPSC.

Figure 44:
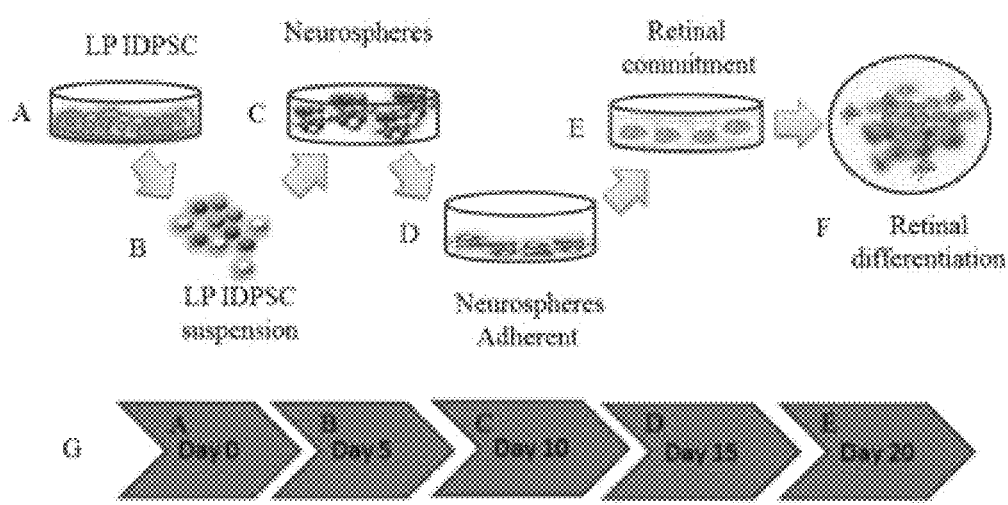

FIG. 44 depicts LP IDPSC differentiation toward retinal cells. A)-F) Stages of differentiation. In F) the final stage of retinal cells differentiation is presented preferentially by photoreceptors. Following differentiation the cell number decreases significantly. G) Time line of differentiation.

Figure 45:
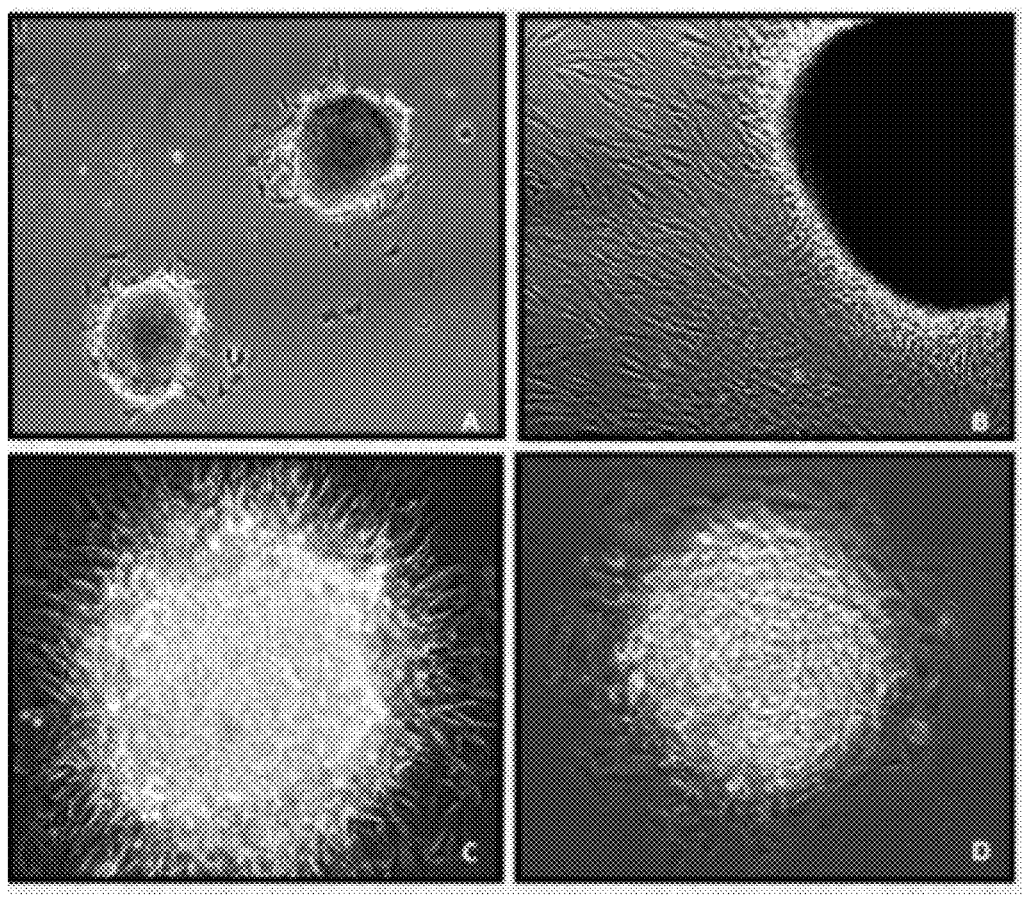

FIG. 45 depicts EP IDPSC, adherent neurospheres, which were not able to progress through retinal differentiation. A) 10×; B)-D) 40×.

Figure 46:
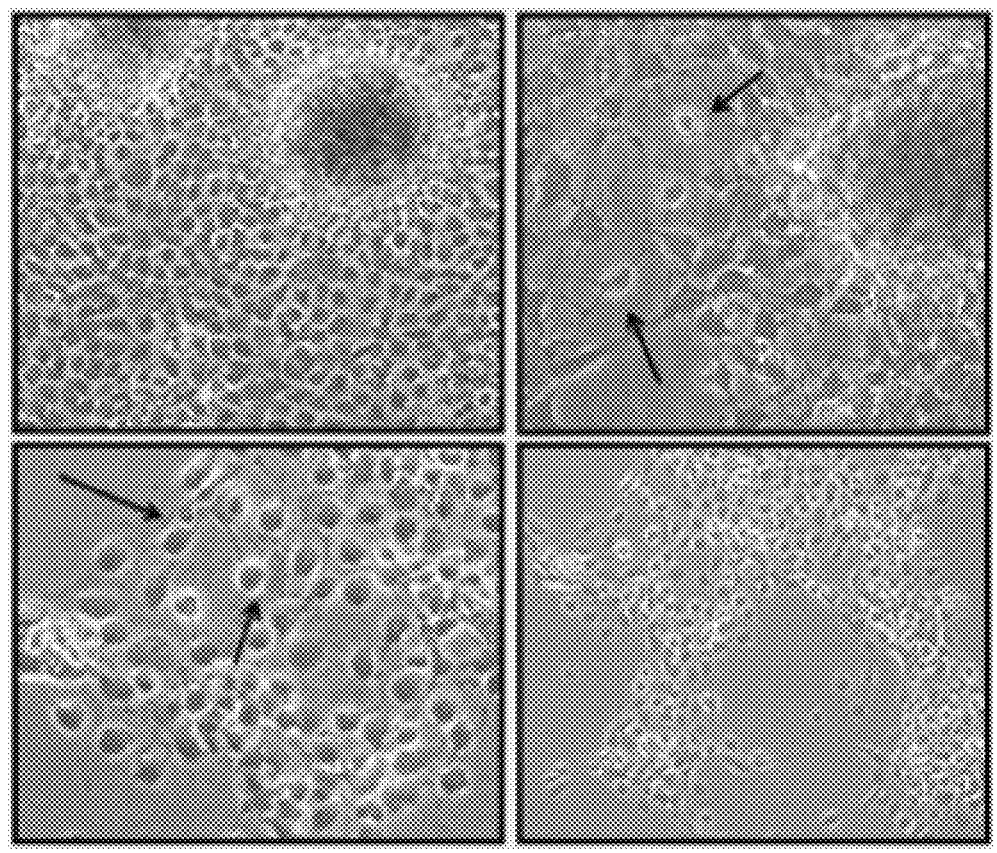

FIG. 46 depicts LP IDPSC, adherent neurospheres, which were able to progress through retinal differentiation. A) 10×; B)-D) 40×.

Figure 47:
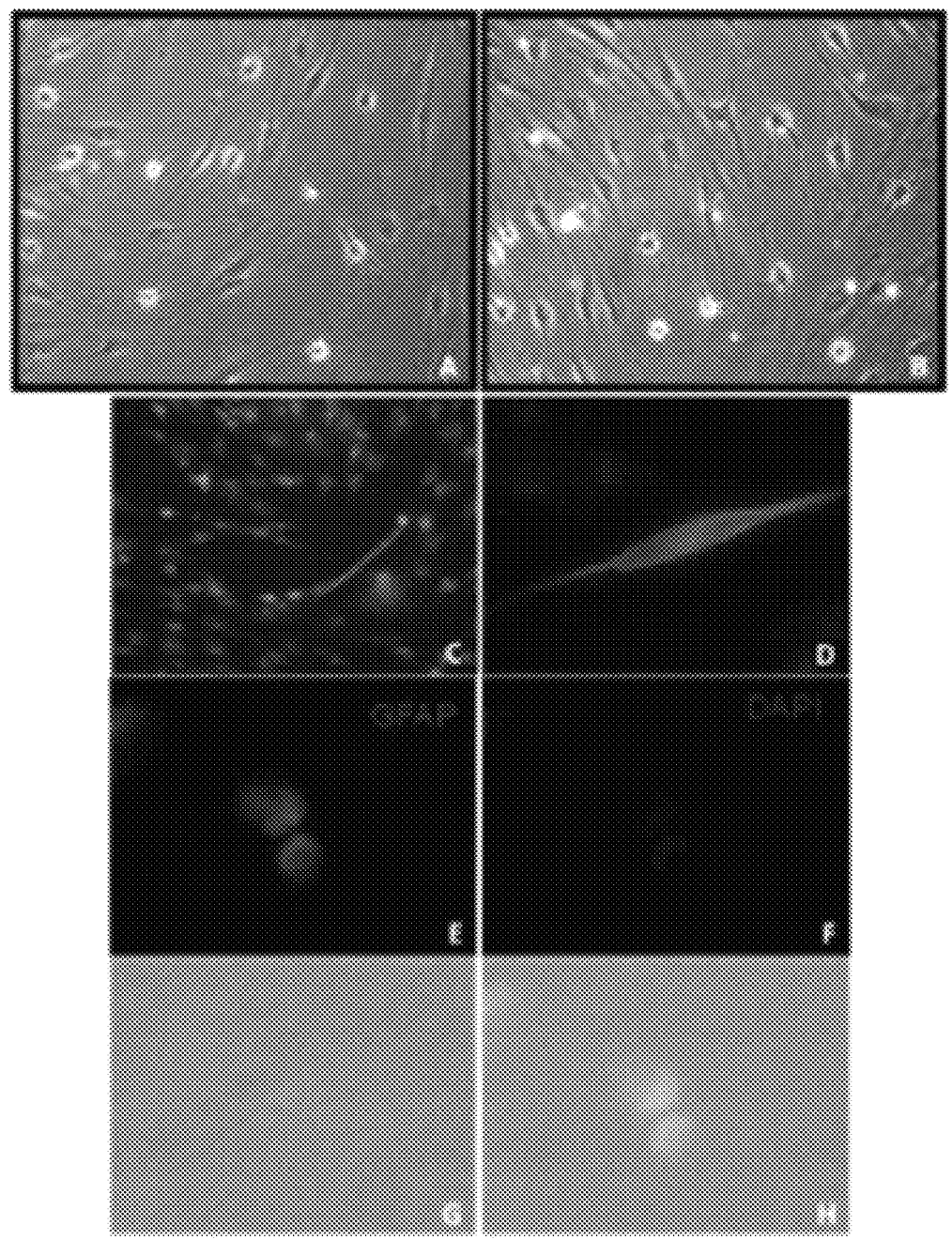

FIG. 47 depicts neuronal differentiation of EP IDPSC. A)-B) Phase contrast showing cells with glial-like morphology—10× objective. C)-D) Immunofluorescence showing expression of β-III-Tubulin. C) 10× objective. D) 60× objective. E)-H) Expression of GFAP—40×. E) GFAP immunostaining of body and cell nucleus. F) Nuclei stained with DAPI. G) Brightfield demonstrating the morphology of glial-like cells. H) Overlay of all filters (DAPI+Rhodamine, Brightfield).

Figure 48:
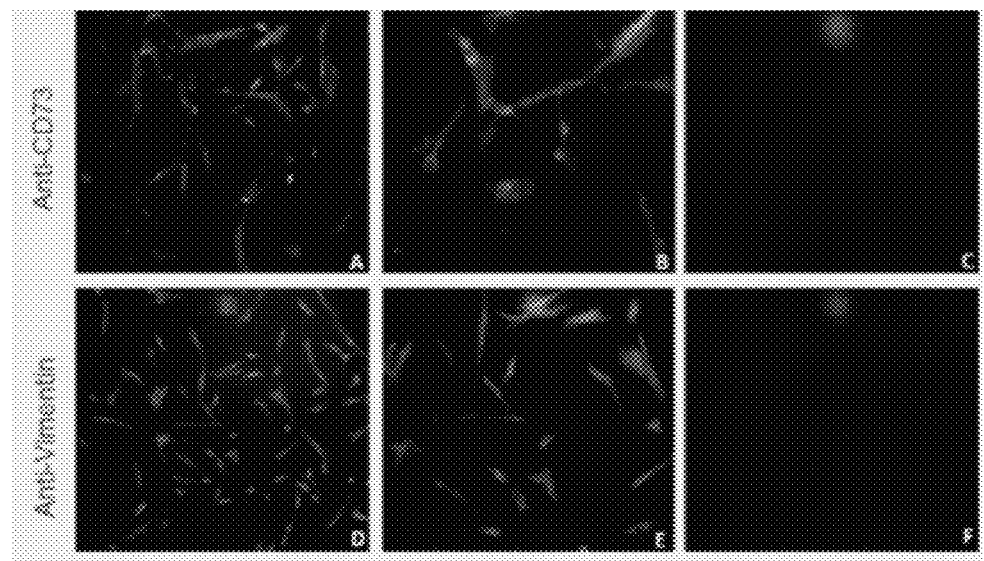

FIG. 48 depicts expression of CD73 (A, B) and vimentin (D, E) by undifferentiated IDPSC. C)-F) Secondary antibody controls. Nuclei were stained with DAPI (blue).

Figure 49:
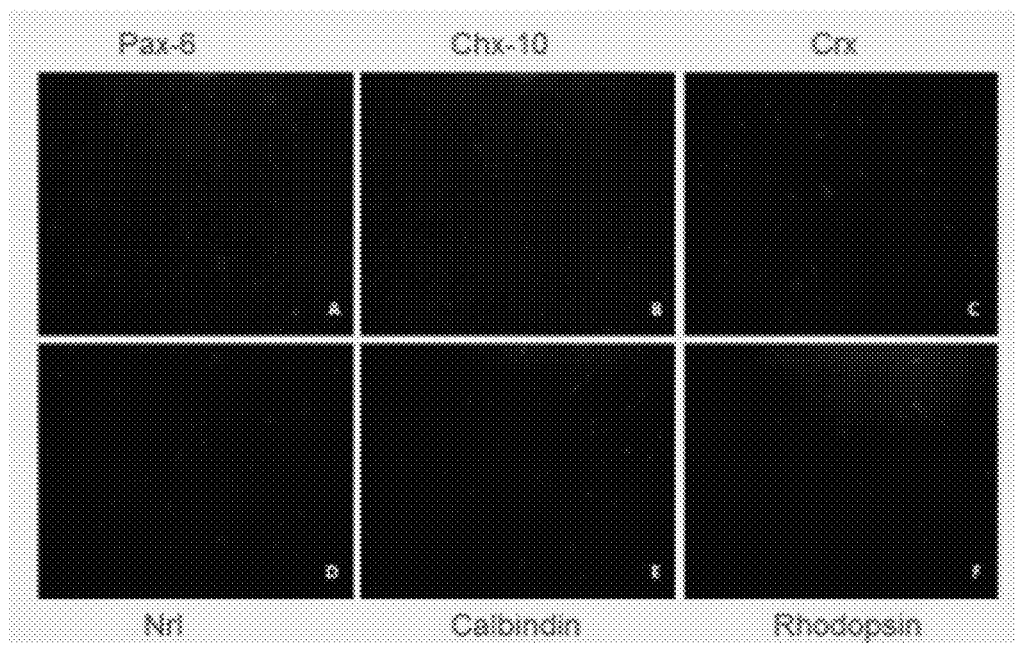

FIG. 49 depicts immunofluorescence and lack of expression of specific markers of retinal cells such as Pax-6, Chx-10, Crx, Nrl, calbindin and rhodopsin in undifferentiated LP IDPSC.

Figure 50:
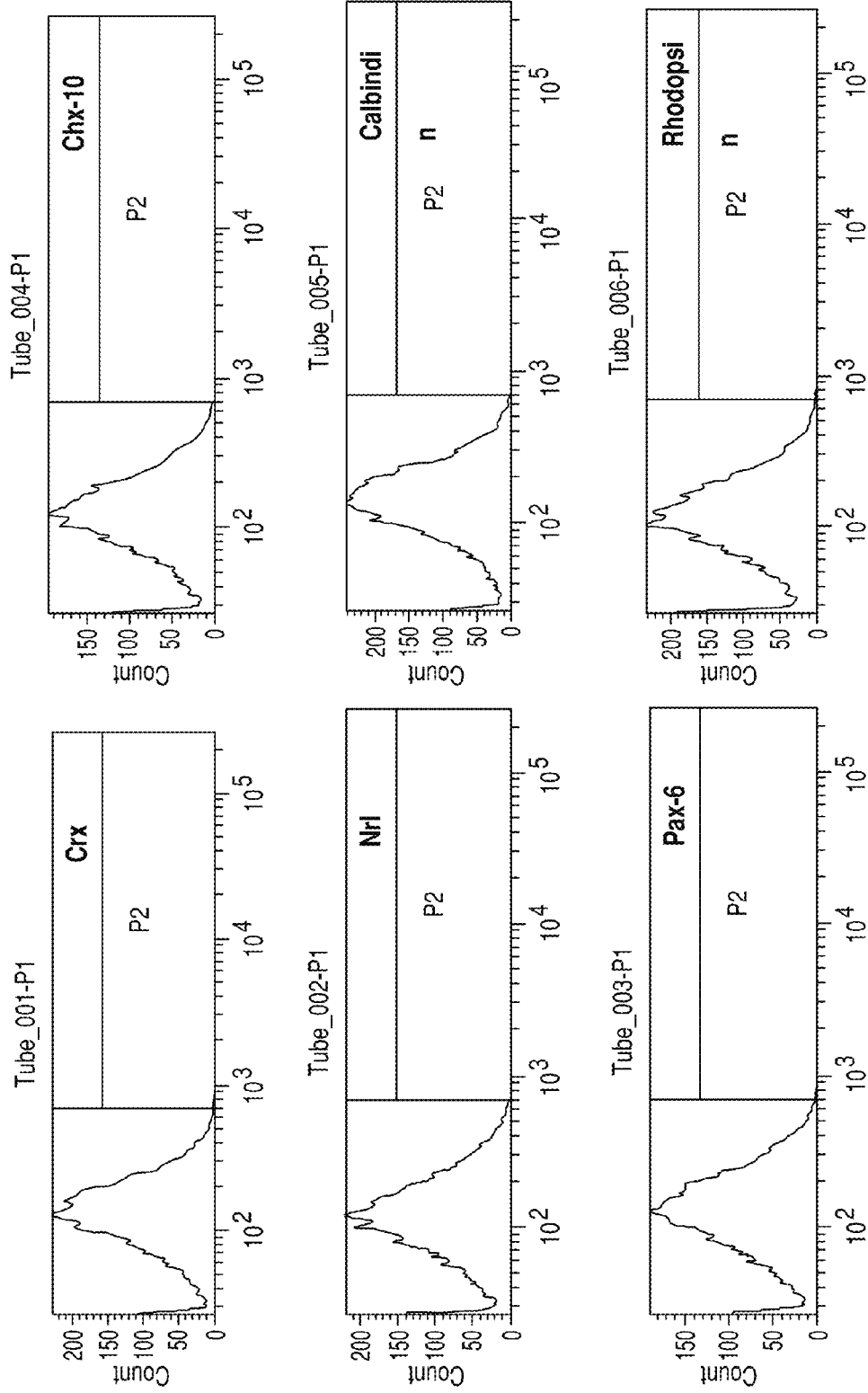

FIG. 50 depicts flow cytometry and lack of expression of specific markers of retinal cells such as Pax-6, Chx-10, Crx, Nrl, calbindin and rhodopsin in undifferentiated LP IDPSC.

Figure 51:
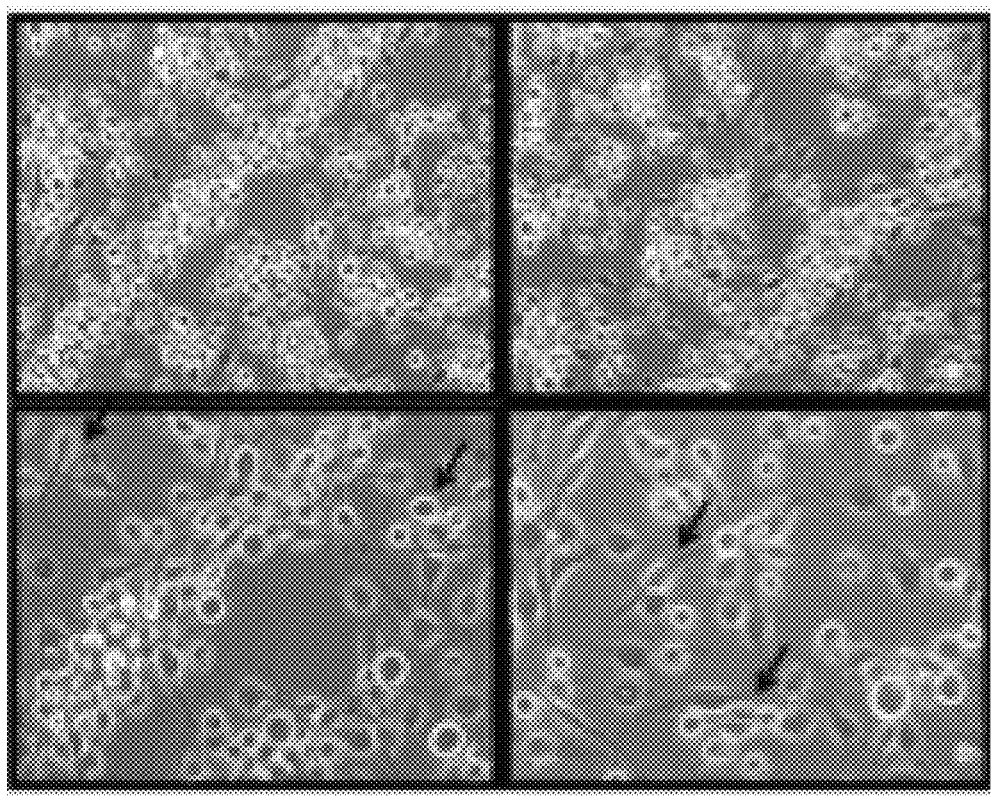

FIG. 51 depicts differentiated LP IDPSC showing different types of neuronal morphology, such as neuron- and ganglion-like cells.

Figure 52:
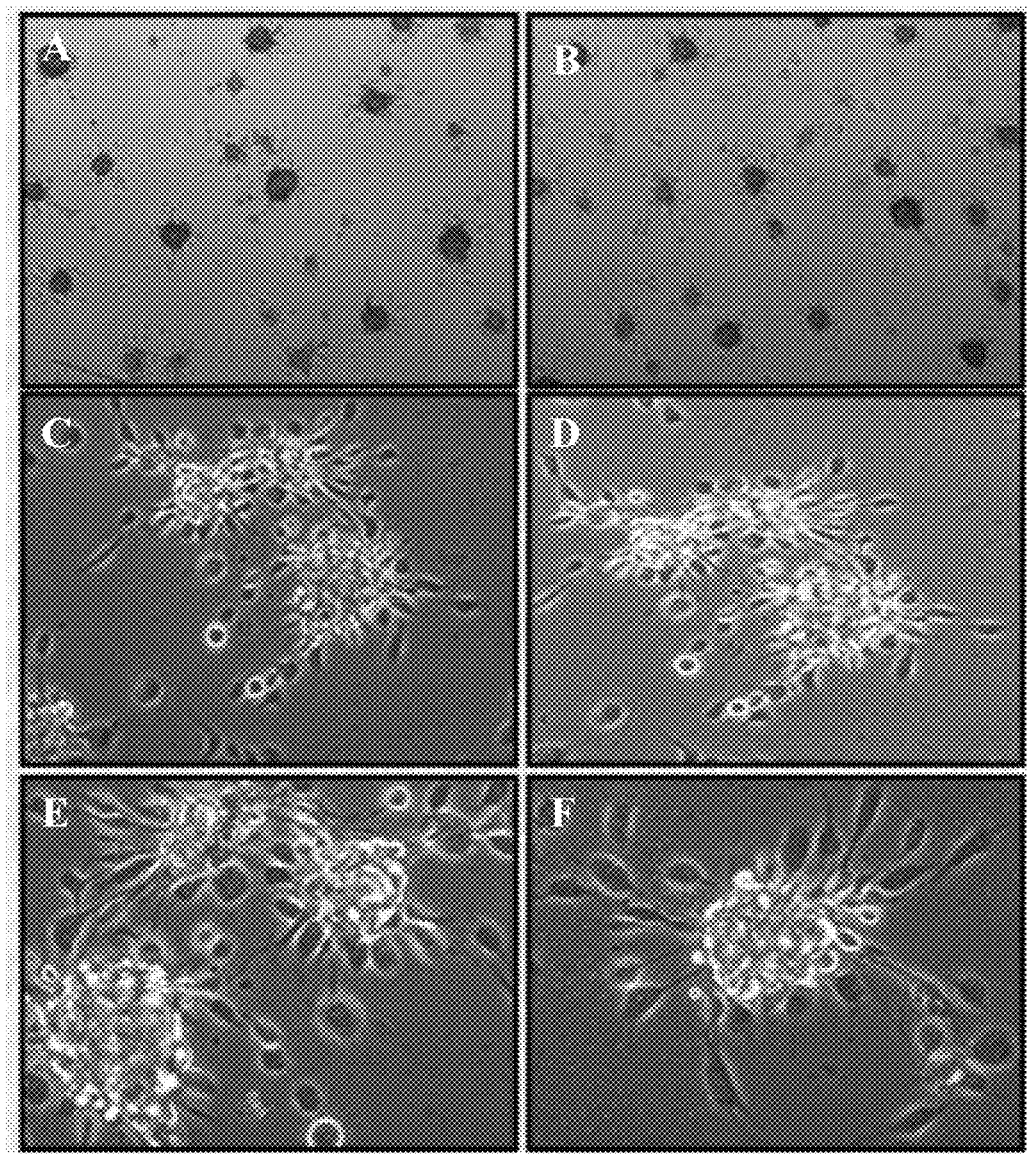

FIG. 52 A)-B) Secondary neurospheres in suspension—20× objective. C)-D) Secondary neurospheres adhered—objective 10×. E)-F) Rosette-like morphology—20× objective.

Figure 53:
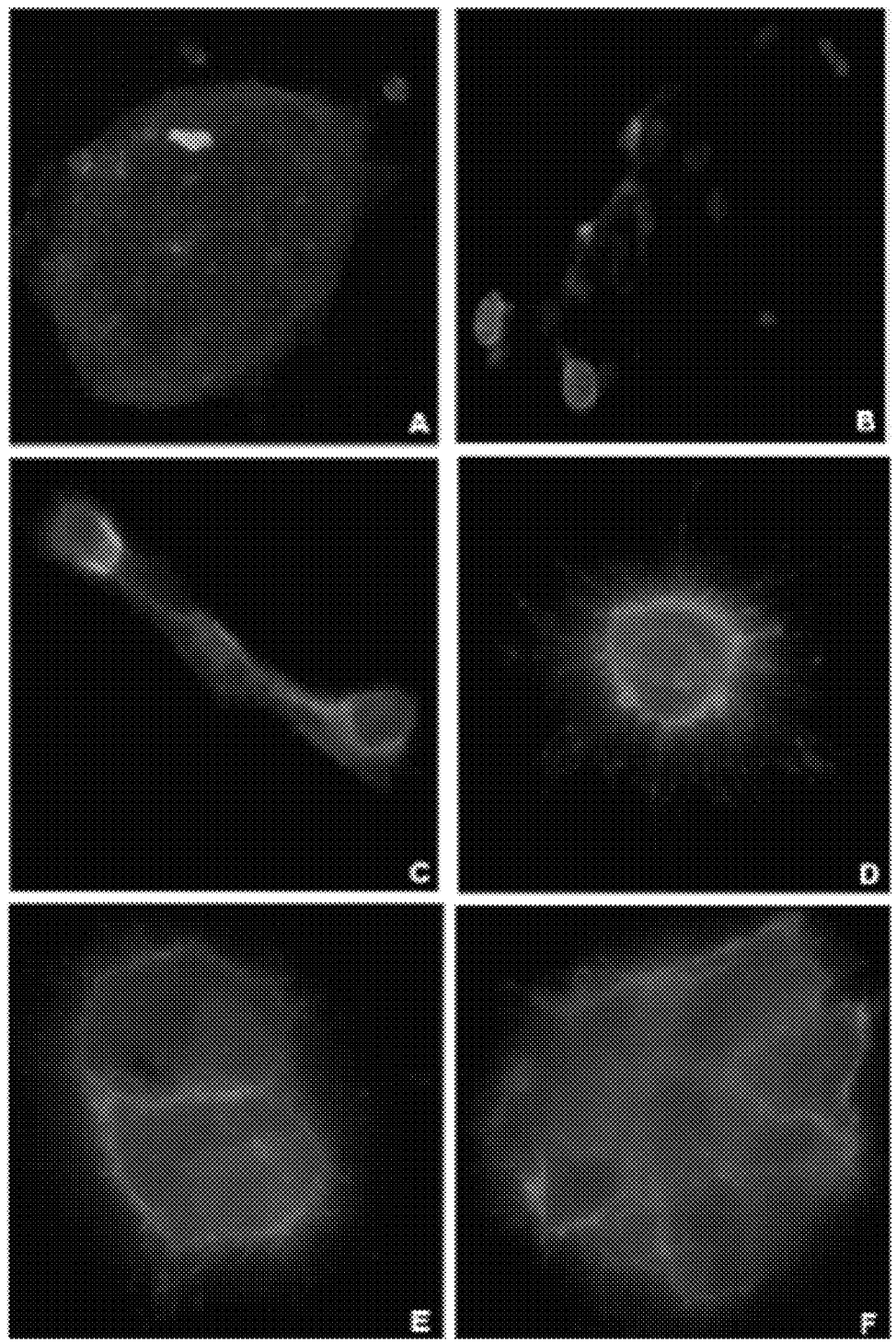

FIG. 53 depicts expression of CD73 in differentiated LP IDPSC neurospheres and migratory neurons (A-F). In (B) some cells, which are negative for this marker, can be observed.

Figure 54:

FIG. 54 depicts expression of Pax6 in LP IDPSC derived retinal precursor cells, which are organized into neurosphere-like structures. Anti-Pax-6 antibody showed positive immunostaining in 50% of differentiated cells.

Figure 55:
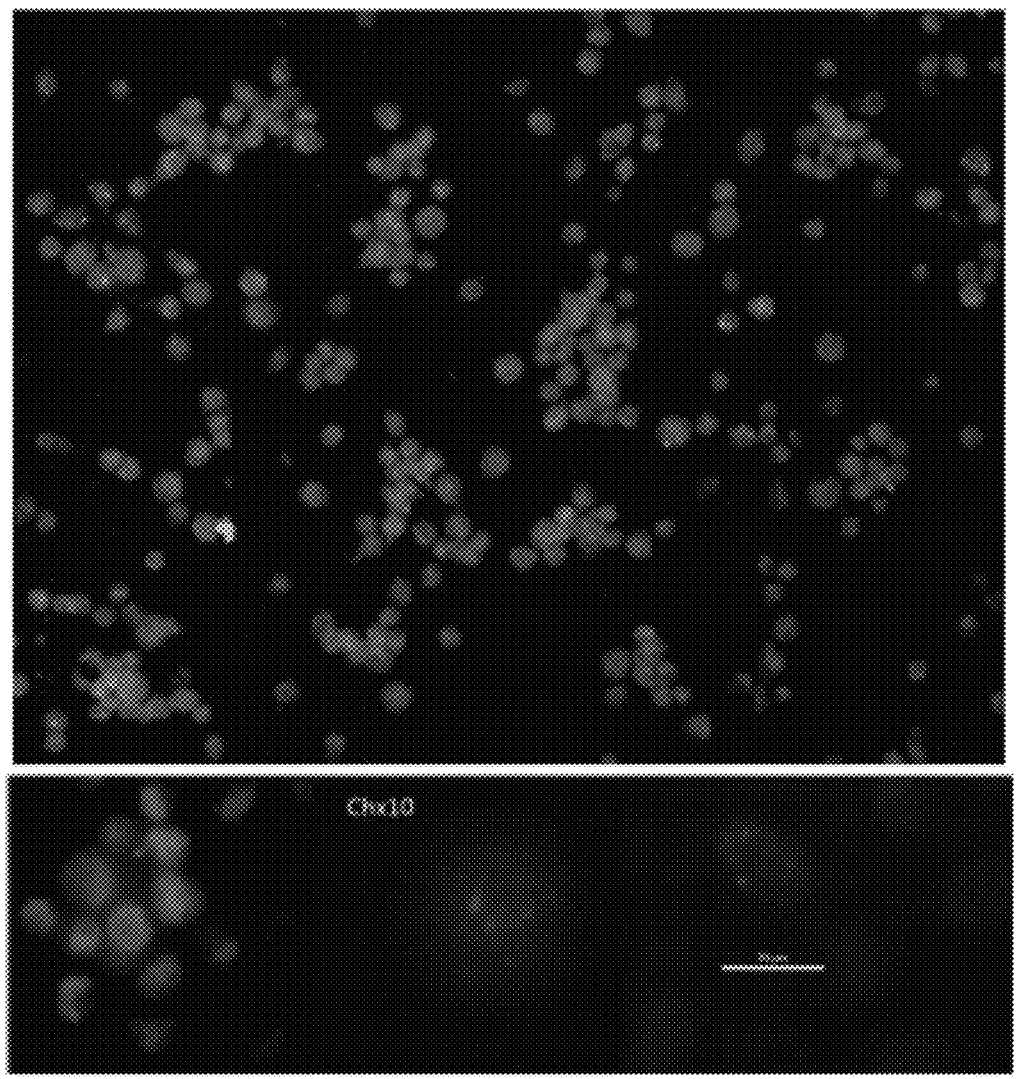

FIG. 55 depicts expression of Chx10 in LP IDPSC derived retinal precursor cells, which are organized into neurosphere-like structures. Anti-Chx-10 antibody showed positive immunostaining in 80% of differentiated cells.

Figure 56:
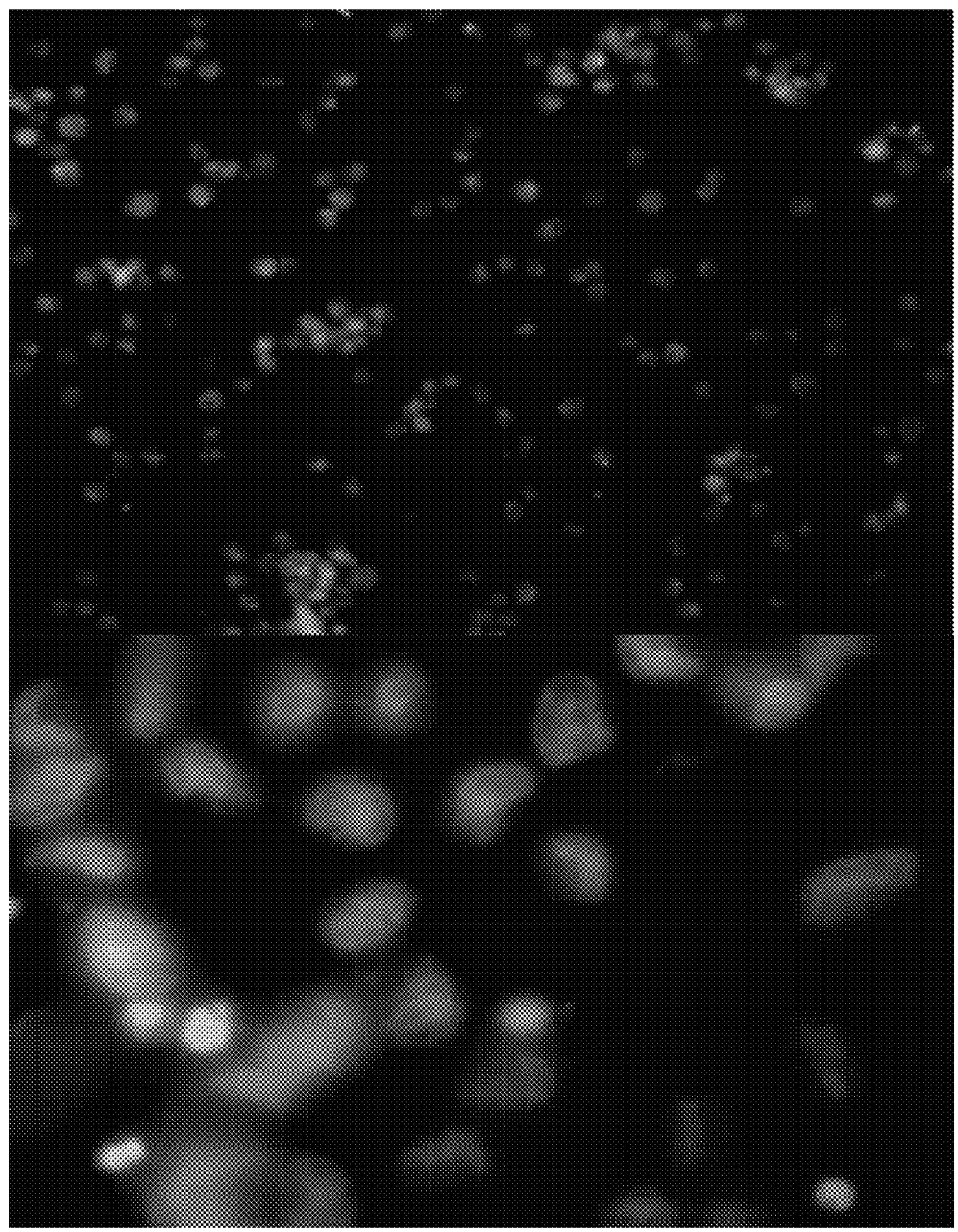

FIG. 56 depicts expression of Crx in LP IDPSC derived retinal precursor cells, which are organized into neurosphere-like structures. Higher magnification showed nuclear localization of this protein. Anti-Crx antibody showed positive immunostaining in 80% of differentiated cells.

Figure 57:
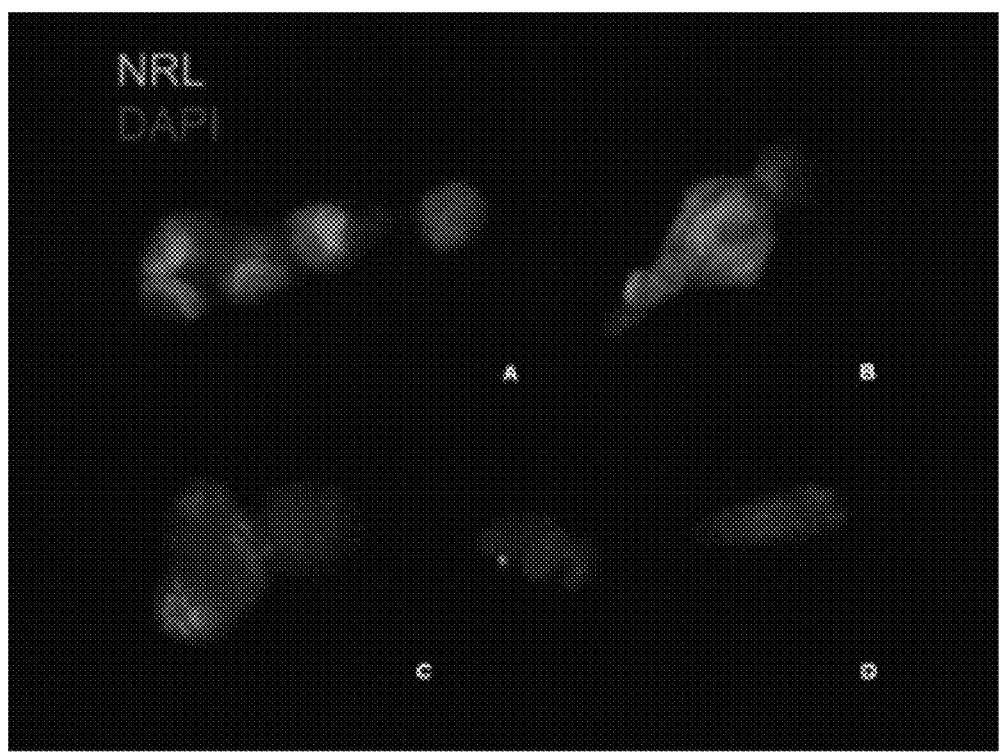

FIG. 57 depicts expression of NRL (nuclear and perinuclear localization) in LP IDPSC derived retinal precursor cells, which are organized into neurosphere-like structures. Anti-NRL antibody showed positive immunostaining in 20% of differentiated cells.

Figure 58:
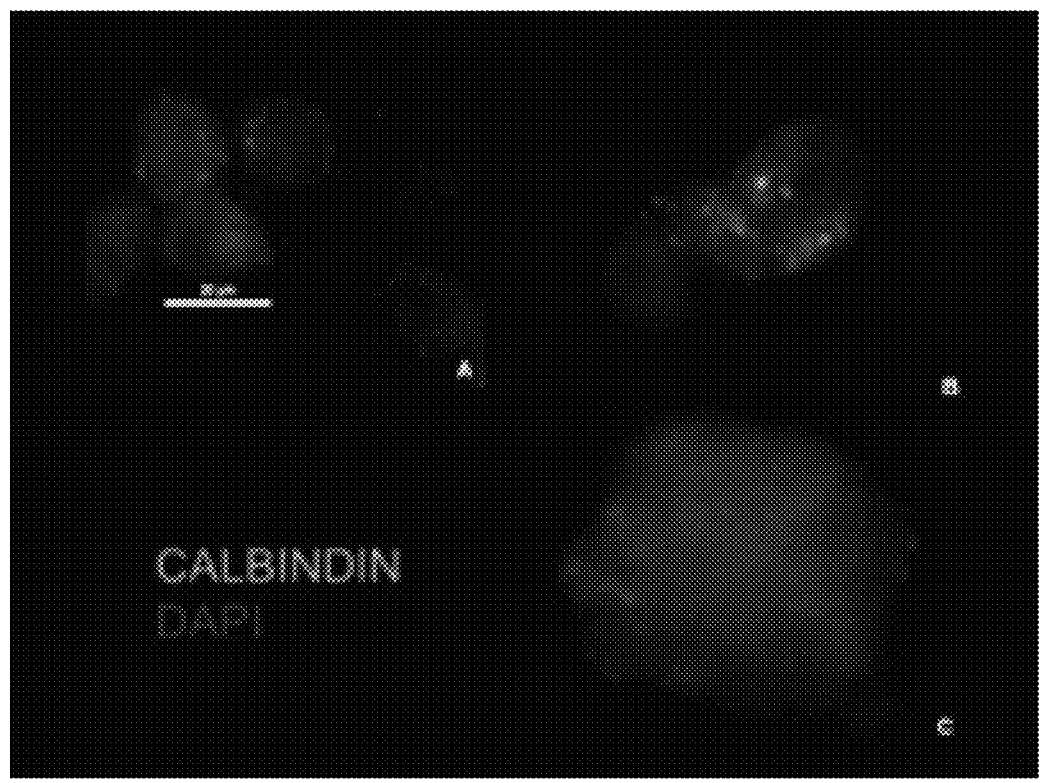

FIG. 58 depicts expression of calbindin (cytoplasm localization) in LP IDPSC derived retinal precursor cells, which are organized into neurosphere-like structures. Anti-calbindin antibody showed positive immunostaining in 20% of differentiated cells.

Figure 59:
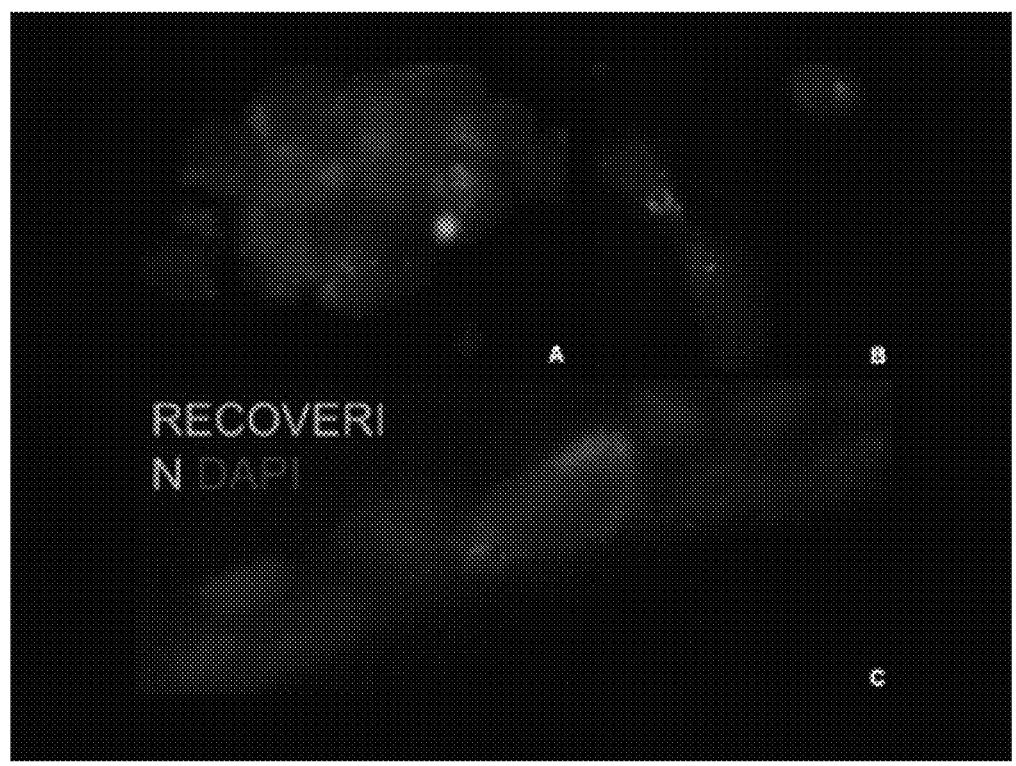

FIG. 59 depicts expression of recoverin (cytoplasm localization) in LP IDPSC derived retinal precursor cells, which are organized into neurosphere-like structures. Anti-recoverin antibody showed positive immunostaining in 20% of differentiated cells.

Figure 60:
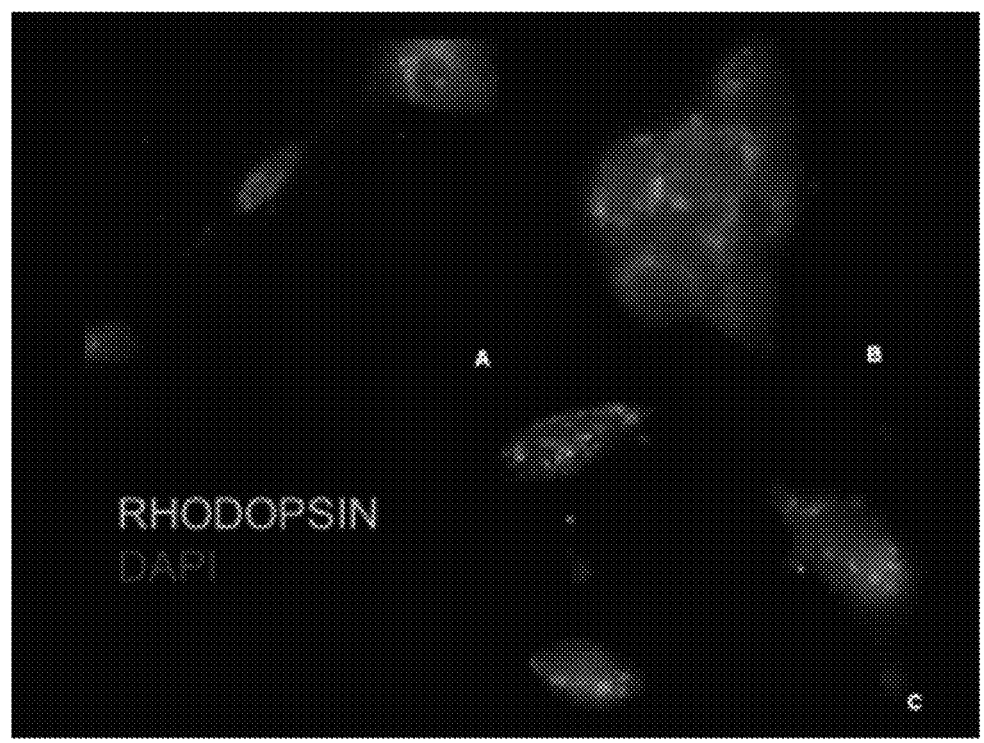

FIG. 60 depicts expression of rhodopsin (cytoplasm localization) in LP IDPSC derived retinal precursor cells, which are organized into neurosphere-like structures. Anti-rhodopsin antibody showed positive immunostaining in 20% of differentiated cells.

Figure 61:
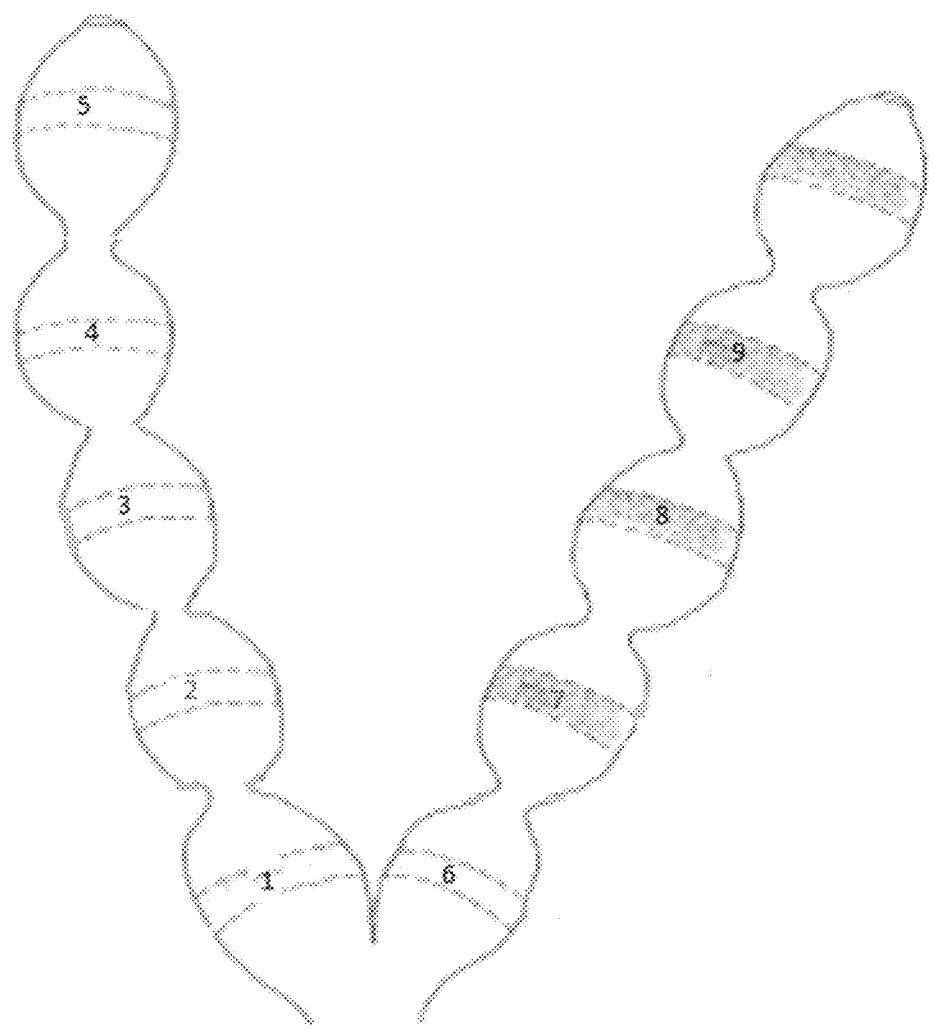

FIG. 61 depicts a Scheme 1 exemplifying the uterine horns of the experimental model: the group of treated fetuses were in 1, 3, 4 and 5 of the right uterine horn (Cud); these fetuses received transplantation of EGFP LP IDPSC. The control group of fetuses were in 2 and 7 of the left uterine horn (Cue); these were collected for the experimental control.

Figure 62:
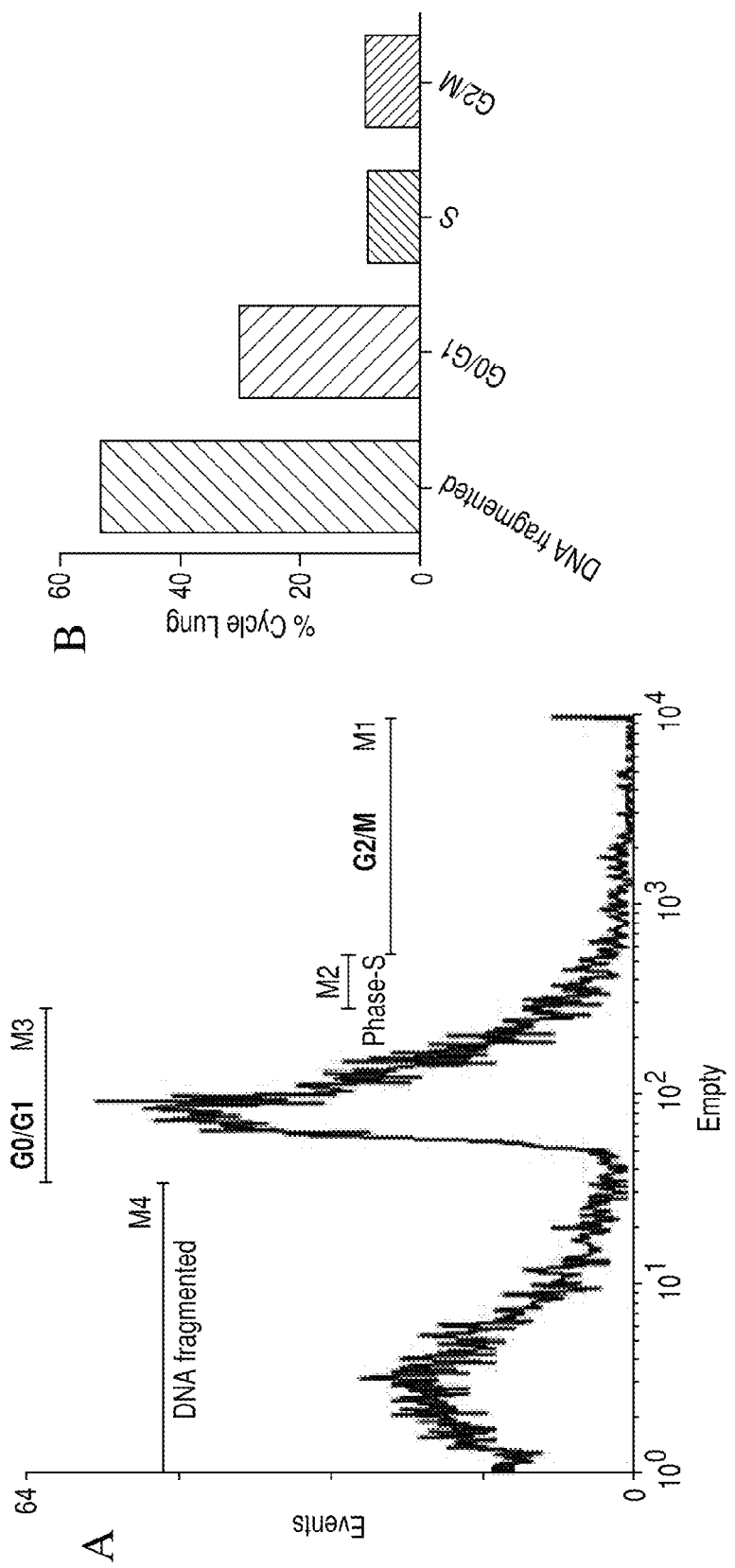
Figure 62:
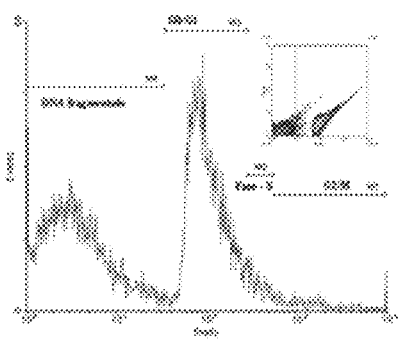
Figure 62:
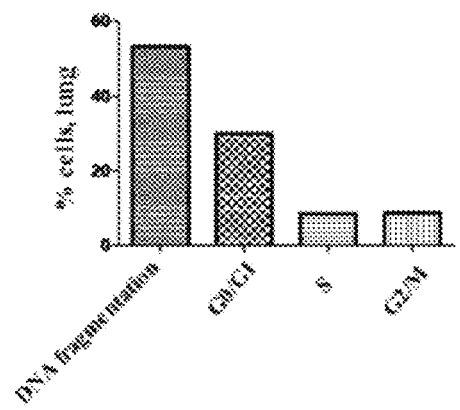

FIG. 62 depicts Quantification of EGFP LP IDPSC grafting and evaluation of these cells proliferation after transplantation performed by flow cytometry A, B) Quantification of grafting EGFP LP IDPSC in a fragment of lung tissue. A) anti-IDPSC (52.8%) and B) anti-HuNu (50.2%) antibodies. C) Schematic evaluation of EGFP LP IDPSC at different phases of cell cycle after transplantation into dog fetus. D) Quantitative and comparative analysis of EGFP LP IDPSC at different phases of the cell cycle.

Figure 63:
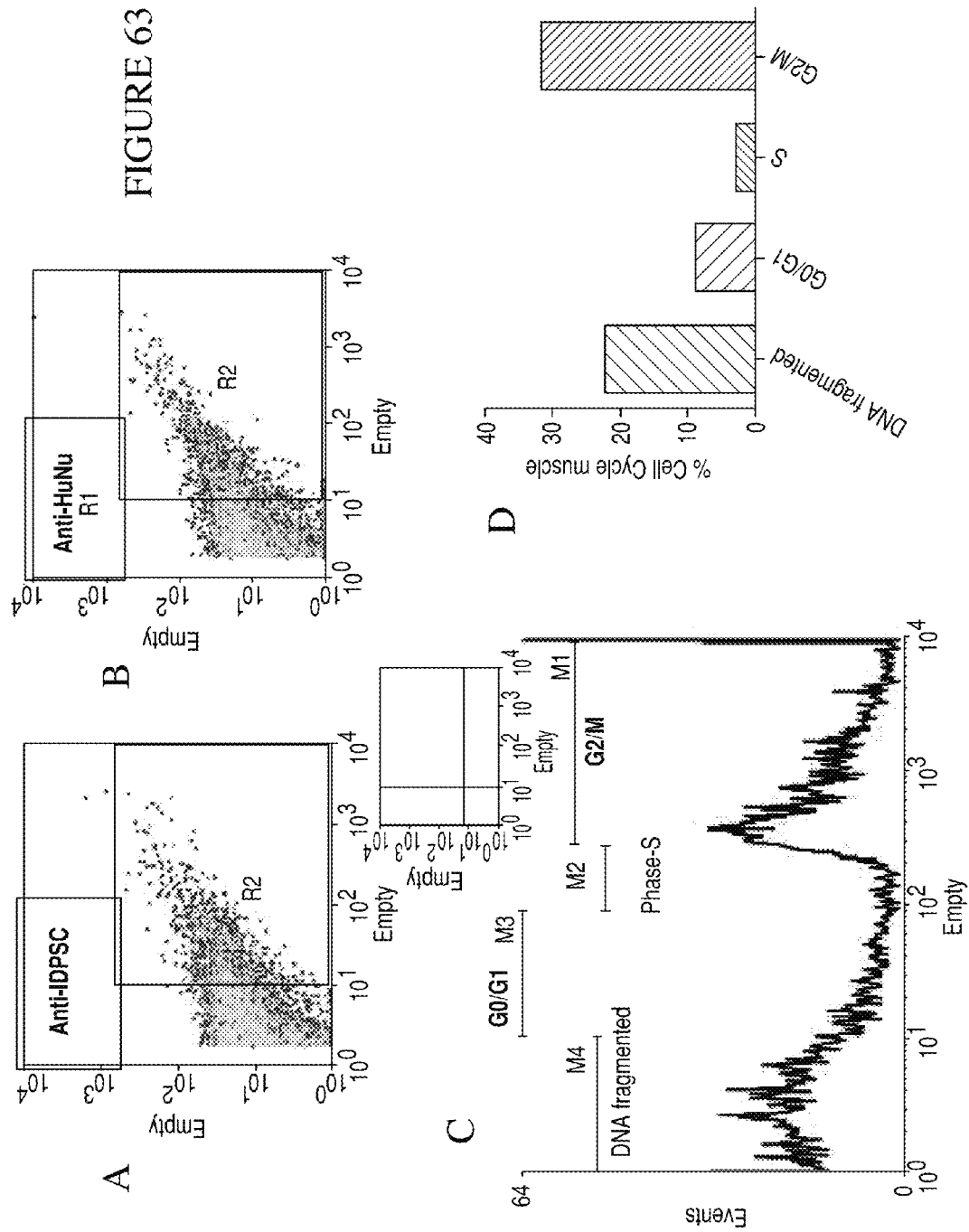

FIG. 63 depicts quantification of EGFP LP IDPSC grafting and evaluation of these cells proliferation after transplantation performed by flow cytometry A, B) Quantification of grafting EGFP LP IDPSC in a fragment of muscle tissue. A) anti-IDPSC (52.8%) and B) anti-HuNu (50.2%) antibodies. C) Schematic evaluation of EGFP LP IDPSC at different phases of cell cycle after transplantation into dog fetus. D) Quantitative and comparative analysis of EGFP LP IDPSC at different phases of the cell cycle.

Figure 64:
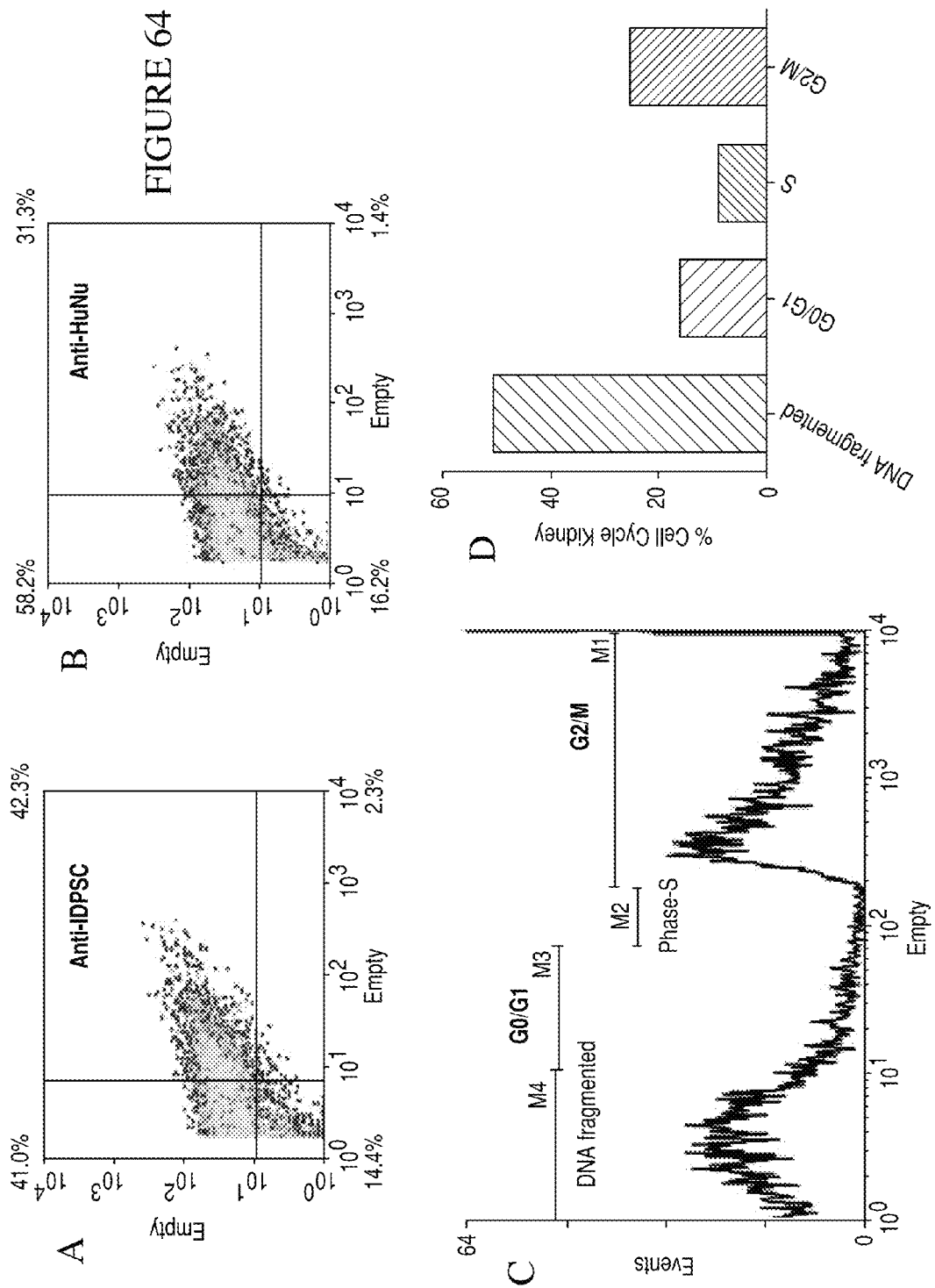

FIG. 64 depicts quantification of EGFP LP IDPSC grafting and evaluation of these cells proliferation after transplantation performed by flow cytometry A, B) Quantification of grafting EGFP LP IDPSC in a fragment of renal tissue. A) anti-IDPSC (42.3%) and B) anti-HuNu (31.3%) antibodies. C) Schematic evaluation of EGFP LP IDPSC at different phases of cell cycle after transplantation into dog fetus. D) Quantitative and comparative analysis of EGFP LP IDPSC at different phases of the cell cycle.

Figure 65:
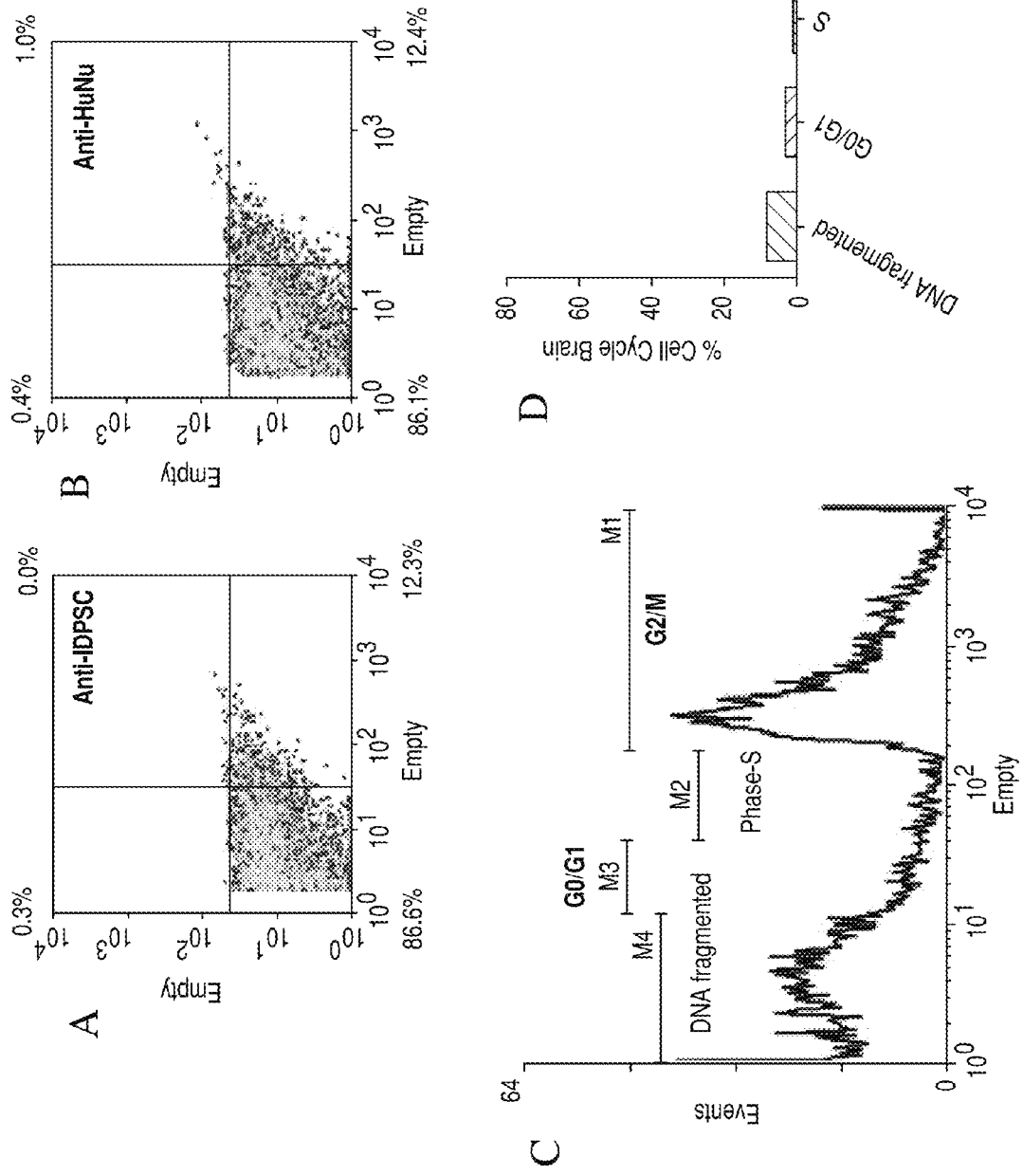

FIG. 65 depicts quantification of EGFP LP IDPSC grafting and evaluation of these cells proliferation after transplantation performed by flow cytometry A, B) Quantification of grafting EGFP LP IDPSC in a fragment of brain tissue. A) Anti-IDPSC (13.1%) and B) anti-HuNu (13.4%) antibodies. C) Schematic evaluation of EGFP LP IDPSC at different phases of cell cycle after transplantation into dog fetus. D) Quantitative and comparative analysis of EGFP LP IDPSC at different phases of the cell cycle.

Figure 66:
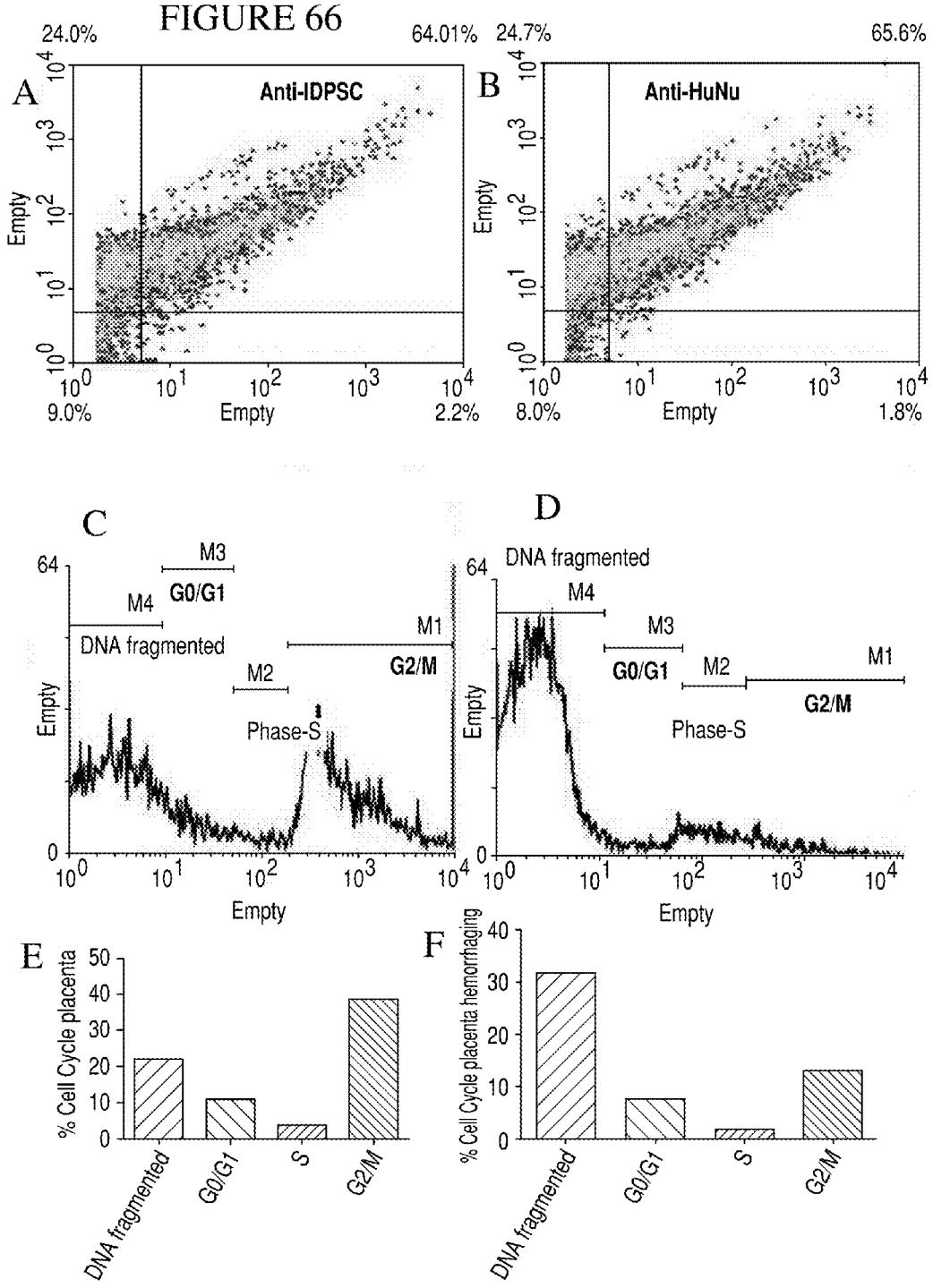

FIG. 66 depicts quantification of EGFP LP IDPSC grafting and evaluation of these cells proliferation after transplantation performed by flow cytometry A, B) Quantification of grafting EGFP LP IDPSC in a fragment of placenta maternal tissue. A) Anti-IDPSC 64.8%) and B) anti-HuNu (65.6%) antibodies. C, D) Schematic evaluation of EGFP LP IDPSC at different phases of cell cycle after transplantation into dog fetus. E,F) Quantitative and comparative analysis of EGFP LP IDPSC at different phases of the cell cycle.

Figure 67:
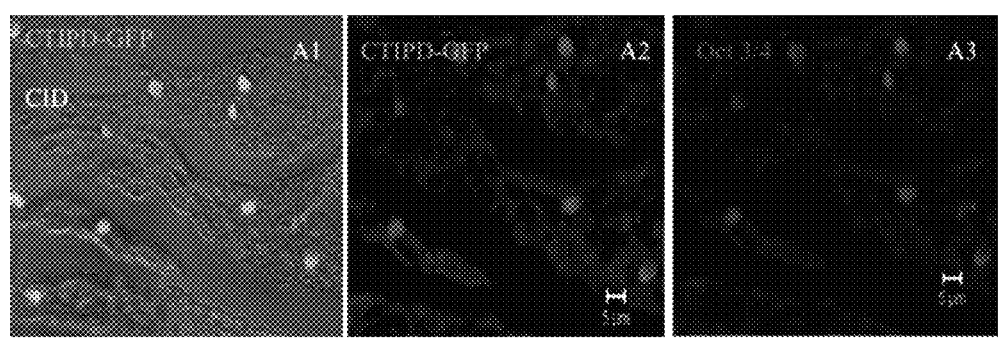

FIG. 67 depicts expression of human protein OCT3/4 (red) in EGFP LP IDPSC (green) grafted between muscle fibers of the fetal canine myocardium (A1-A3). A1—Overlaping between Oct3/4 and EGFP LP IDPSC demonstrating nuclear and cytoplasmic localization A2) Expression of EGFP protein in LP IDPSC. A3) Positive immunostaining for Oct3/4 showing myocyte-like localization. A1-A2=Fcm. A3—Fcm+CID. Barra de escala: A1-A3=5 µm.

Figure 68:
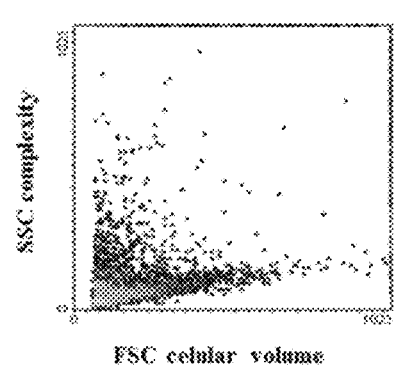
Figure 68:
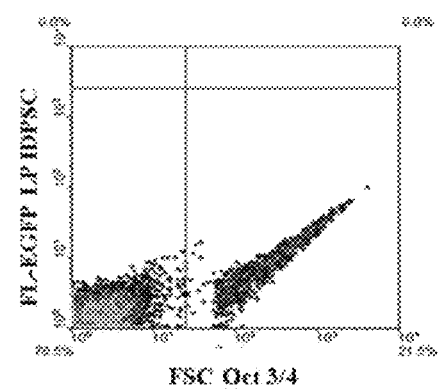
Figure 68:
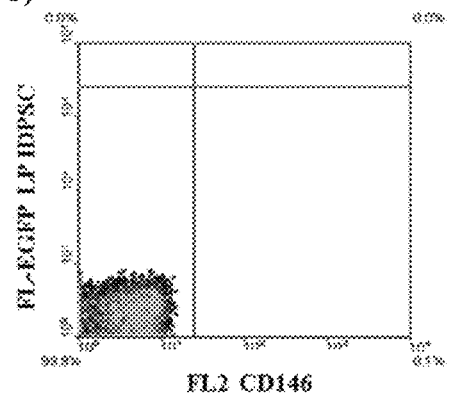
Figure 68:
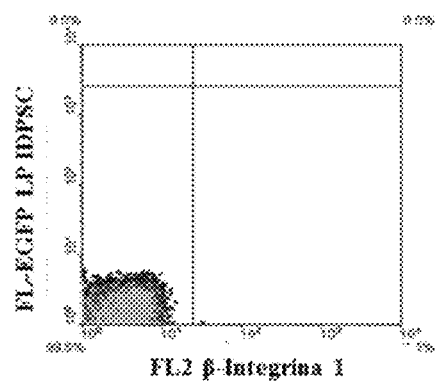

FIG. 68 depicts a flow cytometry analysis. Expression of markers of undifferentiated cells (MSCs and ES cells) in EGFP LP IDPSC grafted in myocardium. A) Control of cell volume. B-D) Expression of Oct3/4—21.5% (C) CD146—0.0% and (D) β1-integrin—0.0%.

Figure 69:
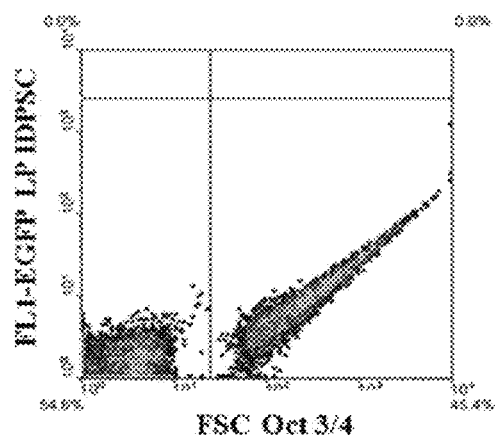
Figure 69:
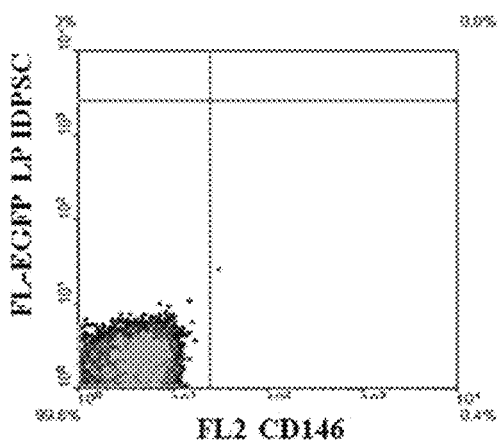
Figure 69:
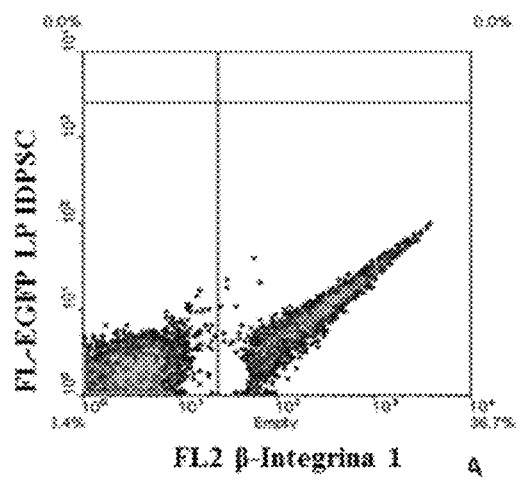

FIG. 69 depicts a flow cytometry analysis. Expression of markers of undifferentiated cells (MSCs and ES cells) in EGFP LP IDPSC grafted in skeletal muscle tissue—Biceps. A) Expression of Oct3/4 (45.4%) (B) Expression of CD146 (0.4%) and (C) expression of β1-integrin (36.7%).

Figure 70:
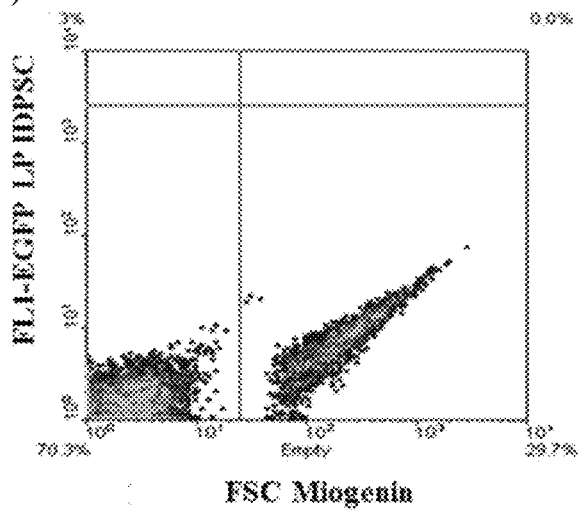
Figure 70:
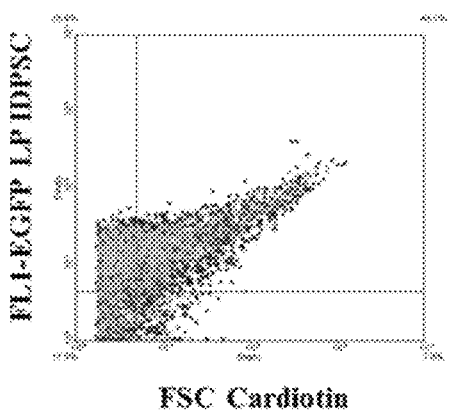
Figure 70:
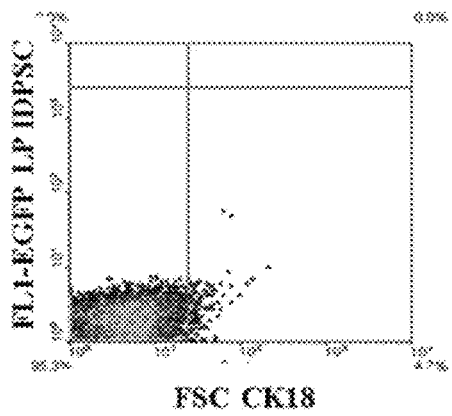
Figure 70:
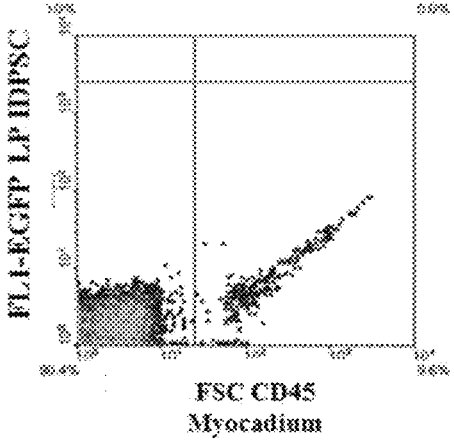
Figure 70:
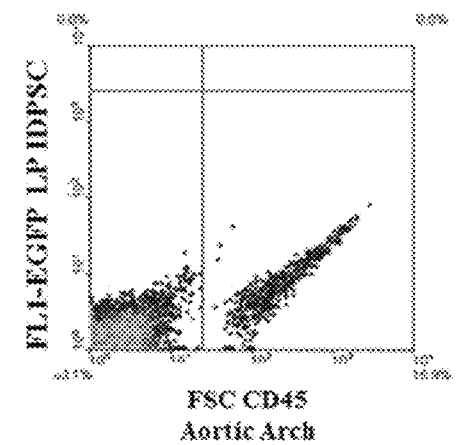

FIG. 70 depicts a flow cytometry analysis. Expression of markers of differentiated cells in cardiac tissue. The positive expression of cardiac proteins: myogenin (A), cardiotin (C) and negative for CK-18 (B). We observed positive expression of CD45+, which quantity varies in myocadium (D) and in the aortic arch (E).

Figure 71:
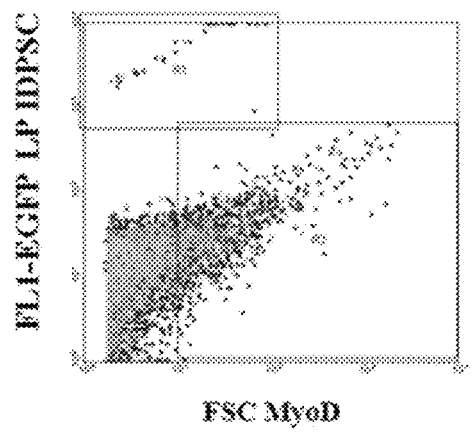
Figure 71:
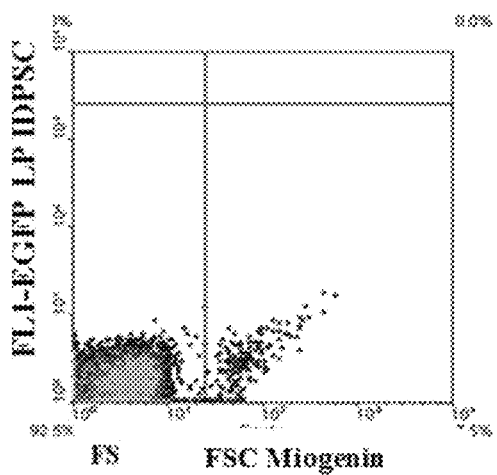
Figure 71:
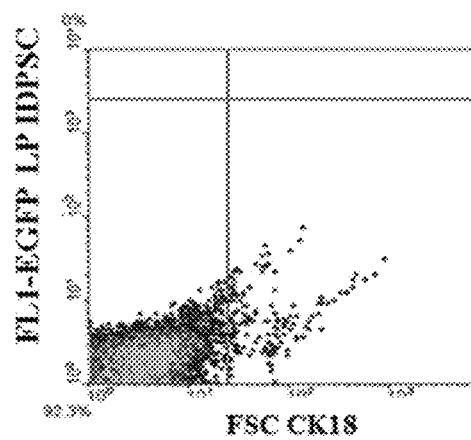
Figure 71:
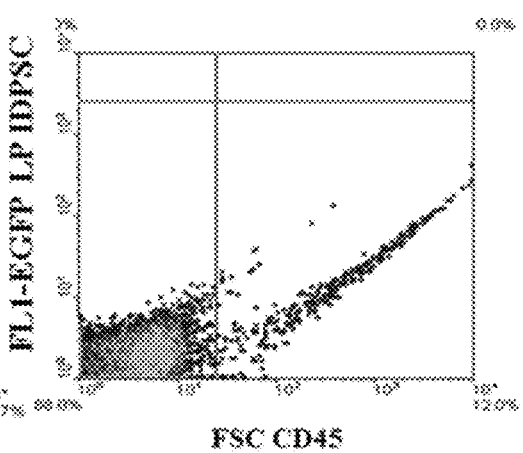

FIG. 71 depicts a flow cytometry analysis. Expression of markers of differentiated cells in the skeletal muscle tissue—Biceps Femoris. The positive expression of the muscle proteins: (A) Myo D1, (B) 7.5% Myogenin, (C) CK-18 with 7.7% and (D) 12.0% with CD45.

Figure 72:
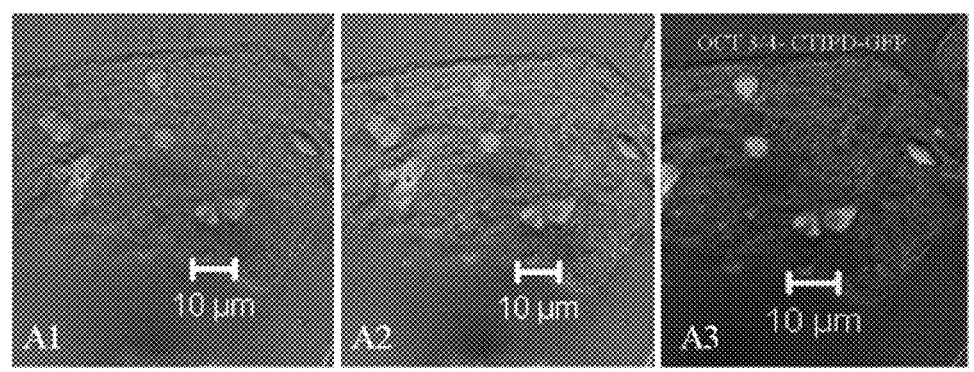

FIG. 72 depicts expression of human Oct3/4 (red) protein in EGFP LP IDPSC (green) grafted in maternal fetal placental canine tissue (A1-A3). A1) Positive immunostaining for Oct 3/4. A2) direct GFP fluorescence observed in LP IDPSC, A3) Overlap between Oct3/4, and EGFP LP IDPSC I observed. FCM CID=A1+, A2-A3=FCM; Scale bars: A1-A3=10 µm.

Figure 73:
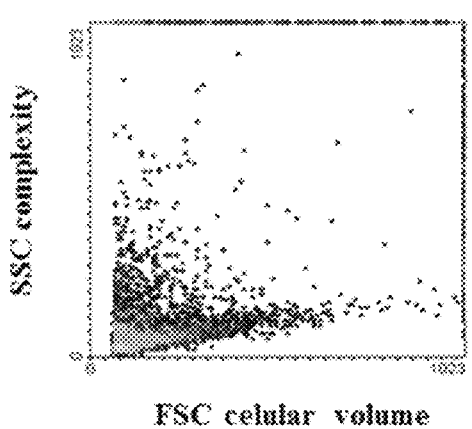
Figure 73:
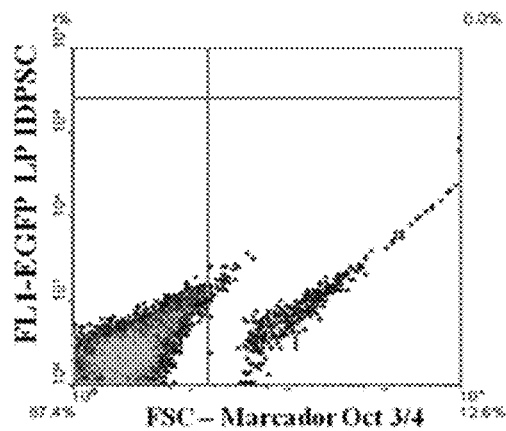
Figure 73:
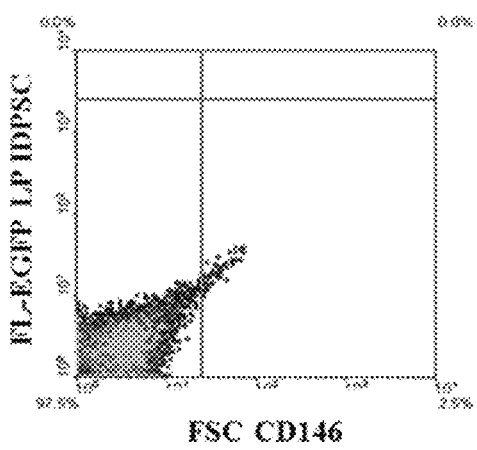
Figure 73:
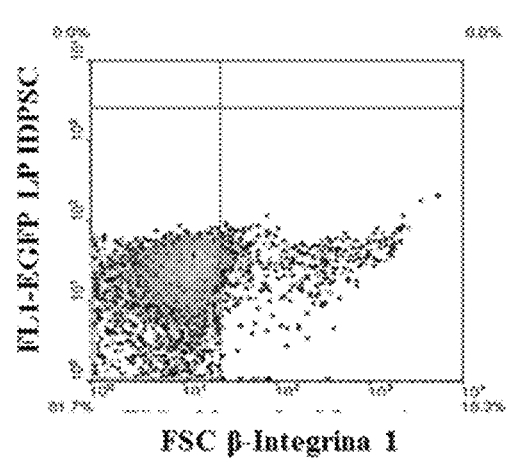

FIG. 73 depicts a flow cytometry analysis. Expression of markers of undifferentiated cells (MSCs and Es cells) in EGFP LP IDPSC in the placental tissue. A) Control cell volume (B) Expression of proteins Oct3/4 with 12.6% (C) CD146 with 2.5% and (D) β-integrin with 18.3%.

Figure 74:
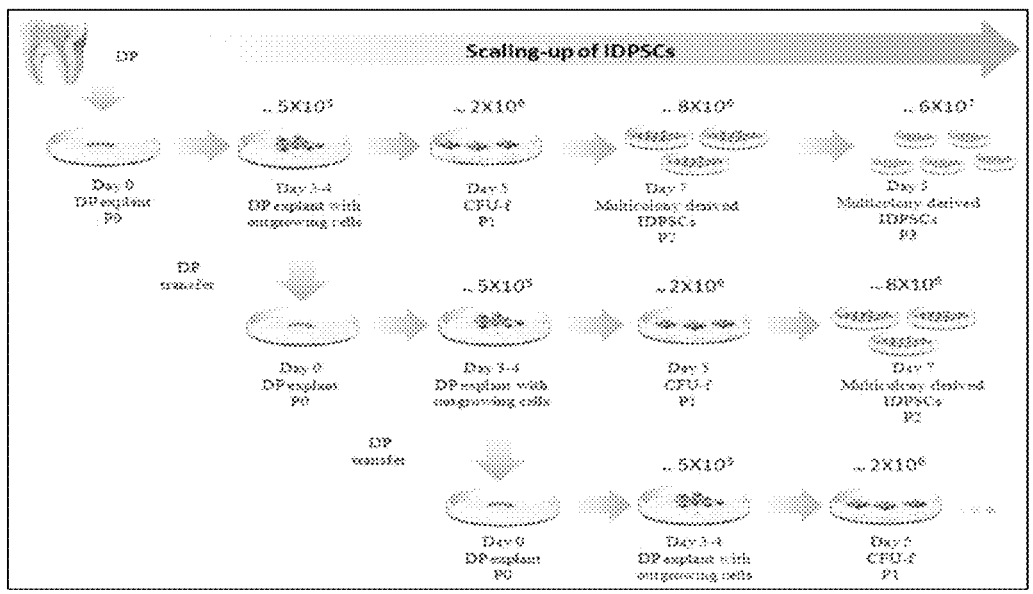

FIG. 74 depicts scaling-up of IDPSCs. Horizontally, the process of DP in vitro plating (Day 0, P0) followed by DP adherence and cells outgrowth (Day 3-4) is shown. This process is followed by enzymatic treatment (P1) of the cells and formation of multiple colonies (CFU-f: Colony Forming Units-fibroblast). After 5 days, enzymatic treatment is performed to harvest a population of multicolony-derived IDP-SCs (P2). Next, in vitro expansion of IDPSCs (P3) is performed. The numbers above each plate in the figure represent approximate quantities of harvested IDPSCs in each passage. Vertically, the same process is shown albeit after multiple mechanical transfers of DP.

Figure 75:
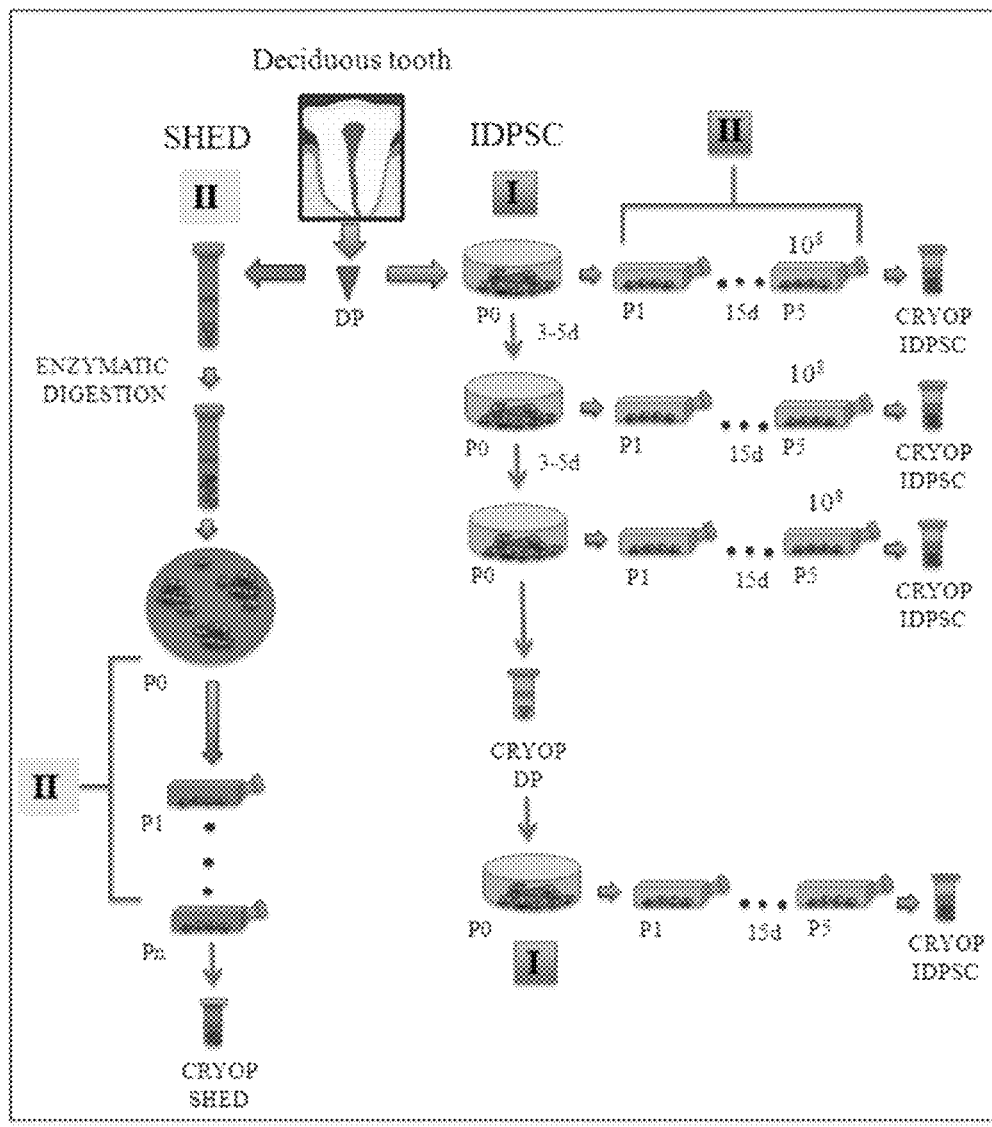

FIG. 75 depicts strategies of isolation, in vitro expansion, and banking of SHED and IDPSC. The process of SHED isolation by enzymatic treatment of the DP, SHED in vitro plating (Day 0, P1), and formation of multiple colonies in a heterogeneous population is shown at left. The process of IDPSC isolation, shown at right, includes DP in vitro plating (Day 0, P0) followed by DP adherence and cells outgrowth (Day 3-4). Scaling-up of IDPSCs is a process that includes enzymatic treatment (P1) of the cells and formation of multiple colonies (CFU-f: Colony Forming Units-fibroblast). After about 5 days, enzymatic treatment is performed to harvest a multicolony-derived IDPSCs (P2) population. Next, in vitro expansion of IDPSCs (P3) is performed. The numbers above cell culture flasks in the figure represent approximate quantities of harvested IDPSCs in each passage. Vertically, the same process is shown albeit after multiple mechanical transfers of DP.

Figure 76:
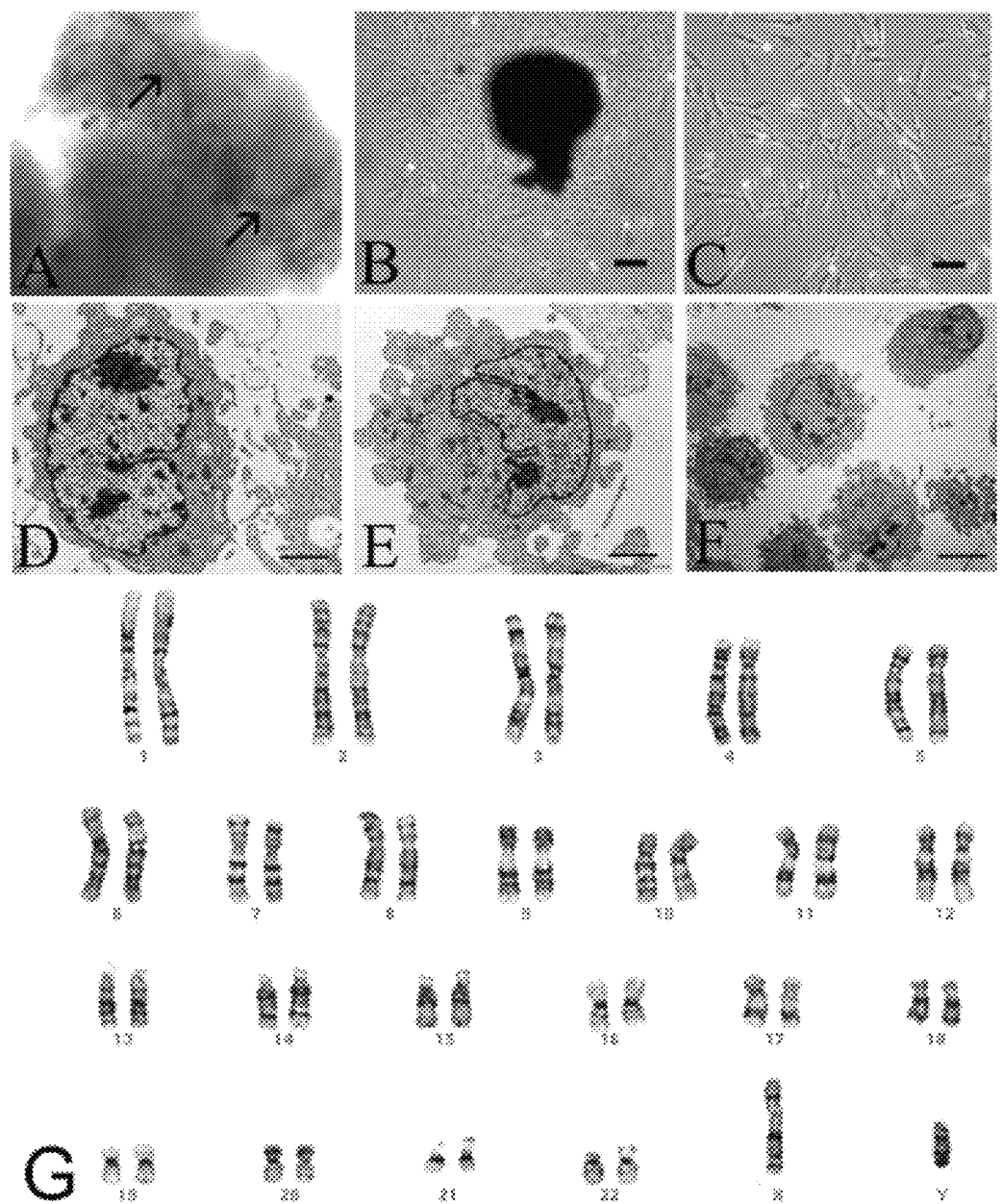

FIG. 76 depicts dental pulp and IDPSCs. A) Highly vascularized (black arrows) DP just after extraction. B) Explant culture of DP with outgrowing IDPSCs. C) Culture of IDPSCs at 1st passage. D) IDPSCs showing ES-like cells morphology with a large nucleus. E) IDPSCs showing MSC-like morphology with several pseudopods. F) IDPSCs showing uniform morphology resembling ES cells and MSCs. G) Karyotype analysis of IDPSCs (LP) showing chromosomes in pairs and ordered by size and position did not reveal any numerical changes in chromosome number as shown by the routine G-banding analysis. FIGS. 3A-3C and 3G were generated with light microscopy while FIGS. 3D-3F resulted from Transmission Electron Microscopy. Magnification for FIG. 3A=20× and for FIG. 3G=63×; the scale bars are for FIG. 3B=20 mm; for FIGS. 3C and 3F=10 mm; and for FIGS. 3D and 3E=3 mm.

Figure 77:
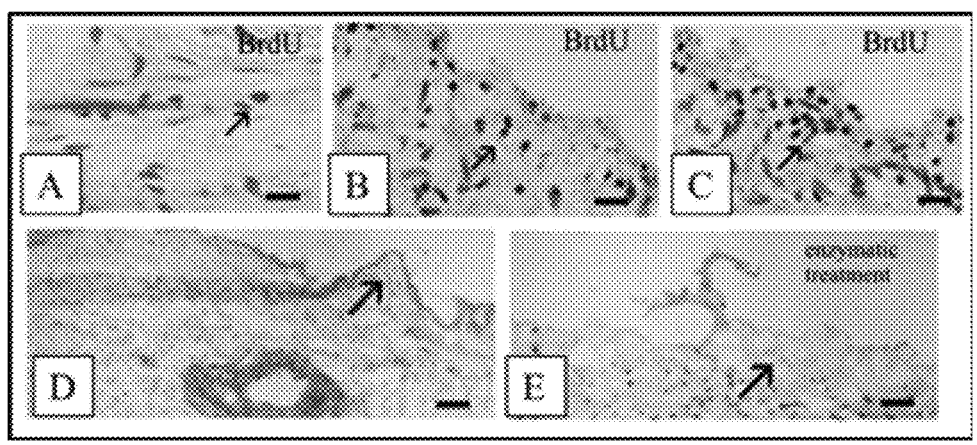

FIG. 77 depicts BrdU immunostaining of DP. A) DP about 6 hours after plating in culture medium. B) DP about 48 hours after in vitro cultivation. C) DP about 72 hours after in vitro cultivation. D) DP without enzymatic treatment. E) DP with enzymatic treatment showing that the external cell layer of DP is destroyed by such treatment. Light microscopy was used for all images. The scale bars in FIGS. 4A-4C=20 μm and in 4D-4E=50 μm.

Figure 78:
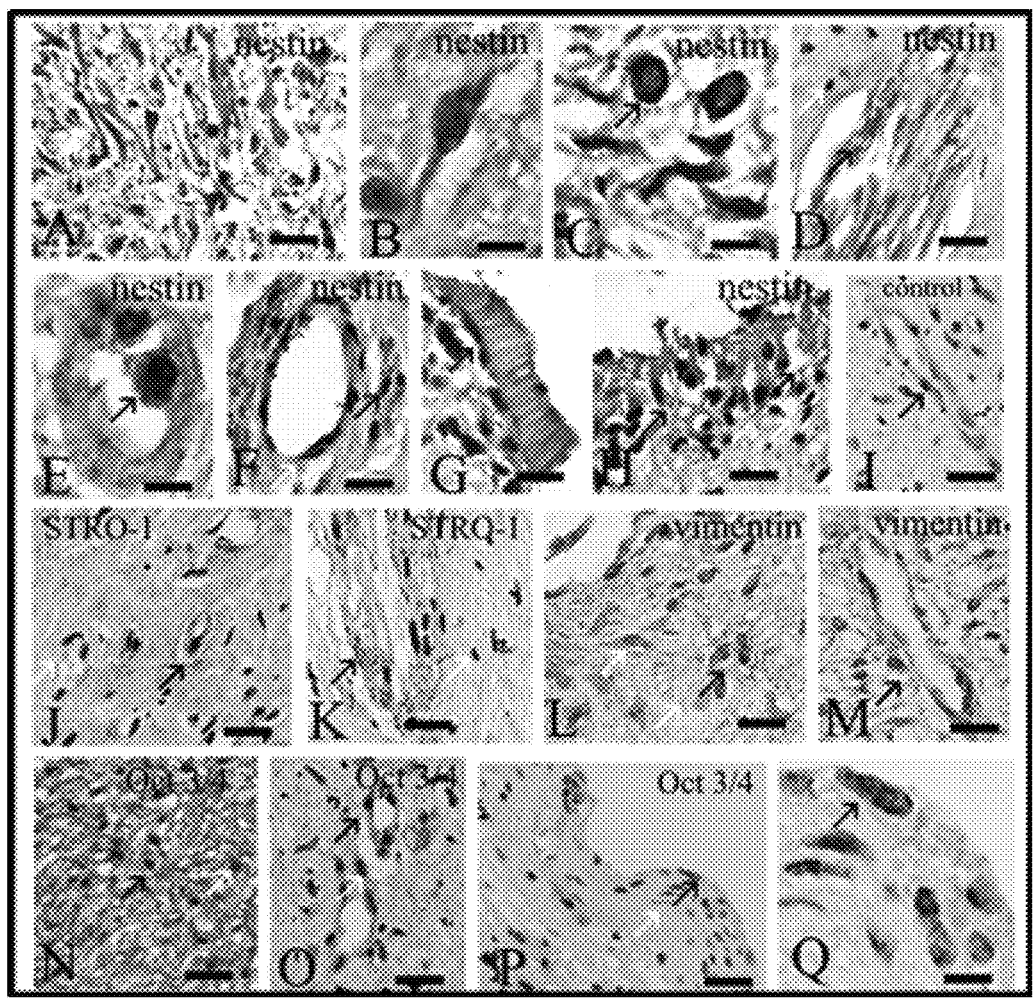

FIG. 78 depicts expression of nestin, STRO-1, vimentin, and Oct3/4 in DP. FIGS. 5A-5H show nestin expression in the cell-rich zone (FIGS. 5A-5C), the cell-free zone (FIGS. 5D-5F) and in the odontoblastic layer (FIGS. 5G-5H). A) Multiple nestin positive cells can be observed. Here and below black arrows indicate immunopositive, and white arrows indicate immunonegative cells. B) Apparently undifferentiated MSCs show nestin cytoplasm localization. C) Nestin positive cells with two distinct morphologies: round epithelial-like (ES-like) and fibroblast-like cells. D) Nestin showing intermediate filament staining in the nerve plexus. E) A small capillary with two intensively stained nestin positive cells. F) Same as in E) with nestin positive cells in the lateral of the capillary (arrow). G) and H) Nestin positive obontoblasts can be observed. I) Negative control: only secondary antibody was used. J) STRO-1 positive cells within capillaries (perivascular niche) in the cell free zone. K) Very poor STRO-1 immunostaining was observed within the nerve plexus of the cell free zone. L) and M) Vimentin positive (black arrows) cell localization in cell rich (L) and cell free (M) zones. N)-Q) Oct3/4 positive cells localization in cell rich (N) and cell free (O-Q) zones. Light microscopy was used with scale bars for 5A, 5D, and 5F-5P=20 μm; and for 5B, 5C, and 5Q=5 μm.

Figure 1:
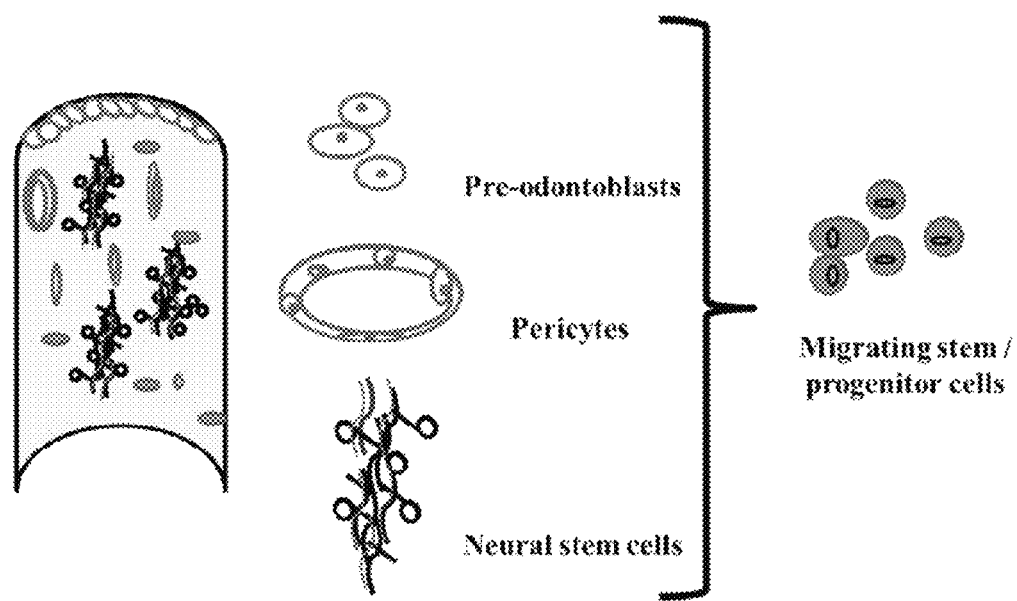
FIG. 1 depicts stem cell niches in dental pulp (at left) and production of a mixed population of migrating stem/progenitor cells that are isolated at immature dental pulp stem cells (IDPSCs).
Figure 79:
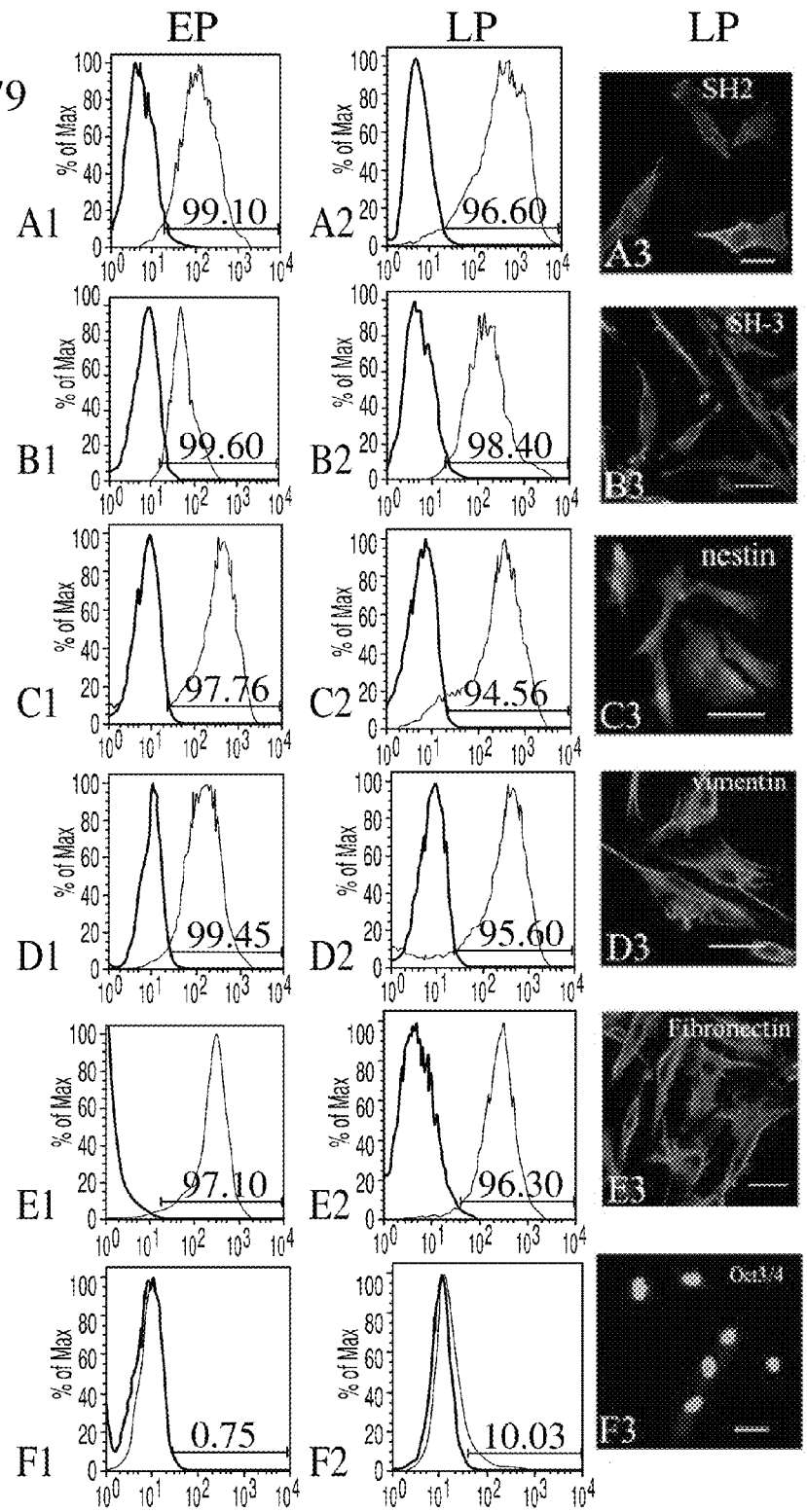
Figure 80:
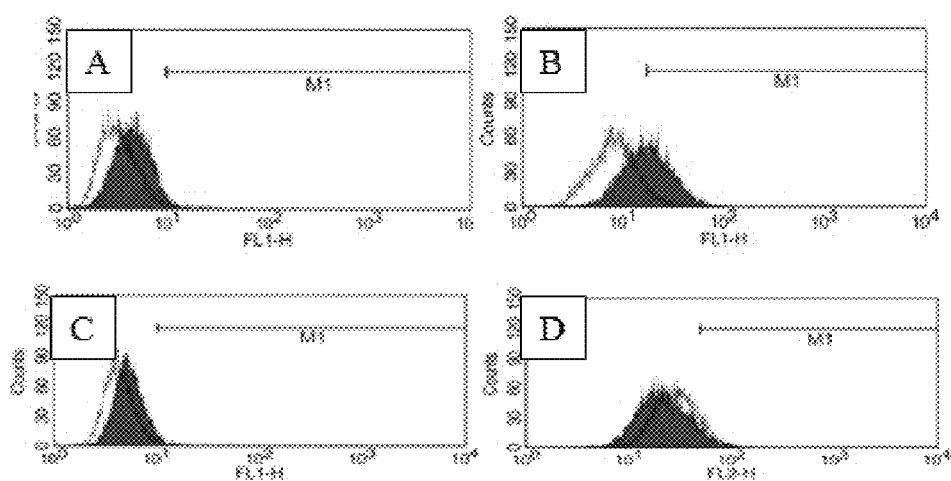

FIG. 79 depicts characterization of EP and LP of IDPSCs. FIGS. 6A1-6F1) Flow cytometry showing EP of IDPSCs, which highly expressed such markers as SH2/CD105 (A1); SH3/CD73 (B1); nestin (C1); vimentin (D1); fibronectin (E1). F1) Low expression of Oct3/4 in EP; A2-F2) Flow cytometry showing LP of IDPSCs, which expressed the same markers as EP. F2) Higher expression of Oct3/4 in LP than in F1. A3-F3) Immunofluorescence of LP of IDPSCs using the same markers as in (A2-E2). F3) Nuclear localization of Oct3/4 can be observed. A3-F3) Epi-fluorescence, nuclei stained with DAPI (blue). Scale bars for A3, B3, E3, and F3=5 μm and for C3, and D3=10 μm.

FIGS. 80A-D depict expression of Oct3/4 in IDPSC populations each isolated from four unrelated donors. The proportion of Oct3/4 positive cells in each population was A) 25%; B) 47%; C) 12%; D) 5%, respectively.

Figure 81:
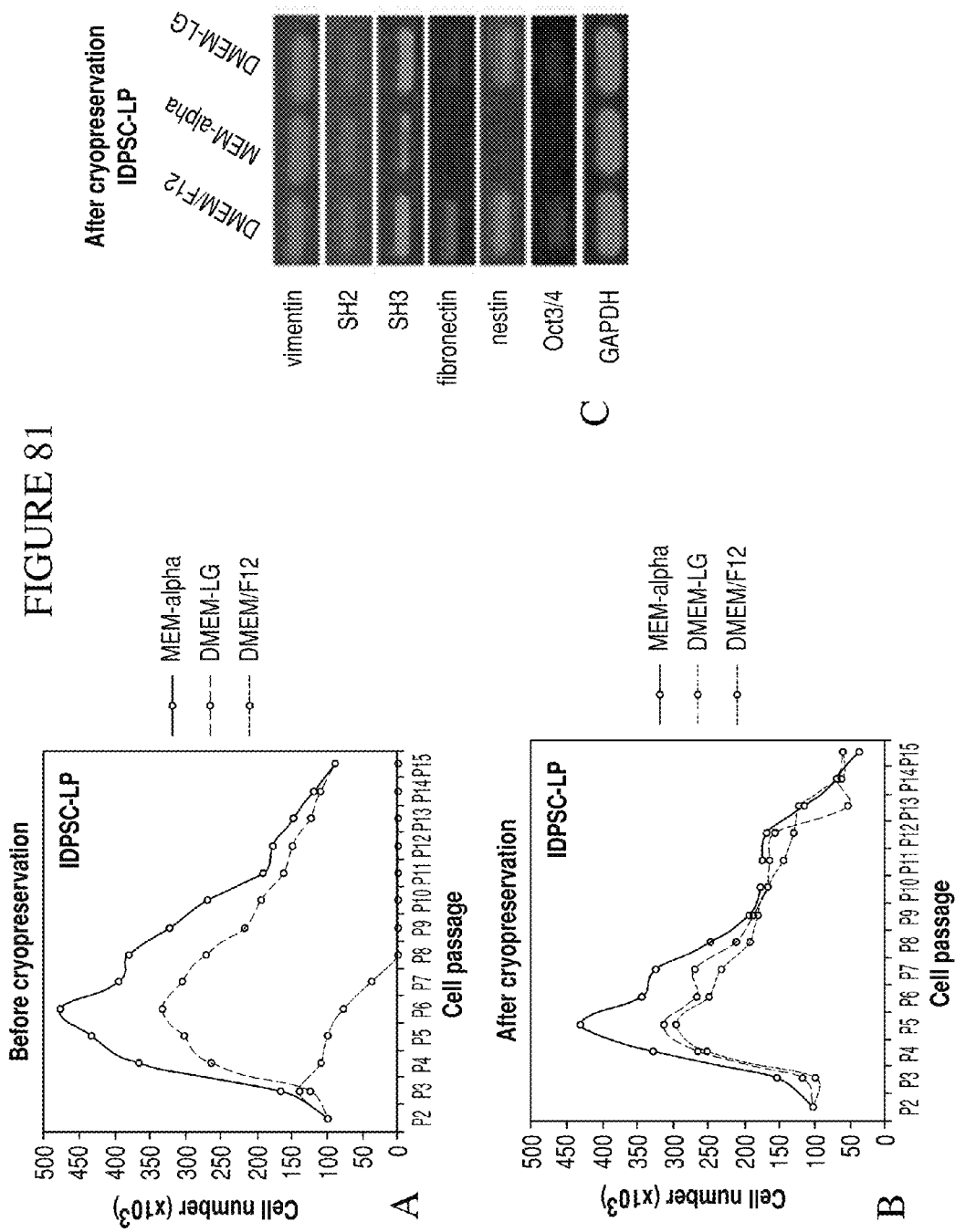

FIG. 81 depicts the proliferation rate and gene expression of IDPSCs after cultivation in three distinct culture media. A) Proliferation curve of LP before cryopreservation; B) Proliferation curve of LP after cryopreservation. C) Gene expression of LP after cryopreservation.

Figure 82:
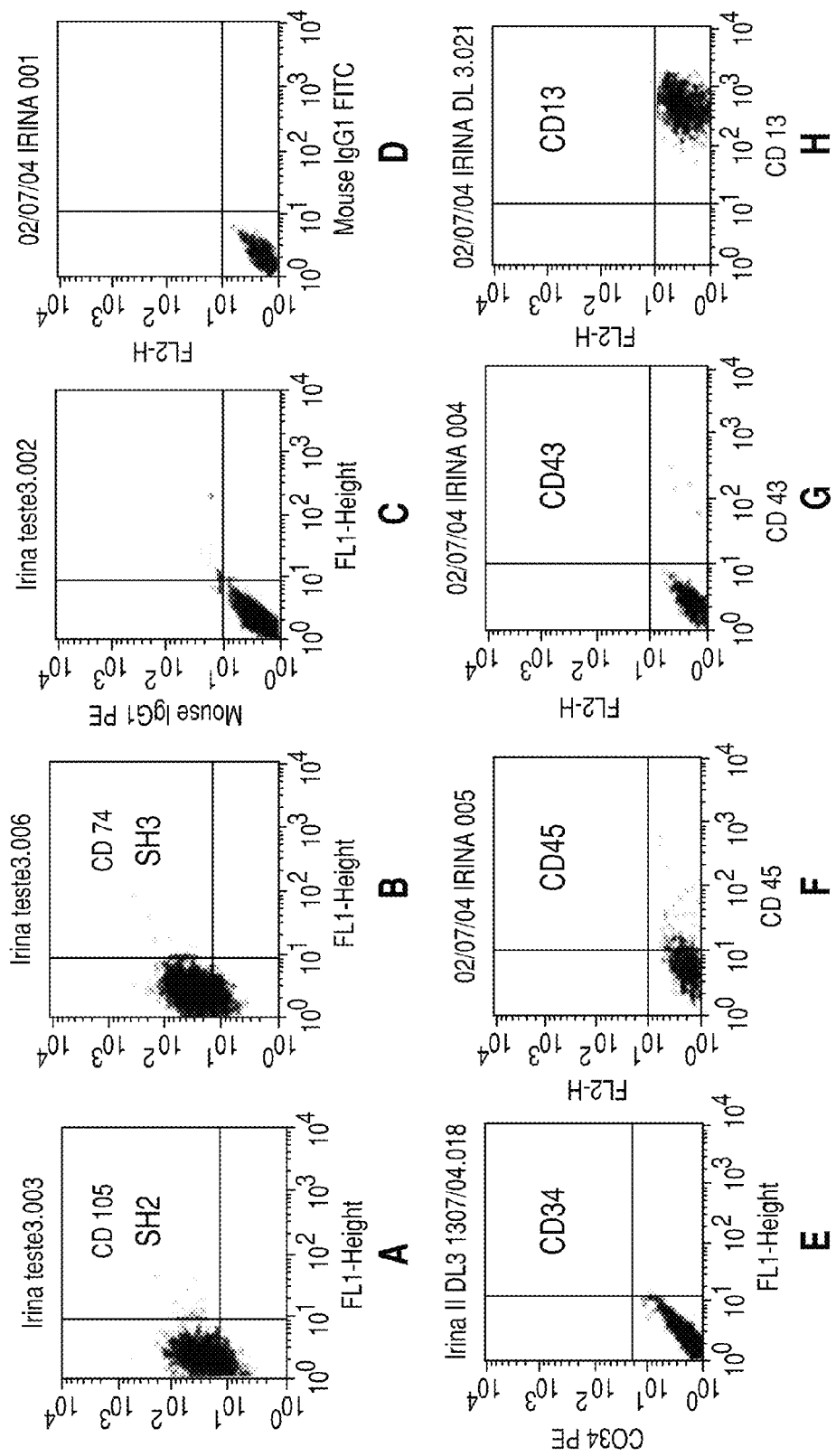

FIG. 82 depicts the flow cytometry expression profiles of IDPSC. A-B) IDPSC positive immunostaining of CD105 and CD73 for human ES cell markers. C-D) Appropriate negative IgG1 controls. E-G) Lack of expression of endothelial and hematopoietic markers such as CD34, CD45 and CD43 by IDPSC. H) Positive immunostaining for CD13. Phycoerythrin (PE) and FITC-conjugated secondary antibody were used.

Figure 83:
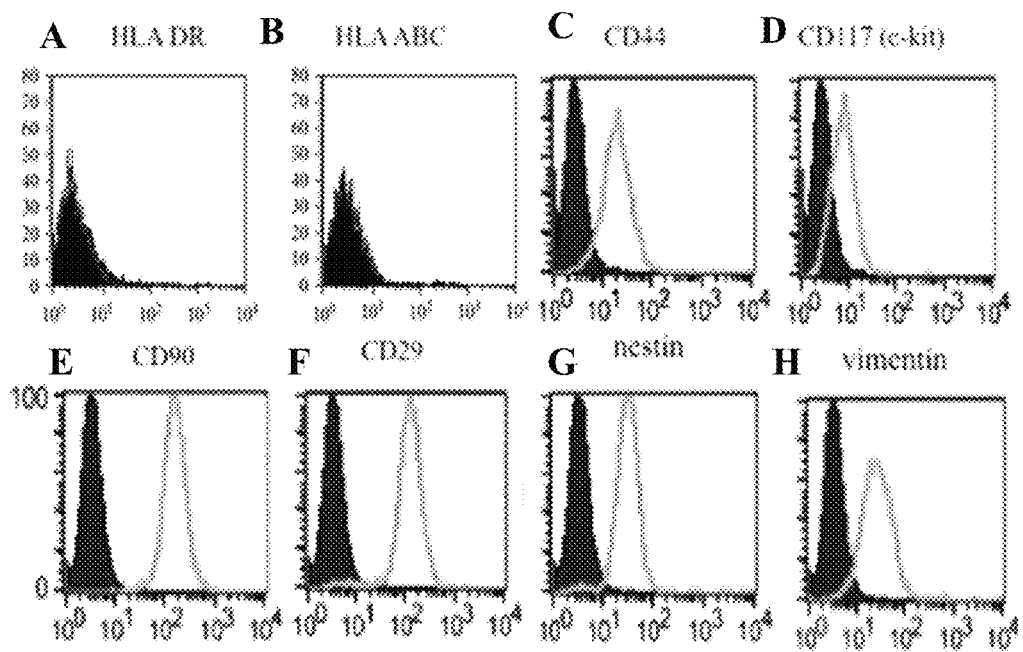

FIG. 83 depicts flow cytometry expression profiles of IDPSC. A-B) Lack of expression of HA-DR and HLA-ABC by IDPSC. C-H) Positive immunostaining for CD44 (86%), CD117 (80%), CD90 (100%), CD29 (99.5%), Nestin (99.2%), and Vimentin (95.6%).

Figure 84:
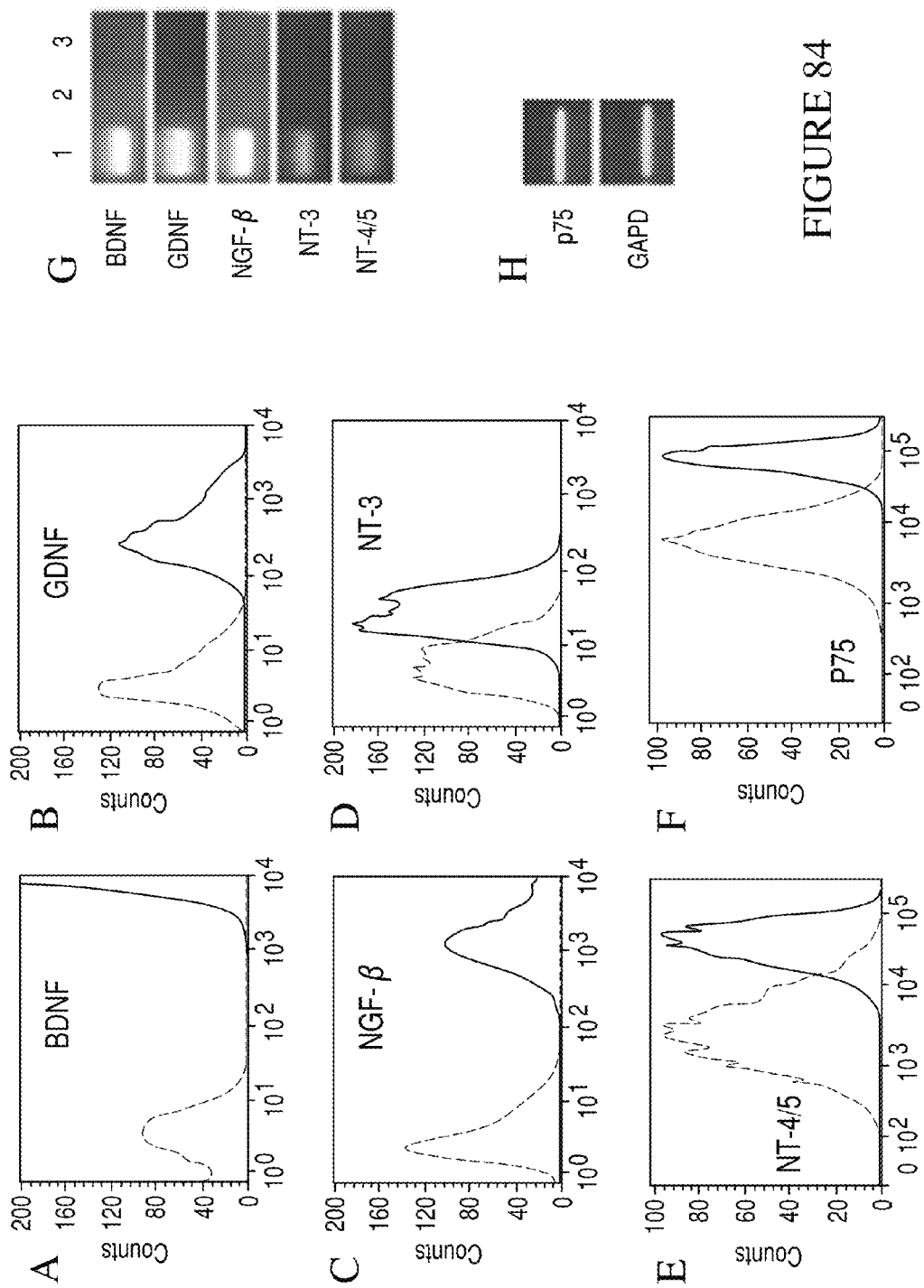

FIG. 84 depicts flow cytometry and RT-PCR analyses of IDPSCs. A-E) Flow cytometry expression profiles for neurotrophic factors BNDF (brain-derived neurotrophic factor), GNDF (glial cell line-derived neurotrophic factor), NGF-β (nerve growth factor), NT-3 (Neurotrophin-3), NT-4/5 (Neurotrophin-4/5). F) Flow cytometry expression profile for p75 by IDPSC. G) Reverse transcription-polymerase chain reaction (RT-PCR) analysis of expression of the neurotrophic factors and p75 in IDPSC. Lane 1—cDNA template; Lane 2—Negative control, no reverse transcriptase; Lane 3—Negative control, no template. H) RT-PCR analysis of p75 expression; GAPD—housekeeping gene.

Figure 85:
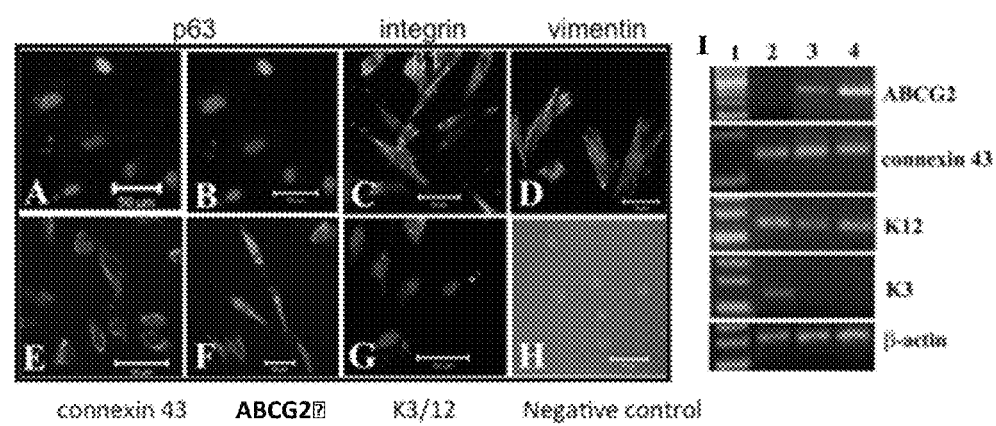

FIG. 85 depicts undifferentiated human IDPSC showing positive immunostaining with human-specific antibodies against limbal stem cells and corneal epithelium. A) Immunopositive reaction with p63 (green) in hIDPSC nuclear localization; B) Merged image of p63 staining with nuclei stained with DAPI; C) Integrin β1 presents localization in the membrane; D) Staining of Vimentin, an intermediate filament; E) Staining of Connexin 43 in the cell membrane; F) ABCG2 staining in the plasma membrane; G) Staining with a K3/12 antibody showed weak positive immunostaining; H) negative control of hIDPSC with primary antibody omitted and hIDPSC incubated with secondary antibody. Confocal microscopy was used for A), fluorescent microscopy (Fcm) for D)-G) Fcm, and Fcm+differential interference contrast (Epi+DIC) for H). Nuclei stained with DAPI are shown in blue. Scale bars=50 μm. I) RT-PCR analysis of expression of limbal stem cell markers in hIDPSC: Lane 1, ladder 100 bp; Lane 2, human corneal tissues; Lane 3, human limbal tissue; Lane, 4 hIDPSC. RT-PCR analyses demonstrated presence of ABCG2, connexin 43 and K12 mRNAs in hIDPSC while those of K3 were not found in hIDPSC.

Figure 86:
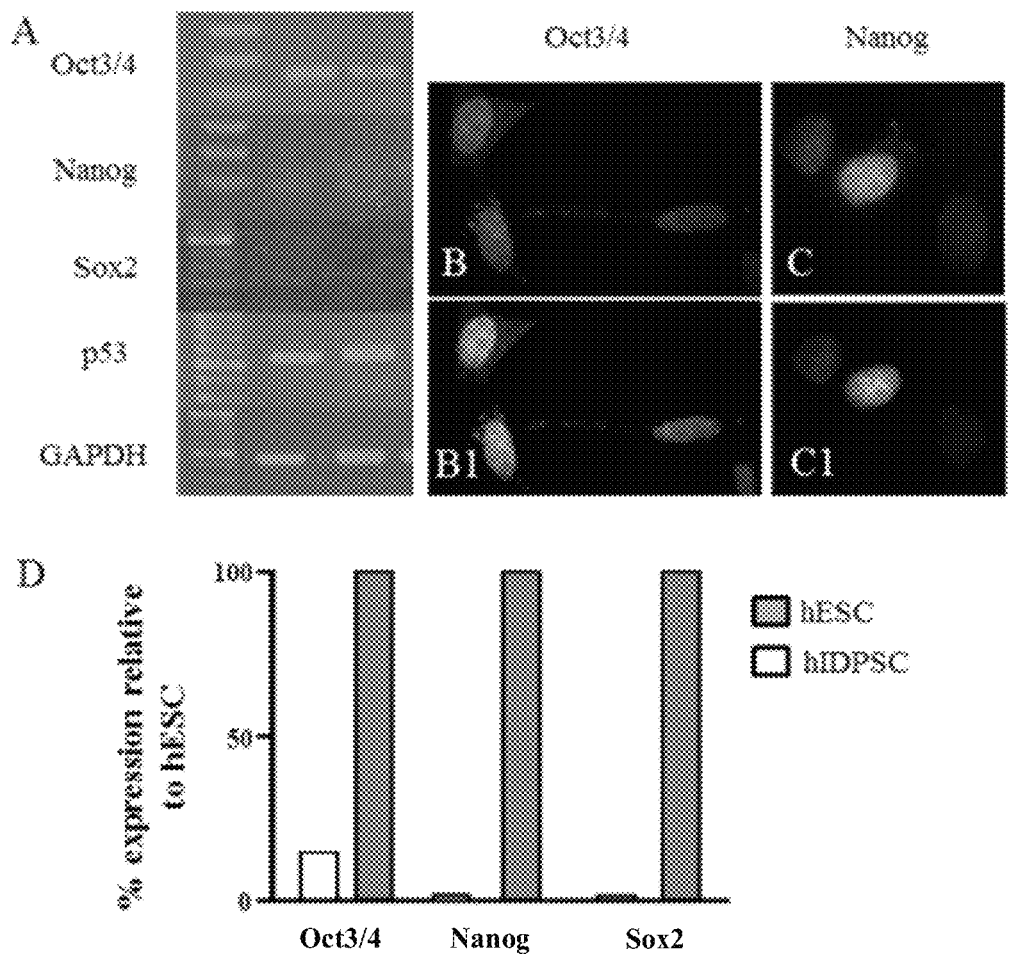

FIG. 86 depicts expression of ES cell markers in IDPSC. A) Reverse transcription-polymerase chain reaction (RT-PCR) analysis of expression of Oct3/4, Nanog, SOX2, and p53. B-C1) Immunopositive reactions with Oct3/4 and Nanog (green) in hIDPSC with nuclear localization; B1 and C1) merged images, showing nuclei stained with DAPI. Magnification 100×. D) Quantitative PCR assay showing relative percentage expression of Oct3/4, Nanog, SOX2 in IDPSC compared to human epithelia stem cells (hESC).

Figure 87A:
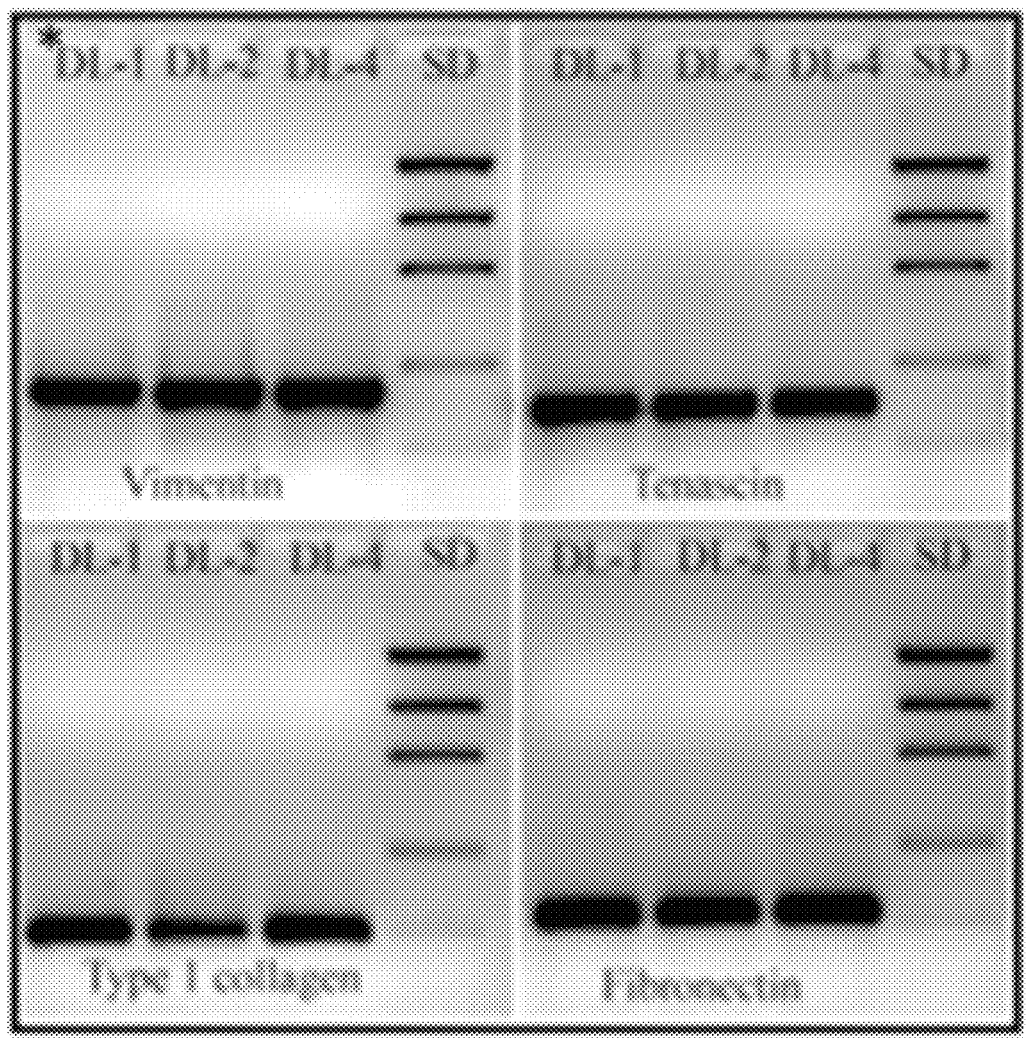
Figure 87B:
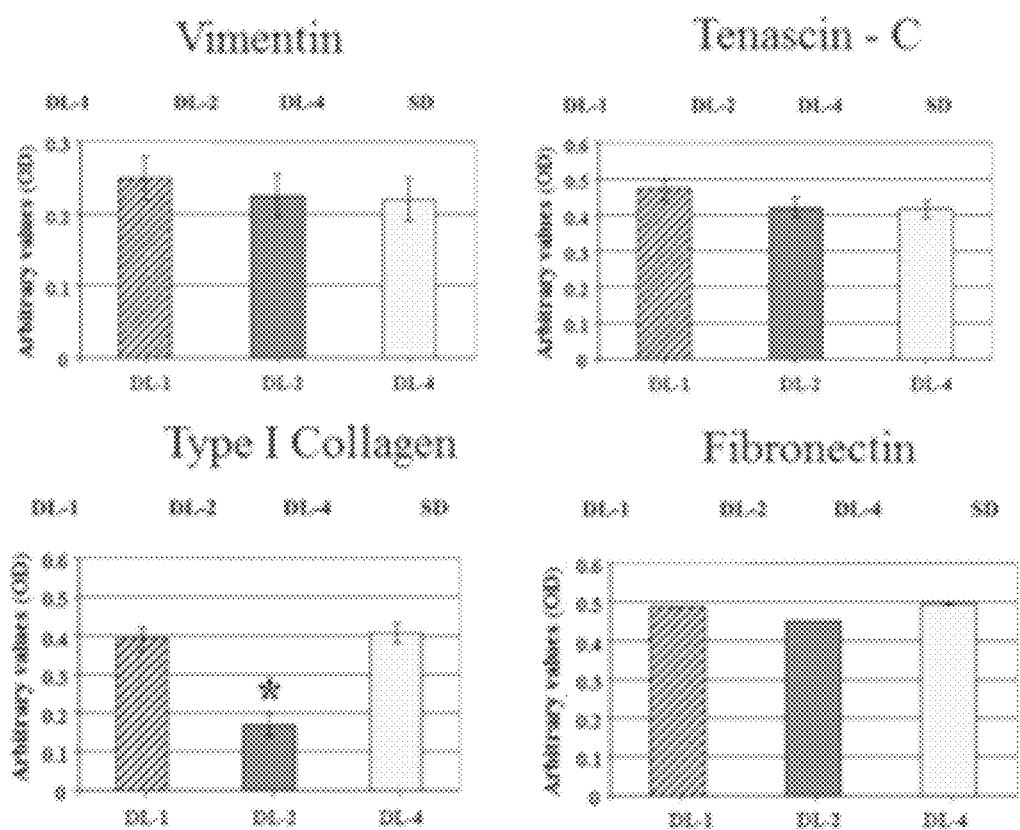

FIG. 87A depicts images of agarose gels with RT-PCR products for vimentin, tenascin-C, type 1 collagen, and fibronectin amplified from hIDPSCs isolated from deciduous teeth (DL-1 and DL-4) and from a third molar (DL-2). FIG. 87B depicts a densitometry analysis of the bands shown in FIG. 87A.

Figure 88:
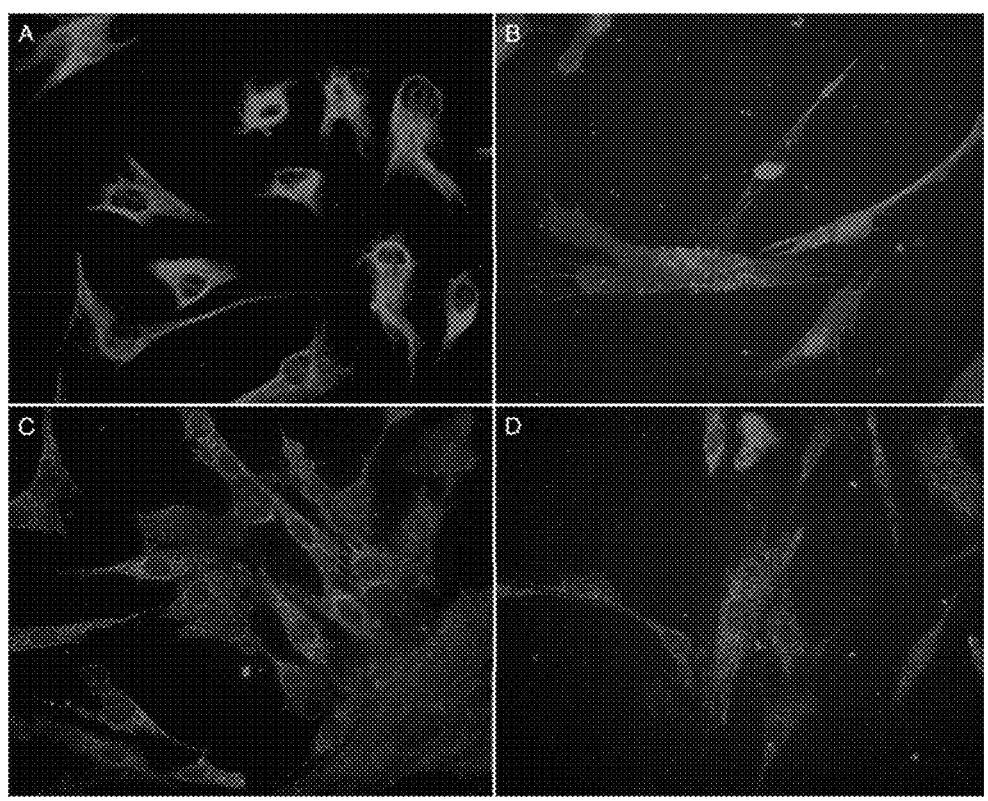

FIG. 88 depicts representative immunofluorescence images of (A) vimentin, (B) type I collagen, (C) fibronectin, and (D) tenascin-C in DL-1 cells (hIDPSCs isolated from a deciduous tooth). (A) Vimentin appears as filament waved bundles branched out from the central body to reach the peripheral domains of the cell. (B) Type I collagen is revealed as dots spread all over the cytoplasm with a higher concentration around the perinuclear area. Fibronectin (C) as well as tenascin-C (D) appears as small dots homogeneously distributed throughout the cytoplasm (original magnification: 400×).

Figure 89:
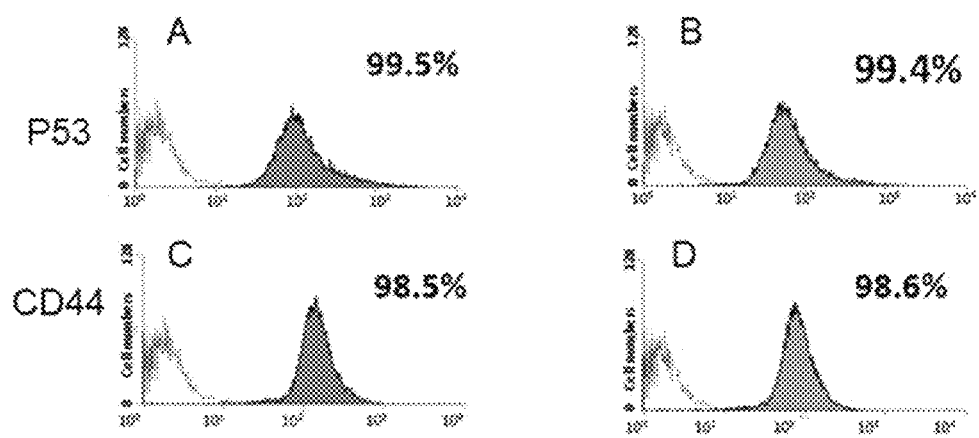

FIGS. 89A-B depict quantification of p53 expression and FIGS. 89C-D depict quantification of CD44 expression in two independent IDPSC populations isolated from different donors. p53 was expressed in 99.5% and 99.4% of the IDPSC cells of the two populations while CD44 was expressed in 98.5% and 98.6% of the IDPSC cells of the two populations.

Figure 90:
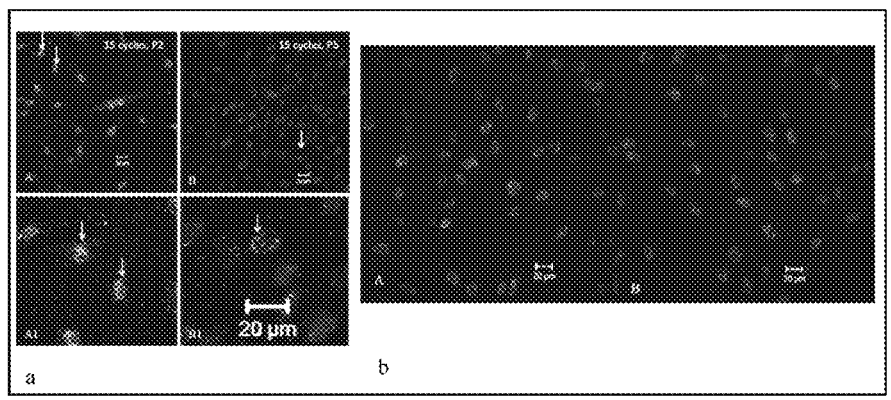

FIG. 90 depicts expression of SOX2 protein in IDPSC after varying cycles. FIG. 90a depicts expression of SOX2 protein in IDPSC after 15 cycles of mechanical transfer and after in vitro culturing, passages 2 (A) and 5 (B). FIGS. 90A1 and 90B1 demonstrate cell passage dependent intracellular localization of SOX2: A1—nuclear, A2—perinuclear. FIG. 90b depicts expression of SOX2 protein in IDPSC after 45 cycles of mechanical transfer and after in vitro culturing, passages 2 (A) and 5 (B).

Figure 91:
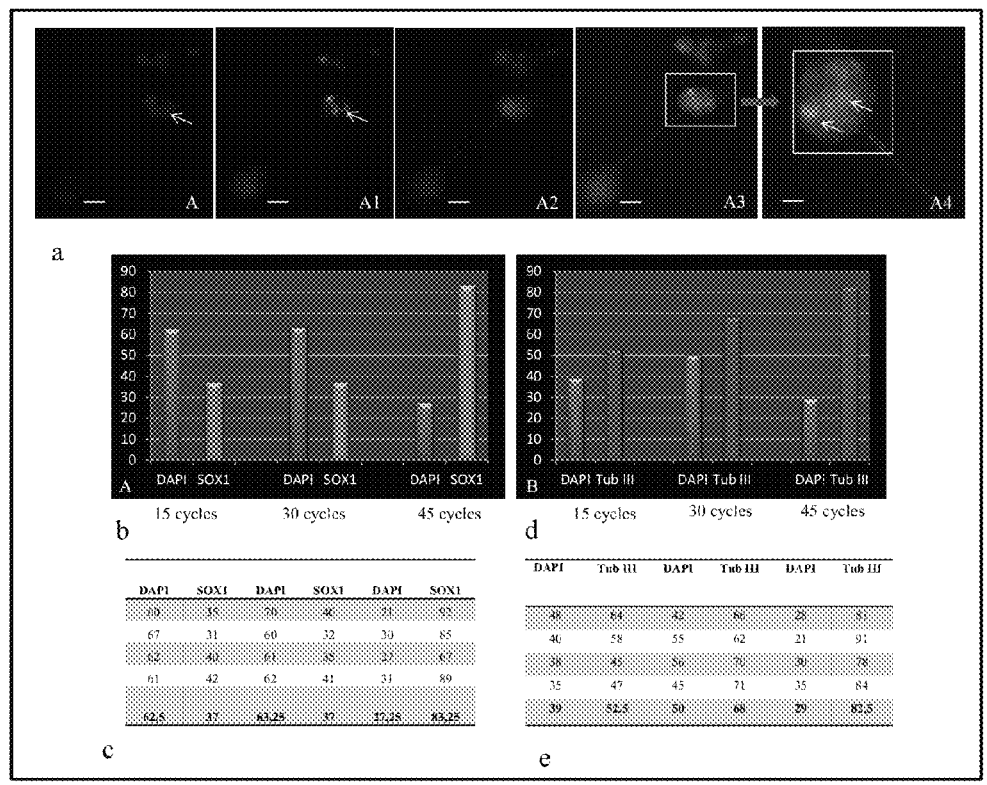

FIG. 91a depicts expression of SOX1 and β-tubulin proteins in late population (LP) of hIDPSC derived neurons. A. Nucleus (white arrow) of neurons stained with DAPI; A2. Positive immunostaining for SOX1 observed in the nucleus (white arrow) of neurons; A3 Positive immunostaining for β-tubulin; A3. Merged images A-A2; A4. Major magnification of inset in A3 demonstrates superposition of DAPI and SOX1 in the nucleus of neurons (white arrow). Epifluorescence, Scale bar=5 μm. FIGS. 91b-e depict enrichment of LP of hIDPSC with neural progenitors and neurons following 15-, 30- and 45 cycles of dental pulp mechanical transfer and induction of neural differentiation. A. Percentage of SOX1 negative cells, nucleus stained only with DAPI (blue). SOX1 positive cells are presented in green. B. Percentage of β-tubulin negative cells, nucleus stained only with DAPI (blue). β-tubulin positive cells are presented in red.

Figure 92:
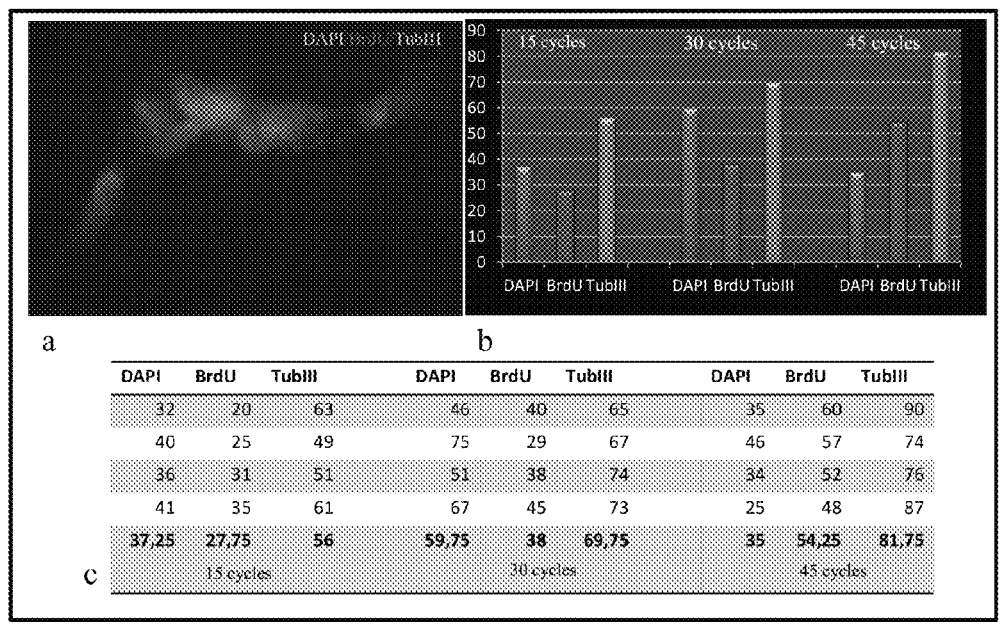

FIG. 92a demonstrates a nucleus of IDPSC-neuroblasts positively immunostained with anti-BrdU antibody and neuronal bodies, which reacts positively with β-tubulin class III.

FIG. 92b-c show the enrichment of differentiated IDPSC population with slightly differentiated neuroblasts following growing cycle numbers of DP mechanical transfer.

Figure 93:
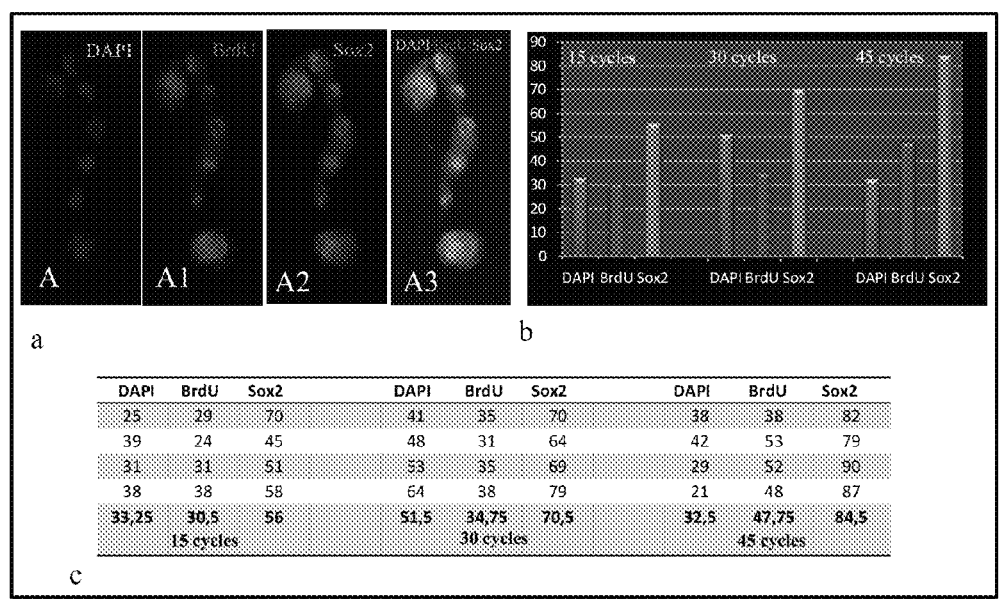

FIG. 93a depicts enrichment of LP of hIDPSC with neural progenitors and neurons following 15-, 30- and 45 cycles of dental pulp mechanical transfer and induction of neural differentiation. BrdU positive cells present red and SOX2 green nucleus, which are also stained with DAPI (blue). FIGS. 93b-c demonstrate percentage of BrdU and SOX2 positive cells shown in relation with nucleus stained with DAPI (blue).

Figure 94:
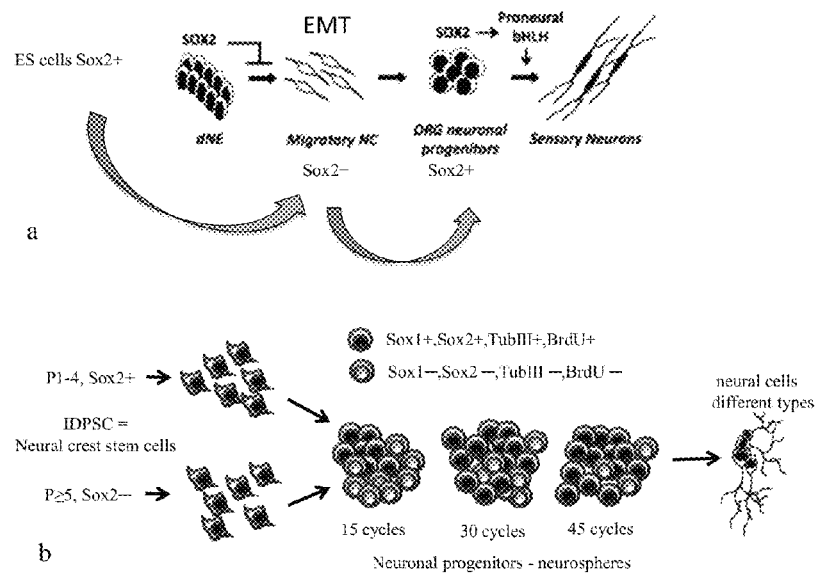

FIG. 94a depicts a graphic abstract from Cimadamore et al., 2011. FIG. 94b depicts a summary of an embodiment disclosed herein.

Figure 95:
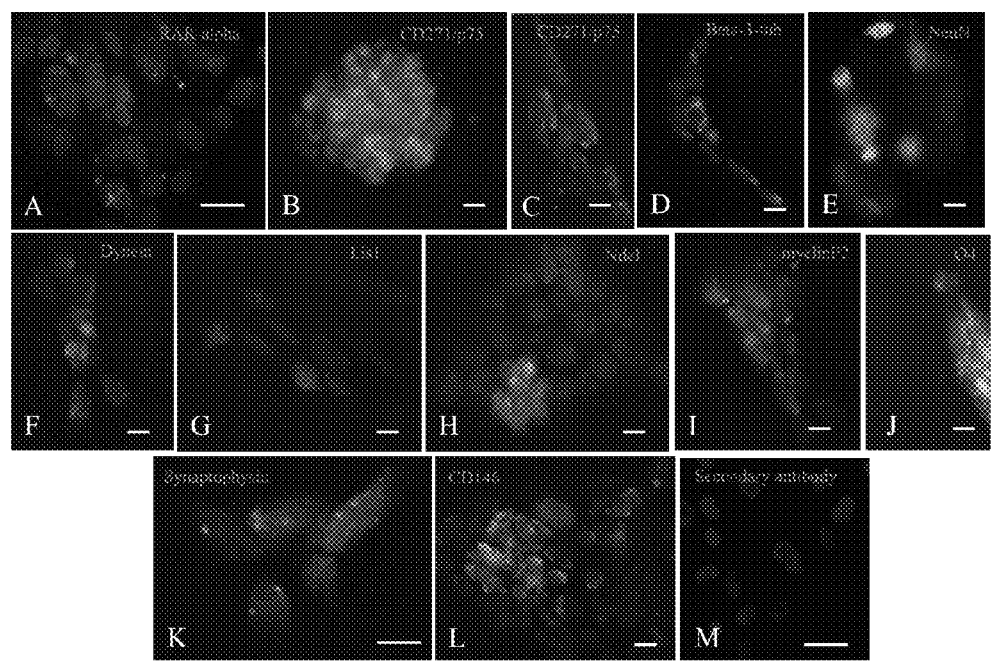

FIG. 95 depicts co-expression of neural markers in IDPSCs derived neuroblasts that form neurospheres and rosettes. A) RAR-alpha expression (green) within IDPSCs derived neuroblasts induced towards neural differentiation. B) and C) Expression of CD271 (P75) in neurospheres and differentiated neurons, respectively. D) Beta-3-tubulina expression. E)NeuN antibody, nuclear localization in neurospheres. F), G) and H) Dynein—Lis1-Ndel complex expression. I) and J) myelin P2 and O4 expression, respectively. K) Synaptophysin expression. L) CD146 expression and in M) control. Scale bar=10 μm, Nucleus stained with DAPI (blue).

Figure 96:
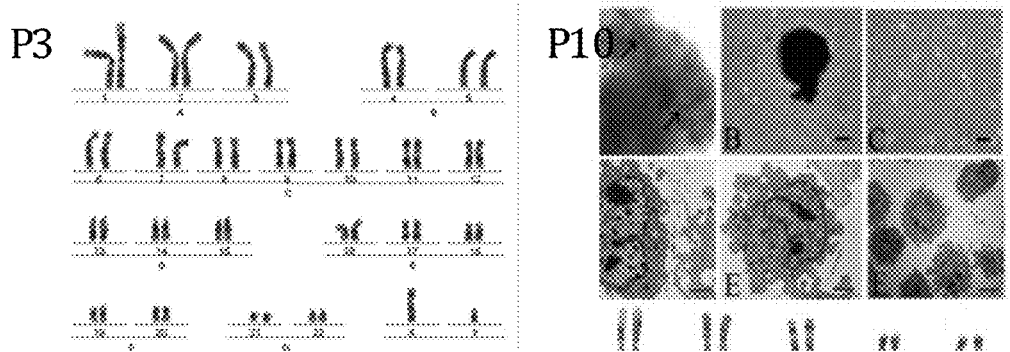

FIG. 96 depicts male karyotypes of in vitro cultured LP IDPSC at early and late passages.

Figure 97:
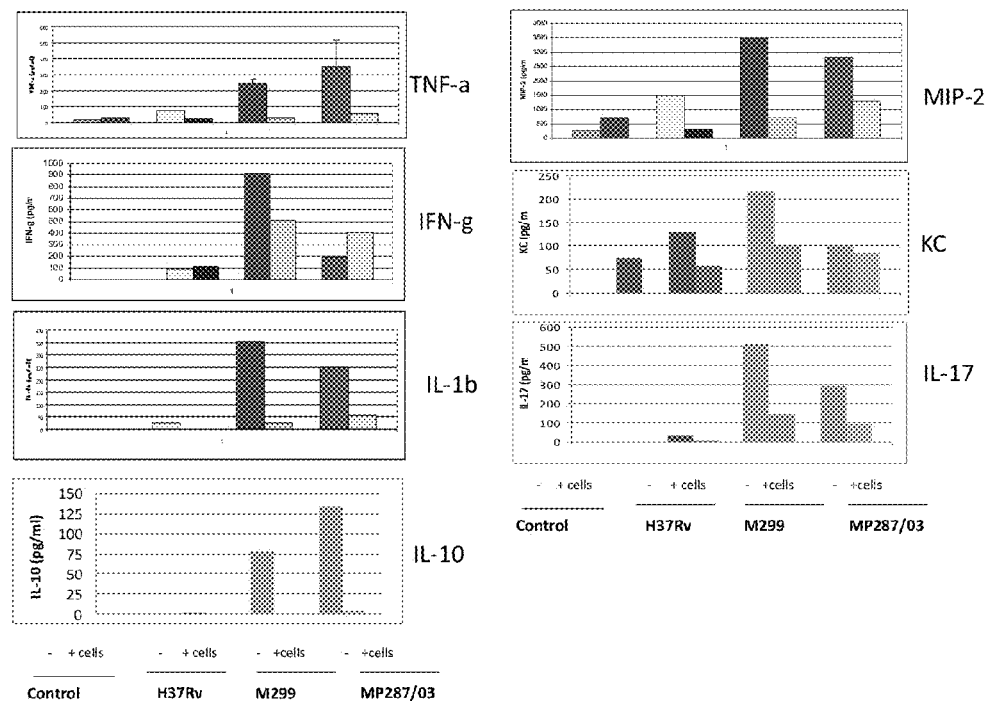

FIG. 97 depicts an effect of IDPSCs i.p. inoculation on cytokine production by lung cells of C57Bl/6 mice i.t. infected with Mtb and M. bovis strains differed in virulence.

Figure 98:
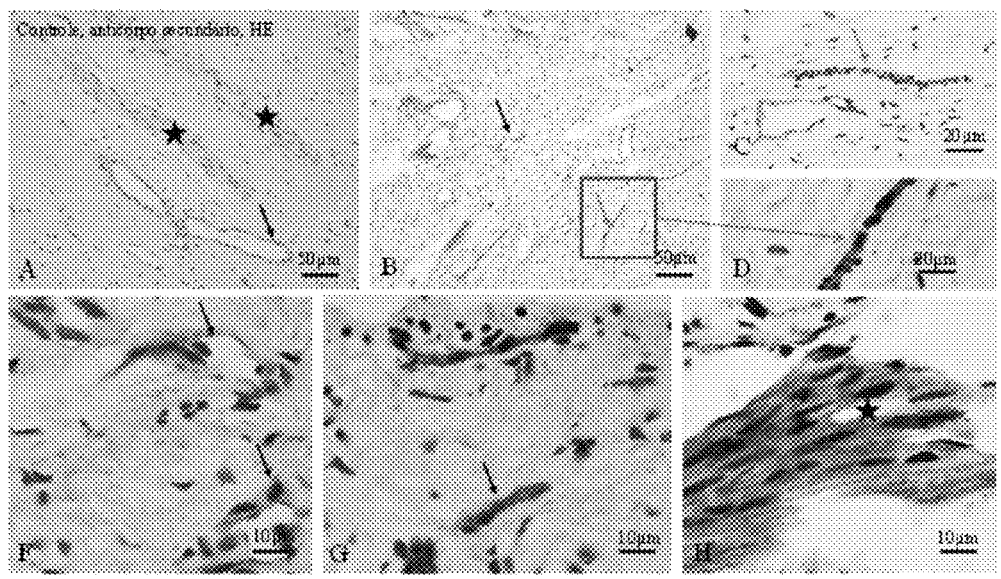

FIG. 98 depicts wisdom tooth pulp tissue and immunohistochemical staining for CD105. A. General aspect of the tissue, HE staining; the arrow indicates the perivascular niche and the star indicates nerve plexus. Negative control reaction, only the secondary antibody was used. B. Positive staining for CD105, observed in perivascular (black arrow) and vascular plexus (orange arrow). C, D, F and G even in B at higher magnification. H. Positive staining for CD105— nerve plexus. Contracorado with hematoxylin and eosin (HE).

Figure 99:
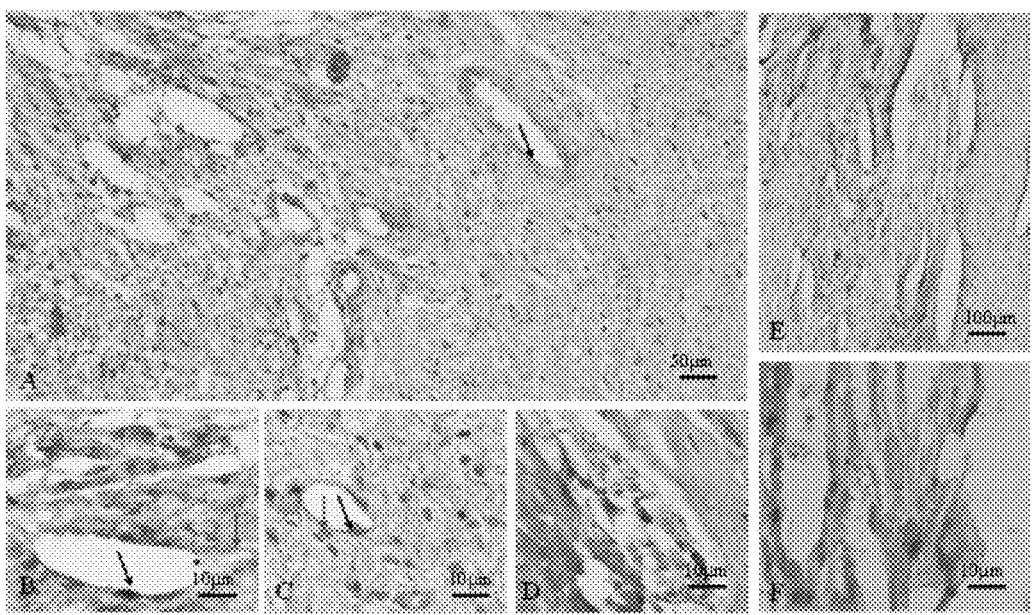

FIG. 99 depicts wisdom tooth pulp tissue and immunohistochemical staining for CD73—SH3 and SH4. A. General aspect of the tissue, HE staining, arrow indicates the perivascular niche. B, C. Positive staining for SH3 observed in vascular (black arrow) and perivascular (orange arrow). D—nerve plexus, neuronal cells simile. E, F—very weak staining for SH-4.

Figure 100:
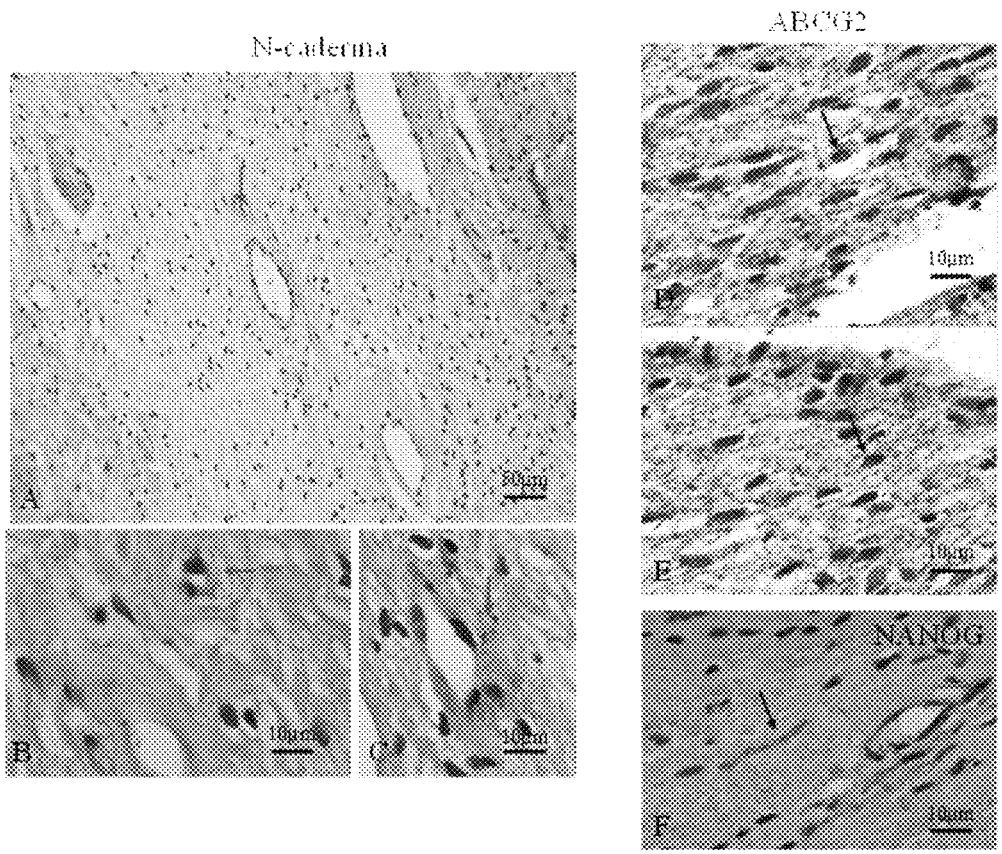

FIG. 100 depicts wisdom tooth pulp tissue and immunohistochemical staining for N-cadherin (AC), ABCG2 (D, E) and Nanog (F). A. General aspect of the tissue, HE staining, positive staining for N-cadherin. B, C. Largest increase, positive staining for N-cadherin observed in perivascular niche (black arrow) (B) and site of pericytes (orange arrow) (C). D, E, positive expression of ABCG2 shows location on the membrane (black arrow). F. Positive staining for Nanog-transcription factor, less intense compared with ABCG2, cytoplasmic localization (black arrow).

Figure 101:
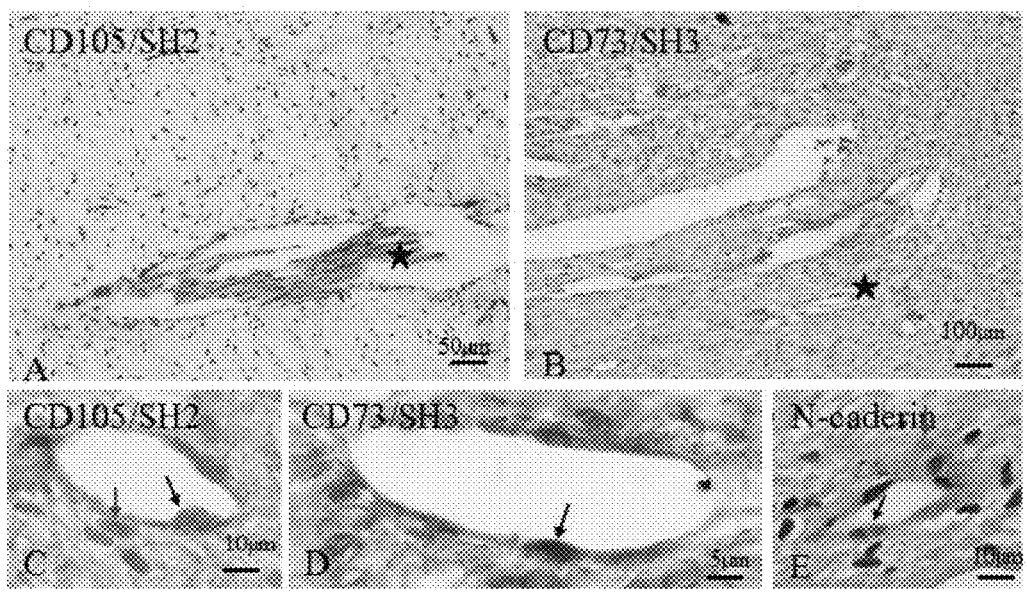
Figure 101:
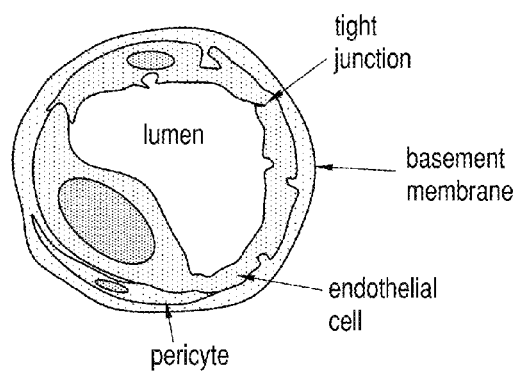

FIG. 101 depicts pulp tissue wisdom tooth comparative analysis of immunohistochemical staining for CD105+ and +CD73/SH3 and N-cadherin. A. General Appearance tissue, HE staining, marking CD105+. B General appearance of the fabric, HE staining, marking CD73/SH3+. C Same as in (A), greater increase. Perivascular niche: black arrow indicates endothelial cells, red arrow—pericytes. Even in D. C. (B) greater increase. Perivascular niche: black arrow indicates endothelial cells. E. Positive expression for N-cadherin. Red arrow indicates location of pericytes, black arrow—endothelial cells.

Figure 102:
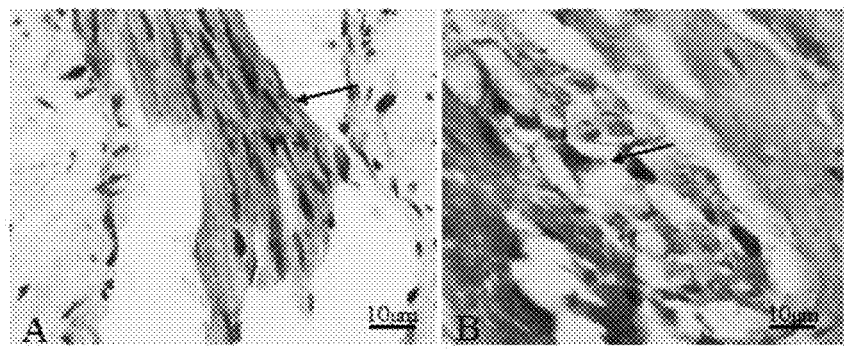

FIG. 102 depicts fibroblastoid morphology of the cells immunopositive for CD105 (A) and neuronal cells immunopositive for CD73/SH3+ (B). Black arrows.

Figure 103:
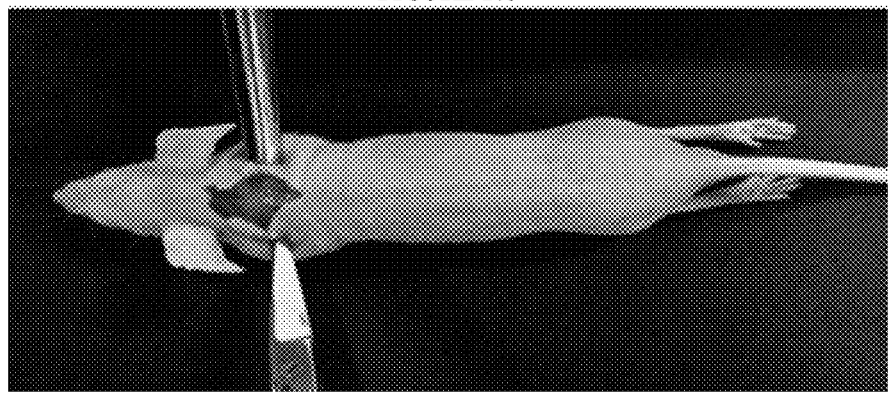

FIG. 103 depicts a dorsal region of a nude mouse without forming cell masses and/or teratoma after subcutaneous application of human IDPSC.

Figure 104:

FIG. 104 depicts a third molar tooth.

Figure 105:
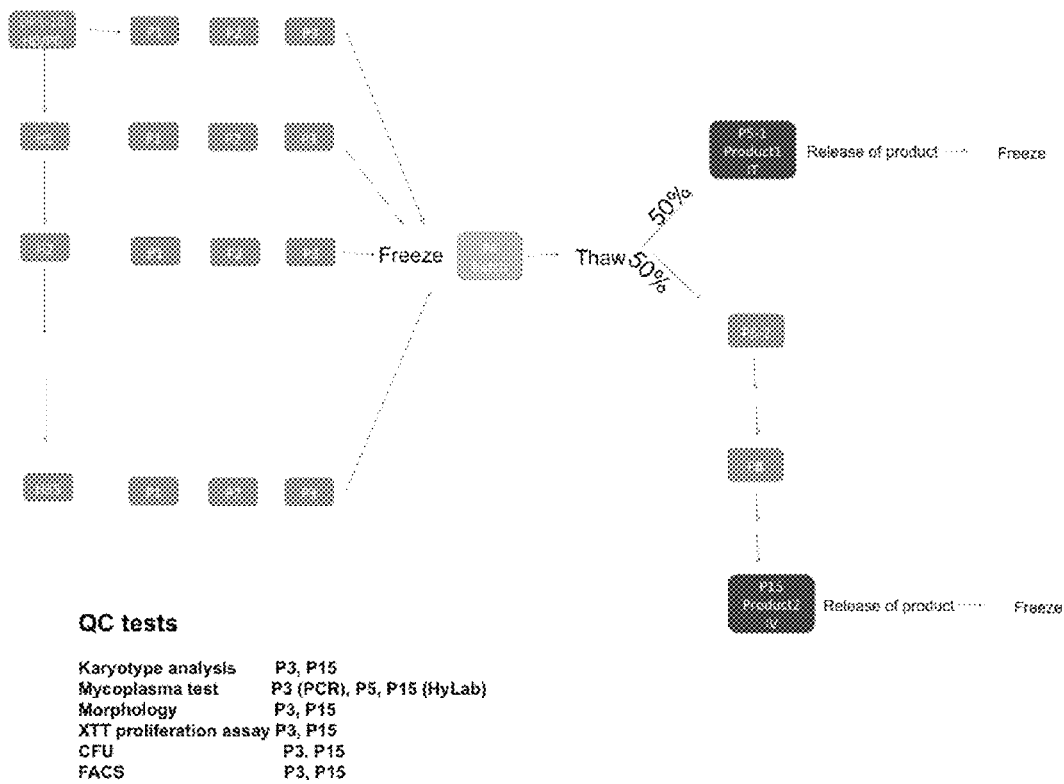

FIG. 105 depicts an exemplary flow chart for a batch release process for industrial scale-up of hIPDSC by LP method in order to obtain clinically relevant quantities for multiple patient dosing.

DETAILED DESCRIPTION OF INVENTION

All publications, patents and patent applications, including any drawings and appendices, herein are incorporated by reference to the same extent as if each individual publication or patent application was specifically and individually indicated to be incorporated by reference.

The following description includes information that may be useful in understanding aspects of the disclosures. It is not an admission that any of the information provided herein is prior art or relevant to the presently claimed inventions, or that any publication specifically or implicitly referenced is prior art.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

As used herein, the term "Matrigel" refers to a gelatinous protein mixture secreted by Engelbreth-Holm-Swarm (EHS) mouse sarcoma cells that resembles the complex extracellular environment found in many tissues.

A "harvesting cycle" constitutes a transfer of the DP to a new cell culture container after adherence and outgrowth of the IDPSCs followed by preservation (e.g. cryopreservation) and/or sub-culturing of the outgrowth of IDPSCs.

As used herein, "hypoxic conditions" comprise culturing the cells under culture conditions comprising or equivalent to:
  (i) a maximum of between about 0.5% and 1%, or a maximum of between about 0.5% and 15% oxygen ($O_2$);
  (ii) about 0.05%, 0.1%, 0.2%, 0.3%, 0.4%, 0.5%, 0.6%, 0.7%, 0.8%, 0.9%, 1% or 2% or 5% of oxygen ($O_2$);
  (iii) between about 0.1% and 2% oxygen ($O_2$); or
  any of (i), (ii) or (iii) with 5-7% $CO_2$.

As used herein, the term "stem cells" refers to immature, unspecialized cells that, under certain conditions, may differentiate into mature, functional cells.

As used herein, the term "hIDPSC" refers to an undifferentiated stem cell that is capable to differentiate into a wide spectrum of cell types, including but not limited to cells from central and periphery neural systems, e.g. neurons, astrocytes, ganglial cells, and/or oligodendrocytes.

As used herein, the term "LP" refers to IDPSCs after multiple DP transfer at least 15 cycles. The term "EP" refers to IDPSCs isolated just after DP extraction.

As used herein, the terms "cell culture" or "cultured cell" refer to cells or tissues that are maintained, cultured, cultivated or grown in an artificial, in vitro environment.

As used herein, the term "pluripotent" refers to precursor cells that have the ability to form any adult cell.

As used herein, the term "undifferentiated" refers to cultured cells that display morphological characteristics of undifferentiated cells, distinguishing them from differentiated cells.

As used herein, the term "substantially homogenous" population of cells refers to a population of cells wherein the majority (e.g., between about 50% to about 90%) of the total number of cells have a specified characteristic of interest (for example, expression of SOX1, SOX2 and beta tubulin).

As used herein, the term "co-express" refers to the simultaneous detection of two or more molecular markers, e.g., SOX1 and SOX2, and beta-3-tubulin in same cell population, preferably in/on same cell.

As used herein, the terms "(cell) culture maintenance," "proliferation", "propagation", "expansion" and "growth", refers to continued survival of a cell or population of cells with an increase in numbers of cells.

As used herein with regard to dental pulp (DP) in vitro cultivation, IDPSCs isolation and expansion, the term "long term" (LT) refers to the cultivation of DP for multiple harvesting cycles of IDPSCs more than 15, preferably >25, more preferably 25-60 cycles, and more preferably 15-45 cycles and more, named "Late Population" (LP).

As used herein with regard to cell cultivation and expansion, the term "large scale" refers to the isolation from DP and cultivation of SC under conditions which permit at least the doubling of cells after each nonenzymatic harvesting cycle.

As used herein, the term "neural progenitor cell" refers to a cell derived from a stem cell that can produce progeny that are capable of differentiating into more than one cell type of CNS and PNS.

As used herein, the terms "neuroprotective factors", "neuronal growth factors", or "neurotrophins" refer to factors that support neurogenesis selected from, without being limited thereto, NGF, BDNF, NT3, NT4.

As used herein the term "neuronal biomarkers" SOX1 (for sex determining region Y-box 1) refers to a transcription factor which is involved in early central nervous system development. SOX1 may be expressed particularly in the ventral striatum.

As used herein, the term "SOX2" refers to a neural progenitor and stemness marker that is a transcription factor expressed by self-renewing and multipotent stem cells of the embryonic neuroepithelium (9). SOX2 may be expressed by actively dividing neural progenitor cells in the neurogenic regions in the adult rat brain and may also be expressed by glial fibrillary acidic protein immunopositive astroglia, widely distributed in the brain parenchyma (10). SOX2 is also known, in conjunction with Oct4, SOX2 as essential transcription factor for pluripotency (Ivanona et al., Nature 442:5330538 (2006); Methods of preparing induced pluripotent stem cells from mouse are also known (Takahashi and Yamanaka, 2006). Induction of iPS cells typically require the expression of or exposure to at least one member from Sox family and at least one member from Oct family.

As used herein, the terms "class III β-tubulin", "beta.3-tubulin", "microtubule-associated protein 2 (MAP-2)", or "neurofilament" refer to microtubule elements expressed exclusively in neurons and serves as a specific neuronal promoter, characteristic of neurons phenotypic marker of early neuronal precursors.

As used herein, the term "bromodeoxyuridine" (5-bromo-2'-deoxyuridine, BrdU) refer to a synthetic nucleoside that is used in the detection of proliferating cells in living tissues. BrdU can be incorporated into the newly synthesized DNA of replicating cells (during the S phase of the cell cycle). Antibodies specific for BrdU can then be used to detect the incorporated chemical, thus indicating cells that were actively replicating their DNA. BrdU can be passed to daughter cells upon replication. BrdU has been demonstrated to be detectable over two years post-infusion.

As used herein, the terms "behavioral tests" and/or "cognitive function" refer to mental processes of an animal or human subject relating to information gathering and/or processing; the understanding, reasoning, and/or application of information and/or ideas; the specification of information; problem-solving, and mental processes such as learning, perception, and/or awareness of ideas and/or information. Cognitive function may be defined via one or more tests or assays for cognitive function, for example valid diagnostic tests and/or computerized cognitive test As used herein, the term "degenerative disorder" includes any disease in which cell death or dysfunction is present. Examples of degenerative disorders include but are not limited to neurodegenerative disorders, cardiac dysfunction, infertility, renal failure, skin disease, autoimmune disease, diabetes, retinal and other ophthalmologic diseases, and hyperproliferative disorders such as cancer.

As used herein, the term "neurogenesis" refers to the proliferation, migration, differentiation, and/or survival of a neural cell in vivo or in vitro.

In the context of some disclosures, the term "neurodegenerative disorder" is defined as disease, in which cells of the central or peripheral nervous system are lost. Examples for neurological and/or neurodegenerative disorders are spinal cord injury, intracranial or intravertebral lesions including, but not limited to, contusion, penetration, shear, compression or laceration lesions of the spinal cord or whiplash shaken infant syndrome.

In the context of the disclosures presented herein, the neurological disorders also include ischaemic events, or ischaemia or ischaemic disorders which can be defined as any local or regional state of hypoxia in cells or tissues which are usually due to an inadequate blood supply (circulation), e.g. caused by a blockage or obstruction of a blood vessel in this area.

The hypoxia can cause acute injury as in hypoxia and/or ischemia including, but not limited to, cerebrovascular insufficiency, cerebral ischemia or cerebral infarction (including cerebral ischemia or infarctions originating from embolic occlusion and thrombosis), retinal ischemia (diabetic or otherwise), glaucoma, retinal degeneration, multiple sclerosis, ischemic optic neuropathy, reperfusion following acute cerebral ischemia, perinatal hypoxic-ischemic injury, or intracranial hemorrhage of any type (including, but not limited to, epidural, subdural, subarachnoid or intracerebral hemorrhage).

According to some aspects, the IDPSCs of the disclosures herein demonstrated a new type of potency, referenced herein as "mixed-maxi-potency". Mixed-maxi-potency is a mix of multipotency characteristics of mesenchymal stem cells (MSC) (about 99% of the IDPSCs carry MSC markers), pluripotency characteristic of human pluripotent stem cells (hPSC) (up to 30%), neuropepithelial stem cell marker enrichment (90%, wherein the nestin expression is in 95% of cells), and relatively low STRO expression in contrast to DPSC derived by other methods. Such mixed maxi-potent compositions of isolated IDPSC populations derived under long-term culturing (LP) result in a synergy of regenerative properties towards neuro-epithelial differentiation. In addition, such mixed maxi-potent compositions of IDPSC populations are characterized by high scalability and safety (immunocompatibility and low risk of tumor formation).

Described herein are the distinct pattern and characteristics of a mixed population of human immature dental pulp stem cells isolated from their niche localized in the central region of the coronal and radicular pulp, which contains large nerve trunks and blood vessels. More specifically this region can be identified as the innermost pulp layer, which is a cell rich zone and contains fibroblasts and undifferentiated stem cells in close association with blood vessels. A new immature dental pulp stem cell phenotype is described and characterized by the expression of hallmarkers of embryonic, mesenchymal, limbal and neuronal/neuroepithelial stem cells. The IDPSCs are multipotent cells, which are able to produce the derivatives of the three germ layers, the endoderm, ectoderm and mesoderm.

During development and in an adult organism, stem cells can be found in a special microenvironment called a stem cell niche. A niche is a specialized anatomic site, which interacts with stem cells. It is hypothesized that a stem cell niche prevents differentiation and thus regulates their fate. During embryonic development, niche factors act on embryonic stem cells inducing their proliferation or differentiation. These changes occur due to alteration of genes and specific proteins expression leading to the development of the fetus and formation of the entire organism. During the post-natal period of human life, especially in childhood, stem cell niches continuously produce specialized cells that are necessary to complete development. In an adult organism, the niche maintains adult stem cells in a quiescent state. Stem cell activation occurs in response to tissue injury when the surrounding microenvironment is sending signals to stem cells to promote self-renewal, proliferation and differentiation to restore damaged tissues. Several factors are involved in regulation of stem cell behavior within the niche. First, cell-cell interactions between stem cells as well as interactions between stem cells and neighboring differentiated cells, interactions between stem cells and adhesion molecules, extracellular matrix components, the oxygen tension, growth factors, cytokines, and the physiochemical nature of the environment including the pH, ionic strength (e.g., $Ca^{2+}$ concentration), and metabolites like ATP are also important. Such reciprocal interaction between stem cells and the niche occurs during development and is maintained during adulthood.

In an adult organism, hematopoietic stem cells of bone marrow have their niche composed of subendoosteal osteoblasts, sinusoidal endothelial cells and bone marrow stromal cells, such as fibroblasts, monocytes and adipocytes. The intestinal stem cell niche is constituted by a subepithelial fibroblast/myofibroblast network which surrounds the intestinal crypts. Such stem cell niches can been found in all adult tissues. Knowledge about stem cell niches in vivo is very relevant because it can help develop cell culture in vitro conditions and to preserve cell stemness after isolation. Identification of such niches within different tissues and discovery of their components and functioning is essential for regenerative therapies. This knowledge will provide information about various components, which is important for cell proliferation and differentiation during stem cells in vitro growing, expansion and differentiation, which must be controlled in flasks or plates in order to provide a sufficient quantity of the proper cell type prior to being introduced back into the patient for therapy. Adult stem cells remain in an undifferentiated state throughout adult life. However, when they are cultured in vitro, they often undergo an "aging" process in which their morphology is changed and their proliferative capacity is decreased. Correct culturing conditions of adult stem cells needs to be improved so that adult stem cells can maintain their stemness over time.

Crowns of the teeth contain coronal pulp. The coronal pulp has six surfaces: the occlusal, the mesial, the distal, the buccal, the lingual, and the floor. Because of continuous deposition of dentin, the pulp becomes smaller with age. This is not uniform throughout the coronal pulp but progresses faster on the floor than on the roof or side walls. The central region of the coronal and radicular pulp contains large nerve trunks and blood vessels. This area is lined peripherally by a specialized odontogenic area which has three layers (from innermost to outermost). The innermost pulp layer is a cell rich zone, which contains fibroblasts and undifferentiated mesenchymal stem cells in close association with blood vessels.

Identification of a stem cell niche also helps to isolate homogeneous population of adult stem cell with unique characteristic similar to those of human embryonic stem cells, so their isolation does not involve any ethical considerations. Such adult stem cells are a promising source for regenerative medicine and have an advantage when compared with recently described induced pluripotent stem cells because these are normal cells, which do not require the use of genetic manipulation or pre-selection methods for isolation.

In one embodiment, a composition comprises an isolated population of immature dental pulp stem cells (IDPSCs), wherein at least 50% of the IDPSCs express a p75 neuroepithelial marker. In some embodiments, at least 55%, at least 60%, at least 65%, at least 70%, at least 75%, at least 80%, at least 85%, at least 90%, or at least 95% of the IDPSCs express a p75 neuroepithelial marker.

In another embodiment, the present invention provides a composition comprising an isolated population of IDPSCs, wherein at least 50% of the IDPSCs express a p53 tumor suppressor marker. In some embodiments, at least 55%, at least 60%, at least 65%, at least 70%, at least 75%, at least 80%, at least 85%, at least 90%, or at least 95% of the IDPSCs express a p53 tumor suppressor marker.

In one aspect, less than 50% of the IDPSCs express a marker selected from CD13 and CD31. In another aspect, less than 45%, less than 40%, less than 35%, less than 30%, less than 25%, less than 20%, less than 15%, less than 10%, or less than 5% of the IDPSCs express a marker selected from CD13 and CD31. In one embodiment, the IDPSCs are negative for CD34, CD43, and CD45 markers.

CD13 is one of the earliest markers of cells committed to the myeloid lineage and is dispensable for normal hematopoiesis and myeloid cell functions. It plays an important functional role in vasculogenesis and is identified as a critical regulator of angiogenesis. In non-hematopoietic cells, CD 13 was found in endothelial cells, epithelial cells, certain renal areas, brain cells, bone marrow, osteoclasts. As an extracellular peptidase, CD13 functions to cleave single neutral amino acids from the N-terminus of small peptides. For example, in the brain CD13 cleaves opioid peptides and enkephalins to regulate neuronal signaling, and in the intestine, it cleaves peptides to facilitate amino acid resorption. CD31 is also known as platelet endothelial cell adhesion molecule (PECAM-1).

In another embodiment, at least 50% of the IDPSCs produce a neurotrophic factor selected from brain-derived neurotrophic factor (BDNF), glial cell line-derived neurotrophic factor (GNDF), nerve growth factor-beta (beta-NGF), neurotrophin-3 (NT3), neurotrophin-4 (NT4), and neurotrophin-5 (NT5). Alternatively, at least 55%, at least 60%, at least 65%, at least 70%, at least 75%, at least 80%, at least 85%, at least 90%, or at least 95% of the IDPSCs produce a neurotrophic factor selected from BDNF, GNDF, beta-NGF, NT3, NT4, and NT5.

Growth factors that are specifically expressed in the brain and that affect neural development in vivo and in vitro include brain derived neurotrophic factor (BDNF), glial derived neurotrophic factor (GDNF), and ciliary neurotrophic factor (CNTF). BDNF is a member of the nerve growth factor family that promotes in vitro differentiation of NSC, human subependymal cells, and neuronal precursors to neurons and promotes neurite outgrowth of hippocarnal stem cells in vivo. BDNF and EGF exclusive differentiation into tyrosine hydroxylase positive neurons has been seen. GDNF is a member of the TGF-superfamily. In early neurogenesis, GDNF is expressed in the anterior neuroectoderm, suggesting that it may play a key role in neuronal development. GDNF promotes survival of motor neurons in peripheral nerve and muscle and has neurotrophic and differentiation abilities.

In certain aspects, at least 50%, at least 55%, at least 60%, at least 65%, at least 70%, at least 75%, at least 80%, at least 85%, at least 90%, or at least 95% of the IDPSCs express nestin. In other aspects, less than 20%, less than 15%, less than 10%, or less than 5% of the of the IDPSCs express Oct3/4.

In one embodiment, a composition comprising a phenotypically uniform multi-lineage population of isolated human post-natal IDPSCs is characterized by a multifunctional molecular profile of:

(a) neuroepithelial stem cell profile IDPSCs wherein at least 80% of the IDPSCs express a marker selected from nestin, p75, ATP-binding cassette sub-family G member 2 (ABCG2), p63, brain-derived neurotrophic factor (BDNF), glial cell line-derived neurotrophic factor (GNDF), nerve growth factor-beta (beta-NGF), neurotrophin-3 (NT3), NT4, and NT5; and (b) pericyte profile IDPSCs wherein less than 20% of the IDPSCs express a marker selected from STRO-1 and CD146;

(c) mesenchymal stem cell profile IDPSCs wherein at least 80% of the population express a marker selected from CD105, CD73, CD90, CD29, CD44, CD117, vimentin, fibronectin, alkaline phosphatase (ALP), alpha-fetoprotein (AFP), tenascin-C, matrix metalloproteinase-1 (MMP-1), MMP-2, MMP-9, syndecan 1 (SDC1), SDC2, SDC3, SDC4, p53, and collagen type 1;

(d) pluripotent stem cell profile IDPSCs wherein from 2% to 30% of the IDPSCs express at least one marker selected from Oct3/4, SOX2, Nanog, TRA1-60, TRA1-81, and SSEA4; and (e) mesenchymal stem cell profile IDPSCs wherein the IDPSCs are negative for HLA-ABC and HLA-DR major histocompatibility (MHC) antigens.

HLA (human leukocyte antigens) were originally defined as cell surface antigens that mediate graft-versus-host disease, which resulted in the rejection of tissue transplants in HLA-mismatched donors. Tenascin is abundant in embryonic tissues and during the tissue-repair process.

In some embodiments, at least 50%, at least 55%, at least 60%, at least 65%, at least 70%, at least 75%, at least 80%, at least 85%, at least 90%, or at least 95% of the IDPSCs express a marker selected from nestin, p75, ATP-binding cassette sub-family G member 2 (ABCG2), p63, brain-derived neurotrophic factor (BDNF), glial cell line-derived neurotrophic factor (GNDF), nerve growth factor-beta (beta-NGF), neurotrophin-3 (NT3), NT4, and NT5.

In other embodiments, less than 20%, less than 15%, less than 10%, or less than 5% of the of the IDPSCs express a marker selected from STRO-1 and CD146. In some aspects, from 2% to 30% or any range therein (e.g., from 5% to 30%, from 10% to 30%, from 2% to 10%, from 2% to 20%) of the IDPSCs express at least one marker selected from Oct3/4, SOX2, Nanog, TRA1-60, TRA1-81, and SSEA4.

In another aspect, a composition comprises a phenotypically uniform multi-lineage population of isolated human post-natal IDPSCs, wherein said population of human post-natal IDPSCs is obtained as an outgrowth from DP cultured for at least 10 harvesting cycles under hypoxic conditions.

In certain embodiments, LP IDPSCs are transferred mechanically without enzymatic treatment. This may preserve the DP and allow for a hypoxia-induced multi-lineage orientation of the IDPSCs.

In some embodiments, the IDPSCs are cultured with an extracellular matrix (ECM) substrate comprising fibronectin, collagen, laminin, vitronectin, polylysine, heparan sulfate proteoglycans, entactin, or a combination thereof. The ECM substrate may be Matrigel.

The IDPSCs may be isolated as an outgrowth from DP cultured for at least 5 harvesting cycles, at least 10 harvesting cycles, at least 15 harvesting cycles, at least 20 harvesting cycles, at least 25 harvesting cycles, at least 30 harvesting cycles, at least 35 harvesting cycles, at least 40 harvesting cycles, at least 45 harvesting cycles, at least 50 harvesting cycles, at least 55 harvesting cycles or at least 60 harvesting cycles.

The IDPSCs may be isolated from dental pulp (DP) from a tooth selected from a deciduous tooth, a permanent tooth, and a third molar.

According to some aspects, this disclosure also provides a method of producing an isolated population of IDPSCs. Unique advantages provided by this method relate to the ability to scale up production of IDPSCs and the resulting clinical utility of the IDPSCs. The published therapeutic doses of cells used in central nervous system (CNS) clinical trials with stem cells are in the range of $10 \times 10^6$ to $10 \times 10^9$ cells per dose.

In one embodiment, the average numbers of cells generated after 5-10 passages of the IDPSCs are as follows.

Starting from $5 \times 10^5$ cells following enzymatic digestion after 5 passages, $3 \times 10^8$ IDPSCs will be produced, and after 10 passages $5 \times 10^9$ cells of IDPSC will be produced. One dental pulp (DP) after 15 harvesting cycles (about 1.5 month with harvesting cycles occurring once about every 3 days) will produce $5 \times 10^{12}$ IDPSCs at passage 5 using EP IDPSCs cultured with enzymatic treatment. Using LP IDPSCs and mechanical transfer without enzymatic treatment, after 15 harvesting cycles about $3 \times 10^{13}$ IDPSCs will be produced at passage 5. An additional $3 \times 10^{13}$ IDPSCs are produced after 30 harvesting cycles and an additional $5 \times 10^{13}$ after 50 harvesting cycles using LP IDPSCs and mechanical transfer without enzymatic treatment.

An additional advantage of the method is that the proliferation rate of cells isolated from DP by explant culture is maintained constant and usually quadruples each 3-4 days. Proliferation rate of cells isolated from DP using enzymatic treatment usually triple each 3-4 days.

In one embodiment, this disclosure provides a method of producing an isolated population of IDPSCs comprising:
  (a) extracting DP from a tooth;
  (b) placing the DP in a sterile container and washing the DP with a sterile solution with antibiotics;
  (c) optionally, removing the sterile solution with antibiotics and mincing the DP in a basal culture medium;
  (d) mechanically transferring the DP into another container with a culture medium;
  (e) culturing the DP until outgrowth and adherence of the IDPSCs is observed; and
  (f) repeating steps (d) and (e) at least 5 times to allow outgrowth and adherence of IDPSCs from multiple niches within the DP.

Culturing of the DP may proceed for at least 1 day, at least 2 days, at least 3 days, at least 4 days, at least 5 days, at least 10 days or at least 15 days. Steps (d) and (e) may be repeated at least 10 times, at least 15 times, at least 20 times, at least 25 times, at least 30 times, at least 35 times, at least 40 times, at least 45 times, at least 50 times, at least 55 times or at least 60 times.

The DP may be cryopreserved and thawed prior to mechanically transferring the DP explant into another container with a culture medium. In some aspects, clonogenicity is preserved both before and after cryopreservation. The efficiency of clonogenecity before and/or after cryopreservation may be greater than 75%, greater than 80%, greater than 85%, greater than 90%, greater than 95%, greater than 96%, greater than 97%, greater than 98% or greater than 99%.

A method of this disclosure may comprise passaging the IDPSCs into a subculture with or without protease treatment. Subculture may be repeated a maximum of 10 times, a maximum of 9 times, a maximum of 8 times, a maximum of 7 times, a maximum of 6 times, a maximum of 5 times, a maximum of 4 times, a maximum of 3 times, a maximum of 2 times or a maximum of 1 time.

In some embodiments, culturing of the DP for about 3 days generates an isolated population of at least $1 \times 10^5$ IDPSCs, at least $2 \times 10^5$ IDPSCs, at least $3 \times 10^5$ IDPSCs, at least $4 \times 10^5$ IDPSCs, at least $5 \times 10^5$ IDPSCs, at least $6 \times 10^5$ IDPSCs, at least $7 \times 10^5$ IDPSCs, at least $8 \times 10^5$ IDPSCs, at least $9 \times 10^5$ IDPSCs or at least $1 \times 10^6$ IDPSCs.

In certain aspects, the culture medium is DMEM/F12 medium or MEM-alpha medium. The culture medium may be supplemented with about 5% to about 20% fetal bovine serum, about 1% of non-essential amino-acids, about 1% of L-glutamine or an L-glutamine substitute, and about 1% of an antibiotic.

Aspects of this disclosure also encompass an isolated population of IDPSCs generated by any of the methods disclosed herein.

In some embodiments, the stem cells of the disclosed method are dental pulp stem cells. Dental pulp stem cells are a kind of somatic stem cells which is present in dental pulp tissue inside the dentine of teeth, and which is capable of differentiating into dental pulp, dentine and the like (capable of differentiating mainly into odontoblasts). Dental pulp stem cells can be obtained by extirpating dental pulp tissue from (i) a tooth extracted for the sake of convenience in orthodontic treatment or a tooth extracted because of periodontal disease and the like, or from (ii) a wisdom tooth (aka a third molar) extracted for the sake of convenience in orthodontic treatment or of treatment of wisdom tooth periodontitis and the like.

Although any tooth retaining dental pulp tissue can be used as a source of dental pulp stem cells, it is preferable to select a tooth that is rich in dental pulp stem cells with a high potential for proliferation.

One suitable source of dental pulp stem cells is dental pulp tissue derived from a wisdom tooth of a young person (for example, in humans, about 12-16 years) having the wisdom tooth extracted for orthodontic purposes. Wisdom teeth at these ages are still in the midst of dental root formation during the initial stage of dental differentiation, and are characterized by a high abundance of dental pulp tissue, a relatively high density of dental pulp stem cells, and a very high potential for their proliferation.

Because wisdom teeth are sometimes extracted for orthodontic purposes in other age groups, and also because dental pulp tissue can be obtained from teeth other than wisdom teeth, extracted for the sake of convenience, the availability of these extracted teeth is high.

Other potential sources of dental pulp stem cells include teeth extracted for the treatment of periodontal disease, wisdom teeth extracted because of wisdom tooth periodontitis and the like. In this case, there are disadvantages of an increased risk of contamination and a smaller amount of dental pulp tissue obtained. Because of the ease of obtaining these teeth from adults (particularly the elderly), however, these materials can serve as a major source of dental pulp stem cells when autologous transplantation of cells or tissue differentiated from these cells is desired.

The dental pulp stem cells that can be used in the present invention may be derived from any animal species, including mammals. Although dental pulp stem cells can be collected from any animal species, it is particularly preferable that the dental pulp stem cells be collected from the patient or from another person sharing the same type of human leukocyte antigen (HLA) because of the absence of graft rejection, when the stem cells obtained are used for human regenerative medicine. When the stem cells are not administered (i.e., transplanted) to a human, but are used as, for example, as a source of cells for screening to determine the presence or absence of the patient's drug susceptibility and adverse drug reactions, the dental pulp stem cells must be collected from the patient or from another person sharing the same gene polymorphism correlating to the drug susceptibility and adverse drug reactions.

Various companies have set up of tooth banking in order to isolate MSCs/pericytes from dental tissues and to tap the potential of this new and innovative approach for preserving stem cells from deciduous teeth and other dental sources. In the USA, StemSave, BioEden and Store-A-Tooth are companies involved in banking of tooth stem cells. In Japan, the first tooth banks were established in Hiroshima University and Nagoya University.

Aspects of this disclosures described herein relate to a method for derivation of unique and previously non-isolated mixed population of human adult stem cells derived from dental germ (the dental germ are primitive embryonic cells that are the precursors of teeth), primary dental pulp of deciduous, third molar and permanent teeth (see Lizier et al. (2012) PLoS ONE 7:e39885).

Said mixed population comprises MSCs/perycites/neuroepithelial/pluripotent stem cells capable to differentiate into endoderm, ectoderm and mesoderm embryonic germ layers.

More specifically said mixed population comprises of mesenchymal stem cells (MSCs) at least 96%-99% characterized by CD105+, CD73+, CD90+, CD29, CD44, CD117 (c-kit), Vimentin, Fibronectin, alkaline phosphatase (ALF), Alpha-Fetoprotein (AFP), tenascin, matrix metalloproteinases 1,2,9, syndecans 1,2,3,4, p53, collagen type 1 and 52% CD13, as well as CD45-, CD34- and HLA ABC (low), HLA DR-expression signature. Said biomarker defined cell signature fingerprint is typical for MSCs with classic multipotent cell type characteristics.

Additionally said mixed population comprises MSCs/pericytes at least 24% characterized by STRO-1 and 36% characterized by CD146 (MUC18) and expression signature. Said biomarker defined cell signature fingerprint is typical for MSCs with perivascular niche derived multipotent cell type characteristics.

Further, said mixed population comprises MSCs/pluripotent stem cells at least 2% to 30% characterized by an Oct3/4, SOX2, Nanog, TRA1-60, TRA1-81, and SSEA4 expression signature. Said biomarker defined cell signature fingerprint is typical for pluripotent cell type characteristics.

Unexpectedly, said mixed population comprises MSCs/neuroepithelial stem cells at least 95% Nestin, at least 85% p75 (nerve growth factor receptor, CD271/p75(NTR) inhibits the differentiation of mesenchymal stem cells into osteogenic, adipogenic, chondrogenic, and myogenic lineages), ABCG2 (ABCG2 is a member of the ATP binding cassette (ABC) transporters, lays an important role in promoting stem cell proliferation and the maintenance of the stem cell phenotype), p63 (p63 is essential for the Proliferative Potential of Stem Cells in Stratified Epithelia; p63 and ABCG2 expression in the corneoscleral limbus: Implications for stem cell purification), Brain-derived neurotrophic factor (BDNF), Glial cell line-derived neurotrophic factor (GNDF), Nerve growth factor-beta (beta-NGF), Neurotrophin-3 (NT3), NT4,5, at least 20% β-tubulin III (weak), Connexin 43 and cytokeratin-K12 expression signature. The enrichment of the mixed population IDPSCs with said biomarker defined cell population signature fingerprint is unique and unexpected. This population of cells holds promise of enormous research and therapeutic applications.

Therefore, according to an aspect of these embodiments, there is provided a population of IDPSC cells comprising enriched stem cells characterized by MSCs/neuroepithelial biomarkers preferably various neuroprotective factors such as p75 and p63, BDNF, GNDF, beta-NGF, NT3, NT4/5.

A further embodiment relates to a method of continuous derivation of IDPSC from prolonged cultivation of dental DP explant ex vivo through multiple harvesting cycles.

Said method allows an unexpected and almost unlimited number of harvesting/derivation cycles and therefore may reduce passage number of IDPSCs in order to obtain a similar number of cells as previously reported methods.

Said disclosed method is easy to perform and diminishes the probability of occurrence of spontaneous genomic mutations and eventual karyotype abnormalities, which may arise during multiple passages in stem cells which occur in traditional methods for derivation of IDPSCs using enzymatic digestion of dental pulp.

Furthermore, aspects of this disclosure refer to the process for differentiation realized from said cells and concentrates containing these cells, as well as, to the differentiated cells obtained from said process and concentrates containing these cells.

The number of stem cells that present a MSC/pericyte phenotype is diverse in different populations of MSCs from dental tissue and it presents individual variations. Therefore it is a significant advantage for single donor-derived culturing for multiple batches including reduced variability, consistency and reproducibility.

As an example, using said method it is possible to derive a therapeutically sufficient quantity of low passage IDPSCs derived from a single donor's DPs which may be obtained from at least one deciduous tooth or optionally four upper teeth and four lower "milk" teeth that may be stored or preserved and used as needed.

It is generally accepted that pericytes are isolated from the perivascular niche; this niche has also been found in dental pulp (Shi and Gronthos, 2002). Surprising finding herein is the derivation of IDPSCs from both non-perivascular and perivascular niches. Neuroepithelial markers enriched IDPCSs derived from non-perivascular are herein for the first time obtained using prolonged culturing methods.

A further embodiment relates to a method of prolonged culture of DP explants under hypoxic conditions for derivation of IDPSCs from the perivascular stem cell niche.

A further embodiment relates to a method of prolonged culture of DP explants under reduced nutrition supply conditions for derivation of IDPSCs from the non-perivascular stem cell niche.

Also disclosed herein are cell populations with pluripotency potential as demonstrated by nuclear localization of Oct3/4 expression, which may be reduced from 10% to <2% during prolonged culture.

When propagating stem cells for cryopreservation or use in a patient, the FDA recommends that cells will not be passed through over 15 passages.

This is in order to lower the risk of karyotype mutation and tumorogenicity related to high passage number and to reduce in vivo differentiation plasticity. Therefore, after cryopreservation 2-5 more passages may be expanded before clinical administration depending on the required procedure. This limitation on the number of passages limits the number of stem cells that can be collected for clinical applications.

An additional embodiment relates to a method of wherein a clinically sufficient number of IDPSCs can be obtained at low passage number.

In an additional embodiment, a single donor explant is biopreserved in culture up to six months or more with preferable derivation of IDPSCs at P0 for three days until viable, uni-clonal colonies are formed. Said explant is then replaced for the next sequential harvesting derivation cycle, such continuous cultivation may lead to 10 cycles per month for at least five months to a total of 50 transfers and derivation cycles at P0. From each transfer and derivation cycle IDPSCs are propagated and passaged a maximum of 5 times prior to cryopreservation or use.

As noted above, aspects of the disclosures presented herein are based in part on the surprising discovery that immature dental pulp stem cells (IDPSC) can be isolated from stem cell niches present in the teeth. These niches can be found in but are not unique to dental pulp from deciduous teeth. Additional niches have been found localized in nerve networks of the cell free zone, in the innermost pulp layer of the cell rich zone, and in the outermost layer, which contains the odontoblasts in the cell free zone (see FIGS. 1 and 2). The existence of these niches is consistent with the neural crest origin of dental stem cells (DSC) and isolation of a mixed population of neuroepithelial and mesenchymal stem cells in the IDPSC.

An important advantage of using the isolated IDPSC for regenerative medicine is the fact that they present less of risk of tumorogenicity. The inventors have developed a novel strategy for IDPSC isolation, manipulation, and cryopreservation, which leads to long-term culture of these cells with a limited number of in vitro passages. With this strategy, practically unlimited numbers of IDPSC at early passages (5 or less) can be produced. See Lizier et al. (2012) PLoS ONE 7:e39885.

It has been shown that adipose tissue derived stem cells (ASC) have an affinity to produce tumor in vivo. It seems that this affinity of ASC correlates with their isolation from the perivascular niche (Zhang et al. 2010). IDPSCs can be isolated from different niches in dental pulp thus minimizing the risk of tumor formation. Lizier et al. (2012) PLoS ONE 7:e39885. In this disclosure, we disclose a new lineage of DSCs from deciduous teeth (hIDPSC) can be isolated from different (non-perivascular) distinct niches in dental pulp or from ischemic/vascular-nutrient/oxygen deprived internal tissue of DP explant, thus putatively minimizing the risk of tumor formation.

The IDPSC compositions of some embodiments are administered in a pharmaceutically effective amount. As used herein, the phrase "pharmaceutically effective amount" refers to an amount sufficient to treat a disease, condition, or disorder. The level of the effective dosage can be determined according to the severity of the disease; the age, weight, health, and sex of a patient; the drug sensitivity in a patient; the administration time, route, and release rate; the treatment duration; or elements including drugs that are blended or simultaneously used with the composition of the some embodiments, or other elements well-known in the medical field. For example, the dosage of the IDPSCs varies within a wide range, and is determined according to the requirements of the individuals in specific cases. Generally, in the case of parenteral administration, the IDPSCs are usually administered in an amount of about $1\times10^6$, about $1\times10^7$, about $1\times10^8$, about $1\times10^9$, or about $1\times10^{10}$ cells/kg of a body weight of the individual. Further, the composition of some embodiments and other disease-treating substances known in the art can be simultaneously or sequentially administered to an individual.

The IDPSC compositions of some embodiments can be administered locally or systemically, may require ex vivo or in vivo manipulations to obtain therapeutic activity in order to induce a local effect (e.g., a direct regenerative effect of IDPSC in contact with degenerative tissue affecting cell proliferation/cell death, tissue integrity and functionality) and/or due to a systemic effect (e.g., by releasing protective trophic factors and reducing levels of pro-inflammatory cytokines).

IDPSCs administration routes are selected from known medical methods of treating degenerative, reproductive clinical or aesthetic damage, and/or to preventing subject, tissue, cells from future damage. IDPSC treatment herein encompass abrogating, substantially inhibiting, slowing or reversing the progression of a condition, substantially ameliorating clinical or aesthetical symptoms of a condition or substantially preventing or reduce the appearance of clinical or aesthetical symptoms of a condition. According to another aspect, there is provided a use of a IDPSC composition in conjunction with another therapeutic cells or another medicament for protecting a subject from degenerative clinical or aesthetic damage, or loss of tissue, cell functioning, or to relief of an existing symptom and/or of a future symptom of any disease mentioned here but not limited to the described herein examples.

In some embodiments, administration of the composition is performed in accordance with any of the methods and/or treatments described in co-filed Provisional Patent Application by the present inventors, titled "MULTIFUNCTIONAL IMMATURE DENTAL PULP STEM CELLS OBTAINED BY A ROBUST, LONG-TERM CULTURING SYSTEM", and having U.S. Ser. No. 61/791,594, the contents of which are incorporated herein by reference in their entirety. More particularly, the aspects of this disclosure relate to a method for obtaining a clinically sufficient number of a patient's own DTSCs without aberrant genetic and biologic changes based on tissue explant culture and mechanical (nonenzymatic) transfer in long-term culture of DP.

According to an embodiment, DP is maintained in culture following mechanical transfer during several months. The following characteristics were evaluated: morphology, expression of specific MSC-phenotypes and ES cell proteins and genes, karyotype, growth rate and differentiation ability of IDPSCs just after DP extraction (early population, EP) and after multiple DP transfer (late population, LP). Some of these parameters were evaluated after cryopreservation and with culturing IDPSCs in three distinct culture media. The used of antibody against BrdU incorporated in DP just after plating and three days after DP cultivation gave insight into the mechanism of IDPSCs generation by explant culture. Additionally, to distinguish SCs in DP, immunohistochemical staining against nestin, vimentin, Oct3/4 and STRO-1 has been performed.

Also disclosed herein is a method of obtaining of a pure population of typical MSCs, which also almost pure in respect of neuro-crest stem cells (NCSC) and neuro-epithelial stem cells. A part of this population (no more than about 24%) may be presented as SHED and another part is presented by MSCs+NCSC+Pluripotent stem cells. It is impossible to separate these populations with such methods as flow cytometry and magnetic beads.

Another embodiment of offers the possibility to separate SHED cells, following LP method, by a more robust approach and with higher cell numbers than using traditional DP enzymatic dissociation technology or a EP DP outgrowth method.

Notably, the enrichment of neuroepithelial population is progressively enriched with these markers following harvesting cycles.

DP may also overcome some mechanical treatment such as perforation, or mincing as an alternative method to obtain such cells. Usually the first cells appear outgrowing about one week after DP plating; it is hypothesized that from nervous plexus the cells can migrate later because they are deeper into the DP than blood vessels. On the other hand, the subodontoblastica niche, which can also produce these cells, is peripherally located and enzymatic treatment can destroy it. Mechanical treatment such as DP mincing is especially useful when the pulp is big.

In addition, the neuroepithelial markers can be induced by external cell culture media formulation components or gas equilibrium, inducing "stress"/hypoxic cell culture conditions. For example, the pluripotent stem cells marker expression may be induced by hypoxia.

An additional embodiment relates to the use of the disclosed methods to produce a new lineage of DPSCs that are derived from multiple niches of perivascular and non-perivascular origin. The derivation from non-perivascular origin is induced due to deprivation of nutrients and oxygen to inner DP niches during prolonged culture/hypoxic conditions, and therefore inner niche cells migrate to the surface. Such cells are characterized by nuclear expression of OCT 4 and robust expression of ectodermal/NPC markers such as nestin, p75, p63 and more.

According to some aspects, the IDPSC compositions of this disclosure are administered at a therapeutically effective amount that is sufficient to result in a reduction of the degenerative damage or disease or aesthetic symptoms can be administered through various administration routes including topical (dermal, and intraocular), local, transmucosal (including buccal, sublingual,), parenteral/systemically (including subcutaneous, intradermal, intramuscular, intravascular, and intraarticular), and, and preferably parenteral administration.

IDPSCs undifferentiated or induced to undergo special differentiation (progenitors) may be administered to a subject having degenerative disease may, for example, be injected directly into the disease loci/cavity/mileau, transplanted elsewhere in the body, or may be adhered to a scaffold or delivery vehicle and surgically inserted/transplanted/grafted into an acceptable location in the body. hIDPSC are NOT immunogenic and do not need, in most cases, the use of immunosuppression protocol, but in some immuno-over reactive or sensitive cases, immunomodulation may required or immuno-matched donors are preferably used. IDPSCs can be administered to a subject with abnormal or degenerative symptoms obtained in any manner, including those obtained as a result of age, trauma, preferably (neuro)degenerative disease. The present inventors have found that the IDPSCs are very effective for treating neurological diseases among other ailments.

IDPSCs may be introduced locally or systemically into the subject in order to treat a degenerative disorder, such as, but not limited to, a neurodegenerative disorder, reproductive disorder, ectodermal, or diabetes, in a subject by administering a therapeutically effective amount of a differentiated or undifferentiated IDPSCs.

U.S. Pat. Application Nos. 2003/0219898, 2003/0148513 teach the implantation of stem cells for different therapeutic treatments of neuro degenerative conditions. IDPSCs are preferably via a surgical procedure or injection, intrathecally, or intra-ventriculary. U.S. Pat. Nos. 5,762,926; 5,650, 148; 5,082,670 teach methods of neural transplantation or grafting involves transplantation of cells into the central nervous system or into the ventricular cavities or subdurally onto the surface of a host brain (i.e. extraprenchymal transplantation). Additional intrabrain delivery methods include intraparenchymral transplantation achieved by injection. Multiple injections may be made using this procedure. Multiple grafts may consist of a mixture of cell types, and/or combine transgenes inserted into the cells. Transplantation into cavities may be preferred for spinal cord grafting. Grafting of transplanted cells into brain will require suction or cleaning of the cavity or filling of the lesion, etc. Most preferable parenteral administration is intrathecal administration. To treat diabetes, IDPSCs undifferentiated or differentiated to beta-like cells can be administered by injection, subcutaneous injection, intraperitoneal injection, injection under the kidney capsule, injection through the portal vein, and injection into the spleen, or by implantation under the kidney capsule, through the portal vein of the liver, or into the spleen, IDPSC may be implanted using delivery vehicle/scaffold or encapsulation techniques.

The IDPSC compositions of some embodiments can be administered through various administration routes including topical (including buccal, sublingual, dermal, and intraocular), parenteral (including subcutaneous, intradermal, intramuscular, intravascular, and intraarticular), and transdermal administration, and preferably parenteral administration. Most preferable parenteral administration is intrathecal administration. The present inventors have found that the IDPSCs are very effective for treating neurological diseases among other ailments.

Hair Renewal and Restoration

The hair follicle, when growing passes through three phases: a growth phase (anagen), regression phase (catagen), and a resting phase (telogen). Hair growth is a continuous process, which lasted during organism life. Therefore, hair follicle must have a stem cell niche, which are constantly active and especially in the time of hair follicle regeneration. According to current knowledge, the hair follicle stem cells, which originated from neural crest, reside in the bulge area of the hair follicle near the sebaceous gland. These cells express in nestin in undifferentiated state, which is a marker of neural and hair follicle stem cells. Such nestin-expressing stem cells found in the bulge area of the hair follicles were to form the outer and inner route sheath of the hair follicle during anagen. It has been shown that these stem cells can not only produce the hair follicle but can regenerate or at least heal wounds in the epidermis. Moreover, hair follicle stem cells can be converted into neurons. They formed neurospheres, which in turn, formed neurons, glial cells, keratinocytes, smooth muscle cells, and other cell types. When hair follicle stem cells were injected subcutaneously in mice, they formed neurons. After transplanted into mice, in the bulge area of the hair follicle they gave rise to blood vessels indicating the potential of the hair follicle stem cells to form endothelial cells. The hair follicle stem cells can also greatly enhanced the rate of nerve regeneration and the restoration of nerve function. These results demonstrate the pluripotency of hair follicle stem cells and their potential use in regenerative medicine. These stem cells have characteristics that combine some advantages of embryonic and adult stem cells. Similar to embryonic stem cells, they have a high degree of plasticity, can be isolated at high levels of purity, and can be expanded in culture.

Human immature dental pulp stem cells are also originated from neural crest. It has been shown that shared similar characteristics with embryonic stem cells and hair follicle stem cells, expressing nestin and other embryonic stem cell markers. They are capable to form neurospheres and differentiate into neurons, glial cells, epithelium, keratinocytes, smooth muscle cells, and other cell types, presenting a high degree of plasticity. They are also can be isolated at abundant quantity from the central region of the coronal and radicular dental pulp, specifically from the region, which can be identified as a innermost pulp layer a undifferentiated stem cells cell rich zone, presenting high level of purity and can be expanded easily in culture. When these human immature dental pulp stem cells (IDPSC), when reintroduced into developing embryo, formed chimeric fetuses and showed contribution into different tissues and organs, especially dense engraftment into epidermis. Surprisingly LP cultured IDPSCS maintain their stemness also after cryopreservation. After transplantation of GFP (green fluorescent protein) expressing IDPSC subcutaneously into mice they populated hair follicle and produced several GFP expressing yarn hairs.

These cells are readily accessible and could lead to using a patient's own teeth as a source for therapy in the case of baldness without the controversy or medical issues of embryonic stem cells. Based on these finding IDPSC may also be useful to treat Parkinson's disease, multiple sclerosis, Hirschsprung's disease, stroke, peripheral neuropathies and ALS. Certain defects of the heart, and bone defects (degeneration, craniofacial birth defects) could also be treated through neural crest stem cell replacement therapy. They can be also expanded in culture into millions of cells without losing stem cell markers.

The IDPSC may become the stem cells of choice, able to substitute other source of epidermal neural crest stem cells in the future for regenerative medicine, since (1) they are readily available from essentially anyone, (2) they are easily cultured and expanded, (3) they are highly pluripotent, (5) they do not carry the ethical issues that embryonic stem cells and fetal stem cells, (6) they do not produce teratomas, (7) they are immune-compatible.

Skin Regeneration

Stem cell-based therapies open new avenues for skin regeneration following injury and disease. There are several functional stem cell niches in skin, which are known to be collectively responsible for physical and chemical microenvironmental cues that enable all layers of human skin regenerative potential. Preclinical studies have demonstrated that paracrine factors secreted by stem cells after their topical delivery into injured site may improve chronic wound healing and are the major mechanism by which stem cells can enhance repair. Even conditioned media from mesenchymal stem cells (MSCs) have been shown to promote wound healing via activation of host cells.

IDPSC are already express several markers, which are associated with skin stem cells niches. Thus epithelial stem cells from the bulge and IDPSC have common features, including expression of cytokeratins, integrins and p63. On the other hand, recent studies showed that a cell population within the dermal papilla of hair follicles may function as adult stem cells. This dermal stem cell niche contains a unique population of progenitor cells, which express of the transcription factor SOX2 that is also expressed by IDPSC. Therefore IDPSC-based therapy may hold promise in overcoming wound healing, including burns and other skin degenerative disorders. The regenerative (self-renewal and differentiation plasticity) and paracrine (protective factors release) effects of IDPSCs can promote the progress of skin remodelling. Creating a suitable microenvironment is the key issue for stem cells to survive and participate in regeneration and repair skin tissue. The success of tissue regeneration depends on optimal local vascularization and the successful integration of the implant into extracellular matrix and antiscarring effects.

In one embodiment, IDPSC is used to overcome wound healing and skin remodeling challenges, such as:
1. Wound healing, such as untraceable skin ulcers resulting from diabetes, ischemia and collagen diseases represent significant problems with few solutions.
2. The burn wounds is an extremely difficult challenge, burn injury has been reported to be an important cause of morbidity and mortality globally.
3. Bio-dermocosmetic therapy for which improves skin firmness, reduces wrinkles, as well as delays the aging process resulting in aged tissue that have the appearance, growth and differentiation similar to young skin.

Disclosed herein are remarkable results suggesting that engraft of these cells into blood vessels can support neovascularization, which is critical for the process of tissue remodeling. In addition, collagen regeneration prove potential treatment of loss of integrity of the wounded or/and aged skin. The absence of immunological response suggests the use of IDPSC for the treatment of immunological disorders (e.g. Vitilligo) or for the patients with skin burn.

In one embodiment, the disclosed IDPSC therapy may be applied as the cell implantation, or through local delivery, or systemic infusion, of autologous or allogeneic IDPSCs to restore the viability or function of deficient tissues.

Spermatogenesis

It has been shown that the transplantation of spermatogonial stem cells from fertile mice to testicles of infertile recipient mice results in donor-derived spermatogenesis and also the transmission of genetic material from the donor to the offspring recipient animals. Germ cell transplantation provides a bioassay to study the biology of male germ cells develop systems of isolation and culture of spermatogonial stem cells to examine defects in spermatogenesis and to treat male infertility. Although most widely studied in rodents, the transplantation of germ cells was applied to larger mammals. In domestic animals, including pigs, goats and cattle as well as in primates, germ cells can be transplanted into a recipient testis guided by ultrasonographic cannulation in testicles. Germ cell transplantation was successful between unrelated species (pigs and goats) and without using the protocol of immunosuppression, while transplantation in rodents requires the use of animals syngeneic or immuno-compatible partners.

However, SSC has been more extensively characterized in mice and the biology of human SSC is unknown, once there are no methods available for their study. The characterization of human stem cells, regardless of tissues origin, has been difficult because the experiences of transplant and manipulations involving humans are ethically problematic.

In this sense, the use of experimental animals in the transplantation of human stem cells is being used as a practical alternative for studying the biology of these cells. For example, there was realized the xenotransplantation of hematopoietic cells from human bone marrow in immunodeficient mice and used to identify markers of HSC human origin, as well as the efficiency of human gene transfer by HSC. Xenogeneic transplants using experimental animals is a powerful approach to understanding the biology of stem cells and the development of stem cells clinical applications, minimizing the ethical concerns associated to experimentation in humans.

Recently, an attempt to transplant human germ cells into testicles of mice has been reported. The results indicated that no human germ cell survived in mouse testicles, suggesting that these cells probably died because of the incompatibility between human germ cells and the animal testicular environment, or immunological rejection. In contrast, previous studies have demonstrated that germline stem cells of primates (baboon) can colonize testicles of immunodeficient mice, at least for six months. Although these cells differentiated only by spermatogonia this result showed that stem cells of primates not only survived in mouse testis, but were also capable of proliferating.

Germ line stem cells called spermatogonial stem cells (SSCS) which are found in postnatal period in mammals, are essential for spermatogenesis (process of sperm production), and with females oocytes, are essential to species continuity. SSC reside in the seminiferous tubules basal membrane of the testicles and are surrounded by somatic Sertoli cells, which form a microenvironment or niche. Inside the niche, growth factors and extracellular signals regulate the differentiation of SSC for self-renewal or for expansion and the beginning of spermatogenesis differentiation process, resulting in the production of mature sperm after 40 days in mouse and 64 days in humans (Loeffler et al., 1997, Harrison et al., 1980). The timing of sequential steps in spermatogenesis is tightly regulated by genes of germ cells and Sertoli cells that support the differentiation process.

In addition, the transplantation of stem cells in the animal testicles is a powerful tool for studying the biological capacity of stem cells to differentiate to male gametes, to assess the factors that influence this process, to investigate the testicles functionality and the reasons that cause infertility. These studies will significantly increase our understanding of the testicles functionality and the ability to control and preserve male fertility.

The disclosed results suggest the differentiation potential of hIDPSC to germ cells and germ fate supporting cells. These data indicate IDPSC possible use restoration of human fertility after, for example cancer, which frequently lead to infertility due to chemotherapy application. This data suggest that IDPSC are able to engraft in different compartments mouse seminiferous tubes. IDPSC differentiation appears to be faster in fertile mice, suggesting the importance of the environment for cellular engraftment and differentiation of stem cells. When transplanted into mice testis, IDPSC following sequential order of differentiation of mice seminiferous epithelium and cells resembling round spermatids, elongated and even sperm can be observed, albeit at low efficiency. Our data also suggest that the use environment of the seminiferous tubules of animals could be a model tool to achieve donor-matched human sperm cells. We found that the fusion between mouse cells and human cells can occur, however fusion between nucleuses was not detected.

We hypothesize that for the reconstruction of spermatogenesis in xenotransplantation (infertile animal model), first, we must restore the environment. The cells that support spermatogenesis produce human proteins, which affect SSC progression and facilitate the spermatogenesis. Analyzing the published data we can conclude that to date the efforts of scientists were directed predominantly in the use of SSC to check their ability to enter in spermatogenesis. SSC are cells committed to spermatogenesis and therefore was a failure in differentiation, and these cells did not receive the normal signal of the environment in which they were transplanted. Sertoli cells are sustentacular cells, i.e.—cells 'nurses' located on the periphery of a seminiferous tubule. They are also called "stem cell", once they provide nutrition and mechanical support for the spermatogonial cells. They are also responsible for establishing and maintaining the niche of germline stem cells, ensuring their renewal and differentiation into mature spermatogonial cells regulating the progress that finish in the release of sperm.

hIDPSC are NOT immunogenic and do not need the use of immunosuppression protocol. They are migratory cells and can be widely distributed in mouse testicles, while SSC cannot migrate.

Renal Failure

Renal failure (RF) (also kidney failure or renal insufficiency) is a medical condition in which the kidney to fail to adequately filter waste products from the blood. To test whether high level of expression of ectodermal markers will enable IDPSC therapy on cat RF veterinary patients (RF representative case example is described based on written analysis of treatment/symptoms by veterinary experts, other examples, not described here, were applied to treat RF disease in several pets via request/informed concern by the hosts).

We disclose a IDPSC cell therapy composition comprising IDPS and a method to treat RF disease in mammalian species including humans, using in vitro cultured, preferably LP-derived IDPSC. Notably, it is shown that IDPSC express CD146 and VEGF after transplantation in rat model of renal failure indicating endothelial markers importance. Taken together these both studies demonstrate renal-protective effect and clinical benefits of IDPSC transplantation in acute (rat) and chronic (cat) renal disease.

One embodiment local intra-renal administration may be proposed. In other embodiment, IDPSCs are administered i.v./systemically at a dose of approximately $0.01\text{-}1\times10^6$ cells per kg body weight by i.v. infusion in buffered saline or any other known in the state of the art other suitable vehicle for systemic administration. Infusions are repeated subsequently at therapeutically active levels, for example each every 1-3 week basis until significant improvement in renal function, then infusion interval increased to 1-6 months as per patient condition. In additional embodiment, the composition may include other cells, or/and active therapeutic agents or/and genes to deliver to treat RF patient.

Renal failure is a disease, which shows high incidence in dogs and cats, causing considerable morbidity and mortality among these species (Lees, G E, 2004). Even using conventional therapies, structural injury occurs, favoring the reduction of renal mass associated with impaired metabolism and consequent loss of the physiological functions of the kidneys, thus culminating in organ failure. The conventional medical therapies, fluid and dietary counseling, as well as corrections to the medical complications they cause disease, are usually ineffective when serum creatinine exceeds 6 mg/dl and urea exceeds 90 mg/dl, leading to this point, a significant impairment quality of life of the animal (Fischer, Jr., et al, 2004).

We describe herein an IDPSCs containing composition and a method to treat chronic kidney disease in cats and other species, including dogs and humans, using in vitro expanded allogenic human IDPSCs. In this sense, the stem cell therapies show a possibility of great prospects, since the regeneration of damaged tissues, is an expectation of plausible permanent cure of this disease.

Enrichment of Late Population of hIDPSC with Neural Progenitors and Neurons

Other aspects of this disclosure relate to enrichment of late population of hIDPSC with neural progenitors and neurons following 15-, 30- and 45-cycles of dental pulp mechanical transfer and induction of neural differentiation. The CNS is originated from ectoderm, more precisely from the pool of multipotent neuroepithelial stem cells (NSCs). This cell's population is composed at least by two different groups of neural precursors: a first group can grow in monolayer cultures; a second group generally form neurospheres (i.e. grow in suspension culture). In spite of this difference, both of cell types demonstrate the same differentiation potential (Noble et al., 2011, Kempermann, 2011).

NSCs are symmetrically dividing and under appropriate conditions can be rapidly conversed into neuroblasts, asymmetrically dividing precursors, which are able to develop into neurons after a migration phase. Neuroblasts are slightly more differentiated than NSCs and can produce transit amplifying cell population. The ability to divide is main difference between neuroblasts and neurons, which are postmitotic. Neuroblast differentiates and matures into neurons but not in other cell types.

NSCs fate, among other mechanisms, is regulated through signals that emanate from surrounding tissues. NSCs are found in specific regions, so-called stem cell niches that provide the microenvironmental cues that regulate stem cell proliferation, self-renewal and differentiation.

Known today are two potential sources of stem cell with neural potential of differentiation: first, fetal neuronal precursors obtained from abortion and, second, pluripotent stem cells (ES cells, iPSCs) induced to differentiated in vitro neuronal precursors. Fetal neuronal precursors raise many ethical problems, while there are certain safety risks associated with human use of ES and iPSCs that delay therapeutic applications. Alternative methods of neurodegenerative therapies from other human types of stem cells are needed to exploit the uses of cell therapy for treatment of neurological diseases. Methods for transplanting stem and progenitor cells are described in U.S. Pat. Nos. 5,928,947; 5,817,773 and PCT Publication Nos. WO 01/176507. These methods include expansion in cell culture and transplantation of undifferentiated neuroprotective stem cells, and/or through by transplantation of neural precursor cells, or/and fully differentiated neuronal cells. Cell therapeutic interventions may involve both cell transplantation and the stimulation of endogenous neural progenitor cells. Conventional methods have multiple disadvantages and limitations and new sources of cells for stem cell neuroprotective/neuroregenerative therapy are required. Also of importance is to predict neuroprotective potential of cells for stem cell therapy using molecular markers.

Stem cells from dental pulp have been isolated by Gronthos et al. 2000, Shi et al. WO 02/07679. Sharpe (WO 01/60981) claimed the production of tooth progenitor cells from embryonic stem cells or adult stem cells or tissue culture. U.S. Patent Publication 2002/0119180 claimed a method and production of a biological tooth from third molar tooth germ (Young et al. 2002). The invention disclosed in U.S. Pat. No. 8,192,987 relates generally to pluripotent stem cells, including embryonic-like pluripotent stem cells derived from teeth.

Aspects of the disclosures presented herein relate to a composition of hIDPSCs which co-express SOX1, SOX2 and beta-3-tubulin markers and especially methods of treating neurological conditions. Also disclosed herein are compositions and methods of enrichment of the co-expressed markers during LT hIDPSCS cell culture therefore increasing neuroectodermal lineage commitment of such LP hIDPSCs. Disclosed herein are new methods to the treatment of neurodegenerative diseases using hIDPSCs obtained through LT harvesting cycles and enriched with specific neuronal biomarkers, such as but not limited to SOX1, and SOX2, beta-3-tubulin. This method is useful to screen for markers that affect neural lineage commitment of hIDPSCs and hold higher potential to treat CNS and PNS diseases, while maintaining normal karyotype and no teratoma formation detected in vivo. Moreover, the contemplated embodiments provide a substantially homogenous population of cells enriched with population of cells that co-express said stemness neuronal markers (SOX1, SOX2 and beta-3-tubulin) while maintaining normal karyotype and carry no risk of teratoma formation. The homogenous population is likely advantageous for treating disease in a human (mammalian). Other advantages of the cell-based therapies disclosed herein include, but are not limited to, incorporation of the cells central nervous system tissue, peripheral nervous system tissue. Such incorporated cells have the potential to differentiate or develop into neuronal, glial or other cells to replace or facilitate repair of the damaged, traumatized or degenerating tissue thereby resulting in a more permanent treatment of the degenerative, acute injury, traumatized, neurological condition.

Incorporated into this document are also the disclosed methods of long term in vitro culturing of dental pulp (DP) tissue in order to produce unlimited number of stem cells named hIDPSCs in U.S. Provisional Patent Application 61/791,594, the contents of which are incorporated herein by reference in their entirety. Oxygen is one of critical signals that can affect stem cell properties under normal tissue homeostasis. Interestingly, low oxygen levels, or hypoxia, are a hallmark of stem cell niches (Panchision, 2009).

Surprisingly, it was observed on biological samples that were stored during long term/LT cell culture of hIDPSCs that during this process the dental tissue gradually shrink, thus creating hypoxia inside the pulp tissue. More surprisingly, immature dental pulp stem cells (IDPSCs) isolated from DP after 30 times of mechanical transfer/harvesting cycle (late population (LP) of IDPSC) and tested for their capacity to produce neurons in vitro demonstrated the increased ability for neural differentiation, as well as enrichment of a population pre-committed LP IDPSC with neuronal precursor when compared with IDPSC isolated after 15 or 25 cycles of mechanical transfer/harvesting (early population (EP)).

According to some aspects, we discovered that the number of actively proliferating neuronal precursors (neuroblasts) in pre-committed IDPSC neural precursor are related with the number of DP transfer cycles.

SOX1 and SOX2 Biomarkers

SOX1 (for sex-determining region Y-box 1) protein is a transcription factor involved in early central nervous system development. SOX1 is a known marker characteristic of a developing central nervous system. The expression of SOX1 in the neural plate and tube seem to correlate with mitotically active progenitors that are not yet committed to a final stage. SOX1 defines the dividing neural precursors of the embryonic CNS and expresses particularly in the ventral striatum (Pevny et al., 1998; Kempermann et al., 2003).

SOX2 is one of the earliest known transcription factors expressed in the developing neural tube and is expressed in certain cells of the adult brain. SOX2 is commonly known to play a critical role in the central nervous system. Recently, Terskikh and colleagues (2011) elucidate role of SOX2 in peripheral nervous system. They developed a hESC-based model in which migratory cells undergo epithelial to mesenchymal transition (EMT) to acquire properties of neural crest (NC) cells. They found that migratory NC progenitor's down-regulate SOX2, but then start re-expressing SOX2 as they differentiate to form neurogenic dorsal root ganglion (DRG)-like clusters. SOX2 down regulation was sufficient to induce EMT and resulted in massive apoptosis when neuronal differentiation was induced. They also showed that SOX2 binds directly to NGN1 (neorogenin 1) and MASH1 promoters and is required for their expression. When neural crest stem cells were prevented from re-expressing SOX2, they die or can give rise to glia or smooth muscle cells. Thus, the function of SOX2 is to keep cells multipotent or pluripotent for become neurons later in development.

SOX2 in Neurodegenerative Disease Models: Huntington Disease (HD) Models

Molero and co-workers (2009) reviewed an HD model. In this model, progressive cognitive deficits develop at the age of 9 months, suggesting possible hippocampal dysfunction (Kandasamy et al., 2010). They observed enhance of NSC self-renewal at late embryonic stages together with high levels of SOX2, a factor that mediates NSC self-renewal, multilineage potential, and neurogenesis. Other groups showed that in hippocampal neural stem cell niche in a transgenic rat model of Huntington disease a disease-associated progressive decline in hippocampal progenitor cell proliferation accompanied by an expansion of the pool of 5-bromo-2-deoxyuridine label-retaining SOX2-positive quiescent stem cells in the transgenic animals.

Upon transplantation to the developing brain they incorporate extensively into the host brain, demonstrate wide spread distribution, migrate along established host brain migratory tracks, differentiate in a region specific manner into progeny of the three fundamental neural lineages, indicating their capability to respond to local cues and participate in the development and histogenesis of the living host.

This combination of defining properties will identify the neural progenitor cell lines of the invention regardless of the method used for their isolation. One method is to transplant undifferentiated stem cells that can differentiate into neural precursor cells, and then into fully differentiated neurons (including neurons, astro-glia, or oligodendrocytes). Another method is to transplant undifferentiated or pre-differentiated IDPSCs that are capable to release neuroprotective factors into affected areas of the nervous system. Moreover, using the described hIDPSCs transplant method of neuroregeneration may be based on administering into patient pre-differentiated ex vivo neuronal precursors or fully differentiated neurons or combinations of thereof.

According to some aspects, a cell culture composition comprises (co-expressing) SOX1 and SOX2 positive hIDPSC, which are neural crest stem cells. The SOX1 and SOX2 may be obtained through LT cell culture. Enrichment of the transcription factors increases towards LP culture, which holds high potential to neuronal differentiation, keeps karyotypes normal, and does not carry the risk of teratoma in vivo.

According to another aspect, a method for obtaining a homogenous population of hIDPSC comprises obtaining the population thorough LT mechanical/non-enzymatic harvesting cycles. The number of harvesting cycles may comprise over 25 cycles, about 45 cycles, or more than 45 cycles. An embodiment of the method may further comprise culturing the taken cells and passaging a plastic adherent cell from the cell culture. The plastic adherent cell typically (i) self-renews, (ii) differentiates into cells of endodermal, mesodermal, or ectodermal lineage, and (iii) expresses markers SOX1, SOX2 and 3-beta-tubulin. An embodiment of the method may further comprise administering the product to a patient as a pharmaceutical composition in a pharmaceutical accepted carrier/vehicle for cell therapy to treat CNS diseases.

According to another aspect, a mitotically active homogeneous neural progenitor's (neuroblasts) composition comprises (co-expressing) such markers as SOX1, SOX2, and beta-3-tubulin that are not yet committed to a final stage.

According to another aspect, a method for obtaining a homogeneous population of pre-differentiated IDPSCs comprises one or more of the following steps. Obtaining IDPSCs-derived neurospheres by culturing IDPSC in non-adherent conditions (suspension). Following adherence to a plastic dish in order to form neural rosette, the cells within the rosettes are presented by (i) transit amplifying cell population of neuroblasts positive for SOX1, SOX2, and BrdU and beta-3-tubulin that are slightly more differentiated than IDPSC; (ii) neuroblasts differentiated terminally into NEURONAL LINEAGES OF CENTRAL AND PERIPHERAL NEURAL SYSTEM—(including neuronal precursors, astroglia and oligodendrocytes and ganglion cells) upon external in vitro- or in vivo-induced microenvironment; (iii) use as a pharmaceutical composition in a pharmaceutical accepted carrier/vehicle for cell therapy to treat CNS diseases by administrating to a patient; and/or (iv) use as a pharmaceutical composition in pharmaceutical accepted carrier/vehicle for anti-cancer therapies, including gene therapy, to treat neuroblastoma and retinoblastoma but not limited to these tumor types.

According to another aspect, substantially homogenous LP of hIDPSCs comprise a cell that co-expresses a marker selected from, but not limited to, the group comprising SOX1, SOX2, or beta-3-tubulin.

Various embodiments of the contemplated disclosures are further illustrated by the following examples that should not be construed as limiting. The contents of all references, patents, and published patent applications cited throughout this application, as well as the Figures, are incorporated herein by reference in their entirety for all purposes.

EXAMPLES

Example 1

Neural Differentiation of IDPSCs

IDPSC were cultured before confluence, which is equal to $2\times10^6$ in 25 cm$^2$ in basal culture medium. Next the cells were washed two times in PBS, and the basal culture medium was changed to Neurobasal culture medium supplemented with 2% B27 (NB+B27). Culture medium should be changed in 3-4 days. After one week, the cells were harvested following a 0.25% trypsin/EDTA treatment for 2-3 min and neutralized with the same culture medium. Following centrifugation at 800×g for 5 min, the cell pellet was obtained and supernatant was removed. Next IDPSC were gently disaggregated in NB+B27 and seeded onto 6 Petri dishes 9.6 cm$^2$. Retinoic acid was added at a final concentration 0.1 µM for 24 hours after which time mature neurons were obtained.

Figure 3:
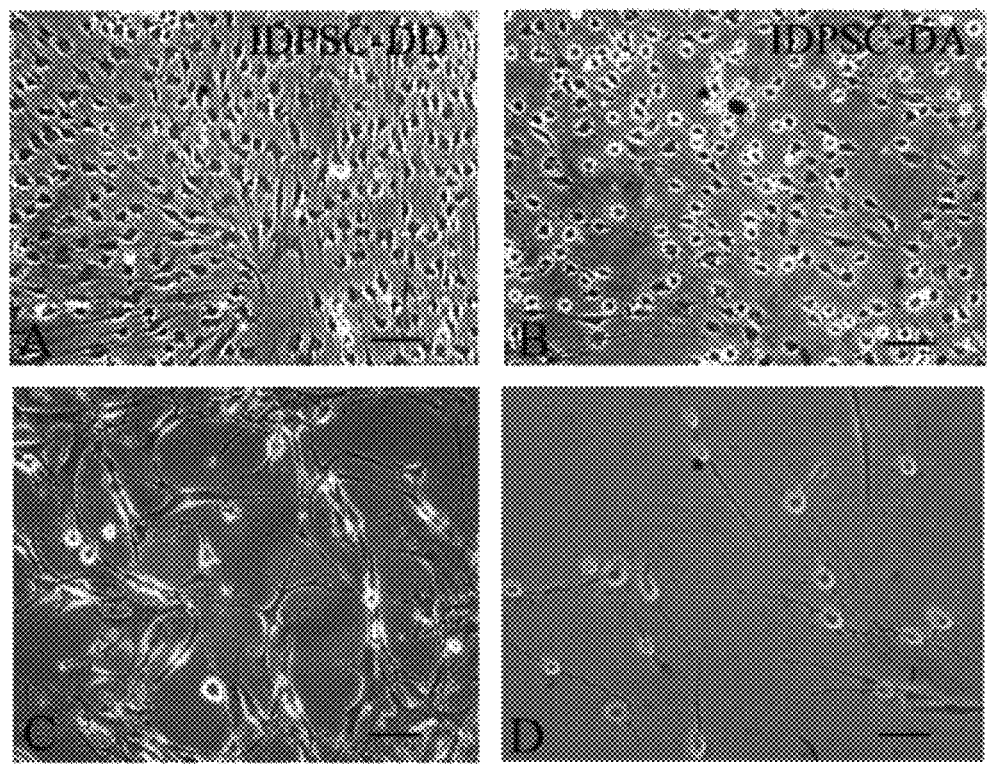
FIG. 3 depicts an image captured with phase contrast microscopy demonstrating the differentiation of IDPSC toward neural lineages. A) and C) show differentiated IDPSC isolated from deciduous teeth (DD). B) and D) show differentiated IDPSC isolated from adult teeth (i.e., permanent teeth) (DA). Note the morphological diversity of the neurons. 20× objective.

Using this protocol for neural differentiation, differentiation of IDPSC into neurons and glial cells, concurrently, in the same culture plate was observed (FIG. 3).

Example 2

Neuronal Phenotype Analysis

Figure 4:
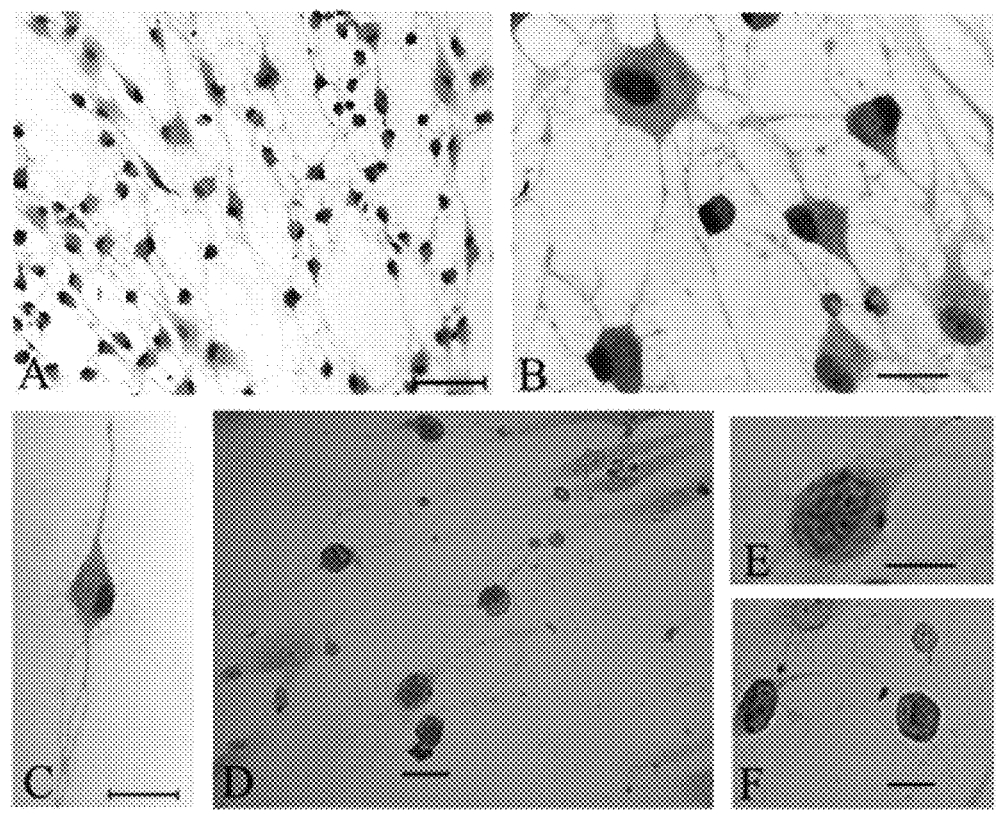
FIG. 4 depicts images of IDPSC after neural differentiation captured with light microscopy and shown with hematoxylin and eosin (HE) staining A) 40× objective. Scale bar 50 μm. (B) 100× objective. (C) Differentiated IDPSC with neuron-like morphology. Typical dendritic spines can be observed. A dendritic spine is a small membranous protrusion from a neuron's dendrite that typically receives input from a single synapse of an axon. 60× objective. Scale bar 40 μm. (D-F) Nissl granules in neurons (shown with dark brown staining) 20× objective. Scale bar 40 μm.

Additionally, in order to study the morphology of neurons hematoxylin and eosin (H & E) staining was used (FIG. 4). It was possible to observe both the network formed by differentiating cells and cells that showed the morphology of those in the process of acquiring a neuronal phenotype (FIGS. 4A-4C). Neutral red was used for staining of Nissl granules in neurons (FIG. 4D-4F), which are rough endoplasmic reticulum with rosettes of free ribosomes and are the site of protein synthesis.

Example 3

Identification of Aneuploidy and Cell Fusion as Important Features for Optional Support of a Subpopulation of Tetraploid Retinal Ganglion Cells (RGCs)

Figure 5:
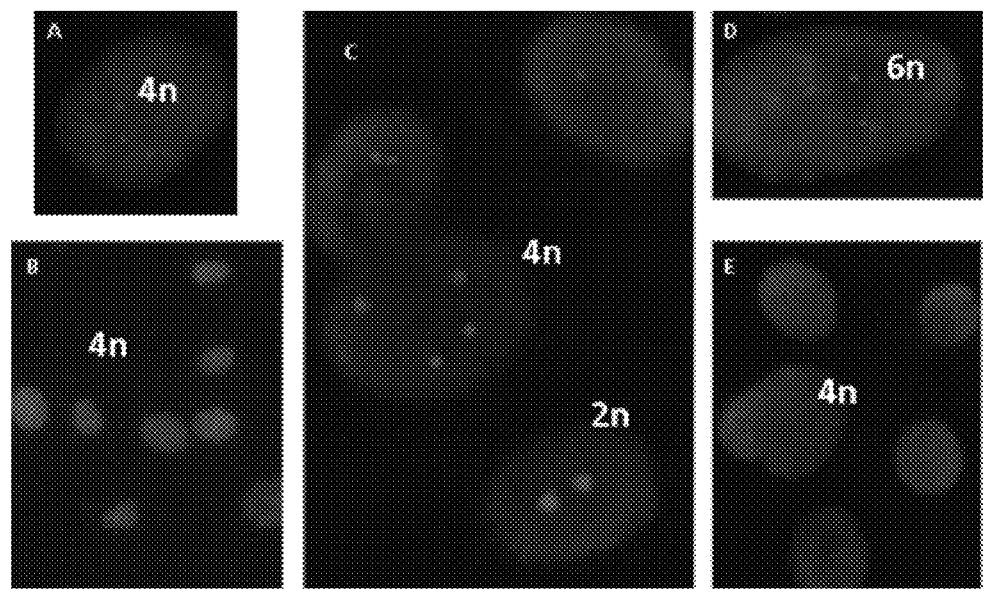
FIG. 5 depicts fluorescence in situ hybridization (FISH) analyses during IDPSC neuronal differentiation. A red fluorescent hybridization probe for chromosome 21 was used. Nuclei are stained with DAPI and appear blue. Note the presence of polyploid cells (4n and 6n) and normal nuclei (2n). Objectives: A), D) and E) 40×; B) 20×; C) 63×.

During the process of neural differentiation, it was found that some cells were binuclear (or multinuclear). This fact would be an indication that cell fusion occurred in IDPSC during differentiation. In FIG. 4E a neuron with multiple nucleuses can be observed. These cytological data were confirmed fluorescence in situ hybridization (FISH) (FIG. 5).

Figure 6:
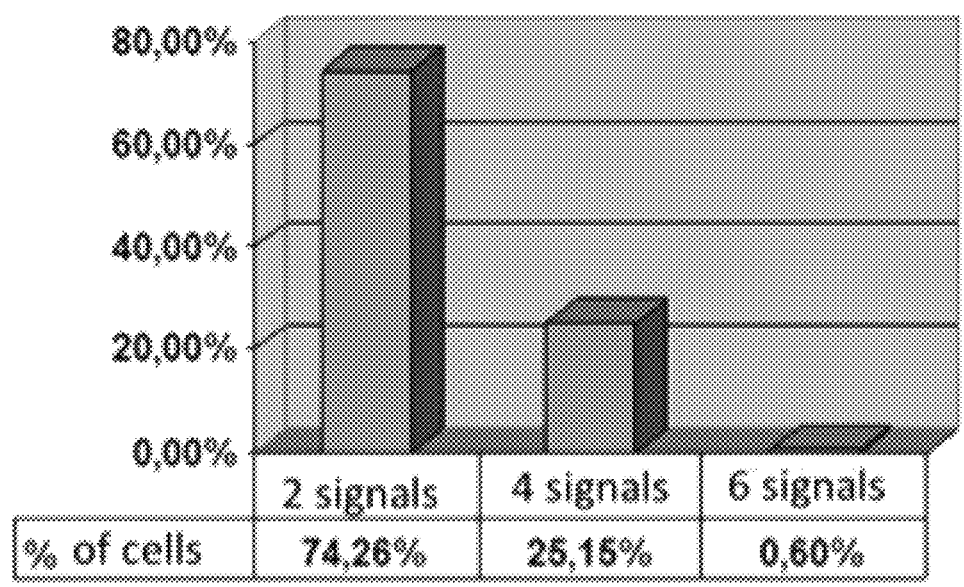
FIG. 6 depicts the quantification of polyploid cells during in vitro neuronal differentiation of IDPSC. The percentages of cell nuclei with two, four and six hybridization probe signals are indicated.

Counts of hybridization signals for human chromosome 21 in the nuclei of differentiated IDPSCs was performed by FISH and demonstrated a rate of cell fusion estimated around 25% of cell nuclei with more than two hybridization probe signals (FIG. 6). Overall, 250 nuclei were counted.

To carry out the FISH analysis a specific probe LSI 21 (Vysis) to the region of chromosome 21 associated with Down's syndrome was used. The FISH protocol was used according to the manufacturer's instructions (Vysis-Abbott) as briefly described below.

After washing with PBS the coverslips, these differentiated cells were fixed in 4% formaldehyde for a week and stored at 4° C. Next, the material on the coverslips was dehydrated in serial alcohol (70%, 90% and 100%, Merck) for 3 minutes each at room temperature, and the coverslips were air dried. The material was denatured at 72° C. with denaturation solution (70% formamide in 2×SSC, NaCl/sodium citrate; Sigma). The material was again dehydrated in serial alcohol for 3 minutes each in ice and air dried. The probes were added to this material and the coverslips were kept in a humid chamber at 37° C. for hybridization, for a period of 16 hours (overnight). After this period, the coverslips were washed twice in a solution containing 50% formamide in 2×SSC, followed by two washes in 2×SSC and 1% Tween 20 (Merck) diluted in 4×SSC, for 3 minutes each wash. Finally, the coverslips were mounted with DAPI containing Vectashield, and analyzes were performed under a fluorescence microscope.

Example 4

Expression of Neuronal Biomarkers Following Differentiation Protocols

Figure 7:
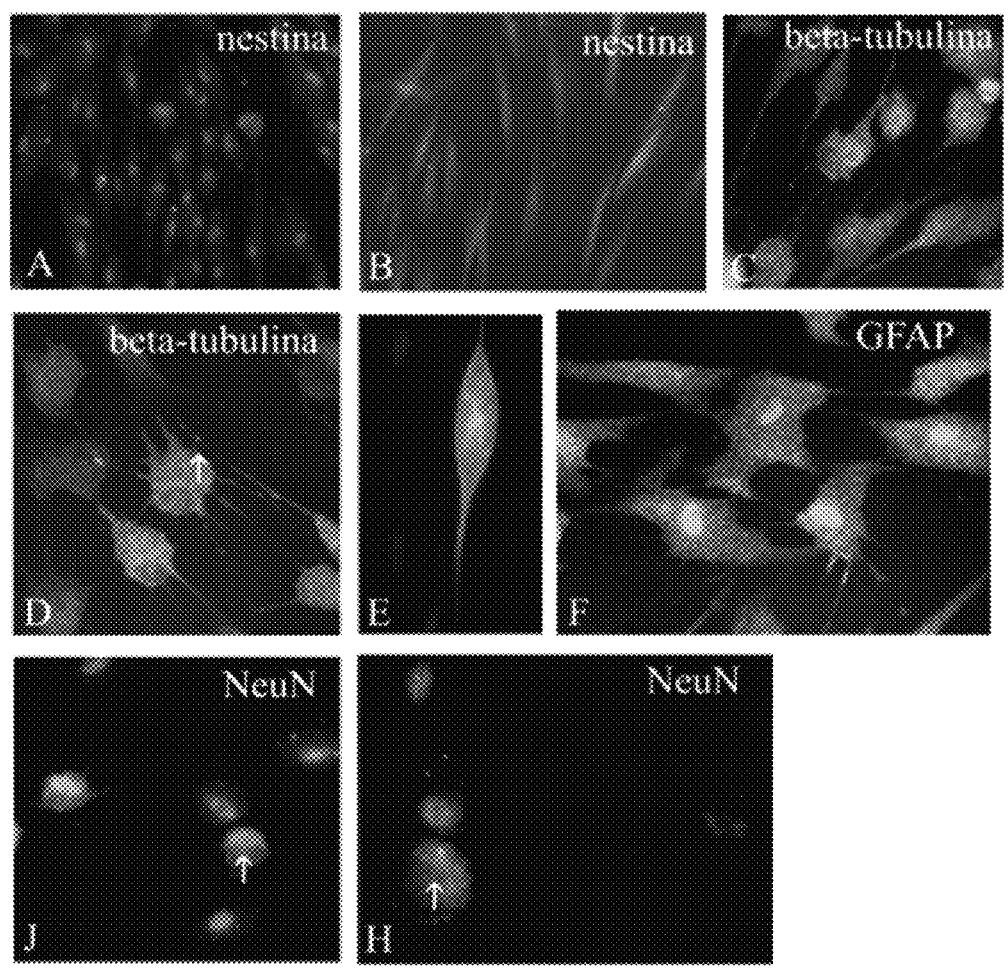
FIG. 7 depicts expression on neuronal lineage markers in differentiated IDPSC. A) Nestin (aka nestina) expression in undifferentiated IDPSC. B) Expression of nestin in IDPSC after induction of differentiation. C)-E) Expression of beta-tubulin (aka beta-tublina) in IDPSC that acquired a neuronal morphology. F) Expression of glial marker, glial fibrillary acidic protein (GFAP) in differentiated IDPSC. J) and H) Expression of NeuN, a marker of mature neuronal cells, in differentiated IDPSC. DAPI (blue) was used for nuclear visualization. A)-B) 20× objective. C)-H) 40× objective.

Expression of specific proteins of neural differentiation were performed using immunofluorescence with antibodies against an early marker of neuronal differentiation, nestin (FIGS. 7A-7B); against a marker of neuronal cells, beta-tubulin, (FIGS. 7C-7E); against a glial protein, glial fibrillary acidic protein (GFAP) (FIG. 7F); and against a marker of mature neuronal cells, NeuN (FIGS. 7J-7H) in IDPSC-derived neurons. All of these markers were expressed in IDPSC neuron-like cells.

We used mouse monoclonal nestin and glial fibrillary acidic protein (GFAP) antibodies purchased from Santa Cruz Biotechnology (Santa Cruz, Calif., USA) and β-tubulin III from Chemicon. The following immunostaining protocol was used: IDPSC growing on coverslips were washed twice in rinse buffer (20 m M Tris-HCl, pH 7.4, 0.15 M NaCl, 0.05% Tween-20), fixed with 4% paraformaldehyde, and permeabilized with 0.1% Triton X-100. After blocking with 5% bovine serum albumin, the cells were incubated with diluted primary antibodies for 1 hr at room temperature. Primary antibodies were diluted at a 1:100. After washing three times in rinse buffer, fluorescein isothiocyanate (FITC)- or Cy3-labeled appropriate secondary antibodies were added for 30 min at a 1:100 dilution. Microscope slides were mounted in Vectashield mounting medium (Invitrogen) with or without DAPI. Analysis was performed with digital images that were acquired with a cooled CCD camera (PCO, VC44) and processed with ISIS software (MetaSystem, Belmont, Mass., USA).

Figure 8:
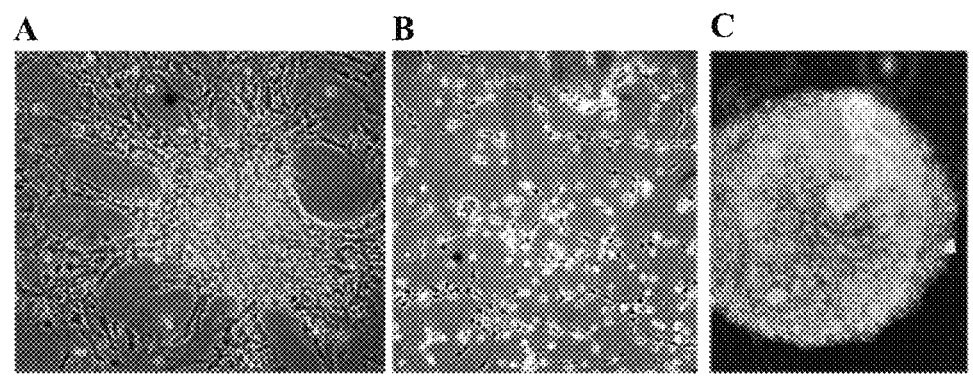
FIG. 8 depicts microscopic images of neurosphere-like structures formed from differentiated IDPSC. A) and B) depict images using phase contrast microscopy. C) shows positive immunofluorescence for Nestin. Objectives were 40× for A) and B) and 63× for C).

During IDPSC neural differentiation the formation of neurosphere-like structures was also observed (FIGS. 8A-8B). When we performed immunofluorescence against nestin, the interior of these structures was found to be nestin positive (FIG. 8C), which indicates the presence of neural progenitors within these spheres.

Figure 9:
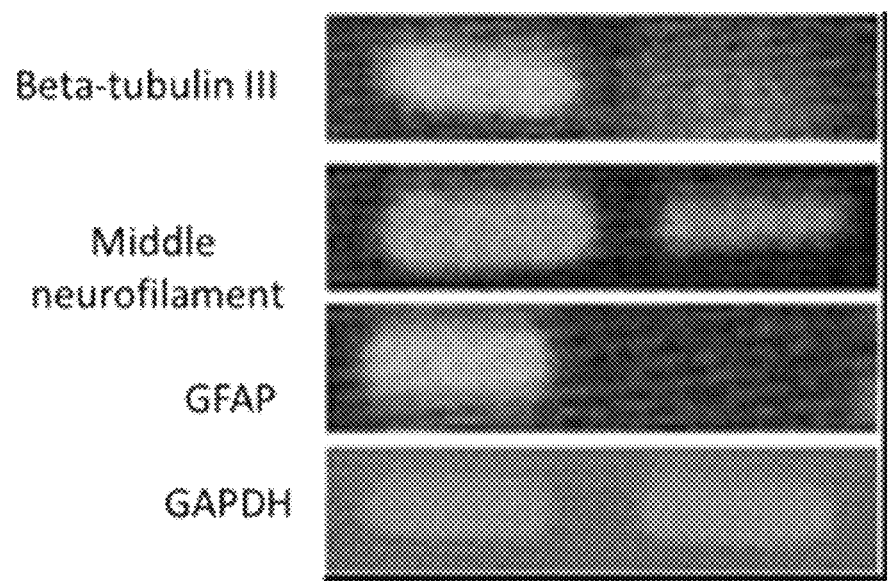
FIG. 9 depicts RT-PCR analysis of expression of neuronal genes in differentiated (lane 1) and undifferentiated (lane 2) IDPSC. Lane 1 demonstrates the presence of mRNAs for beta-tubulin III, middle neurofilaments, and GFAP. Lane 2 shows expression of middle neurofilaments. Glyceraldehyde 3-phosphate dehydrogenase (GAPDH) is a housekeeping gene that was used as a loading control.

Neural differentiation was also confirmed by expression of neural genes such as beta-tubulin, middle neurofilaments, and GFAP using reverse transcriptase polymerase chain reaction (RT-PCR) (FIG. 9).

Figure 10:
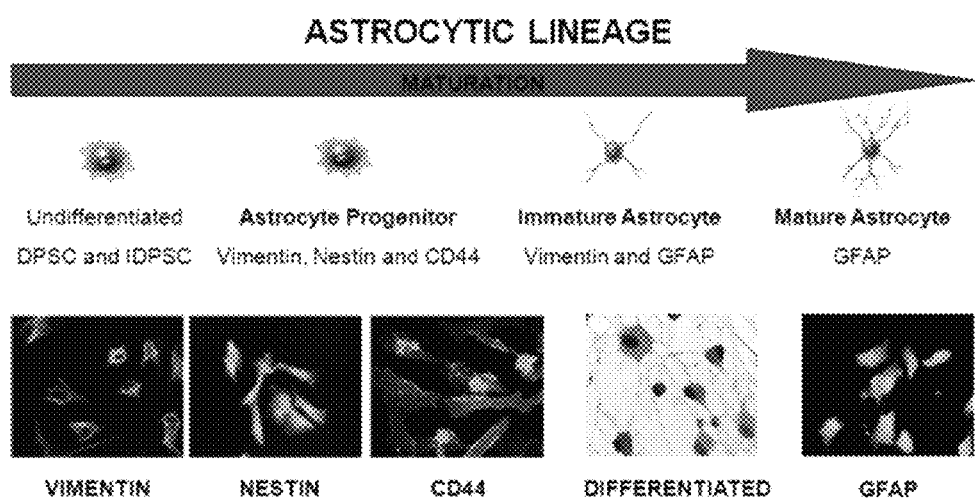
FIG. 10 depicts a spectrum of glial IDPSC derived precursors. Undifferentiated IDPSC express vimentin. Following astrocyte differentiation, the cells express a subset of markers, such as vimentin, CD44 and nestin. Mature astrocytes express GFAP.
Figure 11:
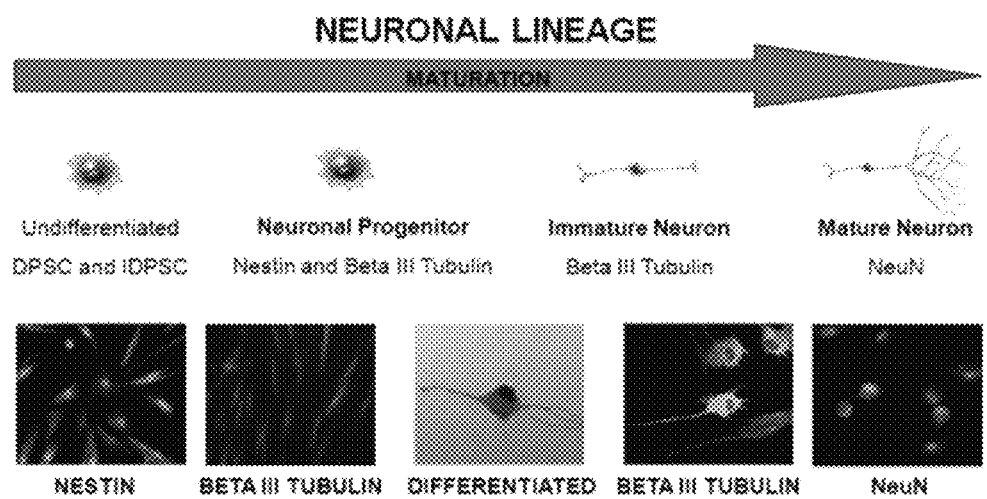
FIG. 11 depicts a spectrum of LP IDPSC derived neuron-like cells. LP IDPSC express nestin, an early marker of neuroepithelial lineage. Following differentiation, IDPSC change their morphology and start to express nestin and beta-tubulin III (neuronal progenitors). Immature neurons express beta-tubulin III while more mature neurons express NeuN and neurofilaments during the maturation period.

The results regarding the ability of IDPSC to differentiate into neuronal cells is summarized for the astrocyte and neuronal cell fates in FIGS. 10 and 11, respectively.

Example 5

Therapeutic Use of IDPSC in a Mouse Model of Spinal Cord Injury

Adult female mice 6-8 weeks old were anesthetized with ketamine and xylazine (100 and 15 mg/kg, respectively) and subjected to a compression injury for 1 min at the T9 level, by means of a 30-g vascular clip (Kent Scientific Corporation, Torrington, Conn.), as previously described by Marques and coworkers (2009). After surgery, the animals were allowed to recover on a warm pad and received 1 mL of saline solution to compensate for dehydration and loss of blood and enrobaytril injections (2.5 mg/kg/d SC). The bladders were manually expressed twice a day until spontaneous urinary function returned.

IDPSC transplantation was performed as follows. The cells were transplanted at two different time points in order to compare the recovery between a subacute and a chronic lesion. The subacute group received treatment 7 days after the injury: injection of the medium in a total volume of 4 μL (subacute+DMEM, n=8) or IDPSC ($8 \times 10^5$ in 4 μL, n=8, subacute+IDPSC). The chronic group received the medium 28 days after the lesion (chronic+DMEM, n=8) or IDPSC (chronic+IDPSC, n=8) with the same concentration and volume. In all groups, the cells were injected into the epicenter of the lesion, using a 10-μL Hamilton syringe. A sham group that received no cells but was subjected to all surgical procedures was included as a control.

Figure 12:
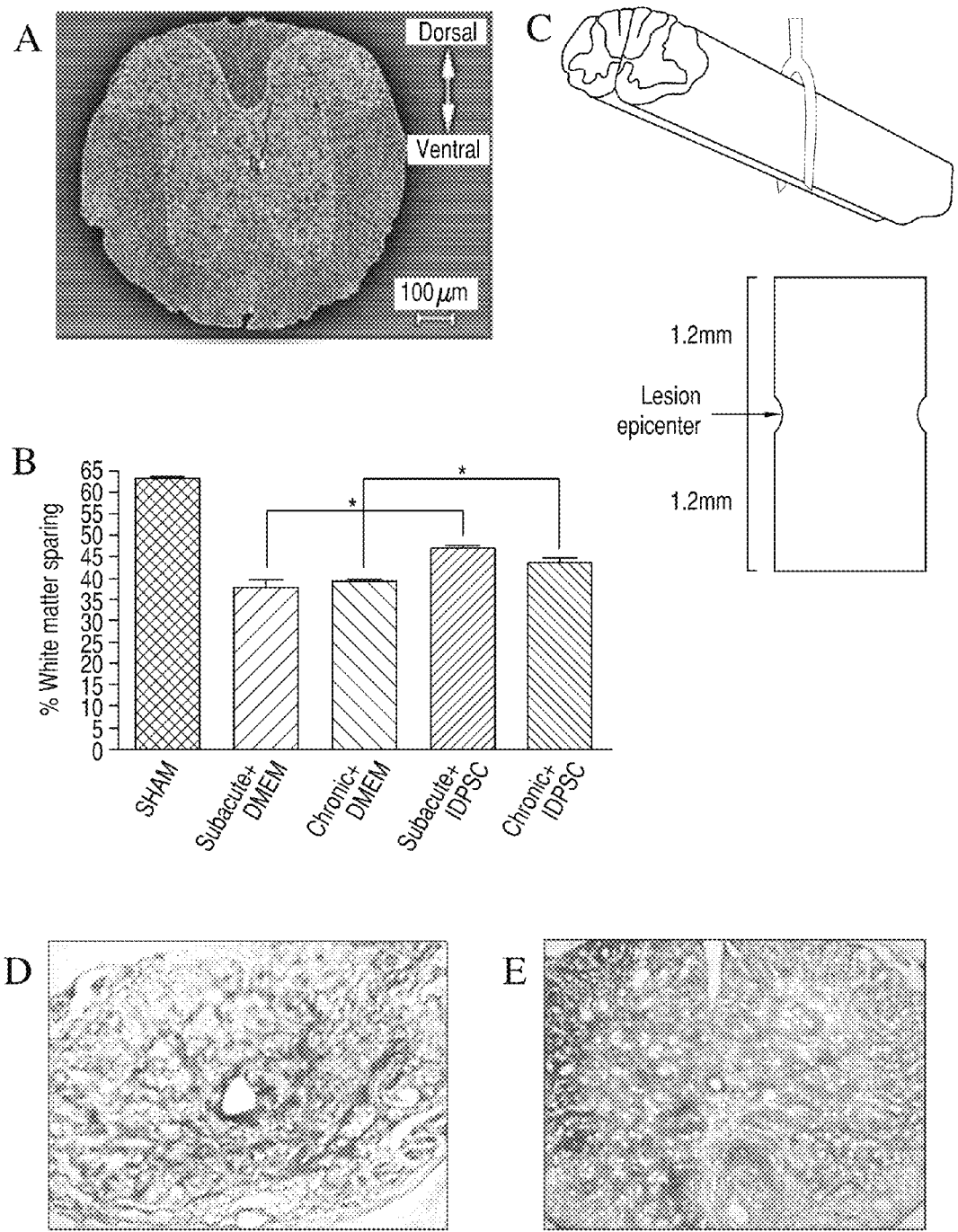
FIG. 12 depicts quantification of spared white matter. A) Luxol fast blue (LFB)-stained area used for white-matter quantification. B) The graph represents the mean values of spared white matter showing higher values in the human immature dental pulp stem cell (IDPSC) groups ($*p<0.05$). C) Diagram of spinal cord injury compression at the T9 level (upper part of figure), and the segment of spinal cord used for quantification of the serial sections (lower part of figure). D) and E) Images illustrating spinal cord sections stained by LFB used for quantification of spared white matter from the subacute+DMEM (D) and subacute+IDPSC (E) groups (DMEM, Dulbecco's modified Eagle's medium).
Figure 13:
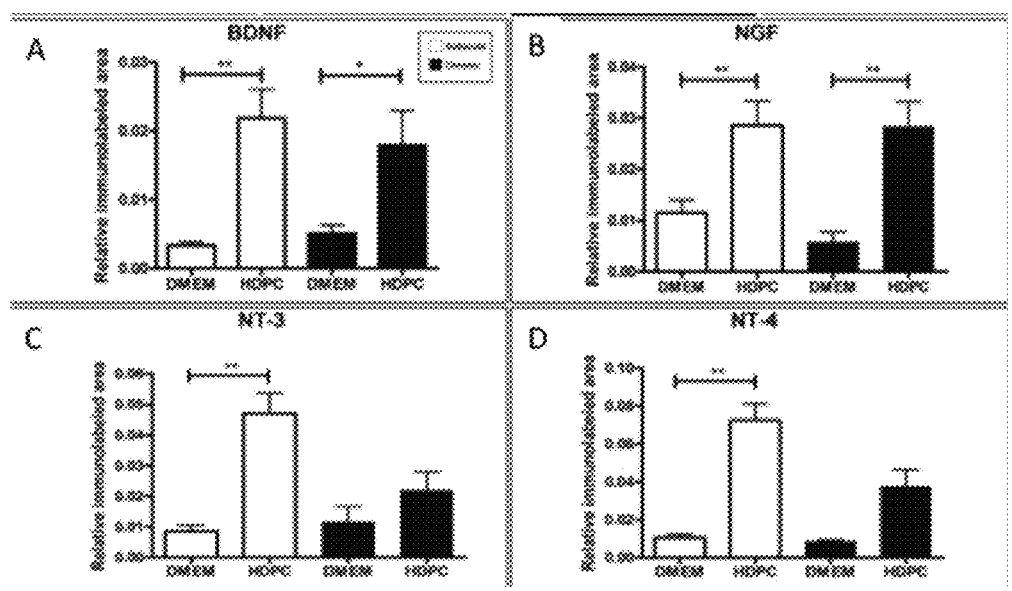
FIGS. 13A-13D depict quantification of the immunolabeled trophic factors brain-derived neurotrophic factor (BDNF), nerve growth factor beta (NGF), neurotrophin-3 (NT-3), and neurotrophin-4 (NT-4). Note the stronger staining in IDPSC- (aka human dental pulp stem cells or HPDC) treated animals for all analyzed trophic factors in comparison to DMEM-treated animals, especially BDNF and NGF, which showed more strongly immunolabeled areas both in the subacute and chronic groups ($*p<0.05$; $**p<0.01$). Subacute groups are indicated by white bars while chronic groups are indicated by black bars.

White matter preservation was measured as follows. Analysis of this quantification showed a better preservation of white matter areas in the IDPSC groups than in the DMEM groups (FIG. 12). The sham group exhibited normal and superior values (63.23±1.2%) in comparison to the lesion groups with normal distribution. The IDPSC-treated animals showed values around 46.85±1.97% for the subacute and 43.49-2.89% for the chronic group, while the animals that received only DMEM as treatment showed lower values of about 38.03±4.28% and 39.00±2.54% for the subacute and chronic groups, respectively. The white-matter preservation was calculated in terms of the percentage of spared white matter in the injured area. All the values are illustrated in FIG. 12, which also shows a schematic view of the injury site and the spinal cord samples used for this quantification (FIGS. 12D and 12E).

Quantification of the immunolabeled trophic factors brain-derived neurotrophic factor (BDNF), nerve growth factor beta (NGF), neurotrophin-3 (NT-3), and neurotrophin-4 (NT-4) was also performed on the spinal cord sections (FIGS. 13A-13D). The primary antibodies used were: rabbit anti-human BDNF (1:100; PreproTech, Rocky Hill, N.J.), rabbit anti-human NGF (1:100; PreproTech), goat anti-mouse NT-3 (1:100; PreproTech), or goat anti-mouse NT-4 (1:100; PreproTech). After primary incubation, the slides were washed and incubated with the appropriate antibodies: Alexa 488 goat anti-rabbit (1:600; Sigma-Aldrich) or Alexa 488 rabbit anti-goat (1:600; Sigma-Aldrich) for 2 hr at room temperature, followed by three washes and cover-slipped with Fluoromount (Sigma-Aldrich). For quantification studies, 12 animals (3 per group) were used. The immunofluorescence images were analyzed with Image-Pro Plus (version 6.0), by evaluating the ratio between the stained area and the total field area. Six sections from each animal were used, and these sections were 100 μm apart. From each section, two photos were captured using the 10× objective in order to encompass the whole spinal cord cross-section. After that, the trophic factors BDNF, NGF-b, NT-3, and NT-4 were quantified using these images. The data were statistically analyzed using GraphPad Prism software with a one-way ANOVA and Tukey's.

Although trophic factor staining showed low immunoreactivity because the trophic factors are soluble and therefore spread very quickly in the tissue, a difference in the staining pattern among the groups could be observed (data not shown). In general, the IDPSC-treated group showed an increased immunoreaction per area compared to the DMEM-treated group, especially in the subacute group, which showed higher levels of all analyzed trophic factors. For the chronic group we only observed differences between the IDPSC-treated group and the DMEM-treated group for BDNF and NGF quantification. The stronger staining was observed in IDPSC-treated animals for all analyzed trophic factors in comparison to DMEM-treated animals, especially BDNF and NGF that showed significantly higher immunolabeled area in both subacute and chronic groups (FIGS. 13A-13D).

All the statistical analyses were performed with Graph Pad Prism 4.0. Results are expressed as mean±SEM, and p values ≤0.05 were considered significant.

For electron microscopy, eight weeks after the animals received the cell transplantation, they were anesthetized with ketamine and xylazine as described above, and perfused intracardially with a solution of 4% paraformaldehyde and 1% glutaraldehyde in 0.1 M phosphate buffer (pH 7.4). The spinal cords were extracted, divided into three different segments (epicenter of the lesion, and rostral and caudal to it), and post-fixed by immersion in 1% osmium tetroxide in cacodylate buffer with 0.8% potassium ferrocyanide for 6 hr at room temperature. The samples were washed three times with 0.1 M phosphate buffer (pH 7.4), dehydrated with a graded acetone series, embedded in resin, and polymerized for 48 hr at 60 C. Semi-thin (500 nm) and ultra-thin sections were made using an RMC ultramicrotome. The semi-thin sections were stained with toluidine blue and observed under a Zeiss microscope (Axioscop 2 Plus), and the images were acquired using the Axiovision Program version 4.5 (Zeiss). The ultra-thin sections were collected on copper grids, stained with uranyl acetate and lead citrate, and observed in a Zeiss 900 transmission electron microscope.

Figure 14:
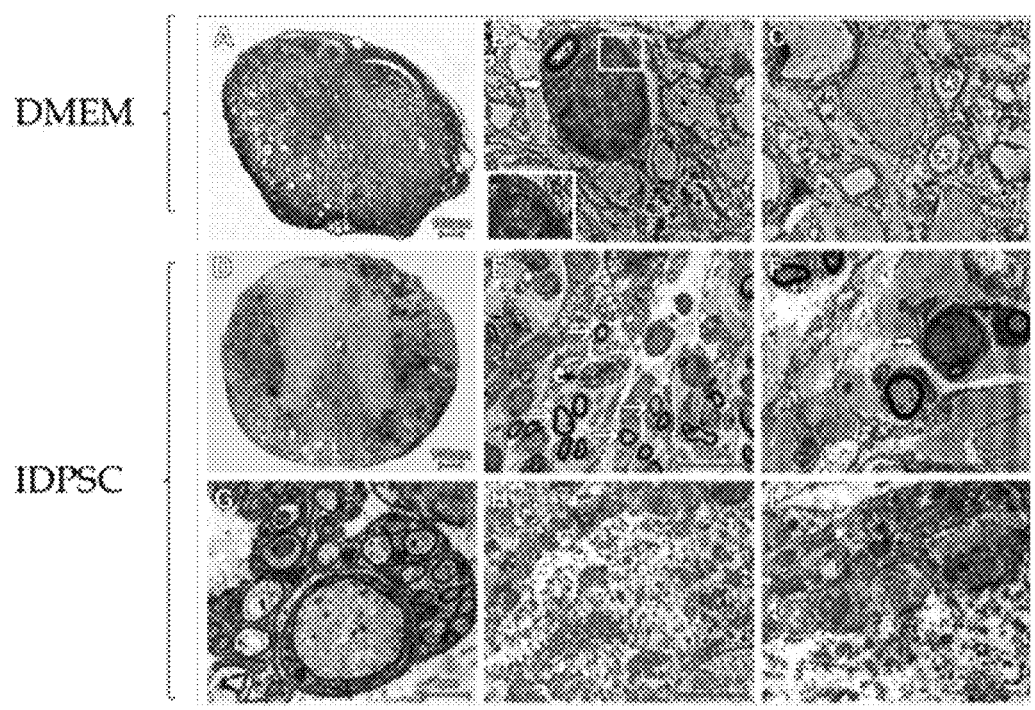
FIG. 14 depicts semi-thin and ultra-thin sections of spinal cords from subacute DMEM-treated animals A)-C) and LP IDPSC-treated animals D)-I). In A), a semithin section, there are several cavitations (short red arrows). In B) is shown a Schwann cell (solid white arrow) with its typical basal laminae (inset), and in C) astrocyte processes (arrowhead), and several microcavitations (asterisks) are indicated. D) shows a semi-thin section from an IDPSC-treated animal with a more preserved morphology. E) shows many preserved fibers (long white arrows) and macrophages (black short arrows). In F) Schwann cells (solid arrows) and oligodendrocytes (long black arrow) myelinating axons are seen. G) shows an example of regenerative islands, and H) represents a preserved healthy-appearing neuron with intact terminals making synaptic contacts on its cell body, which are shown at higher magnification in I). DMEM: Dulbecco's modified Eagle's medium.
Figure 15:
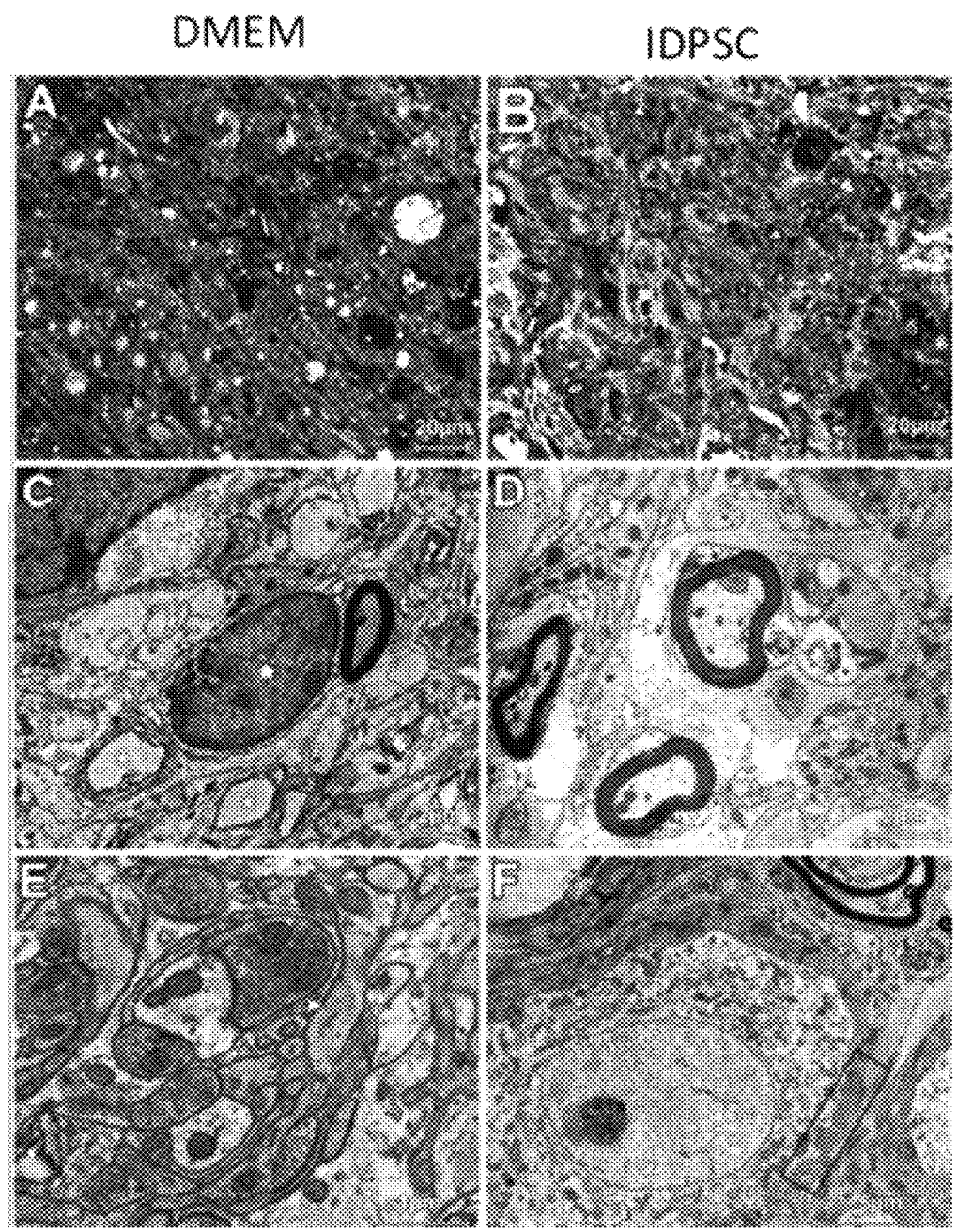
FIG. 15 depicts semi-thin and ultra-thin sections of spinal cords from chronic DMEM-(A, C, and E), and LP IDPSC-treated (B, D, and F) animals. A) Macrophages (red solid arrows). B) Preserved fibers in white matter (long arrows) and macrophages (red short arrows). C) Schwann cells (star) and many cavitations (asterisks). D) Some preserved fibers (white arrows). E) Intense astrocytosis (arrowhead) typical of a chronic lesion. F) Preserved neuron cell body with many synaptic contacts terminating on it (rectangle area). DMEM: Dulbecco's modified Eagle's medium.

FIGS. 14 and 15 show semi-thin and ultra-thin sections from all groups. We observed that in general, the ultrastructural analysis of the animals that received DMEM in the subacute phase (FIGS. 14A-14C) or in the chronic phase (FIGS. 15A, 15C, and 15E) revealed tissue disorganization with many cavitations (short red arrows in FIG. 14A, and asterisks in FIGS. 14C and 15C), and strong astrocytosis (arrowhead in FIG. 15E), few preserved fibers (FIGS. 14B and 14C), and some myelinating Schwann cells with their typical basal laminae (solid arrow in FIG. 14B and star in FIG. 15C).

Both the subacute and chronic groups that received IDPSC transplantation showed better tissue preservation. In the IDPSC subacute group (FIGS. 14D-14I), we could observe a large number of preserved fibers inside the white matter (large arrows in FIG. 14E), and a notable number of macrophages with many cytoplasmic inclusions, myelin debris, and lipids in their interior (black arrow in FIG. 14E). Intact Schwann cells (solid arrow in FIG. 14F) and oligodendrocytes remyelinating axons (black arrow in FIG. 14F); regenerative islands (FIG. 14G), and some preserved neurons were also observed. Some of these neurons showed several preserved synapse contacts (artificially colored portions in FIG. 14H). The ultrastructural analysis of the IDPSC chronic group (FIGS. 15B, 15D, and 15F) showed many preserved fibers (long arrows in FIG. 15B), some Schwann cells myelinating axons (arrows in FIG. 15D), and preserved neurons with synapse contacts (rectangle in FIG. 15F).

Behavioral analysis was performed as follows. The animals were evaluated before injury, 1 d after injury, and weekly up to 8 weeks after cell transplantation. To analyze the recovery, the global mobility test described by Marques and coworkers (2009) was used, which evaluates locomotor improvement by recording the animals in an open field for 1 min with a webcam (5 frames per sec). After that, the velocity (cm/sec) that the animals reached during this 1-min period was measured using ImageJ software. The Basso Mouse Scale (BMS) test was also performed (Basso et al., 2006), which is a 9-point scale that indicates the locomotor ability and locomotion features such as ankle movement, paw position, weight support, plantar steps, hindlimb and forelimb coordination, and trunk stability. For statistical analysis, the mean of the scores obtained from the left and right hindlimb (HL) was used to establish a single score per animal. One-way ANOVA and Tukey's test for post-hoc comparisons were determined.

Figure 16:
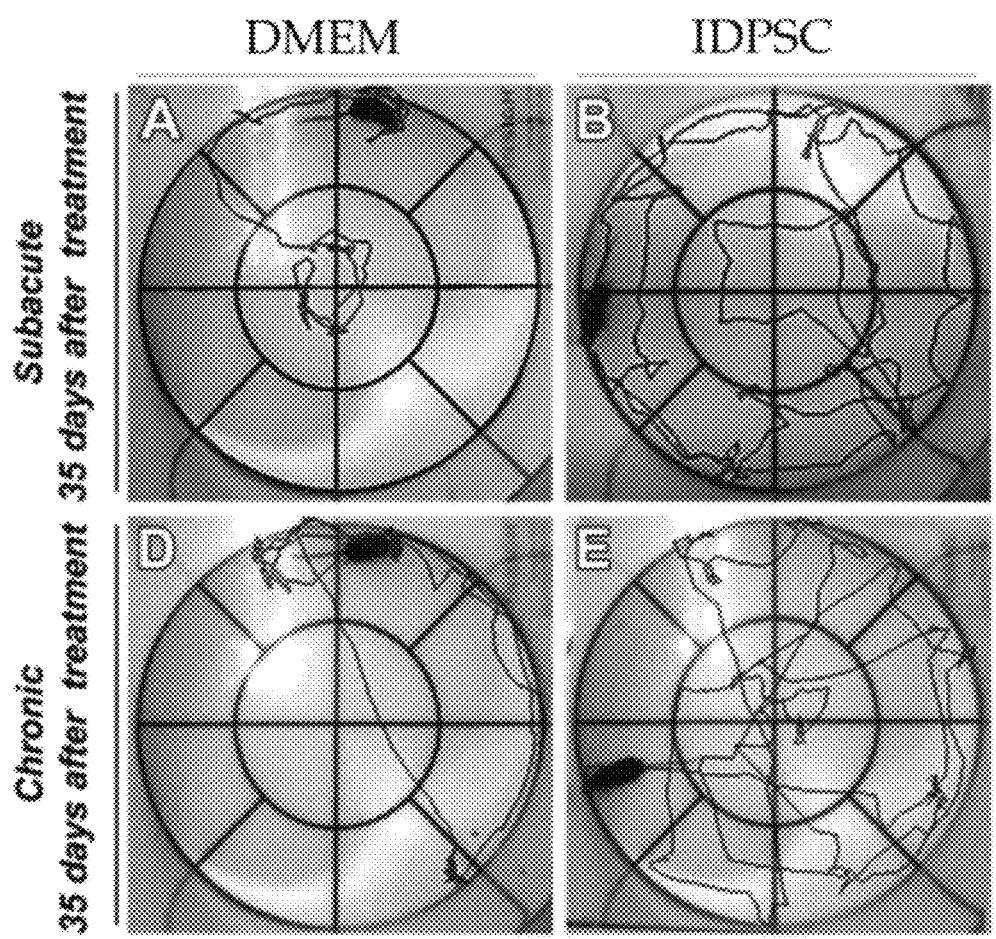
FIG. 16 depicts functional analysis of the DMEM-treated and LP IDPSC-treated groups. The global mobility test showed a progression of global mobility of the subacute and chronic groups 35 days after treatment. The IDPSC-treated animals (B and E) walked longer distances (blue lines) in the open field than did the DMEM-treated animals (A and D) during the assessment period.

For the global mobility test, the sham animals did not show any alteration in their locomotion and exhibited normal values around 16.21±1.73 cm/sec. The subacute group that received IDPSC (6.94±1.85 cm/sec) showed higher values compared to the DMEM group (3.71±0.95 cm/sec), and the improvement in locomotion began 7 days after cell transplantation (i.e., 14 days after spinal cord injury (SCI)) and was maintained throughout the subsequent weeks of the study. The chronic animals showed a slight improvement 7 days after the treatment. However, 14 days after cell transplantation, they exhibited higher locomotion speed with an average around 6.6±2.03 cm/sec versus 4.15±1.07 cm/sec in the DMEM group. In both groups that received the IDPSC, the animals did not reach normal rates, but they showed a better exploratory pattern, walking much more and crossing the open field several times during the test. FIG. 16 illustrates the displacement of these animals 35 days after IDPSC transplantation.

The functional improvement shown by IDPSC-treated animals can also be attributed to the release of neurotrophic factors by these cells. This may act by stimulating collateral sprouting, which may bypass the lesion area and make new synaptic contacts, enhancing the functional outcome (Cummings et al., 2005). This is a plausible explanation because many healthy neurons, intact synapse contacts, and preserved axons were found in the ultrastructural analysis. This study demonstrated an important therapeutic potential of IDPSC transplantation, as applied in both subacute and chronic stages of a mouse compressive SCI. IDPSC appeared as excellent candidates for stem-cell-based treatments to be used in human trials in the near future.

Example 6

Pre-clinical Study of Neurologic Potential of IDPSC in Clinical Cases of Canine Distemper and Hard Pad Disease Canine distemper is a viral disease of dogs, and this virus belongs to the paramyxovirus group. In humans, measles virus is also a member of this group. In approximately half of the cases, it is fatal. Impossible to cure, canine distemper is a serious viral illness that attacks a dog's body on all fronts. It can cause a persistent infection of the dog's central nervous system resulting in a progressive, multifocal demyelinating disease. Once an animal develops neurological symptoms of the disease, such as seizures or paralysis, its chances of surviving are slim and its quality of life is bound to become progressively worse. Thus, these animals are usually euthanized.

Case Histories

The animals were enrolled in an experimental procedure after having obtained informed consent signed by the animals' owners and in accordance with international animal care guidelines. The treatment was realized also without any cost for the owners and animals received long-term follow-up after the treatment.

Eight dogs of variable breeds aged between 4 to 6 years and with a weight between 8 kg to 16 kg in which canine distemper was diagnosed and who presented such symptoms as vomiting, diarrhea, and fever and others were enrolled. Before cell transplantation, these dogs received antibiotics to fight the cough and pneumonia, which did not provide any clinical amelioration. Following the dog's own ability to fend off the effects of the virus, they acquired the symptoms of a neural form of this disease, such as paralysis of the hind paws or of both hind and front paws.

Xenogeneic IDPSC transplantation was performed only after the effect of the virus was ended. Undifferentiated IDPSC, which were cryopreserved at passages 3-5 were used. The cells were thawed just before transplantation and washed twice in pre-warmed (37 C) sterile PBS following centrifugation for 5 min at 800×g. At that moment, the viability of the cells was tested using Trypan blue staining and was approximately 98% of live cells. Cell number used in each application was established in accordance with the dog weights and varied between $2 \times 10^6$ (8 kg) to $4 \times 10^6$ (16 kg). The cells were suspended in a mean volume of ±0.5 mL of sterile physiologic solution for subsequent intravenous injection. The dog received an injectable anesthetic, which dose was computed according to the weight of the dog and sensitivity of certain breeds to anesthetic. According to disease severity the dogs received single or multiple (no more than three) applications. IDPSCs were transplanted without any immunosuppressive protocol. None of the animals showed signs of immune rejection following single or multiple IDPSC transplantations.

Soon after the first IDPSC application, all animals showed significant amelioration of symptoms of the neurological form of Canine distemper. The animals, which were able only to crawl, started to half-rise, while those that were able to half-rise started to get up and walk. The animals, which were able only to crawl, started to rise up while those that were able to rise up started to walk slowly. Each animal had its own dynamics of healing and those that had their musculature stronger demonstrated accelerated dynamics of amelioration. The dogs that presented more advanced clinical symptoms and were able only to crawl demonstrated significant amelioration after the third IDPSC application and even with difficulty, but these animals were able to walk. Next, in order to obtain the best clinical result they were submitted to physiotherapy procedures.

Figure 17:
FIG. 17 depicts progress in the treatment of a mild case of canine distemper, a viral disease, after LP IPDSC transplantation. A) and B) show before IDPSC transplantation. C) and D) show one month after a single application of IDPSCs.
Figure 18:
FIG. 18 depicts progress in the treatment of a severe case of canine distemper, a viral disease, after LP IPDSC transplantation. A) and B) show before IDPSC transplantation. C) and D) show one month after a single application of IDPSCs.

In representative FIGS. 17 and 18 two animals with mild and severe neurological forms of canine distemper (before cell application) and their progression of healing (after cell application) are presented. The animal with a mild neurological form showed paralysis of the hind paws (FIGS. 17A and 17B), which were completely restored after a single IDPSC application (FIGS. 17C and 17D), and the animal was able to walk and to stand during sufficient time periods. The animal with a severe neurological form showed both seizures and paralysis of the front and hind paws (FIGS. 18A and 18B). Seizures disappeared after the first IDPSC application, and the dog was able to walk a short distance even presenting the symptoms of the disease of being unable to move paws correctly (FIGS. 18C and 18D). This dog was almost completely restored to all movement after the third IDPSC application.

At a follow up 4 months later, all animals recuperated their movement and even running capacities. At a follow up 2 years later, the animals demonstrated that IDPSC transplantation was safe and were able to maintain physical performance of dogs, which apparently were healthy. None of the animals demonstrated tumor formation, which supposedly can be caused by stem cell transplantation.

Example 7

Myogenic Differentiation of IDPSC

Figure 19:
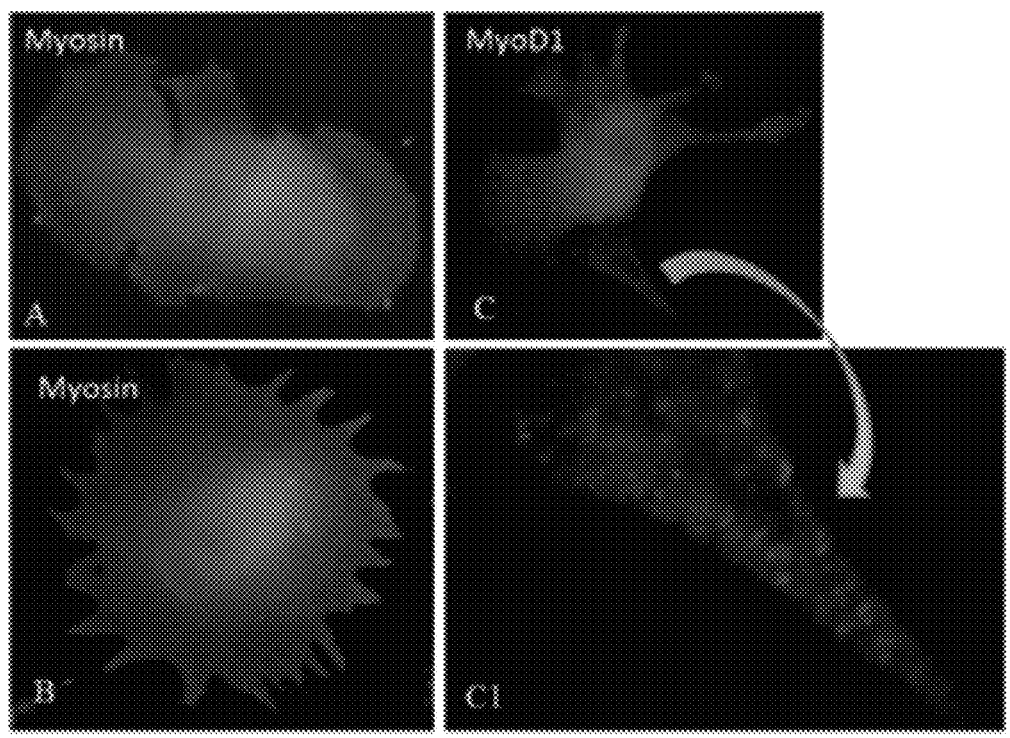
FIG. 19 depicts cardiomyocyte (CM)-like cells obtained from LP IDPSC. A) Spontaneous fusion of differentiated IDPSC. B-C1) CM-like phenotype and morphology of differentiated IDPSC.

Additionally, differentiation of IDPSC into cardiomyocytes (CM)-like cells was observed (FIG. 19). IDPSC can adopt a CM-like phenotype and morphology in vitro following fusion (FIG. 19A) or differentiation (FIGS. 19B-19C1).

Figure 20:
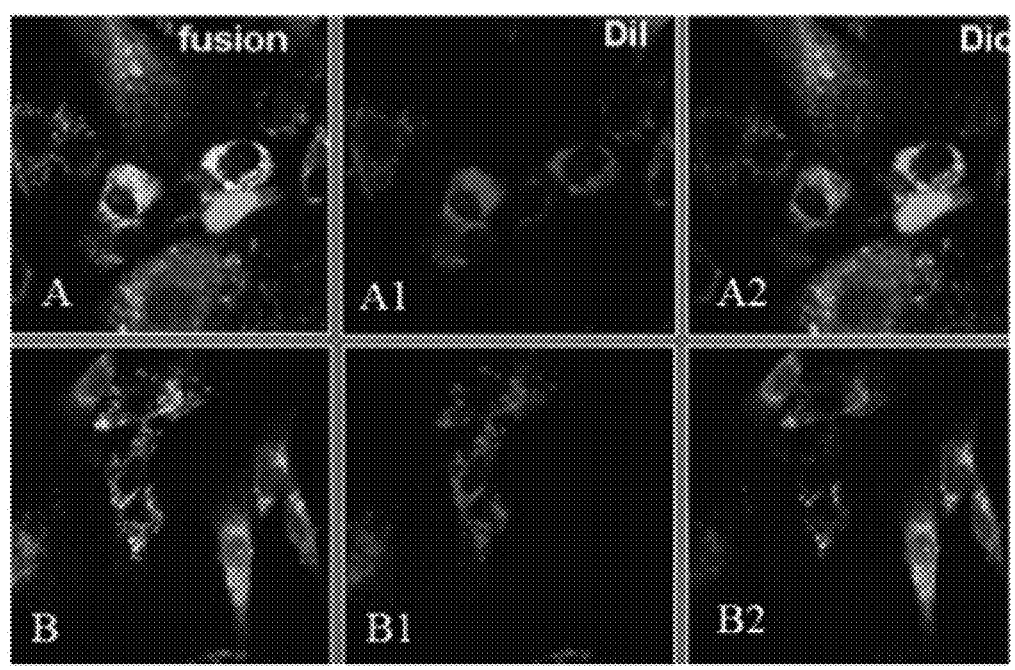
FIG. 20 depicts LP IDPSC spontaneous cell fusions through co-culture with other cell types. A), A1), and A2) show mouse bone marrow cells crossed with IDPSC. A) Merged image. A1) IDPSC. A2) Mouse bone marrow cells. B), B1), and B2) show human fibroblasts crossed with IDPSC. B) Merged image. B1) IDPSC. B2) Human fibroblast.

Cardiomyocyte apoptosis is critical for the progressive cardiac dysfunction that culminates in congestive heart failure. Bone marrow cells can help to restore cardiac function following ischemia through their fusion with cardiomyocytes thus rescuing heart cells from apoptosis. Cell fusion preserves cardiomyocytes from apoptosis following myocardial infarction, thus providing a new approach for targeting cardiac regenerative therapies. (Yang et al., 2012). IDPSC can also be a good option for use in heart failure due to their natural spontaneous fusion capacity, which can be demonstrated in vitro (FIG. 20). Primary human skin fibroblasts (PHSF), mouse bone marrow cells (MBMC) and IDPSC were isolated and washed twice in calcium- and magnesium-free Dulbecco's phosphate-buffered solution (DPBS, Invitrogen) and dissociated with 0.25% trypsin/EDTA solution (Invitrogen). The suspension was centrifuged and the cell pellet was resuspended in DMEM (Invitrogen) with 10% fetal bovine serum (FBS) (Invitrogen) containing a green (Dio) fluorescent dye (Vybrant CM-Dio Cell-Labelling Solution; Molecular Probes, Invitrogen) while the IDPSC suspension was resuspended in the same solution containing red (DiI) fluorescent dye. Cells were incubated for 15 minutes at 37° C., washed twice in DPBS, and mixed cells IDPSC:PHSF and IDPSC:MBMC were seeded at a 1:1 ratio. Efficient spontaneous cell fusion was observed in both experiments (FIG. 20).

Figure 21:
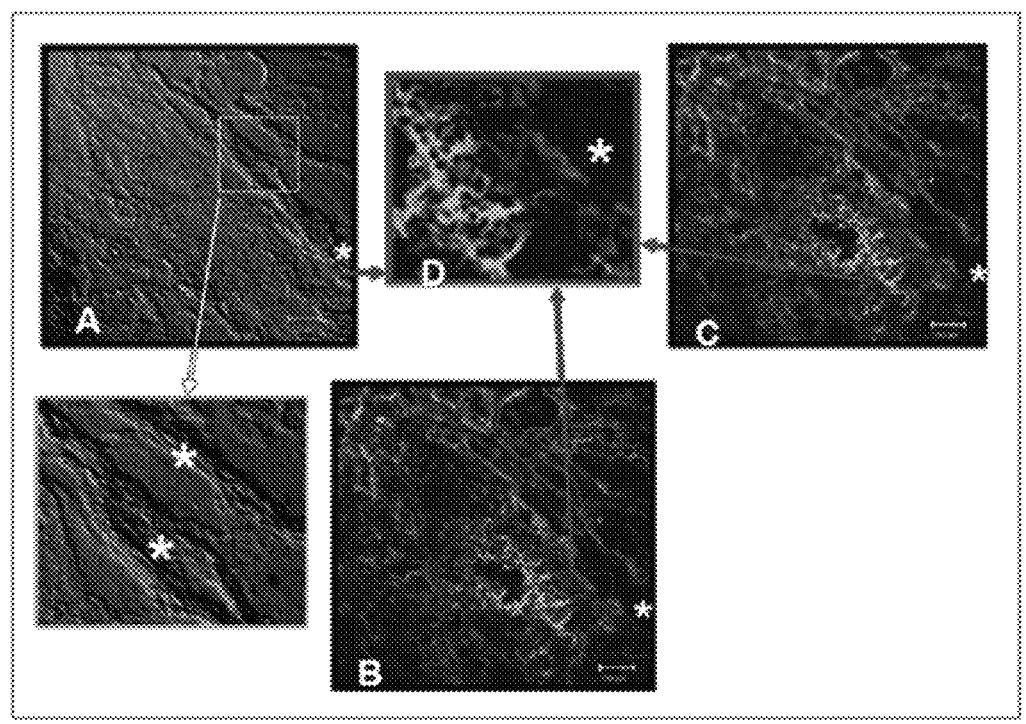
FIG. 21 depicts LP IDPSC (green) homing in muscle myocardium in a rat model of myocardial infarction by coronary artery ligation.

These undifferentiated IDPSC ($10^6$) were also transplanted in rat model of myocardial infarction by coronary artery ligation, which was induced as described (Selye H, Bajusz E, Grassos S, Mendell P. Simple techniques for the surgery occlusion of coronary vessels in the rat. Angiology. (1960) 11: 398-407). All procedures were performed in accordance with International Guidelines for Ethical Conduct in the Care and Use of Animals. Five young Wistar males were used, which weighed between 200-250 grams. The cells were administrated by direct intramyocardial injection just after induction of myocardial infarction. After one month, IDPSC homing was in muscle myocardium (FIG. 21). Anti-IDPSC antibody, which was obtained as described in Kerkis et al., (2006) Cells Tissues Organs 184:105-116, was used to analyze IDPSC homing.

Figure 22:
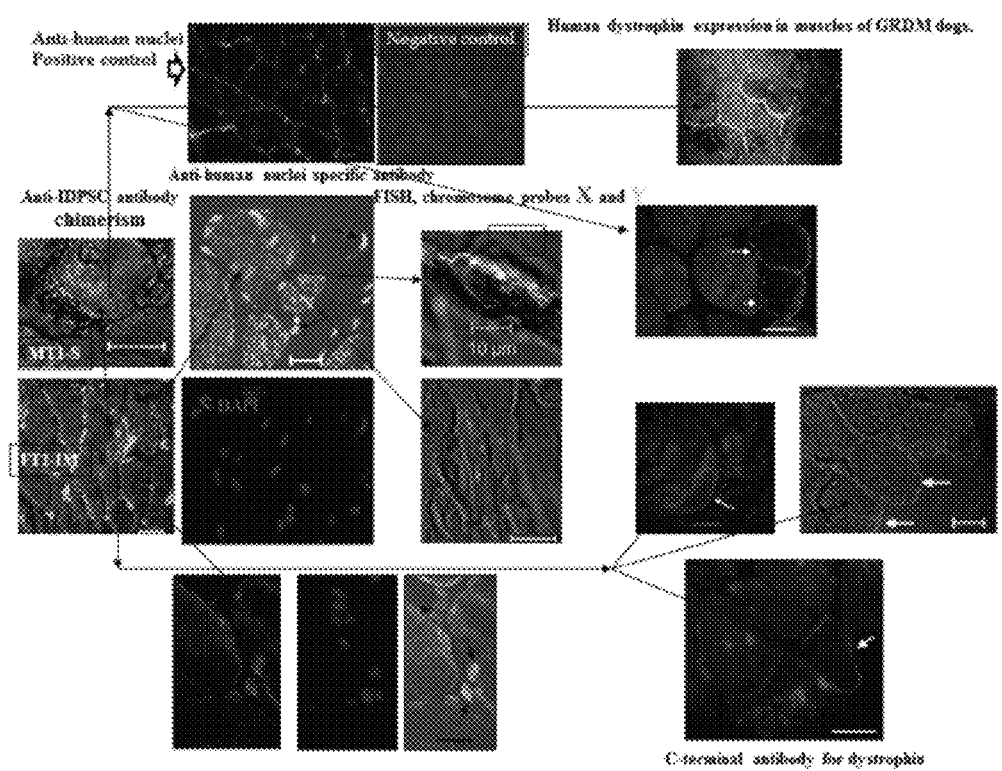
FIG. 22 depicts the results of an analysis of the myogenic potential and spontaneous fusion of LP IDPSC in golden retriever muscular dystrophy (GRMD) dogs. Different markers, such as anti-human nucleus, anti-human dystrophin antibodies and DNA fluorescent probe against human Y chromosome, provide evidences of LP IDPSC homing in dog muscle.

In vivo myogenic potential and spontaneous fusion capacity of IDPSC with recipient cells and muscle tissues was also demonstrated in golden retriever muscular dystrophy (GRMD) dogs. To minimize the effects of inter and interfamilial variability previously observed in GRMD dogs from the same litter were used. Six affected animals (3 males and 3 females) born after the breading of an affected male with a carrier female through artificial insemination were used. Each gender received $6 \times 10^7$ IDPSC via arterial injection. One non-injected male and one non-injected female were analyzed as age-matched controls. To verify the potential effect of long-term treatment with IDPSC, the animals were treated monthly, starting at 44 days old. At different time points, biopsies were obtained and homing and differentiation of IDPSC were studied. As seen in FIG. 22, IDPSC differentiated into and fused with myocytes in the injected GRMD dogs indicated by staining of human dystropin in the dog muscles.

Example 8

IDPSC Homing in Mice Bone Marrow

Figure 23:
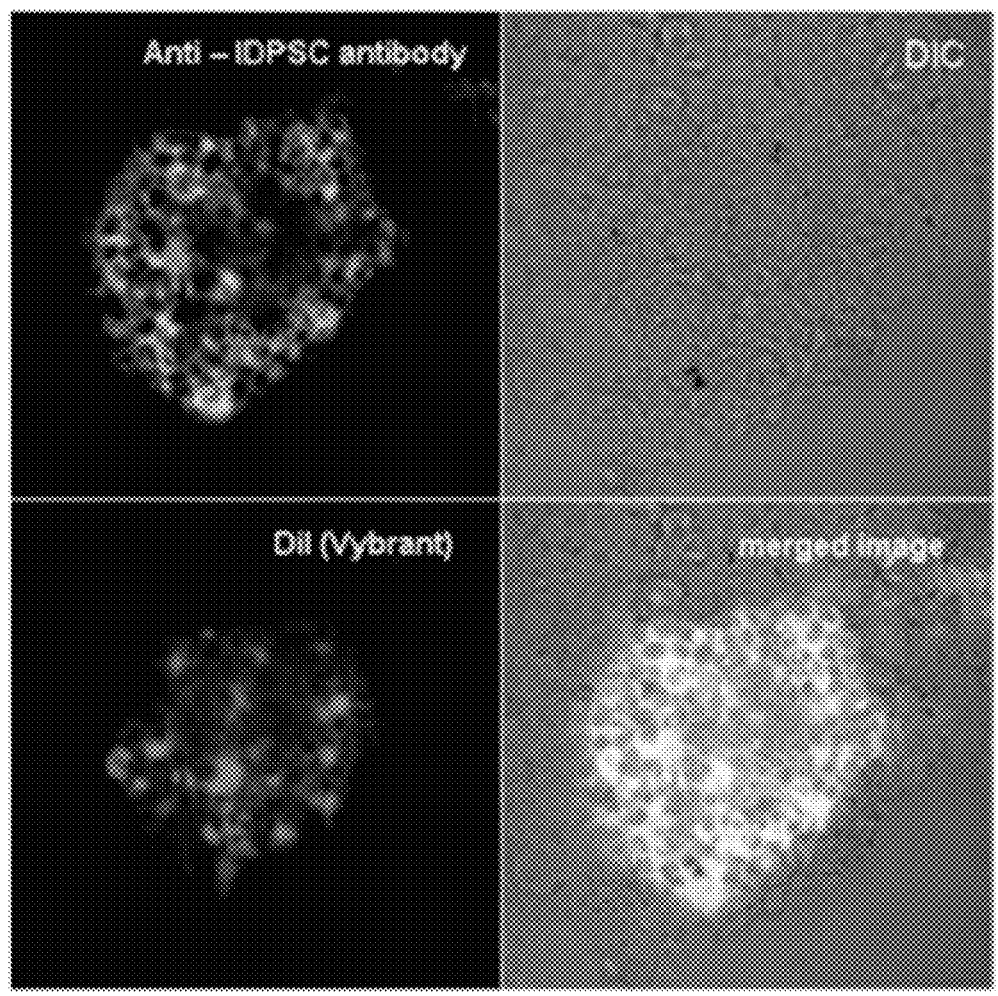
FIG. 23 depicts engraftment of LP IDPSC into the bone marrow of mice. LP IDPSC were recognized by a specific antibody, and the cells in the bone marrow were identified with Dil, a lipophilic membrane stain.

IDPSC were further characterized by their ability to engraft following intraperitoneal injection of BALB/c nude mice (n=15) with $10^6$ cells of each tested line (n=4). When mice were sacrificed 2 weeks later following IDPSC injection, dense engraftment of these cells was observed in mouse bone marrow (FIG. 23).

Example 9

Figure 24:
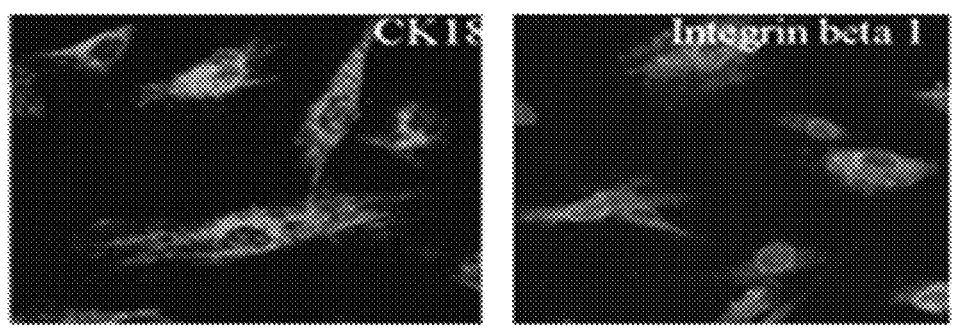
FIG. 24 depicts expression of CK18 and integrin beta 1 (CD29) Sertoli cells markers in undifferentiated LP IDPSC.
Figure 25:
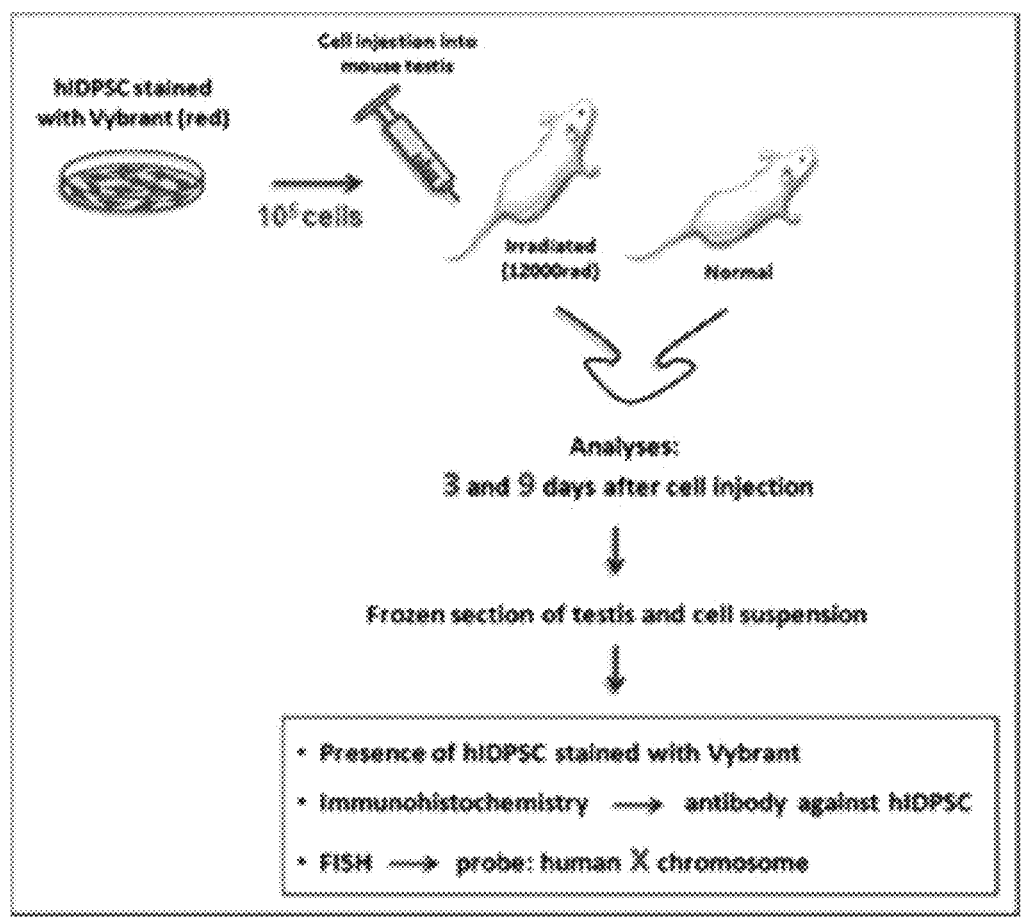
FIG. 25 depicts a schematic representation of LP IDPSC transplantation into mouse testes.

Differentiation of IDPSC into Support Cells of Spermatogenesis and Spermatogonial-like Cells after Transplantation in Mouse Testicle It was curious that IDPSC express key markers of Sertoli cells when undiffereniated, such as desmin, vimentin and cytokeratin-18 and CD29 (Integrin beta 1) (FIG. 24). From this data, it seemed likely that these cells have all the advantages that justify testing their ability to differentiate into Sertoli cells and other types of spermatogonial cells. In a pilot experiment, two cultures of human IDPSC (hIDPSC) were transplanted into fertile and infertile (by irradiation) mice testicles as outlined in FIG. 25.

The cell suspension ($10^5$ cells) was stained with fluorescent dye Vybrant (FIG. 26A-26B) and injected into normal mouse testes or mouse testes sterilized by gamma irradiation (strain CD-1). Irradiation (150 rads) was performed three times (1 month) and cells were applied one month after irradiation. Control mice were injected with saline solution. Animals were sacrificed 3 and 9 days after injection. The thin frozen sections (5 μm) were prepared using a routine protocol. The presence of IDPSC in the testes of mice was evaluated by fluorescence emitted by the dye Vybrant.

Figure 26:
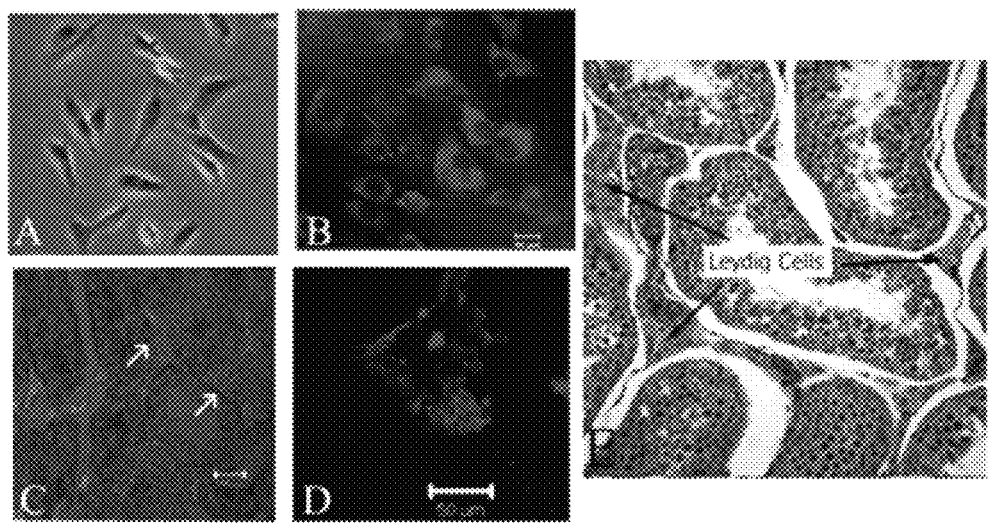
FIG. 26 depicts LP IDPSC transplantation into testes of a fertile mouse. IDPSC morphology (A). IDPSC stained with Vybrant (B). (C, D) On day 1 after transplantation, IDPSC were detected mainly in the cell compartment where Leydig cells are usually located (E). Scale bar: (A,B,E) 20 µm; (C) 100 µm; (D) 50 µm.
Figure 27:
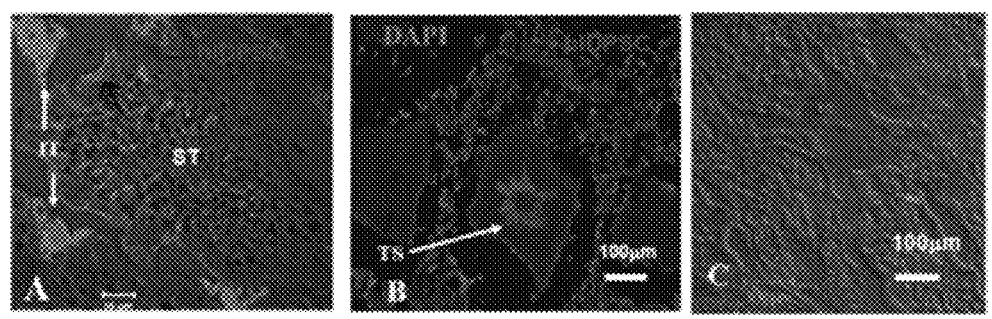
FIG. 27 depicts LP IDPSC transplantation into testes of a fertile mouse. (A, B) On day 9 after transplantation IDPSC (red) were detected in the intratubular (IT) and tubular regions (TS) in fertile mice testes. A) Confocal Microscopy: epi-fluorescence and digital interference contrast (DIC). (B)

In fertile mice, 1 day after injection the cells were mainly detected in the Leydig compartments and Sertoli cells (FIGS. 26C-26E). After 3 and 9 days, the IDPSC were found near the lumen where more differentiated spermatogonial cells are usually localized (FIGS. 27 and 28). IDPSC demonstrated a cluster distribution within these compartments and the fluorescence was observed only in some tubular regions (TS) indicating the presence of IDPSC; however most of the TS in the mice did not show any sign of cells. In control mice, in TS where saline was injected no fluorescence signal was observed (FIG. 27C). In infertile mice, on day 9 after injection of IDPSC into irradiated testes the IDPSC were mainly observed in the peripheral part of the TS grafted in the tunica albuginea, which is composed of dense connective tissue (FIG. 29).

On day 9 after injection of IDPSC the formation of human germ-like cells was observed. Analyses were performed using anti-IDPSC antibody (green) that specifically recognizes IDPSC (FIG. 29C). The presence of tetrads was observed indicating the occurrence of meiosis (FIGS. 29D-29D1).

Formation of germ-like cells at different stages of development from IDPSC stained with Vybrant (red) was also observed (FIGS. 30 and 31). FISH analyses with human X chromosome probes demonstrate the presence of the human X chromosome in compartments of interest (FIG. 32). However, fusion between human and mouse cells could occur, and it is difficult to imagine how tetraploid cells will progress through meiosis (FIG. 33).

We observed fusion between Vybrant stained IDPSC (red) and cells isolated from mouse testes stained in green when they were co-cultured in vitro. The fusion between these cells was observed with double staining of the cytoplasm as well as with the presence of two bi-nuclear cells with the nucleus, showing distinct morphologies that correspond to human and mouse cells (FIG. 33A-33B1).

Additionally, we showed that hIDPSC were able to populate the site of Sertoli, Leydig and myoid cells after 60 days in infertile mice presenting the aforementioned morphological characteristics (data not shown).

Example 10

Treatment of Renal Failure in Cat with IDPSC

A male Persian cat, age 11, male arrived at the Veterinary Hospital for clinical care by presenting symptoms of moderate dehydration, polyuria, polydipsia, appetite loss, apathy and loss of weight. Physical examination of vital parameters showed changes in the degree of hydration, which was around 7%. Assessment of renal function was performed measuring urea >250 mg/dl, creatinine 11.1 mg/dl, urine specific density 1012 and by ultrasound evaluation of the kidneys, both of which showed partial loss of the corticomedullary boundary, small size, elevated cortical echogenicity. Measurement of the kidneys, left and right respectively, were 1.7 cm wide by 2.0 cm long and 2.0 cm wide by 2.5 cm long. No hematological changes were observed.

After stating a clinical diagnosis of Chronic Renal Failure (CRF), electrolytes (Na) 155 mg/dl, (K) 3.0 mg/dl, (Ca) ionized 8.4 mg/dl, and (P) 7.7 mg/dl were measured. Immediate support treatment was started by intravenous injection of 250 ml of Ringer's lactate (RL) plus 3.5 ml of potassium chloride (KCl solution at 19.1%), 2 mL of compound B and 0.5 mL of ranitidine. Except for potassium, this therapy was maintained during the first 12 days, and then subcutaneous (SC) administration of 0.5 mL of ranitidine was initiated. In this period, the clinical improvement observed occurred 5 days after initiation of the support therapy and the concentrations of urea and creatinine reached the minimum of 174.1 mg/dl and 5.3 mg/dl respectively. The animal ran off to play and presented normorexia but still had polyuria/polydipsia.

IDPSC therapy

The first human IDPSC therapy was made 27 days after initiation of therapy support, with the second and third after 41 days and after 50 days. During the first cell therapy, the animal received $2\times10^6$ of undifferentiated LP IDPSC diluted in 1 mL of sterile phosphate solution: 0.6 mL was applied via intrarenal (only the right kidney) and 0.4 mL was applied subcutaneously. For this procedure the animal received analgesia with 5 mg/kg morphine and was induced with an inhaled anesthetic, isoflurane, in an aquarium.

During the 12 days after IDPSC therapy and while still receiving the supporting treatment described above, the animal had a clinical picture without changes and without any other specific treatment. One month after the IDPSC therapy, 80% of improvement was observed. The animal demonstrated a decrease in urine output and water intake. In this period the concentrations of urea and creatinine reached the minimum of 172 mg/dl and 4.4 mg/dl, respectively.

A second IDPSC therapy was made 43 days after the first under the same conditions. During the 29 days after the second cell therapy, the animal remained well. Thirty days after the second CT scan showed a picture of apathy and normocytic/normochromic not regenerative.

The third cell therapy was performed fifty days after the second cell therapy under the same conditions, and the animal was good. Seven days after the third cell therapy, the animal was fine, playful, gained weight, normorexia, and normúria normodipsia. In this period the concentrations of urea and creatinine reached the minimum of 136.2 mg/dl and 3.8 mg/dl, respectively.

Four months and twelve days after the third cell therapy, the animal presented the concentrations of urea and creatinine in 198.1 mg/dl and 4.4 mg/dl respectively. After this period, the animal began to show apathy with frequent episodes of emesis and pale mucous membranes, but had no polyuria/polydipsia and weight remained stable. A treatment with erythropoietin was instituted at 2000 IU dose of 100 IU/kg three times per week and Combirom prescribed at 24 mg/mL and ½ mL BID until new recommendations. Sixteen days after treatment, the blood count returned to normal and the animal was fine.

In FIGS. 34-36 are summarized the fluctuations in urea, creatinine and electrolytes during the cell therapy. Measurements were performed 12 times, and the numbers 4, 7 and 9 corresponds to IDPSC transplantations. FIG. 35 shows that IDPSC cell therapy stabilized the level of creatinine, which was maintained low and stable. Although urea's level presents fluctuations during this period, it presents the tendency to decrease over a time (FIG. 34) as well as electrolytes (FIG. 36).

After an additional month the animal arrived, presenting with muscle weakness ventro-cervical flexion and emesis. Fluid therapy was instituted with intravenous Ringer lactate, 0.3 mL of Plasil, and potassium supplementation 3 mL (19.1% KCl solution) without exceeding a speed of 0.5 mEq/kg/hour. Four hours later, the animal had a seizure and died. The exams performed when the animal has arrived demonstrated potassium 4.1 mg/dl urea 156 mg/dl and creatinine 4.4 mg/dl, with a mean of the values maintained during the whole treatment and, therefore, indicated that the probable cause of death was not the renal failure.

Soon after the death, with the permission of the owner, the kidneys were removed and fixed in 10% formaldehyde. Macroscopically there was a significant difference in size of the right and left kidneys (FIG. 37A) with the left kidney marked by a neoformation of irregular appearance (FIG. 37B) and consistency similar to the left kidney. This difference was observed previously by ultrasonography.

Figure 2:
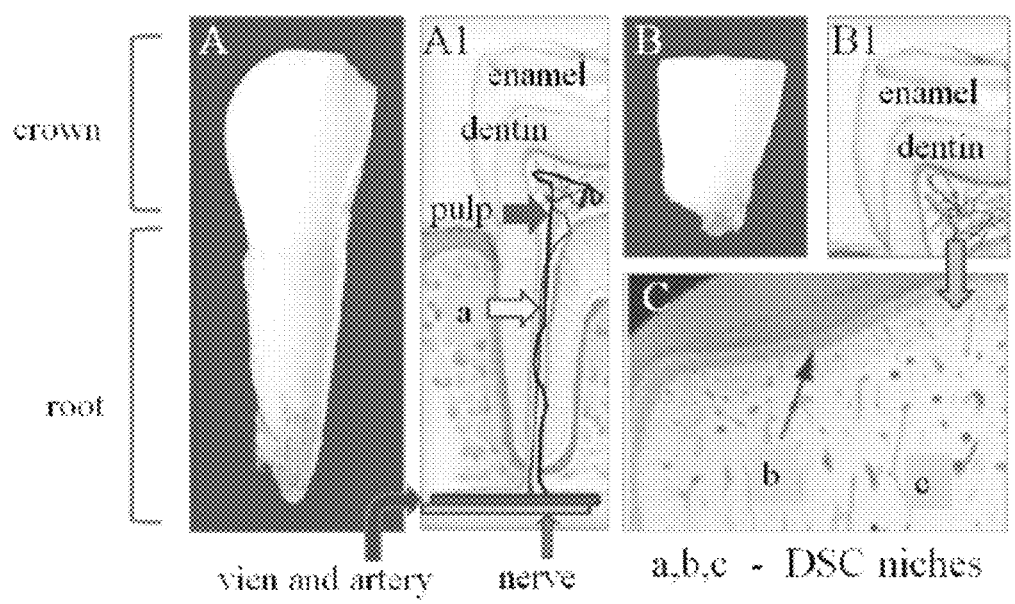
FIG. 2 depicts niches of dental stem cells (DSC) in deciduous teeth. A) Primary teeth are composed of a crown and a root. A1) A longitudinal section of a primary tooth shows the perivascular niche (a) indicated with an arrow. B) Resorption of the root in a primary tooth is shown. B1) A longitudinal section of the crown shown in B) demonstrates two other niches of DSC in the subodontoblastic cell rich zone (b) and the cell poor zone containing unmyelinated nerve fibers and fibroblasts (c) and traversed by blood capillaries. C) A magnification of the DSC niches from B1) is shown.

Histological evaluation demonstrated a significant difference between the right kidney, which received IDPSC transplantation via intrarenal injection and the left kidney (FIG. 38). The left kidney shows extensive fibrosis (FIGS. 38A-38A1) with thickened glomerular basement membranes and mesangial proliferation in a glomerulus (FIG. 38A2). The right kidney shows a more preserved morphology (FIG. 38B) with minimal fibrosis (FIG. 38B1) and a preserved glomerulus (FIG. 38B2). Among other positive effects of IDPSC transplantation, blood infiltration (red) in the right kidney was evident as observed in FIGS. 38B1 and 38B2. In addition, FIG. 38B2 shows preservation of glomerular endothelial cells, which are not visible in FIG. 38A2.

The presence of IDPSC in the cat's kidney was confirmed by immunofluorescence analysis using an anti-IDPSC antibody (FIGS. 49A-39C).

Example 11

Effect of IDPSC in Rapid Skin Remodeling and Prevention of Scarring

LP Enhanced Green Fluorescent Protein (EGFP)-tagged IDPSC (EGFP-IDPSC) were cultured as described (Lizier et al., (2012) PLoS ONE 7:e39885)). Swiss mice (8 weeks old; female; body weight, 20-23 g) were used. The animals were randomly divided into three groups, and an excisional wound splinting model was generated. In brief, after hair removal from the dorsal surface and anesthesia, two 5-mm full thickness excisional skin wounds were created on each side of the midline in 12 mice. Each wound received $10^5$ cells (LP EGFP-IDPSC) diluted in 100 µL of PBS and the cells were injected intradermally around the wound at four injection sites. A control group received only PBS. No immunosuppression protocol was applied. The incision was saturated with nylon (4-0). The animals were housed individually. We tested the adhesive on the skin in mice prior to this experiment and did not observe any skin irritation or allergic reaction. The animals were euthanized after 7 days.

Histologic examination was performed as follows. Tissue specimens were fixed in 3% paraformaldehyde for 24 hours and embedded in OCT, an embedding medium used for frozen tissue to ensure Optimal Cutting Temperature. Six-micron-thick sections were stained with H&E and Masson's Trichrome for light microscopy. Analysis of GFP expression in LP EGFP-IDPSC engrafts was performed by confocal microscopy.

Histologically, the best aspect was observed in the group that received LP EGFP-IDPSC via topical delivery. In this group, well-organized tissue, provided epidermis, dermis, and hypodermis formation were observed. No signs of graft immunorejection were detected.

Collagen, in the form of elongated fibrils, can be normally found in skin. The staining by Masson's Trichrome demonstrated the presence of collagen in skin, which was remodeled by topical delivery of EGFP-IDPSC to the injured site. In contrast, the control group did not show skin remodeling (FIG. 40).

Confocal microscopy showed robust engraftment of LP EGFP-IDPSC around small vessels, buds of hair follicles, and in sebaceous glands (FIG. 41). Images captured with confocal microscopy of skin cells treated with PBS only are shown in FIG. 42 for comparison.

Example 12

In Vitro Retinal Differentiation of LP IDPSC

Since the neural retina consists of ectodermal cells and of the same origin that DP and DP derived IDPSC, both of these cells, retinal and IDPSC, may preserve a common embryonic "memory" that can permit IDPSC to give rise not only the neurons of the central nervous system (CNS) but to retinal stem cells and retinal neurons-like cells.

Studies of neurogenic potential of LP IDPSC demonstrated that these cells present a more controlled type of differentiation need and responded adequately when neurogenic induction was induced with retinoic acid. When induced LP IDPSC were plated in vitro, further differentiation was observed and the majority of cells expressed β-Tubulin III, a marker for immature neurons. In addition, many plated cells expressed markers for mature neurons or glial cells.

In vertebrates, the retina is considered part of the central nervous system (CNS). However, retina is a special class of neuronal cells, and it is a layered structure with several layers of neurons interconnected by synapses. Retina produce photoreceptor cells, which are neurons that are directly sensitive to light. Three types of retinal neurons can be identified: rods, cones, and ganglion cells. The rods provide black-and-white vision, cones support daytime vision and the perception of color, and the photosensitive ganglion cell is important for reflexive responses to bright daylight.

Neuronal and retinal cells differ in their spectrums of specific markers and while retinal cells can express early neuronal cell markers, the neuronal cells are limited by expression of only neuronal markers (e.g., nestin and beta-tubulin III) (FIG. 43). EP IDPSC were able only to differentiate into neural cells, while LP IDPSC showed both neuronal and retinal differentiation (FIGS. 45-47).

Protocol of LP IDPSC Differentiation toward Retinal Cells In Vitro

LP IDPSC were maintained and in vitro expanded as described in Lizier et al., 2012. Neurospheres were obtained from LP IDPSC, which were grown in culture flask of 25 cm$^2$ until they reach a semiconfluence of 70%. Then, cells were trypsinized and split into two 35 mm petri dishes, pre-treated with 1% agarose (Sigma), which formed a thin layer on the bottom of the plate. Neurobasal culture medium supplemented with 3% B27 (both from Gibco) was used. The dishes were incubated at 37° C. for 3 days in the humid atmosphere in a 5% $CO_2$ incubator. Once formed, the neurospheres were transferred to other dishes and were plated on coverslips for adhesion in IDPSC basal culture medium, which was changed on the next day for NB+B27. Adhered neurospheres were maintained in NB+B27+0.5 µM retinoic acid culture medium for five days until the cells started outgrowth from neurospheres. Next, an enzymatic digestion using 0.25% trypsin was carried out, and the cells were seeded in a new petri dish of 35 mm, keeping the same culture medium for another 10 days but without addition of 5 µM retinoic acid, and culture medium was changed every 3 days. The cell culture was maintained for another five days and then fixed in 4% formaldehyde. A summarized protocol is shown in FIG. 44A-44F and a timeline of differentiation is presented in FIG. 44G.

At day 15 of differentiation the difference in differentiation toward retinal cells between EP and LP was observed and is shown in FIGS. 45 and 46. EP IDPSC showed robust neuronal differentiation, expressing principal markers such as beta-tubulin III and GFAP (FIG. 47).

The expression of CD73 (ecto-5'-nucleotidase) in LP IDPSC was assessed by immunofluorescence, which was recently reported to be also precursor of retinal cells. The expression of vimentin, a marker of MSC, was also evaluated. Both markers were positive in LP IDPSC (FIG. 48).

In view of the proposed neural crest embryonic origin of IDPSC, the expression of specific markers of retinal cells such as Pax-6, Chx-10, Crx, Nrl, Calbindin and Rhodopsin was also determined by immunofluorescence (FIG. 49) and flow cytometry (FIG. 50). These markers were not expressed in undifferentiated LP IDPSC.

The adhered neurospheres formed by LP IDPSC subsequently released cells in large quantities, among which some had cells with morphology similar to neurons. After about five days of culture, we observed that adherent neurospheres presented highly concentrated areas of cells around the spheres. We passaged the cells and in order to enrich the dish with retinal like cells, we cultured these cells in NB+B27 and RA for ten more days. The cells exhibited morphology similar for different types of neuronal cells (FIG. 51).

When we varied the quantity of LP IDPSC and the time of enzymatic dissociation, we observed that, depending on this variation, the result can be quite different. We observed that under short times of enzymatic digestion the formation of secondary neurospheres, which showed very similar morphology to that, derived from neuronal cells of the CNS itself or from embryonic stem cells occurred (FIG. 52).

To evaluate the differentiated cells, we performed an immunofluorescence assay, first checking the expression of CD73, also known as ecto-5'-nucleotidase, which catalyzes the conversion of extracellular adenosine 5'-monophosphate to adenosine. It is a marker cell surface of precursors of both cones and rods (KOSO et al., 2009). FIG. 53 demonstrates the expression of CD73 in neurospheres and in differentiated cells.

Next, we analyzed PAX-6, which is a transcription factor, and its localization is mainly in nuclear and perinuclear areas of the cell. On precursor cells, the cytoplasmic expression can also be viewed because of the high ratio between the nucleus and cytoplasm, which is characteristic for this differentiation stage. The expression of this marker did not occur in all cells. There are many cells that were negative for this marker (50%) depending on the stage of maturation they had reached (FIG. 54).

Just as Pax-6, Chx-10 is also a transcription factor involved in differentiation of precursor of retinal early development. We observed that the number of Chx-10 positive cells was higher than of Pax-6 and reached around 80% of Chx-10 positive cells (FIG. 55). Chx-10 activates transcription factor Crx. The gene Crx encodes a transcription factor that coordinates the expression of photoreceptors and is considered a marker of photoreceptor precursors, and it is expressed in the nucleus and the perinuclear region (FIG. 56).

The gene Crx activates another factor transcription, Nrl (FIG. 57), which expressed in retinal neurons and promotes expression of rhodopsin by its connecting the rhodopsin gene promoter. It is expressed throughout the central nervous and peripheral systems during development, but in adulthood is restricted to the neocortex and retinal neurons. The next marker expressed in retinal cells is Calbindin, which is also known as calcium binding vitamin D dependent protein and is expressed in neural tissues and horizontal retina cells. Recoverin is a calcium ligand photoreceptor protein and is implicated with the regulation of rhodopsin kinase activity, an enzyme needed for luminous adaptation. We found a few cells expressing this protein. Both calbindin and recoverin are localized in the cell cytoplasm (FIGS. 58-59).

Finally Rhodopsin, which is a visual pigment of photoreceptors, is responsible for the absorption of photons, more specifically, for adapting light/dark. Its location is more in the cellular cytoplasm, which can also be viewed on the core. The amount of cells expressing this protein also was much lower in the retinal precursor (FIG. 60).

Thus we can conclude that we have reached a breakthrough in vitro differentiation of LP IDPSC in retinal precursor and mature cells.

Protocols of immunofluorescence and Flow cytometry are the same that used in other examples and in Kerkis et al., 2006 and Lizier et al., 2012. The list of antibodies used is presented below in Tables 1-3.

TABLE 1

Antibodies used for imaging of differentiated IDPSC cells.

| Anticorpo | Origem | Diluição | Fabricante |
|---|---|---|---|
| CD73 | Mouse | 1:100 | * |
| Viamentina | Mouse | 1:100 | Santa Cruz Biotechnology |
| Pax-6 | Goat | 1:100 | Santa Cruz Biotechnology |
| Chx-10 | Goat | 1:100 | Santa Cruz Biotechnology |
| Crx | Rabbit | 1:100 | Santa Cruz Biotechnology |
| Nrl | Rabbit | 1:100 | Santa Cruz Biotechnology |
| Calbindin | Rabbit | 1:100 | Santa Cruz Biotechnology |
| Recoverin | Goat | 1:100 | Santa Cruz Biotechnology |
| Rhodopsin | Rabbit | 1:100 | Santa Cruz Biotechnology |

TABLE 2

Antibodies used for imaging of differentiated IDPSC cells.

| Anticorpo | Origem | Diluição | Fabricante |
|---|---|---|---|
| Nestin | Goat | 1:100 | Santa Cruz Biotechnology |
| Beta-III-Tubulin | Mouse | 1:100 | Chemicon |
| GFAP | Goat | 1:100 | Santa Cruz Biotechnology |

TABLE 3

Antibodies used for imaging of differentiated IDPSC cells.

| Anticorpo | Origem | Diluição | Fabricante |
|---|---|---|---|
| FITC anti-goat | Rabbit | 1:200 | Santa Cruz Biotechnology |
| FITC anti-mouse | Goat | 1:200 | Santa Cruz Biotechnology |
| FITC anti-rabbit | Goat | 1:200 | Santa Cruz Biotechnology |

Example 13

Production of Pancreatic Cell Precursors from LP IDPSC

Previously, it has been shown that pancreatic β-cells, which are of endodermal origin share common features with those of neurons that are of ectodermal, neural crest origin (Yang et al., 1999, Teitelman and Lee, 1987; Baekkeskov et al., 1990; De Vroede et al., 1990). These data suggest that dental tissue may be a possible source of stem cells for generation of insulin producing cells. Accordingly, it was reported that DPSC from deciduous teeth, which were obtained using enzymatic digestion, can be differentiated into pancreatic like β-cells (Govindasamy et al., 2011). Thus, this work raised several questions. The islets of Langerhans are the regions of the pancreas that contain its endocrine (i.e., hormone-producing) cells, which constitute approximately 1% to 2% of the mass of the pancreas. These islands are composed by 5 different cell types, which produced hormones.

The majority of the currently employed differentiation protocols, which used ES cells, rely on the sequential activation or inhibition of embryonic signaling pathways, through treatment with their respective ligands. Alternative approaches have been undertaken to identify biologically active small chemical compounds that can functionally mimic cellular signaling molecules.

We demonstrated that LP IDPSC express a set of different neural markers such as NGF, BDNF, NT-3, NT-4, as well as the low-affinity receptor, p75NTR (CD271). Accordingly normal pancreatic neural tissue also expresses some of the neurotrophins (Schneider et al 2001). Alternatively, NGF is able to induce neuron-like differentiation of an insulin-secreting pancreatic beta cell line (Polak et al., 1993). Once pancreatic beta cells arise from the embryonic endoderm, the induction of differentiation of insulin-secreting pancreatic beta cells by NGF indicates that endocrine and neuronal cells share a developmental pathway. LP IDPSC showed robust differentiation into neural and retinal cells, which strongly support the potential capacity of LP IDPSC population into pancreatic cells.

In Table 4 expression patterns of several neurotrophins and early neural markers in undifferentiated LP IDPSC and in different pancreatic cells are presented. The overlap between the expression patterns of these markers in pancreatic cells and LP IDPSC is evident. This indicates that LP IDPSC is a potential unlimited source of stem cells, which shows commitment to insulin-producing endocrine cells as well as to exocrine cells (duct/ductules) and pancreatic neurons.

Some authors did not accept the statement about similarities between pancreatic β-cells and neurons due to their distinct anatomic origins (Hebrok, 2012). In contradiction to this assumption, LP IDPSC contributed to three germ layers, including endodermal tissue, during fetal development was demonstrated and presented in the following Example 15 (Intrauterine Transplantation of LP IDPSC). LP IDPSC can produce insulin producing (endocrine) cells or provide cellular basis for exocrine cells or both. They or supernatant of these cells rich of neurotrophins can be used in combination with ES cells, providing a diverse factor useful for pancreatic cell differentiation creating an appropriate cell niche. An additional advantage of LP IDPSC over ES cells is that they are MSC and also can act via multiple paracrine mechanisms.

Taken together, these facts indicate that LP IDPSC form the basis of a therapeutic treatment for some types of diabetes by inducing the proliferative differentiation of islet cells.

TABLE 4

Expression of common markers observed in LP IDPSC and pancreatic cells.

| Neurotrophins | Exocrine | Endocrine | Pancreatic neurons | LP IDPSC |
|---|---|---|---|---|
| p75NTR | ---- | ---- | +++ | +++ |
| Anti-NGF | ++ | + | ---- | +++ |
| Anti-BDNF | ---- | ---- | ---- | +++ |
| Anti-NT-3 | ---- | ---- | ---- | +++ |
| Anti-NT-4 | +++ ducts/ductules | + Insulin secreting cells | ---- | +++ |
| Other markers | | | | |
| Nestin | +++ | +++ | +++ | +++ |
| Beta-tubulin III | ---- | +++ alpha- and beta-cells precursors | ---- | +++ |
| Pax 6 (also marker of retinal precursors) | ---- | +++ alpha- and beta-cells precursors | ---- | +++ |
| GFAP | n/a | +++ Insulin secreting cells | n/a | +++ |

---- negative;
+ week;
++ moderate;
+++ strong;
n/a—not analyzed

Example 14

Intrauterine Stem IDPSC Transplantation (IUSCT)

We show herein that once IDPSC are transplanted into a fetus in utero they are distributed throughout the fetus while remaining viable in undifferentiated and differentiated forms and develop into multiple cellular types due to their unique multilineage orientation that was characterized with multiple tissue-specific molecular markers and robust differentiation potential in the other examples.

Also surprisingly, IDPSCs and their differentiated progeny were not rejected by immunocompetent hosts and did not transform into inappropriate differentiation but were differentiated accordingly in the relevant host niche-coordinated manner. Therefore we conclude that the multilineage orientation of IDPSC is proven by in vivo distribution and engraftment of IDPSC into multiple tissues and organs.

The disclosed results support the use of IDPSCs for cellular therapy by administration via an intrauterine route to a fetus in an amount effective for treatment.

Surprisingly, the transfected GFP-tagged IDPSCs distributed over the fetal and placental tissues. In one embodiment, the present disclosure relates to a method of obtaining genetically modified IDPSCs, comprising transducing IDPSCs with exogenous genetic material and the use of these modified IDPSCs as a delivery system for therapeutic proteins encoded by the exogenous gene for treatment of inherited genetic and/or acquired disorders.

Multipotent adult progenitor cells (MAPC), progenitors that were isolated from bone marrow but subsequently established in other tissues, including brain, muscle, and cord blood, but not dental pulp, have been shown to treat lysosomal disorders in utero (see U.S. Pat. No. 7,927,587). Surprising different characteristics between MAPC and LP IDPSCs include:

IDPSCs never express Rex1.
MAPC are also negative for CD44
MAPC do not express nestin and many other factors LP IDPSCs are characterized by.
MAPC plurality require the use of cell selection methods to obtain high purity population as in IDPSC, but this step is not necessary with IDPSC.
This is a principal difference, that IDPSC have sufficient multilineage orientation without the necessity of purification methods.
In addition, with MAPC pre-differentiated cells only were used and the comparative level of the engraftment of MAPC was low.

IDPSCs showed high level of engraftment without any selection, which means they are "stem cells". For example, disclosed herein is the use of undifferentiated IDPSC, which have a capacity to home in stem cell niches, for example, muscle tissue—satellite cells—which is not the tissue of their origin (DP). In other words, they are TRUE stem cells!

Notably, we detected during in utero experiments distribution and engraftment of differentiated and undifferentiated LP IDPSC. When they differentiate, they do this appropriately, for example, in heart tissue they express appropriate markers, but not CK18, which is a marker of epithelium. They showed differentiation into human lymphocytes expressing CD45. Disclose herein is the robust multi-organ engraftment and tissue-matched differentiation. In comparison MAPC demonstrate a more limited potential to differentiate:

- IUT transfer of MAPCs did not result in differentiation to an epithelial cell type.
- Similar to lung engraftment, MAPCs were present in the intestine; however, cytokeratin staining was also negative, indicating that the MAPCs did not differentiate into intestinal epithelia.
- MAPCs were also found in the cardiac and skeletal muscle, as well as in the spleen and skin but did not show any differentiation.
- In the brain, MAPCs differentiate into astrocytes and oligodendrocytes but not neurons and did not express neurotrophic factors. In contrast, with IDPSC Purkinje cells and brain vessels were observed.

To summarize, disclosed herein is a robust method of administration of multilineage-oriented IDPSCs, or differentiated progeny thereof, in the pharmaceutical carrier as a single or combined biological treatment (i.e, they can be mixed with other regenerative or therapeutic agents) to promote differentiation to a preferred cell type. This can be advantageous when engraftment or gene delivery is desired according to the developmental progression of the organ systems in the fetus.

Cells of different origins have been used for in utero transplantation in a number of models. In utero transplantation of $1\times10^8$/kg CD34+ paternal canine bone marrow-derived cells in a canine model achieved a low level of microchimerism (1%) in various tissues (Blakemore et al., 2004). Transplantation of human cord blood-derived CD34+-enriched stem cells into the peritoneal cavity of 45- to 60-day-old ovine fetuses achieved 18% engraftment at 1-3 months after birth (Young et al., 2003). Human fetal liver mononuclear cells or fetal bone marrow-derived CD34+ cells transplanted into NOD/SCID (non-obese diabetic/severe combined immunodeficiency) mice on day 13 or 14 of gestation resulted in multilineage human hemopoietic engraftment in 12% of recipients at 8 weeks of age, respectively (Turner et al., 1998). Transplantation of human fetal mesenchymal stem cells into fetal mice with Duchenne muscular dystrophy on day 14-16 resulted in wide-spread long-term (19 weeks) engraftment in multiple organs (Chan et al., 2007). Embryonic stem cells transplanted into murine fetuses achieved low level (0.4%) chimerism (Moustafa et al., 2004). Human placenta derived, amnion and chorion cells from term placenta also successfully engrafted in neonatal swine and rats after transplantation showing low level of chimerism (Bailo et al., 2004, Chen et al., 2009).

Liechty and co-authors (2000) performed IUT of human bone marrow mesenchymal stem cell in sheep at the beginning of gestation. This study demonstrated xenogeneic MSC grafting in several tissues, which persisted during 13 months after transplantation. Transplanted cells underwent differentiation into chondrocytes, adipocytes, myocytes and cardiomyocytes, bone marrow and thymus stromal cells in graft site. This study demonstrated that MSC were able to maintain their multipotential capacity and yet their unique immunological characteristics without immunological rejection (Almeida-Porada, et al. 1996, b, 2002; LIECHTY et al. 2000). Subsequently, MacKenzie & Flake (2001 a, b 2002) confirmed these results. However, in both studies a low level of chimerism was observed.

Another group performed allogeneic MSC transplantation in sheep's uterus on day 14 of gestation, which also resulted in low level of chimerism, but showed engraftment in multiple organs (SCHOEBERLEIN et al., 2005).

When human bone marrow MSC were transplanted into a mouse uterus on day 14 of gestation, they showed engraftment in all tissues derived from the three germ layers, which was maintained after four months. It is important to mention that CD45+ cells (a human lymphocyte marker) were detected in the peripheral blood of mice (Chou et al. 2006). This work suggests that the population of MSC may contain precursor cells that are capable, in an appropriate environment, to differentiate into blood cells.

To investigate the usefulness of bone marrow MSC for cardiac development in mammals, these cells from fetal and adult origin were intraperitoneally injected in sheep fetuses. No difference was observed between the grafts of MSC isolated from adult bone marrow or fetal liver and brain. Most human cells grafted in the Purkinje fibers. Approximately 43.2% of Purkinje fibers were of human origin, in contrast, only 0.01% of cardiomyocytes were of the MSC (Airey et al. 2004).

The human fetal CTM isolated from peripheral blood in the first trimester of pregnancy, were applied in the uterus of homozygous mice with osteogenesis imperfecta (HI), which results in multiple fractures and is currently treated only symptomatically. Donor cells were found in animal bones, and express genes of osteoblastic lineage producing extracellular structural protein bone—osteopontin. After treatment a marked reduction of fractures and skeletal abnormalities was observed (GUILLOT et al., 2008).

MSCs derived from human amnion and placenta were also used in animal model of IUT, albeit migration and localization in various organs were evidenced, the graft remained low level (Han et al., 2008, Chen et al. 2,009). Adipose tissue derived MSC showed similar low engraftment (Martínez-González, 2012).

Autologous transplantation of MSC derived from amniotic fluid was performed in sheep using GFP positive stem cells, which were detected in fetal tissues including heart, liver, placenta membrane, umbilical cord, adrenal gland and muscle (Shaw et al. 2010).

The allogeneic MSC derived from fetal rabbit liver was performed by two routes of administration: intra-hepatic and intra-amniotic. The graft was studied after 10 and 16 days and low grafting of these cells were observed which nevertheless persisted for 16 weeks (Moreno et al., 2011).

To check the capacity of human ES cells to differentiate into functional neurons in vivo, these cells were transplanted on day 14 of gestation in mice fetus in the lateral ventricle of the brain. This study demonstrated that ES cells were able to integrate in mouse brain and produce astrocytes localized predominantly in the parenchyma and functional neurons, which were found migrating in the subventricular along facial flow and also in the olfactory bulb, although these grafts in the brain was low >0.1% (Muotri et al. 2005).

The advantage of dental pulp stem cells came from the embryonic origin of the pulp tissue. Craniofacial tissues originate from the neural crest, which is a transient embryonic structure. According to current knowledge, the neural crest stem cells (NCSC) have a high auto renewal ability and differentiation potential similar to ES cells.

Post-migratory NCSC originate most cells and tissues which generate the peripheral nervous system, as well as various non-neural cell types such as smooth muscle cells of the cardiovascular system, epithelial cells of the skin, craniofacial bones, cartilage and connective tissue, corneal epithelium and dental pulp and others (LE DOUARIN, DUPIN, 2003; DOUARIN LE et al., 2004, 2008).

Intra-uterine stem cells transplantation (IUSCT) is a method for the treatment of genetic, congenital, hematological, and immunological diseases. In basic research it provides a model for studying the dynamics of migration, graft and functional status of different types of stem cells. The cells can be transplanted in different moments of gestational period, which can be divided into quarters that are not functionally equivalent. The choice of the cells and quarter where the stem cells will be applied can influence cells behavior and results of transplantation. Fetal and adult hematopoietic or bone marrow derived mesenchymal stem cells (MSCs) were mainly used for IUSCT. We previously obtained human immature dental pulp stem cell (IDPSCs), which showed pluripotent potential and immune-compatible properties.

The goal of our study was to evaluate migration capacity, proliferation, homing and differentiation of IDPSCs after IUSCT during the third fetal period in dogs. All experimental procedures were approved by the Ethical Committee of the School of Veterinary Medicine and Animal Science of Sao Paulo University and were performed under appropriate anesthesia. $1 \times 10^6$ of undifferentiated GFP-positive human IDPSCs were transplanted following laparotomy and intraperitoneal injection under intra-operative ultrasound control into 5 fetuses at the 45 days of gestation. Five fetuses, which did not receive IDPSCs, were used as a control. Ultrasound analyses were performed daily before collection of the fetuses. After 7 days ovarian hysterectomy was performed, fetuses were collected; organs and tissues were isolated and fixed in 4% paraformaldehyde or cryopreserved.

Biodistribution of EGFP LP IDPSCs within the organs and tissues were analyzed on cryosections (5 µm) under Confocal Microscopy. Homing of EGFP LP IDPSCs was observed in organs derived from three germ lines, endoderm, ectoderm and mesoderm.

In stomach and in intestine EGFP LP IDPSCs were found in the intraglandular space as well as in muscularis mucosae. In liver they appeared in hepatic parenchyma; in heart in myocardium and in brain in bold vessels, in cerebellum within Purkinje cells. Using Flow cytometry assay EGFP LP IDPSCs graft was quantified. Among the different organs an expressive homing was observed in myocardium of heart (~50%), in spleen and liver. The EGFP LP IDPSCs were also found in canine placenta, especially in blood vessels. These data were confirmed using anti-human nucleus (HuNu), anti-GFP and anti-IDPSCs anti-bodies. Human EGFP LP IDPSCs showed high migration capacity and proliferation potential after IUSCT in dog fetuses. Undifferentiated EGFP LP IDPSCs demonstrated homing in fetal hematopoietic (placenta), epithelial (gastric glands) and perivascular stem cells niches. Our data suggest that EGFP LP IDPSCs is a new promising source for genetic, congenital, hematological, and immunological treatment for those diseases through IUSCT.

Experimental Group—Animals

We used the canine model (*Canis lupus* familiar), SRD (mongrel), female, 3-4 years old, pregnant with approximately 43 days of gestation.

Abdominal Ultrasound to Estimate Fetal Age

The sonographic examinations were performed on days 3, 2 and 1 prior to the surgical procedure, with a handset GE® brand, model Logic 100 MP, equipped with transducers: 7.5 MHz linear, convex 5.0 MHz and another endocavitary. The images were digitally documented.

The 7.5 MHz linear array transducer was used in all tests for clinical evaluation of organs and uterus, while the 5 MHz transducer was useful for evaluating the fetal body in its length and dimensions, especially when it exceeds the limits of zonary placenta, such as CR (body length-Crow-Rump) was measured from the distance between the most rostral skull to the base of the tail (DTC transverse diameter of the fetus) was obtained from the distance dorsum and ventral-lateral-lateral fetus. The measurement of PE (thickness of placenta) was obtained in defining the structure in relation membranes.

In order to determine the fetal age, making sure that the fetuses were aged less than 43 days, obtained through evaluation of ecogenicidades lung and liver. We also measured heart rates (HR) making sure fetal viability before and after the cell transplantation.

Mapping and Location of the Uterus Placenta Belts

Scheme 1 exemplifies the uterine horns of the experimental model: Group treatment fetuses 1, 3, 4 and 5 of the right uterine horn (Cud)-received transplants GFP-tagged IDPSC. The control group of fetuses were in 2 and 7 of the left uterine horn (Cue); these were collected for the experimental control (FIG. 61).

Procedures for Intra Uterine Transplantation in Fetal Canine Model

We divided the surgical procedures employed in this research three different times:

1ST Time Beginning 3 Days Prior to the Surgical Procedure I

1—Clinical assessment of the pregnant female

2—Abdominal ultrasound (US) to determine age and fetal viability

3—Collecting blood for CBC

4—Fast food 12 hours before surgery and 4 hours of fluid deprivation.

5—Anesthetic Technique in both surgical procedures:

Pre-anesthesia with acepromazine (Univet, São Paulo, SP) at a dose of 0.1 mg/kg associated with Meperidine (Cristália Chemicals and Pharmaceuticals, Itapira) 5 mg/kg IM (intra muscular), 15 minutes after proceeded to the induction of anesthesia with ketamine at a dose of 7.5 mg/kg dose associated with diazepam 5 mg/kg, then used the Epidural anesthesia with morphine at a dose of 1.0 mg/3 kg associated with Lidocaine 2% without vessel constrictor (Cristália Chemicals and Pharmaceuticals, Itapira) via lumbosacral with hypodermic needle 40×8. During surgery was used Fentanyl (pain reliever) (Hipolabor, Sabará) at a dose 4.4 mg/kg IV (via inta-venous) and Ampicillin Sodium (antibiotic) 20 mg/kg IV.

1—Surgical Procedure 1—Exploratory Laparomia

2—Mapping to count uterine fetuses and identification of fetuses paraplacentary right uterine horn (CUD)

3—Guided by US-endocavitary probe to identify the peritoneal cavity of the fetus 4—Transplant intrauterine IDPSC $1 \times 10^6$ cells resuspended in 1.0 ml sterile saline via intraperitoneal fetuses 1, 3, 4 and 5 Cud.

5—Daily Care: ATB (antibiotic therapy) therapy Enrofloxacin 10% at a dose 5.0 mg/kg SC (subcutaneously) BID (every 12 hours) and Anti-flamatório Meloxicam 0.2% at dose 0.2 mg/kg on day 1 and 0.1 mg/kg in the 2nd and 3rd days after SC SID (every 24 hours) and dressing area with liquid Iodine and Dakim polyidine 6—Animal was kept in a kennel with food and water ad libitum, and Elizabethan collar as mechanical restriction animal.

$2^{nd}$ Time Conducted 7 Days after the Transplantation of Uterine GFP-tagged IDPSC 1—abdominal ultrasound to determine fetal viability (heart rate—HR, peristalsis fetal movement fetal)

2—Collection of the mother's blood for CBC

3—Fast food 12 hours before surgery and 4 hours of fluid deprivation.

Surgical Procedure II—Ovariosalpingohisterectomy within 3 Days Subsequent Proceeded:

1—Abdominal ultrasound on days 1, 2 and 3 post-surgery clinical evaluation

2—Daily Care postoperative similar to previous (ATB, Healing and Anti-flamatório site)

3—Animal kept in kennels for 3 days with food and water ad libitum and Elizabethan collar.

4—High return the animal to its owner.

$3^{rd}$ Time Immediately after the Removal of the Uterus Carried out:

Fetal autopsy—collection of organs and tissues of fetuses 1, 3, 4 and 5 (treatment group—CUD) for later analysis of Xeno-transplantation, as well as the fetuses 2 and 7 control group—CUE+2 CUD fetus.

Immediately after autopsy of fetuses were collected the following organs: Tongue, esophagus, thymus, lung, heart, diaphragm, abdominal aorta, Stomach, Small Intestine (Jujuno), Spleen, Kidney Law, gonad (ovary or testis), Brain, Cerebellum Placenta and collected as follows:

SAMPLE 1—⅓ of the organ paraformoldehyde was previously included in the 10% and immersed in paraffin.

Sample 2—⅓ paraformoldehyde also be set at 10%, but will be included in OCT ("optimal cutting compound" Tissue-Tek®)

SAMPLE 3—⅓ of the organ was kept frozen in cryotubes in the Freezer at −80 C.

Flow Cytometry Analysis

The cells were harvested by trypsinization and trypsin was inactivated with fetal bovine serum, the cells were placed in 15 ml tubes. Then, the material was centrifuged at 1500 rpm for 10 minutes to form the cell pellet. After centrifugation, the supernatant was discarded and resuspended in 5 ml 0.9% saline solution to wash centrifuged at 1500 RPM for 10 minutes and the supernatant again discarded and the FACS buffer Flow added, the suspension was transferred to tubes cytometry, and added all specific anti-human antibodies, such as Anti-HuNu anti-IDPSC, CD 45, CK18, CD 146, OCT 3/4, β1 integrin, Cardiotin, MyoD1 and Myogenin, human, incubated for 15 minutes at 4° C. The expression analyzes were performed on FACS Calibur flow cytometer for 10,000 events and analyzed by the acquisitions program Mdi Win 2.8. The marker expression was determined by comparison with an isotype control labeled with FITC unspecific fluorochrome.

The evaluation of the expression of cytoplasmic and nuclear markers Anti-IDPSC Anti-HuNu and Oct3/4 cells were permeabilized with previously 10 µl of Triton X-100 (0.1%) for 30 minutes prior to addition of primary antibodies specific.

Analysis of Cell Cycle

After cell isolation from the various organs, they were carefully resuspended in 1 ml 70% ethanol RNAse, transferred to microcentrifuge tubes and stored at a temperature of −20° C. The fixed samples were centrifuged and stored previously at 2000 rpm for 5 minutes. The supernatant was discarded, the cells resuspended in 1 ml cytometry buffer and centrifuged again. After centrifugation, the supernatant was discarded and the cells resuspended in PI solution, prepared from 5 ml of PBS to which was added 5 µl triton 100 (0.01% v/v), 50 mL of RNAse A (2 mg/ml) and 20 µl of propidium iodide (5 mg/ml). Then there was the acquisition of data flow cytometer FACS Calibur on 10,000 events, and analysis program was used Mdi Win 2.8.

After the acquisition of cell populations, cells positive for EGFP protein contained in the gate or quadrant were selected and determined the cell cycle phases using the FL-2 channel for the quantification of PI (propidium iodide) incorporated GFP+cells.

Interpretation of Results

Propidium iodide (PI) is a stoichiometric fluorochrome which intersperses the double strands of DNA. The fluorescence was captured in FL-2, and it is proportional to the DNA content in the cell. Diploid cells that are not replicating (G0/G1 phases of the cell cycle) have 2n cell contents, emitting signals of lower intensity than the cells located in the S phase, during which there is an increase of DNA content. S-phase cells, in turn, generate signals of lower intensity than those located in G2/M until complete replication of the DNA content to 4n, which remains so during the G2 phase to mitosis, in which each mother cell gives rise to two daughter cells.

Cells located at the peak hipodiplóide (Sub-G1) possess DNA content less than 2n, and may represent increased occurrence of cell debris and fragmented DNA, characteristic of cell death events.

All generated signals are amplified and converted into pulses by the apparatus, allowing the construction of distribution graphs of cells in cell cycle. Whereas there is a proportional relationship between the increase in DNA content and area of the pulse generated.

Immunohistochemistry

For immunohistochemical analysis were used paraffin sections mounted on slides. For this procedure the material was previously included in paraformoldehyde to 4%, paraffin-embedded and cut to 5.4 µm (Microtome, LEICA).

The tracking of EGFP LP IDSPC injected via IP, was performed using antibodies: anti-IDPSC: marker of human tooth pulp, and anti-human nucleus—HuNu.

For the realization of the technique of immunohistochemistry, the blades have undergone a process of being immersed in xylene at 50° C. for 30 minutes and then immersed in xylene at room temperature for 20 minutes. To minimize the natural fluorescence of the tissue, it was necessary to immerse slides in Methanol+Acetone "overnight". After this process, the material was hydrated in a series of decreasing alcohols (100%, 95% and 75%) for 2 minutes and incubated for 10 minutes in ammonium hydroxide solution for removal of residual formalin.

During the fixing the process of antigen masking in the tissue can occur, making it harder to detect. To increase the antigen exposure was used for antigen retrieval moist heat which the material was immersed in citrate buffer and placed in water bath for 35 minutes.

In the next step, the blades endogenous peroxidase was blocked with a solution of methanol and hydrogen peroxide (1:1). After this step, the tissues were incubated with primary antibodies in a humid chamber "overnight" 4° C. Past this stage, the material was revealed with the Dako Envision Kit and dehydrated in an ascending series of alcohols (50%, 75%, 95% and 100%). The chromogen used was DAB (Dako®), slides were counter-stained with Mayer's Hematolixina sealed with Permount and visualized by light microscopy.

Quantification of EFGP LP IDPSC and Measurement of Proliferation and Differentiation after Intrauterine Transplantation After we provided a multiple evidences about grafting of EGFP LP IDPSC in various tissues derived from three germ layers we evaluated their possible proliferation and differentiation within recipient tissues.

Analysis of the Endoderm Derived Tissues—Lung

Lung tissue showed high rate EGFP LP IDPSC grafting as measured by red immunopositive staining (FIG. X A,B). The choice of rhodamine secondary antibody was to avoid the interference of fluorescent signal emitted by green EGFP LP IDPSC. The rate of grafting was 52.8% as observed by the expression of anti-IDPSC and 50.2% of anti-HuNu antibodies (FIGS. 62A-62B). Then proliferation was analyzed for EGFP LP IDPSC (FIGS. 62C-62D) by flow cytometry and revealed that 53.17% of EGFP LP IDPSC had their DNA fragmented, 29.88% were in the G0/G1 phase (quiescent cells and in preparation for DNA synthesis), 8.53% was found in stage S of DNA synthesis and 8.65% in the G2 phase of cell division.

Analysis of Tissues Derived from Mesoderm—Striated Skeletal MUSCLE TISSUE—BICEPS FEMORIS Quantification of EGFP LP IDPSC in mesoderm was performed using skeletal muscle tissue (biceps femoris) (FIGS. 63A-63D) and kidney tissue and (FIGS. 64A-64D). The rate of grafting as measured by the expression of anti-IDPSC and anti-HuNu was 34.29% and 36.86%, respectively. The analyzes of cell cycle of EGFP LP IDPSC grafted on biceps femoris revealed that 22.28% had fragmented DNA, 8.82% were in G0/G1 phase (quiescent cells and in preparation for DNA synthesis), and 2.64% were S stage of DNA synthesis and 31.70% in the G2 phase of cell division (FIGS. 63C-63D).

Renal Tissue

In renal tissue the rate of EGFP LP IDPSC grafting was 42.3% (anti-IDPSC) and 31.3% (anti-HuNu) (FIGS. 64A-64B). The analysis of cell cycle of EGFP LP IDPSC in biceps femoris revealed that 50.07% had fragmented DNA, 15.92% were in phases G0/G1, 8.97% were in S phase and in phase 25.25% G2 (FIGS. 64C-64D).

Analysis of Tissues Derived from Ectoderm—Brain and Cerebellum

In brain tissue samples to observe the rate of EGFP LP IDPSC grafting 13.1% (anti-IDPSC) and 13.4% (anti-HuNu) (FIGS. 65A-65B). The cell cycle analysis of EGFP LP IDPSC in brain revealed that 8.52% of the cells had fragmented DNA, 3.24% were in phases G0/G1, 29.1% were in S phase and in G2 phase 66.59% (FIGS. 65C-65D).

Analysis of Extra-Embryonic Tissues—Placenta Maternal and Hematoma Placental

We detected the grafting of EGFP LP IDPSC in PLACENTA MATERNAL AND HEMATOMA PLACENTA. We quantify the grafting of EGFP LP IDPSC only in placental belt and found that this graft was 64.8% (anti-IDPSC) and 65.6% (anti-HuNu) (FIGS. 66A-66B). Then we analyzed the viability and proliferation of EGFP LP IDPSC and in placental belt hematoma placental separately, which was different in there fetal structures. Our data suggest that the environment and function of placental tissue may have the effect on the viability and proliferation of EGFP LP IDPSC. Analysis of the cell cycle in placental central belt revealed that 21.96% of EGFP LP IDPSC had fragmented DNA, 10.83% were in phases G0/G1, 3.59% were in S phase and in 38.64% G2 phase (FIGS. 66C-66D). In bruising marginals or side pockets with respect to the central placental belt demonstrated a higher rate of fragmented DNA 31.82% and lower phases G0/G1, S and G2 was 7.40%, 1.63% and 13 13%, respectively.

Cardiac Tissue

Expression of Oct3/4 and MSC Markers in the Muscle Tissue

It is known that EGFP LP IDPSC expressing Oct3/4 while they are not differentiated (Kerkis et al. 2006). We analyzed the expression of this marker in canine fetal myocardium, due to the present study the EGFP LP IDPSC showing a high grafting in this tissue. Immunofluorescence analysis demonstrated the expression of this protein in EGFP LP IDPSC and demonstrated its location within the nucleus (FIGS. 67A1-67A3). The size of these cells is less than 5 µm, which suggests that they present the characteristics and localization of myocyte also called satellite cells. Flow cytometry allow to quantify the rate of EGFP LP IDPSC, which express anti-Oct3/4 antibody and which was equal to 21.3% (FIGS. 68A-68B). At the same time the rate of expression of MSC markers: CD146 (pericytes) and β1-integrin in the same tissue was very low and was 0.1% and 0.5% respectively.

Additionally we analyzed the expression of these markers in skeletal muscle of the biceps femoral. We observed a high rate of protein expression Oct3/4, CD146, β1-integrin which was equal to 45.4%, 0.4% and 36.7%, respectively (FIGS. 68C-68D).

Skeletal Muscle Tissue—Biceps Femoris

We evaluated whether EFGP LP IDPSC undergone the process of differentiation in muscle tissue of the myocardium. The myogenin and cardiotin proteins expressed in these cells with respective rates of 29.7% and 49.1% (FIG. 69), while expression of CK 18, which is a marker of epithelial cells, was low 4.7% in muscle tissue, as expected. The protein CD45, which is a marker of different types of hematopoietic cells, was expressed in EFGP LP IDPSC in grafted heart tissue. In order to validate this result we compared the expression of this marker in heart muscles and aorta where it is expected to be different. As expected the rate of expression of CD45 on heart muscle was 9.6% vs. 19.5% in the aorta (FIG. 69). The study of the expression of markers of differentiated muscle cells in the striatum of the biceps femoral muscle revealed the presence of MyoD1 and myogenin in 33.87% in 7.5% of analyzed the cells, respectively (FIG. 69). CK 18 was positive in 7.7% of cells, while CD45 in 12% of analyzed cells.

Heart Tissue

Expression of markers of differentiated IDPSC in cardiac tissue showed positive expression of cardiac proteins myogenin and cardiotin and negative for CK-18. We observed positive expression of CD45+, which quantity varies in myocadium and in the aortic arch (FIG. 70).

Skeletal Muscle Tissue—Biceps Femoris

The EGFP LP IDPSC showed positive immunostaining for Oct 3/4, which present nuclear and perinuclear localization (FIG. 72). The rate of EGFP LP IDPSC Oct 3/4 was also assessed by Flow Cytometry and was 12.6%. The expression of markers of MSCs, such as CD146 (pericytes) and β1-integrin was 2.5% and 18.3% respectively (FIG. 73).

In placental tissue we also observed the protein expression of CD45 in CK18 in 9.4% and 2.3% of cells, respectively. The expression of myogenin was registered in 16.6% of the cells that is possibly corresponded to engraftment of EGFP LP IDPSC in the smooth muscle tissue that coats the placental vessels.

Example 15 Isolation and In Vitro Culture of IDPSCs

Human dental pulp (DP) was extracted from ten deciduous teeth of ten healthy subjects (range 6-9 years) through removal of the tooth's apical part using a scalpel as previously described by Kerkis et al. (Kerkis et al. (2006) Isolation and characterization of a population of immature dental pulp stem cells expressing OCT-4 and other embryonic stem cell markers. Cells Tissues Organs 184: 105-116).

Next, DP was gently rinsed in phosphate-buffered solution (PBS) (Invitrogen, Carlsbad, Calif., USA), slightly dissected and placed into 35 mm plastic tissue culture dishes (Corning Inc., Corning, N.Y., USA).

DP tissue explants were cultured in Dulbecco's-modified Eagle's medium (DMEM)/Ham's F12 (DMEM/F12, Invitrogen Corporation—Carlsbad, Calif., USA) supplemented with 15% fetal bovine serum (FBS, Hyclone, Logan, Utah, USA), 100 units/ml penicillin, 100 mg/ml streptomycin, 2 mM L-glutamine, and 2 mM nonessential amino acids (all from Invitrogen) in a 5% CO2 humid atmosphere at 37° C.

After a period of 3 or 4 days, fibroblast-like cells were generated from adherent explants. To generate large numbers of IDPSCs, explants were transferred to another Petri dish under the same culture conditions, and this procedure was repeated several times as shown in FIG. 74. This process of generating IDPSCs is distinct from that in which Stem Cells from Human Exfoliated Deciduous teeth (SHED) are cultured (see FIG. 75). After isolation, SHED are immediately subjected to enzymatic digestion, which prevents the generation of certain populations of stem cells such as those expressing the p53 and p75 biomarkers.

Fibroblast-like cells growing in monolayer were further washed twice with PBS and subjected to 0.5 g/L trypsin and 0.53 mmol/L Ethylenediamine tetra-acetic acid (EDTA) (Invitrogen) for 3 to 5 minutes at 37° C.

Passage 1 was counted after the first enzymatic digestion. Trypsin activity was inactivated by addition of culture medium supplemented with 10% fetal bovine serum (FBS). Approximately $5 \times 10^5$ cells were placed into 25 cm$^2$ cell culture flask (Corning). Sub-culturing was performed every 3 to 4 days, and the culture medium was changed daily.

After isolation and expansion, stem cells from deciduous were cryopreserved (CRYOP) as shown in FIG. 75. For cryopreservation, 90% FBS and 10% dimethylsulfoxide (DMSO) (Sigma, St. Louis, Mo., USA) were used as freezing medium. Frozen cells were maintained in sealed vials at −196° C.

Example 16

Long-term In Vitro Culture of Dental Pulp (DP)

Freshly extracted dental pulp (DP) is a tissue, which contains large nerve trunks and blood vessels in the central region of the coronal and radicular pulp (FIG. 76A). The first outgrowth of fibroblast-like cells appeared between three to four days after DP plating (FIG. 76B). Long-term culture was performed by mechanical transfer of DP into a new culture dish without using enzymatic treatment. After each transfer, DP produced large numbers of outgrowing cells approximately every three or four days, thus allowing constant production of stem cells (SCs) at passage zero (P0) (se FIGS. 74 and 75). We performed multiple mechanical transfers of DP each 3 to 5 days during at least six months. We obtained successful isolations with all samples (n=10) of deciduous teeth.

Example 17

IDPSCs Morphology (Phenotype) Following Long-term Culture of DP

For transmission electron microscopy (TEM), EP and LP of IDPSCs were fixed in 2.5% glutaraldehyde (Sigma) for 48 h, post-fixed in 1% phosphate buffered osmium tetroxide solution (pH 7.4) (Sigma) for 2 h at 4 C, and embedded in Spurr's Resin (Sigma). Ultrathin sections were obtained using an automatic ultramicrotome (Ultracut R, Leica Microsystems, Germany). Sections were double-stained with uranyl acetate (Sigma) and lead citrate (Sigma) (2% and 0.5%, respectively) and analyzed using TEM (Morgagni 268D, FEI Company, The Netherlands; Mega).

During long-term culture of DP the morphology of both, Early Population (EP) (i.e., IDPSCs isolated from outgrowths of cells during the initial mechanical transfers of the DP for 2 weeks or less after extraction) and Late Population (LP) (i.e., IDPSCs isolated from outgrowths of cells during the later mechanical transfers of the DP for greater than 2 weeks after extraction) of IDPSCs was preserved (see FIG. 76C). TEM revealed two types of IDPSCs morphology:

1. ES-like cells with low cytoplasm-to-nucleus ratio, low cytoplasm density, and poor of organelles (FIG. 76D); and
2. MSC-like cells IDPSCs having a high number of stretched out pseudopods serving in substrate exploration with more cytoplasm and organelles compared to ES-like IDPSCs (FIG. 76E).

FIG. 76F documents that IDPSCs showed a relatively uniform population in respect to morphology for these two cell types.

Example 18

Karyotype Analyses

Karyotyping of subconfluent EP and LP of IDPSCs cultured in DMEM/F12 medium (Invitrogen) was performed at passage 3. Before harvesting, Demecolcine (Sigma) at a final concentration of 0.1 mg/ml was added for 1 hour. Cells were harvested, washed in PBS and resuspended in 0.5 ml of medium and mixed with 0.075 M KCl (Sigma) to a volume of 10 ml. After incubation for 20 minutes at room temperature, cells were centrifuged at 400 g for five minutes and the pellet fixed in 5 ml three times (3:1) of cold methanol/acetic acid (Sigma). Three drops of cell suspension were fixed per slide. For chromosome counting, slides were stained in Giemsa for 15 minutes and; >200 cells were analyzed per cell line and reported on a Zeiss II microscope (Zeiss, Jena, Germany) according to the International System for Human Cytogenetic Nomenclature. LP IDPSC karyotype was confirmed here to be unchanged, suggesting that during culture, numerical and gross structural chromosomal abnormalities did not occur as shown by the routine G-banding technique (FIG. 76G).

Example 19

Stem Cell Migration within Dental Pulp: Localization of BrdU Positive Cells in DP During In Vitro Cultivation To examine BrdU positive cells in DP during in vitro cultivation dental pulps were gently rinsed in PBS and sliced. Each slice was placed in a different culture dish. Next, 5-bromo-29-deoxyuridine (BrdU, Sigma) was added directly into the basal culture medium. The first pulp slice was fixed and processed after 6 h of treatment with BrdU. In the second culture dish with a pulp slice, BrdU was added after 42 h and in the third, after 66 h.

After 6 h of treatment with BrdU, all slices were fixed in 10% formalin solution for 48 h. The specimens were embedded in paraffin blocks and sections of 10 mm were obtained. All above specimens were treated by immunohistochemical methods as follows. Paraffin sections of 10 mm were deparaffinized and then hydrated. Endogenous peroxidase activity was measured by incubating the sections for 30 min in a 0.1% solution of hydrogen peroxide (Sigma). For antigen retrieval, sections were incubated with trypsin for 10 min at 37 C. To inhibit nonspecific antigen binding, sections were incubated with blocking serum (5% fetal calf serum, Invitrogen) for 10 min. Sections were then incubated for 12-16 h with the primary antibody in a moist chamber at 4 C.

Primary antibodies were the same used in immunophenotyping of IDPSCs and additionally anti-human STRO-1 (Santa Cruz) and mouse anti-BrdU IGg (Chemicon). The optimal dilution of the primary antibody was found to be 1:10. Slides were again rinsed with PBS and then incubated with biotinylated secondary antibody (DAKO, Glostrup, Denmark) in 1:200 dilution for 30 min. The samples were washed with PBST (PBS with 0.1% of Tween 20) and incubated with StrepABComplex/HRP (DAKO) at 1:100 dilution for 30 min. After one more wash with PBST, the colour was revealed by the chromogen 3 (3-diaminobenzidine DAB Kit, Zymed Laboratories, Inc.) for 5 min, followed by PBST washing, nuclear counterstaining with Harris haematoxylin for 45 s, dehydrated and mounted in Permount. Observation of the sections was conducted using a Carl Zeiss Axioplan fluoromicroscope (Zeiss). Negative control sections were treated identically, except the primary antibody, which was substituted by PBS.

In order to understand the continuous process of IDPSCs generation, DP was treated with BrdU just after extraction and in vitro plating (FIGS. 77A-77C). After 6 h, only a few anti-BrdU antibody positive cells were found in the central part of DP (FIG. 77A). After 48 h, BrdU positive cells were observed in the periphery of DP (FIG. 77B), while after 72 h, BrdU positive cells increased in number and were also found in the periphery of DP in the apical part, close to IDPSCs outgrowing zone (FIG. 77C).

Example 20

DP Tissue after Enzymatic Treatment

At least two methods may be used for tissues-specific stem cell isolation: enzymatic treatment and explant culture. For stem cells isolation, soft tissues are cut into small pieces and treated with enzyme after tissue disaggregation.

We compared morphological characteristics of DP with and without enzymatic treatment (collagenase/dispase) (FIGS. 77D-77E). DP, without any treatment, maintained their integrity especially in the region where BrdU positive cells were observed (FIG. 77D). However after enzymatic digestion this region was destroyed (FIG. 77E). We therefore chose the DP explant method for isolation of DP stem cells (SC). Comparative morphological analysis demonstrated that prior SC isolation enzymatic treatment is not recommended for DP as it probably destroys the SCs "niche".

Example 21

In Vivo Immunophenotype of Dental Pulp Stem Cells

IDPSC immunophenotyping was based on immunofluorescence and flow-cytometry analyses performed by using anti-human specific antibodies: vimentin, nestin, fibronectin, and Oct3/4 (all from Santa Cruz Biotechnology, Santa Cruz, Calif., USA); and CD105/SH-2 and CD73/SH-3 (both from Case Western Reserve University, OH, USA). FITC-conjugated secondary antibodies (Chemicon, Temecula, Calif., USA) were used and respective isotype matched controls. Immunofluorescence was analyzed using the aforementioned antibodies after cell fixation in 4% paraformaldehyde (Sigma) in PBS and permeabilization in 0.1% Triton X-100 (Sigma) in PBS. IDPSCs were incubated with 5% bovine serum albumin (BSA, Sigma), diluted in PBS for 30 minutes, and further incubated for 1 h at room temperature with FITC-conjugated goat anti-mouse or anti-rabbit immunoglobulin (Chemicon) at a final dilution of 1:500 in PBS (Invitrogen).

Microscope slides were mounted in Vectashield mounting medium with 49.6-Diamidino-2-phenylindol (DAPI, Vector Laboratories, Burlingame, Calif.) and immunofluorescence was detected using a Carl Zeiss Axioplan fluoromicroscope (LSM 410, Zeiss, Jena, Germany) or a Nikon Eclipse E1000 (Nikon, Kanagawa, Japan). Digital images were acquired with a CCD camera (Applied Imagingmodel ER 339) and the documentation system used was Cytovision v. 2.8 (Applied Imaging Corp.—Santa Clara, Calif., USA).

Flow-cytometry was performed using EP and LP of IDPSC at passage 3. Cells were detached by using a 10 min treatment at 37 C with PBS 0.02% EDTA, pelleted (10 min at 400 g) and washed in 0.1% BSA in 0.1 M PBS at 4 C. Next, cells at a concentration of $10^5$ cells/ml were stained with a saturating concentration of the aforementioned antibodies (10 ml). After 45 minute of incubation in the dark at room temperature, cells were washed three times with PBS and resuspended in 0.25 ml of cold PBS. Flow-cytometry analysis was performed on a fluorescence activated cell sorter (FACS; Becton, Dickinson, San Jose, Calif.) using the CELL Quest program (Becton, Dickinson). The flow cytometry and/or immunofluorescence analyses were repeated with all samples (n=10), and representative experiments are presented in the figures. All experiments were done performed at least in triplicate.

Using these immunohistochemical assays the niche of nestin, vimentin (markers of MSCs) and Oct3/4 (marker of ES cells) cells within DP (FIGS. 78A-78Q) were identified. Nestin positive cells were found in all zones of DP: in the cell rich zone (innermost pulp layer which contains fibroblasts and undifferentiated mesenchymal cells) (FIGS. 78A-78C); in cell free zone, nestin expression was observed in both capillaries and nerve networks (FIGS. 78D-78F); as well as in the odontoblastic layer (outermost layer which contains odontoblasts and lies next to the predentin and mature dentin) (FIGS. 78G-78H). Nestin positive cells in the cell rich zone showed fibroblast-like as well as ES-like cell morphologies (FIGS. 78B-78C). In the cell free zone, nestin protein was found to be expressed in intermediate filaments in the cells from the plexus of nerves (FIG. 78D). In addition, nestin positive cells were embedded in the wall of small capillaries (FIG. 78E) and in adjacent regions of these capillaries (FIG. 78F).

In the odontoblastic layer, several round ES cell-like and large columnar cells were also nestin positive (FIGS. 78G-

78H). STRO-1 is a specific marker for stem cells/pericytes from DP. STRO-1 antibody was thus used as control. The expression of STRO-1 was mainly observed in small capillaries and middle size blood vessels (FIG. 78J), as well as in the plexus of nerves in the cell free zone (FIG. 78K). We also verified localization of vimentin expressing cells in DP. As expected, vimentin positive cells were localized in capillaries and in the innermost pulp layer, locations where nestin positive cells were also found (FIGS. 78L-78M).

We also examined the expression of Oct3/4 in DP. Initially, only a small percentage (~0.75%) of cells were Oct3/4 positive. This percentage increased with time of DP in vitro cultivation. Strong expression of Oct3/4 was observed in nuclei of cells localized in DP capillaries and in innermost pulp layer (FIGS. 78N-78Q).

Example 22

Immunophenotyping of EP and LP of IDPSCs

Early Population (EP) and Late Population (LP) stem cells were characterized using several markers including SH2/CD105, SH3/CD73 (MSCs markers) and Oct3/4 (ES cells marker). Additionally, expression of MSCs markers such as vimentin, nestin, fibronectin was evaluated in both EP and LP. Representative FIG. 79 (A1-E1, A2-E2) shows that all MSC markers were expressed in both populations (EP and LP) and slightly declined in LP SCs after six months of multiple DP transfer cycles (FIGS. 79A2-79E2) with the exception of Oct3/4.

The percentage of IDPSCs, which showed positive immunostaining for these markers, was evaluated by flow cytometry. The results were: 99.10% to EP and 96.60% to LP for SH2/CD105; 99.60% to EP and 98.40% to LP for SH3/CD73; 97.76% to EP and 94.56% to LP for nestin; 99.45% to EP and 95.60% to LP for vimentin; 97.10% to EP and 96.30% to LP for fibronectin (FIGS. 79A1-79E1 and 79A2-6E2).

Interestingly, in this particular IDPSC population a very low percentage of Oct3/4 positive cells 0.75% was observed in EP. This percentage increased to 10.03% in LP cells (FIGS. 79F1 and 79F2).

Flow cytometry data were confirmed by immunostaining of cells using antibodies against the same MSC and ES cell markers. Expression was observed in both EP and LP of IDPSCs. In FIG. 79, the expression of MSC markers in LP is presented (FIGS. 79A3-79E3). As expected, Oct-3/4 protein expression was observed in the cell nuclei (FIG. 79F3). Except for the case of Oct-3/4, the expression of all these markers in LP was similar to EP (data not shown). LP IDPSCs isolated from four unrelated donors demonstrated variable proportions of Oct-3/4 positive cells from 5% to 47% (FIGS. 80A-D).

Example 23

Culture Media Influence EP and LP Growth Rate

To evaluate the effect of different culture media on cell growth, freshly isolated and the same IDPSC frozen-thawed were equally divided in three groups (DMEM/F12), DMEM low-glucose (1000 mg/ml; DMEM-LG), and Minimum Essential Medium (MEM) Alpha Medium (MEM-alpha). All media (Invitrogen) were supplemented with 15% FBS (Hyclone), 100 units/ml penicillin, 100 mg/ml streptomycin, 2 mM L-glutamine, and 2 mM nonessential amino acids (all from Invitrogen). Cells were seeded at a density of $10^5/cm^2$ and counted for at least fifteen consecutive days to evaluate the growth rate and the effect of cryopreservation. The capacity of the DP tissue explant to produce IDPSC after consecutive rounds of cryopreservation and thawing was also verified. All experiments were performed in triplicate.

Growth curves were constructed using data from cell lines, passage number (P2 to P15), cryopreservation, and growth medium. Cell number data were analyzed by using two-way analysis of variance ("cryopreservation" and "growth medium") complemented by Tukey post hoc multiple comparison tests. The significance level was set at 5% (SPSS 19.0, Chicago, Ill., USA).

Proliferative capacity of EP and LP of IDPSCs before and after cryopreservation was also studied using three different culture media: DMEM/F12, DMEM-LG, and MEM-alpha. Starting from P2, non-cryopreserved cells were harvested following enzymatic dissociation and counted daily during 15 consecutive passages. IDPSCs cultured in DMEM/F 12 and MEM-alpha medium presented a constant proliferative rate during the initial passages, which achieved their peak growth at passage 5±2 (FIG. 82A, Table 5). Based on the growth curves presented in FIG. 81, statistical analyses were performed considering the cell number from passage 3 to 7 (Table 5). Using the same parameters, proliferative rate of EP and LP cultivated in DMEM/F12 and MEM-alpha media were evaluated after thawing and showed similar proliferative potential, when compared with those before cryopreservation (FIG. 81B, Table 5). Non-cryopreserved EP and LP of IDPSCs cultured in DMEM-LG presented spontaneous differentiation into osteogenic lineage (data not shown) and demonstrated rapid decrease of proliferative potential (FIG. 81A, Table 5). Interestingly, EP and LP of IDPSCs, cultured in DMEM-LG after thawing, maintained their proliferative state (FIG. 81B, Table 6). DMEM/F12 and MEM-alpha media did not induce any spontaneous differentiation in non-cryopreserved and cryopreserved EP and LP of IDPSCs.

TABLE 5

Number of IDPSCs cultured in three different growth media and at different passages before and after cryopreservation.

| Cell line | Growth media | Passage number | | | | | | | | | | | | | |
|---|---|---|---|---|---|---|---|---|---|---|---|---|---|---|---|
| | | 2 | 3 | 4 | 5 | 6 | 7 | 8 | 9 | 10 | 11 | 12 | 13 | 14 | 15 |
| Before cryopreservation | MEM-alpha | 100 | 165.5 | 364 | 431.5 | 476.5 | 394 | 378.5 | 321 | 266.5 | 189 | 176.5 | 147.5 | 119.5 | 90.5 |
| | DMEM-LG | 100 | 139.5 | 109.5 | 100 | 78 | 38.5 | a | a | a | a | a | a | a | a |
| | DMEM/F12 | 100 | 125 | 262.5 | 302 | 333 | 305.5 | 273.5 | 218 | 193 | 161.5 | 149.5 | 124.5 | 110.5 | 89 |
| After cryopreservation | MEM-alpha | 100 | 153 | 329 | 433.5 | 345 | 325.25 | 245 | 191.5 | 175.5 | 172.5 | 166.5 | 112.5 | 64.6 | 60.5 |

TABLE 5-continued

Number of IDPSCs cultured in three different growth media and at different passages before and after cryopreservation.

| Cell line | Growth media | Passage number | | | | | | | | | | | | |
|---|---|---|---|---|---|---|---|---|---|---|---|---|---|---|
| | | 2 | 3 | 4 | 5 | 6 | 7 | 8 | 9 | 10 | 11 | 12 | 13 | 14 | 15 |
| | DMEM-LG | 100 | 115.5 | 265 | 314 | 266 | 268.50 | 209 | 186.5 | 165.5 | 162 | 154.5 | 50 | 64.5 | 33.75 |
| | DMEM/F12 | 100 | 99 | 251.5 | 296.5 | 250.5 | 232.5 | 191 | 180.5 | 166.5 | 142 | 128 | 117.5 | 59.5 | 57 | a DMEM-LG did not support cell growth.
doi: 10.1371/journal.pone.0039885.t001

TABLE 6

Cell number (×10³) of IDPSCs (passage range P3-P7) cultured in different growth media before and after cryopreservation.

| Cryopreservation | Growth media | | |
|---|---|---|---|
| | MEM-alpha | DMEM-LG | DMEM/F12 |
| Before | 317.15 ± 101.81[a] | 245.80 ± 75.70[a] | 226.00 ± 74.82[a] |
| After | 366.30 ± 119.88[a] | 93.10 ± 37.68[b] | 265.60 ± 82.52[a] |

[a]Values are mean ± standard deviation, n = 5.
Means followed by the same letter are not statistically different (Tukey, p > 0.05).
doi: 10.1371/journal.pone.0039885.t002

Example 24

Culture Media Influence EP and LP Gene Expression

EP and LP of IDPSCs were cultivated during seven passages in three distinct media (DMEM/F12, MEM-alpha, and DMEM-LG). To evaluate the effect of these different culture media on gene expression, total RNA was extracted using Trizol (Invitrogen): IDPSCs were washed in PBS and RNA extraction was performed according to manufactures instructions. cDNAs were synthesized from 1 μg of total RNA reverse transcribed with the RevertAid M-MuLV Reverse Transcriptase and oligo (dT) (Fermentas Life Science, Amherst, N.Y., EUA) according to the manufactures instructions. The final concentrations of reagents were: 20 μl of PCR reactions were prepared with 2 μl cDNA, 0.2 μM of each primer, 1 unit of Taq DNA Polymerase, 0.2 μM of dNTPs, 1.5 mM of magnesium chloride and buffer Taq DNA Polymerase (Fermentas Life Science). Primer sequences (forward and reverse), and the lengths of amplified products are summarized: Nestin FW 5'-CTCTGACCTGTCA-GAAGAAT-3' (SEQ ID NO:1), and RV 5'-GACGCT-GACACTTACAGAAT-3' (SEQ ID NO:2) (302 bp/54° C.); Vimentin FW 5'-AAGCAGGAGTCCACTGAGTACC-3' (SEQ ID NO:3), and RV 5'-GAAGGTGACGAGC-CATTTCC-3' (SEQ ID NO:4) (205 bp/55° C.); Fibronectin FW 5'-GGATCACTTACGGAGAAACAG-3', (SEQ ID NO:5) and RV 5'-GATTGCATGCATTGTGTCCT-3' (SEQ ID NO:6) (386 bp/56° C.); OCT3/4 FW 5'-ACCACAGTC-CATGCCATCAC-3' (SEQ ID NO:7); and RV 5'-TCCAC-CACCCTGTTGCTGTA-3' (SEQ ID NO: 8) (120 bp/61° C.); SH2/CD105 FW 5'-TCTGGACCACTGGAGAATAC-3' (SEQ ID NO:9), and RV 5'-GAGGCATGAAGTGAGA-CAAT-3' (SEQ ID NO:10) (171 bp/56° C.); SH3/CD73 FW 5'-ACACGGCATTAGCTGTTATT-3' (SEQ ID NO:11), and RV 5'-AGTATTTGTTCTTTGGGCA-3' (SEQ ID NO:12) (391 bp/56° C.). For chondrogenic and myogenic differentiation, following primer sequences were used: COMP FW 5'-CCGACAGCAACGTGGTCTT-3' (SEQ ID NO:13), and RV 5'-CAGGTTGGCCCAGATGATG-3' (SEQ ID NO:14) (91 bp/53° C.); ACTB FW 5'-TGGCACCACACCTTCTA-CAATGAGC-3' (SEQ ID NO:15), and RV 5' GCACAGCT-TCTCCTTAATGTCACGC-3' (SEQ ID NO:16) (395 bp/59° C.); MYOD1 FW 5'-GCCGCCTGAGCAAAGTAAAT-GAGG-3' (SEQ ID NO:17), and RV 5'-TAGTCCATCAT-GCCGTCGGAGC-3' (SEQ ID NO:18) (280 bp/53° C.). GADPH gene FW 5'-ACCACAGTCCATGCCATCAC-3' (SEQ ID NO:19), and RV 5'-TCCACCACCCTGTTGCT-GTA-3' (SEQ ID NO:20) (463 bp/61° C.) was used as control. Undifferentiated IDPSC were examined as negative control for differentiation specific primers. PCR reactions were performed under the following conditions: 1 cycle at 94° C. for 5 minutes, followed by 35 cycles at 94° C. for 1 minute, annealing temperature for 1 minute, and 72° C. for 1 minute. Amplified products were resolved by electrophoresis on a 1.5% agarose gel (Sigma) and visualized using ethidium bromide (Sigma) staining.

The gene expression pattern of pluripotent ES cell and MSC markers were analyzed by RT-PCR in EP and LP after thawing. Overall, both EP and LP showed similar expression pattern of vimentin, SH2/CD105 and SH3/CD73 (FIG. 81C). Similar expression patterns were observed for fibronectin, nestin and Oct3/4, when IDPSCs were cultured in DMEM/F12 and DMEM-LG. However, it was distinct when cultivated in MEM-alpha, in which three of these genes (fibronectin, nestin and Oct3/4) did not show any expression (FIG. 81C).

Example 25

Expression Pattern of MSCs Markers in Immature Dental Pulp Stem Cells

For flow-cytometric analysis, the following antibodies against cell surface molecules and their respective isotype controls were used: monoclonal anti-human CD45, CD13 (Sigma), CD43, and CD34 (BD-PharMingen, San Diego, Calif., USA) and CD105 (Serotec, Oxford, UK). SH-2, SH-3, and SH-4 were from Case Western Reserve University, (Cleveland, Ohio, USA), mouse anti-human HLA-ABC and HLA-DR (Chemicon), CD90, CD146 (BD Pharmigen™), CD29 (Serotec), CD117/c-kit, CD44/Hcam (Santa Cruz, Calif., USA). About 10⁶ cells were incubated with primary antibody for 30 min on ice, washed in PBS+2% FBS and 1M sodium azide (buffer) followed by addition of secondary FITC- or phycoerythrin-conjugated antibody. For staining of intracellular antigens, the cells were fixed and the following protocol of permeabilization. The pellet was resuspended in 1 ml of Tween-20 solution (0.2% in PBS) at room temperature, and the mixture was incubated for 15 min in a 37° C. water bath. Flow-cytometric analysis was performed on a fluorescence-activated cell sorter (FACS, Becton, Dickinson, San Jose, Calif., USA) with the CELL Quest program (Becton, Dickinson).

Flow cytometry revealed that outgrowth cells from DP were uniformly positive for human MSCs-specific antigens, such as SH-2 (CD105), SH-3, and SH-4 (CD73) and CD13 marker of hematopoietic precursors (FIGS. 82A, 82B, and 82H) while human primary fibroblasts were negative for all these markers (data not shown). These cells isolated from DP were also negative for CD34, CD43 and CD45 ruling out contamination with hematopoietic and endothelial cells (FIGS. 82E-82G).

Additionally, the expression of HLA-ABC and HLA-DR major histocompatibility (MHC) antigens was examined by FACS. HLA (human leukocyte antigens) were originally defined as cell surface antigens that mediate graft-versus-host disease, which resulted in the rejection of tissue transplants in HLA-mismatched donors. Similar to MSCs from bone marrow, the expression of both of these proteins was not observed in IDPSC (FIGS. 83A-83B). We also analyzed a set of markers commonly used for MSC characterization:
 i) CD44 is a 80-250 kDa type I (extracellular N-terminus) transmembrane glycoprotein and the hyaluronan receptor plays an important role in MSCs migration and seems to be critical for recruitment of MSCs into wound sites for the proposition of tissue regeneration (Zhu et al., 2006);
 ii) Stem Cell Factor/c-kit (tyrosine-protein kinase Kit) or CD117;
 iii) CD90 or Thy-1 can be used as a marker for a variety of stem cells and for the axonal processes of mature neurons;
 iv) CD29—surface antigen expression revealed neural crest-like and mesenchymal immunophenotypes (Pruszak et al., 2009);
 v) nestin is a marker for multipotent neural stem cells and is also expressed in hair follicle bud stem cells; and
 vi) vimentin is a neural stem cells marker, which is also expressed in immature cells before being replaced later by more specialized networks (Langa et al., 2000).
All these markers were uniformly positive in IDPSC (FIGS. 83C-83H).

Example 26

Expression of neuroepithelial stem cell markers in LP IDPSC

Flow cytometry was performed for BDNF, NGF, NT-3 and NT-4 in LP IDPSC. The same protocol described above was followed, and the primary antibodies used were: rabbit anti-human BDNF (Preprotech, 1:100), rabbit anti-human NGF (Preprotech, 1:100), goat antimouse NT-3 (Preprotech, 1:100), goat anti-mouse NT-4 (Preprotech, 1:100). Expression of p75 protein was monitored by FACS analysis using Ab3125 mouse monoclonal antibody (Abcam, Cambridge, UK) or isotype control. After primary incubation, the slides were washed and incubated with the appropriate antibodies Alexa 488 goat anti-rabbit (Sigma, 1:600) or Alexa 488 rabbit anti-goat (Sigma, 1:600) for 2 hours at room temperature, followed by three washes, and cover slipped with Fluoromount (Sigma).

For RT-PCR analysis total RNA was extracted from dental pulp stem cell cultures with Trizol (Invitrogen) according to the manufacturer's instructions. cDNA was synthesized utilizing the ImProm-II™ Reverse Transcription System (Promega) with Oligo(dT)15, and a control reaction without the reverse transcriptase was also performed. PCR consisted of 35 cycles of 45 sec at 94° C., 45 sec at 55° C. and 1 min at 72° C. with the following primer pairs: BDNF-F (5'-AGA GGC TTGACA TCA TTG GCT G-3') (SEQ ID NO:21), BDNF-R (5'-CAA AGG CAC TTG ACT ACT GAG CAT C-3') (SEQ ID NO:22); GDNF-F (5'-CAC CAG ATA AAC AAA TGG CAG TGC-3') (SEQ ID NO:23), GDNF-R (5'-CGA CAG GTC ATC ATC AAA GGC G-3') (SEQ ID NO:24); NGF-13-F (5'-ATA CAG GCG GAA CCA CAC TCA G-3') (SEQ ID NO:25), NGF-13-R (5'-GTC CAC AGT AAT GTT GCG GGT C-3') (SEQ ID NO:26); NT-3-F (5'-TGG GGG AGA CTT TGA ATG AC-3') (SEQ ID NO:27), NT-3-R (5'-CTG GCA AAC TCC TTT GAT CC-3') (SEQ ID NO:28); NT-4/5-F (5'-AGG AGG CAC TGG GTA TCT GA-3') (SEQ ID NO:29), NT-4/5-R (5'-ATC CCT GAG GTC TCT CAG CA-3') (SEQ ID NO:30). Reactions with no reverse transcriptase and without template were performed as negative controls for absence of amplification from genomic DNA and for absence of contamination, respectively. Amplicons had 147 bp (brain-derived neurotrophic factor, human—BDNF), 335 bp (glial cell derived neurotrophic factor, human—GDNF), 174 bp (nerve growth factor, beta polypeptide, human—NGF-β), 201 bp (neurotrophin 3, human—NT-3), 198 bp (neurotrophin 4/5, human—NT-4/5).

The mRNA expression of p75 was analyzed by RT-PCR using specific primers (forward primer: 5'-tcgtggagagtctgt-gcagt-3' (SEQ ID NO:31), reverse primer: 5'-tggacaggaagt-gtggtcag-3' (SEQ ID NO:32)). Total RNA was extracted with the RNeasy Kit (Qiagen, Valencia, Calif.), reverse transcribed and amplified for 20 cycles on a PTC-100 Programmable Thermal Controller (MJ Research, Inc., Watertown, Mass.) using the Superscript amplification system (Life Technologies, Inc.). PCR products were size fractionated by 2% agarose gel electrophoresis and stained with 2% ethidium bromide (Sigma, St. Louis, Mo., USA). GAPD was co-amplified as a housekeeping gene to normalize p75 expression levels.

Without wishing to be bound to any theory, adult dental pulp stem cells may originate from neural crest stem cells (NCSC) and these dental pulp stem cells with NCSC features might persist until adulthood, able to generate a broad variety of cells depending on their environment. The inventors demonstrated, for the first time, that LP IDPSC naturally constitutively express high levels of neurotrophic factors, such as BDNF (brain-derived neurotrophic factor), GNDF (glial cell line-derived neurotrophic factor), NGF-β (nerve growth factor), NT-3 (Neurotrophin-3), NT-4/5 (Neurotrophin-4/5) that are known to promote sensory and motor axon growth (FIGS. 84A-84E and 84G) as well as p75 (a neurotrophin receptor and marker of NCSC) (FIGS. 84F and 84H). Fluorescence-activated cell sorting (FACS) analysis (FIG. 84A-F) demonstrated a proportion of BDNF (100%), GNDF (99%), NGF-β (99%), NT-3 (70%), NT-4/5 (80%) and p75 (90%) in the LP IDPSC populations.

Example 27

Expression of Limbal Stem Cell and Corneal Epithelial Markers in LP IDPSCs

LP IDPSCs were also shown to express a subset of markers, which are important for epithelial cell fate and especially for the eye surface epithelium. Using immunohistochemical analysis, the presence of several limbal stem cells and epithelial proteins were evaluated in undifferentiated LP IDPSCs. The following antibodies were used: mouse anti-human monoclonal antibodies: anti-integrin beta1 (integrin β1) (Santa Cruz Biotechnology, Santa Cruz, Calif., USA), connexin 43 (Chemicon), ABCG2 (Chemicon) and vimentin (NeoMarkers, Fremont, Calif., USA), and cytoplasmic/nuclear monoclonal antibodies: mouse anti-cytokeratin 3/12 (K3/12) (RDI, Flanders, N.J., USA), reacts with human and rabbit, and mouse anti-human anti-p63 (Chemicon). Cells were grown on glass cover-slips up to 70% confluence, washed in PBS (Gibco) and fixed overnight with 4% paraformaldehyde (Sigma). Coverslips were washed three times in Tris buffered saline (TBS) containing 20 mm Tris-HCl pH 7.4 (Vetec, Duque de Caxias, RJ, Brazil), 0.15 M NaCl (Dinâmica Reagent, Sao Paulo, SP, Brazil), and 0.05% Tween-20 (Sigma). Permeabilization was performed using 0.1% Triton X-100 for 15 min (Santa Cruz Biotechnology). Cells were washed three times and incubated for 30 min in 5% bovine serum albumin (Sigma) in PBS pH 7.4 (Gibco). Primary antibodies were added for 1 h on each slide at different dilutions (connexin 43, ABCG2, vimentin, integrin β1 and K3/12 (1:100), p63 (1:200) and anti-hIDPSC (1:1000)), which were incubated at room temperature. Following washing in TBS (three times), cells were incubated in the dark for 1 h with secondary anti-mouse antibody-conjugated fluorescein isothiocyanate (FITC) at a dilution of 1:500. Microscope slides were mounted in antifade solution (Vectashield mounting medium, Vector Laboratories, Hercules, Calif., USA) with 4',6-diamidino-2-phenylindole (DAPI) and analyzed using a confocal microscope. Control reactions were incubated with PBS instead of primary antibody, followed by washing and incubation with respective secondary antibody.

Primers used for analysis of expression of limbal stem cell markers in LP IDPSCs were as follows with the gene sense primer, anti-sense primer and annealing temperature specified: ABCG2 (379 bp) AGTTCCATGGCACTGGCCATA TCAGGTAGGCAATTGTGAGG (SEQ ID NO:33). 55° C.; Connexin 43 (154 bp) CCTTCTTGCTGATCCAGTGGTAC (SEQ ID NO:34) ACCAAGGACACCACCAGCAT (SEQ ID NO:35) 55° C.; K3 (145 bp) GGCAGAGATCGAGGGTGTC (SEQ ID NO:36) GTCATCCTTCGCCTGCTGTAG (SEQ ID NO:37) 58° C.; K12 (150 bp) ACATGAAGAAGAACCACGAGGATG TCTGCTCAGCGATGGTTTCA (SEQ ID NO:38) 58° C.; 13-actin (208 bp) GGCCACGGCTGCTTC (SEQ ID NO:39); GTTGGCGTACAGGTCTTTGC (SEQ ID NO:40) 55° C. Samples of human limbal and corneal epithelium were donated by patients of the Department of Ophthalmology, Federal University of Sao Paulo, after informed consent and were used as controls in the present work. Total mRNA from these human limbal, corneal epithelium and LP IDPSCs were extracted using TRIZOL reagent (Invitrogen) according to the manufacturer's protocol. Total mRNA was reverse transcribed in cDNA using SuperScript First-Strand Synthesis System and Oligo dT20 primer (both from Invitrogen). About 2 µl of mRNA was used per reaction. Reagents' final concentrations were 1×PCR buffer, 0.2 mM dNTP mix, 0.2 µm of each primer (above); 1.5 mm of $MgCl_2$, and 2 units of Platinum Taq DNA polymerase (Invitrogen), with a final volume of 50 µl. PCR was performed using a MiniCycler (MJ Research, San Francisco, Calif., USA). PCRs were performed under the following conditions: 1 cycle at 94° C. for 5 min, followed by 35 cycles at 94° C. for 1 min, at annealing temperature for 1 min, and at 72° C. for 1 min. PCR products were size fractionated by 2% agarose gel electrophoresis and stained with 2% ethidium bromide (Sigma, St. Louis, Mo., USA). Human β-actin gene was used as control.

Human-specific antibodies, such as p63, integrin β-1 (CD29), vimentin, connexin 43 and ABCG2 presented positive immunostaining with LP IDPSCs while anti-K3/12 antibody showed only weak positive immunostaining in a few cells (FIGS. 85A-85G). Expression of some genes previously analyzed using immunofluorescent proteins was also assessed by RT-PCR. Undifferentiated LP IDPSCs demonstrated expression of ABCG2, connexin 43 and K12, while expression of K3 was not found (FIG. 85I). As expected, ABCG2, connexin 43 and K12 were expressed in human limbal tissue used as control, while mRNAs of K3 were undetectable (FIG. 85I, Lane 3). In human corneal control samples connexin 43, K12 and K3 mRNAs, were present (FIG. 85I, Lane 2). Predictably, expression of ABCG2 was not detected in human control cornea (FIG. 85I, Lane 2).

Example 28

Expression of Embryonic Stem Cell Markers in LP IDPSC

Primary antibodies Oct3/4 and Nanog (Chemicon, Temecula, Calif., USA) were diluted at a 1:40. After Appropriate FITC secondary antibodies were added for 40 min at 1:100 dilution at room temperature. Microscope slides were mounted in Vectashield mounting medium (Invitrogen) with or without 4',6-diamidino-2-phenylindole (DAPI; Vector Laboratories, Burlingame, Calif., USA). Visualization was achieved using digital images that were acquired with a cooled CCD camera (PCO, VC44) and processed with ISIS software (MetaSystem, Belmont, Mass., USA). Total RNA was purified with Trizol reagent (Invitrogen) and treated with Turbo DNA-free kit (Ambion, Austin, Tex., USA) to remove genomic DNA contamination. Human ES cells were used as a control. One microgram of total RNA was used for the reverse-transcription reaction with ReverTra Ace-α and $dT_{20}$ primer, according to the manufacturer's instructions. PCR was performed with ExTaq. RT-PCR Primer Sequence are: (5' to 3') Oct3/4 (End-S) GAC AGG GGG AGG GGA GGA GCT AGG, (SEQ ID NO:41); (End-AS) CTT CCC TCC AAC CAG TTG CCC CAA AC (SEQ ID NO:42); SOX2 (End-S) GGG AAA TGG GAG GGG TGC AAA AGA GG (SEQ ID NO:43), (End-AS) TTG CGT GAG TGT GGA TGG GAT TGG TG (SEQ ID NO:44); Nanog (S) CAG CCC CGA TTC TTC CAC CAG TCC C (SEQ ID NO:45), (AS) CGG AAG ATT CCC AGT CGG GTT CAC C (SEQ ID NO:46); GAPDH (S) GCA CCG TCA AGG CTG AGA AC (SEQ ID NO:47), (AS) TGG TGA AGA CGC CAG TGG A (SEQ ID NO:48).

```
Type I Collagen
                                      (SEQ ID NO: 49)
Primers: 5'-AATGAAGGGACACAGAGGTTTC-3'
and
                                      (SEQ ID NO: 50)
5'-CCAGTAGCACCATCATTTCCAC-3'
Product size: 198 bp
Annealing Temperature: 61 C.
```

Quantitative PCR was used to determine the percent expression relative to human epithelial stem cells (hESC).

LP IDPSC showed expression of Oct3/4, Nanog, SOX2, and p53 with Oct3/4 and Nanog having a nuclear localization (FIGS. 86A-86C1). Quantitative PCR indicated that Oct3/4 had the highest relative level of expression among Oct3/4, Nanog, and SOX2. The relative expression of Oct3/4 in LP IDPSCs varied between unrelated donors (FIGS. 80A-80D). Additionally, the proportion of p53 positive cells in LP IDPSC derived from two unrelated donors was also quantified (FIG. 89A-89B). p53 positive cells were also positive for CD44, a marker of MSC described above (FIG. 10C) and were found in LP IDPSC in similar amounts (FIG. 89C-89D).

Example 29

Analysis of Biomarkers in LP IDPSCs by RT-PCR

Total RNA from cell samples of LP IDPSCs isolated from deciduous teeth (DL-1 and DL-4) and from a third molar (DL-2) were prepared with RNeasy Mini kit (Qiagen, Duesseldorf, Germany) according to the instructions of the manufacturer. Complimentary DNA synthesis was performed on ~800 ng of total RNA by using the QIAGEN OneStep RT-PCR Kit (Qiagen), and the resulting cDNA products were amplified using the gene-specific primers shown below.

```
Type I Collagen
Primers: 5'-AATGAAGGGACACAGAGGTTTC-3'
and

5'-CCAGTAGCACCATCATTTCCAC-3'
Product size: 198 bp
Annealing Temperature: 61 C.

Fibronectin IIIA
                                  (SEQ ID NO: 51)
Primers: 5'-GGTCAGTCCTACAAGATTGGTG-3'
and (SEQ ID NO: 52)
5'-CTTCTCCCAGGCAAGTACAATC-3'
Product size: 223 bp
Annealing Temperature: 61 C.

Tenascin-C
                                  (SEQ ID NO: 53)
Primers: 5'-AGAAGAGGTGTCCTGCTGACTG-3'
and (SEQ ID NO: 54)
5'-TCATGTCACTGCAGTCATAGCC-3'
Product size: 285 bp
Annealing Temperature: 61 C.

Vimentin
                                  (SEQ ID NO: 55)
Primers: 5'-AATCCAAGTTTGCTGACCTCTC-3'
and (SEQ ID NO: 56)
5'-TGTAGGTGGCAATCTCAATGTC-3'
Product size: 327 bp
Annealing Temperature: 61 C.
```

Primers were designed by using Primer3 software v. 0.4.0. The products were electrophoresed on 1.5% agarose gels, stained with ethidium bromide, and visualized with a transluminator Gel Logic 100 Imaging System (Kodak, New Haven, Conn.) using the Software Kodak 1D v.3.6.5K2 (Kodak). Comparative densitometry of bands was obtained with the software Adobe Photoshop CS2.

FIGS. 87A and 87B shows the images of the agarose gels and the graphs of the corresponding optical densities of the bands for the four genes analyzed. All LP IDPSCs studied expressed the vimentin, tenascin-C, type I collagen, and fibronectin genes. The three populations of LP IDPSCs exhibited similar expression of vimentin, tenascin, and fibronectin genes. The densitometry analysis showed that the total RNA for the type I collagen in the DL-2 cells was significantly less than that observed in the other hIDPSCs ($p<0.05$).

Cells were incubated with primary antibodies to detect vimentin, type I collagen, fibronectin, and tenascin-C. All antibodies were diluted in 5% bovine serum albumin solution in PBSA. Optimum antibodies concentrations were determined previously to the experiments using DL-1, DL-2, and DL-4 cells. Vimentin was detected by a mouse monoclonal antibody from Neomarkers (LabVision Corporation, Fremont, Calif.) diluted 1:250. Type I collagen was detected by a mouse monoclonal antibody from Chemicon (Chemicon, Victoria, Australia) diluted 1:25. Fibronectin was detected by a mouse monoclonal antibody from Calbiochem (Calbiochem, San Diego, Calif.) diluted 1:50. Tenascin-C was detected by a mouse monoclonal antibody from Neomarkers diluted 1:100. The secondary antibody was the anti-immunoglobulin G from mouse conjugated to fluorescein diluted in PBSA (1:500) at room temperature. All the incubations were performed for 60 minutes at room temperature and omission of the primary antibodies served as negative controls. The observations and photographic recording were performed on a fluorescence microscope (LSM 410 Zeiss; Oberkochen, Baden-Wurttemberg, Germany). For each reaction, at least 100 cells were observed.

Positive reactions to all antibodies tested were observed independent of the LP IDPSCs analyzed. The LP IDPSC populations expressed vimentin, a cytoskeleton protein from mesenchymal cells. Vimentin appeared as filament waved bundles branched out from the central body to reach the peripheral domains of the cell (FIG. 88A). Type I collagen appeared as dots spread all over the cytoplasm with higher concentration around the perinuclear area (FIG. 88B). Fibronectin (FIG. 88C) as well as tenascin (FIG. 88D) appeared as small dots homogeneously distributed throughout the cytoplasm. The type I collagen appeared less evident in the DL-2 third molar lineage than in the other hIDPSCs whereas DL-4 isolated from deciduous teeth showed less prominent reaction to the fibronectin and tenascin antibodies. Table 7 summarizes the analysis of expression of the four biomarkers in the DL-1, DL-2, and DL-4 cells.

TABLE 7

Immunofluorescence staining of biomarkers in hIDPSCs

| Primary antibodies | DL-1 | DL-2 | DL-4 |
|---|---|---|---|
| Vimentin | +++ | +++ | +++ |
| Type I collagen | ++ | + | ++ |
| Fibronectin | ++ | ++ | + |
| Tenascin | ++ | ++ | + |

+++: strong expression;
++: moderate expression;
+: weak expression

Example 30

Undifferentiated IDPSC Population Enriched with SOX2 Expressing Cells

IDPSC are neural crest stem cells isolated from a young organism. Thus, we verified the expression of SOX2 in these cells at multiple passages in vitro and following mechanical DP transfer, considering a low oxygen environment. Undifferentiated EP IDPSC obtained after 15 cycles of DP transfer demonstrate robust expression if SOX2 protein at passage 2

(FIG. 90a, A-A1), while following in vitro culture, SOX2 expression gradually decreased. At passage 5, expression of SOX2, can be observed only in a few EP IDPSC (FIG. 90a, B-B1).

It was surprisingly found that intracellular localization of transcription factors (TF) is a marker of TFs functional state. Thus, at passage 2 intracellular localization of SOX2 was nuclear, while at passage 5 it can be observed predominantly at perinuclear space. This suggests SOX2 trafficking to cytoplasm (FIG. 90a, A1, B1). Undifferentiated LP IDPSC obtained after 45 cycles of DP transfer demonstrate robust expression if SOX2 protein at passage 2 (FIG. 90b, A) and at passage 5, (FIG. 90b, B). Slight decrease of immunostaining for SOX2 was detected and intracellular localization of SOX2 was nuclear at passages 2 and 5 (FIG. 90b, A,B). These results confirm functional advantage of SOX2 protein expression in LP IDPSC over EP IDPSC following low oxygen culture conditions.

Example 31

Neuronal Progenitor Cells—Neuroblasts Derived from IDPSC

IDPSC are migratory neural crest stem cells which are capable of aggregating into neurospheres. It is known that in development, SOX2 is regained only by those cells fated to become neurons. Neural crest stem cells that remain SOX2-free differentiate into other cell types, but never become neurons.

According to some aspects, it was verified how long term mechanical transfer of DP will affect capacity of IDPSC to express SOX2 and differentiate to neurons. Neural differentiation of IDPSC was induced following protocol described herein. First, it is verified that expression of SOX1 protein correlate with mitotically active progenitors that are not yet committed to a final stage and also that β-tubulin class III is a microtubule element expressed exclusively in early neurons. This marker in combination with BrdU labeling was used as evidence of a correlation between a number of DP transfer cycles and enrichment of IDPSC population with the cells strongly committed to neural differentiation.

FIG. 91a, A-A4 demonstrate expression of SOX1 in the nucleus, while β-tubulin shows cytoplasmic localization in the neural precursors derived from LP of IDPSC, which are organized in neurospheres. More specifically, FIG. 91a depicts expression of Sox 1 and β-tubulin proteins in late population (LP) of hIDPSC derived neurons. The following are also shown in FIG. 91a: A. a nucleus (white arrow) of neurons stained with DAPI; A1. Positive immunostaining for SOX1 observed in the nucleus (white arrow) of neurons; A2. Positive immunostaining for β-tubulin; A3. Merged images A-A2; and A4. Major magnification of inset in A3 demonstrates superposition of DAPI and Sox 1 in the nucleus of neurons (white arrow). FIG. 91b-e demonstrate enrichment of LP of hIDPSC with neural progenitors and neurons following 15, 30 and 45 cycles of dental pulp mechanical transfer and induction of neural differentiation. In FIG. 91b-A, a percentage of SOX1 negative cells, nucleus stained only with DAPI (blue) are shown; SOX1 positive cells are presented in green. In FIG. 91d-B, a percentage of β-tubulin negative cells, nucleus stained only with DAPI (blue); β-tubulin positive cells are presented in red.

The proliferative potential of early neuroblasts obtained following differentiation of IDPSC toward neurons was also confirmed. FIG. 92a demonstrates nucleus of IDPSC-neuroblasts positively immunostained with anti-BrdU antibody and neuronal bodies which react positively with β-tubulin class III. FIG. 92b-c show clearly the enrichment of differentiated IDPSC population with slightly differentiated neuroblasts following growing cycle numbers of DP mechanical transfer.

Surprisingly, transit amplifying IDPSC population of slightly differentiated neuroblasts was obtained. This was confirmed by concomitant expression of BrdU, Sox1 and β-tubulin, which have never been demonstrated before for nether for adult stem cells nor for embryonic.

Even more astonishing was the finding that neuronal progenitor cells derived from IDPSC at advanced passages (5-10) that already lack expression of SOX2 (FIG. 90a, B,B1) start re-expressing SOX2 during neurosphere formation (FIG. 93a). Efficiency of these cells' differentiation into neural cells, however, is lower than IDPSC at passages 1-3. Re-expression of SOX2 was more efficient in IDPSC obtained from DPs, which underwent high number mechanical transfer cycles (≥30) (FIG. 93b,c).

These findings provide strong evidences about identity between IDPSC and neural crest stem cells that can be isolated at early and late embryonic stages. Furthermore, the efficiency of neural commitment increased following DP mechanical transfers supporting our previous observation about the importance of low oxygen atmosphere for IDPSC isolation and maintaining of their self-renewal and differentiation potential (Lizier et al., 2012). Therefore, LP IDPSC has an advantage over EP IDPSC in respect of neuronal commitment, which is important conclusion for the future of stem cell use in neurodegenerative diseases.

Example 31

Simplicity and Advantages of New Methods

FIG. 94a is a graphic abstract from Cimadamore et al., 2011, which suggested the method of isolation of SOX2 cells from human ES cells. This protocol is started from isolation of SOX2+ cells and induction of their migratory capacity in order to induce epithelial mesenchymal transition. At this moment the cells in contrast with IDPSC lack expression of SOX2, which is re-expressed during these cells differentiation into neurons. This protocol, which presents great academic interest to study the mechanism of regulation of SOX2 expression during neuronal differentiation, is sophisticated. It is less probable that this protocol will be used to isolate neuronal cells for the cell therapy.

FIG. 94b depicts a non-limiting embodiment of aspects of this disclosure which clearly demonstrate the simplicity of suggested method as well as underline IDPSC composition utility for the treatment of neurodegenerative disease.

According to some aspects, unique biomarkers fingerprint hIDPSCs-derived neuroblasts and early neurons. Expression of P75NTR (or CD271), a member of the Tumor Necrosis Factor receptor (TNFR) of super family of transmembrane proteins, is described elsewhere in this document. The ligands for CD271 are neurotrophins, which are Nerve Growth Factor (NGF), Brain-Derived Growth factor (BDNF), Neurotrophin 3 (NT3), and Neurotrophin 4/5 (NT4/5). Expression of these in undifferentiated IDPSCs was also demonstrated and described elsewhere in this document. Recent studies have provided evidence that CD271 also serves as a receptor for the pro-forms of these neurotrophins (Rogers M L, Beare A, Zola H, Rush R A. CD 271 (P75 neurotrophin receptor) *J Biol Regul Homeost Agents*. 2008 January-March; 22(1):1-6).

Surprising recent findings also disclosed herein is that CD271 marker is also expressed in hIDPSCs-derived neuroblasts that form neurospheres (3-dimensional clusters of embryonic neural progenitor) and rosettes (neuroepithelial structures reminiscent of early neural tubes-3-D neural islands). Unexpectedly, the cells within rosettes are also express CD 146, which is considered the marker of perycites originally derived from neural capillaries. On the other hand, the multi-functional role of this molecule in biology and pathology was only recently recognized. It has been shown that CD146 is actively involved in development, signaling transduction, cell migration, mesenchymal stem cells differentiation, angiogenesis and immune response. Even more recently, the involvement of CD146 in the development and maintenance of the nervous system was demonstrated. CD 146 interacts with neurite outgrowth factor and involved in neurite extension in vitro. Moreover, CD146 nervous system knockout mice exhibited lower body weights and smaller food intake when compared with wild type (Tu et al., 2013).

FIG. 95 depicts co-expression of neural markers in IDPSCs derived neuroblasts that form neurospheres and rosettes. More specifically, the following are showing in FIG. 95: A) RAR-alpha expression (green) within IDPSCs derived neuroblasts induced towards neural differentiation; B) and C) Expression of CD271 (P75) in neurospheres and differentiated neurons, respectively; D) Beta-3-tubulina expression; E) NeuN antibody, nuclear localization in neurospheres; F), G), and H) Dynein-Lis1-Ndel complex expression; I) and J) myelin P2 and O4 expression, respectively; K) Synaptophysin expression; L) CD146 expression; and M) control. Scale bar=10 μm, Nucleus stained with DAPI (blue).

Immunophenotype of hIDPSCs Derived Neuroblasts SOX1, SOX2, Beta-3-Tubulin, and Early Neurons: CD271+, Beta-3-tubulin+, NeuN+, Dynein+, Lis1+, NDEL+, myelin P2+, O4+, GFAP+, Synaptophysin+ and CD146+. Surprisingly, it was discovered that LP IDPSC culture of pos-natal cells of neural crest origin are characterized by unique properties. These unique properties are usually typical for neural precursors derived from fetal brain or from ES or iPS cells induced to neural differentiation in vitro.

Example 32

IDPSCs Derived Neuroblasts Further Differentiation and Maturation

IDPSCs derived neuroblasts, following in vitro neural maturation, start to express neural key markers:
1. responsible for neurons migration and signaling, outgrowth and maintenance and axoplasmic transport, such as, dynein, Lis1, Ndel1;
2. involved in the generation of the myelin sheath: myelin P2, O4;
3. involved in neural specification and differentiation: RAR-alpha
4. be involved in the regulation of neurotransmitter release: Synapsin Ia/b Dynein is a minus-end directed motor protein which, in the cells, converts the chemical energy contained in ATP into the mechanical energy of movement. Through retrograde axoplasmic transport, dynein carries organelles, vesicles, and possibly microtubule fragments along the axons of neurons toward the cell body.

Lis 1, Platelet-activating factor acetylhydrolase IB subunit alpha, is an enzyme that in humans is encoded by the PAFAH1B1 gene. Lis1 is the protein product of a gene mutated in the human neuronal migration defect lissencephaly, binds to and regulates dynein motor function in the cell.

NDEL-1, Nuclear distribution protein nudE-like 1 is a protein that in humans plays a role in nervous system development, including cytoskeletal organization, cell signaling and neuron migration, outgrowth and maintenance.

Sasaki S, Shionoya A, Ishida M, Gambello M J, Yingling J, Wynshaw-Boris A, Hirotsune S. *A LIS1/NUDEL/cytoplasmic dynein heavy chain complex in the developing and adult nervous system. Neuron.* 2000 December; 28(3):681-96.

Sakakibara A, Ando R, Sapir T, Tanaka T. *Microtubule dynamics in neuronal morphogenesis. Open Biol.* 2013 Jul. 17; 3(7):130061. doi: 10.1098/rsob.130061.

Myelin P2 protein and myelin basic protein together constitute a major fraction of peripheral nervous system myelin protein. They are intimately involved in the generation of the myelin sheath. They are also implicated in a number of neurological diseases, including autoimmune diseases of both the central and peripheral nervous systems.

O4 Monoclonal Anti-Oligodendrocyte Marker O4 recognizes Oligodendrocyte marker O4. Oligodendrocytes are myelinating cells in the central nervous system (CNS) that form the myelin sheath of axons to support rapid nerve conduction.

Retinoic acid receptor-alpha (RAR-alpha) has a high affinity for all transretinoic acids and belongs to the same class of nuclear transcription factors as thyroid hormone receptors, vitamin D3 receptor and ecdysone receptor.

Synapsin Ia/b exists as two alternatively spliced isoforms designated Synapsin Ia and Synapsin Ib, has been characterized as one of the major phosphoproteins in nerve terminals and is thought to be involved in the regulation of neurotransmitter release.

Table 8 presents the type, origin, dilution, and purchase place for various primary antibodies

TABLE 8

| Primary antibody | Type | Origin | Dilution | Purchased From |
|---|---|---|---|---|
| Dynein HC | Monoclonal | rabbit | 1:50 | Santa Cruz |
| Lis1 | Monoclonal | goat | 1:50 | Santa Cruz |
| Myelin P2 | Monoclonal | rabbit | 1:50 | Santa Cruz |
| NDEL-1 | Monoclonal | rabbit | 1:50 | Santa Cruz |
| Anti-O4 | Monoclonal | goat | 1:50 | Millipore |
| RARα | Monoclonal | goat | 1:50 | Santa Cruz |
| Synapsin Ia/b | Monoclonal | goat | 1:50 | Santa Cruz |

Example 33

Karyotype Analysis of LP IDPSCs G Band

Karyotyping of subconfluent LP of IDPSCs cultured in DMEM/F12 medium (Invitrogen) was performed at passage 3 and 10. Before harvesting, demecolcine (Sigma) at a final concentration of 0.1 μg/ml was added for 1 hour. Cells were harvested, washed in PBS and resuspended in 0.5 ml of medium and mixed with 0.075 M KCl (Sigma) to a volume of 10 ml. After incubation for 20 minutes at room temperature, cells were centrifuged at 400 g for five minutes and the pellet fixed in 5 ml three times (3:1) of cold methanol/acetic acid (Sigma). Three drops of cell suspension were fixed per slide. For chromosome counting, slides were stained in Giemsa for 15 minutes and; >200 cells were analyzed per cell line and reported on a Zeiss II microscope (Zeiss, Jena, Germany) according to the International System for Human Cytogenetic Nomenclature.

The karyotype of IDPSC was analysed at early (P3) and late (P10) passages. The karyotype demonstrates stability and no structural or numeric alterations were observed. FIG. 96 depicts male karyotypes of in vitro cultured LP IDPSC at early and late passages, representative figure.

Example 34

Regeneration of Mental Nerve of Rats with the Use of IDPSC

Evaluation was made of the regeneration of the mental nerve that is a general somatic afferent (sensory) nerve. This nerve provides sensation to the anterior aspects of the chin and lower lip as well as the buccal gingivae of the mandibular anterior teeth and the premolars. It is a branch of the posterior trunk of the inferior alveolar nerve, which is itself a branch of the mandibular division of the trigeminal nerve (CNV).

Thirty-six male Wistar rats were used in this experiment and the rats had their right side mental nerve injured by compression. The left side nerve of each rat was used as a positive control. The right side mental nerves were then distributed in two study groups: control group with compression and no treatment (n=18) and experimental group that underwent injury by compression and treatment with IDPSCs (n=18) ($2 \times 10^6$ cells). Animals were euthanized at different times of study: 1, 3, 7, 14, 21 and 42 days after lesion and they had their mental nerves and trigeminal ganglion removed for analysis with transmission electron microscopy. The images of neural fibers were obtained for the measurement of external circumference of mielinic fibers and thickness of mielinic layer. The nerves after 14 days of treatment showed similar morphological aspects to the intact nerve. The use of IDPSCs for mental nerve regeneration was effective in a single application after two weeks of the treatment.

Example 35

Teratoma Formation

Teratomas formation is an essential tool in determining the pluripotency of any pluripotent cells, such as embryonic or induced pluripotent stem cells (ES and iPS cells). A consistent protocol for assessment of teratoma forming ability of the cells was established and then used in studies. Some recently published methods of the inventors are based on subcutaneous co-transplantation of defined numbers of undifferentiated IDPSCs and Matrigel into immunodeficient mice. The method was shown to be highly reproducible and efficient when $10^6$ cells of mouse and human pluripotent cells were used. In 100% of cases we observed teratoma formation in a large number of animals and in long follow-up (up to 6 months). This method for bio-safety analysis of other adult/mesenchymal stem cells (MSC), such as derived from dental pulp of deciduous teeth, umbilical cord and adipose tissue and others.

Also evaluated were the next criterion for a teratoma assay sensitivity and quantitatively:

A. Definitive cell number and single cell suspension production; immunophenotyping of studies cell in respect of expression on pluripotent cell markers and karyotype; co-transplantation of studied cells together with Matrigel; subcutaneous (s.c.) cells transplantation, which allows simple monitoring of teratoma development; the cells were transplanted into NOD/SCID mice.

B. The development of tumors was monitored for 4 month (approximately 16 weeks). For pluripotent cells histological criteria for teratomas was development of tissues derived from all three germ layers. This analysis was performed by a pathologist.

C. For IDPSCs any type or any changes on normal tissue integrity in the site of cell injection were taken in consideration.

The Experimental System(s):

A. Three different LP IDPSC cultures at early (n=10) and late passages (n=10)

B. Human primary fibroblast (negative control)

The IDPSC are composed by population with a variable number of stem cells expressing pluripotent markers (1-25% of cells) (Kerkis et al., 2006; Lizier et al., 2012). These cells were transplanted into NOD/SCID mice (n=20) and the development of tumors was monitored from 4 month (approximately 16 weeks). Any type of changes on normal tissue integrity in the site of cell injection was taken in consideration.

This protocol was adapted for population of IDPSC, especially in respect of cell number used, which was calculated on the basis that 20% of IDPSC express pluripotent markers. In our previous tests with ES and iPS cells we used $10^6$ cells, while in to test IDPSC and control cells teratogenicity $5 \times 10^6$ cells were used.

After 4 months, even if macroscopically the tumors were not observed, the mice were sacrificed and frozen cuts were obtained from diverse organs, such as brain, lung, kidney, spleen, liver and were analyzed by pathologist.

Conclusion: although presence of DNA of IDPSC within all studied organs were found, no tumor formation or any macroscopic morphological changes were observed.

Example 36

Paracrine Effects of LP hIDPSCS: Anti-Inflammatory, Immunomodulatory and Antimicrobial Properties of IDPSCs MSCs assist via paracrine mechanisms and modulate the regenerative environment via anti-inflammatory and immunomodulatory mechanisms. The effect of IDPSCs i.p. inoculation on cytokine production by lung cells of C57Bl/6 mice i.t. infected with Mtb and *M. bovis* strains differed in virulence was observed. BIOPLEX test data is provided in FIG. 97. IDPSCs inoculation reduced production of cytokines by the infected lung cells. Strong reduction of pro-inflammatory (TNF-a, IL-1b, MIP-2, IL-17) and anti-inflammatory (IL-10) cytokines was observed in the lungs infected with highly virulent Mtb strains. Reduction of IFN-g and KC production was less pronounced. Induction of IL-4 production was observed only in the mice inoculated with IDPSCs.

Tumor necrosis factor (TNF, cachexin, or cachectin, and formerly known as tumor necrosis factor alpha or TNFα) is an adipokine involved in systemic inflammation. The primary role of TNF is in the regulation of immune cells. TNF, being an endogenous pyrogen, is able to induce fever, apoptotic cell death, cachexia, inflammation and to inhibit tumorigenesis and viral replication and respond to sepsis via IL1 & IL6 producing cells. Dysregulation of TNF production has been implicated in a variety of human diseases including Alzheimer's disease.

Interferon gamma (IFNγ) is a dimerized soluble cytokine that is the only member of the type II class of interferon, is known as immune interferon a cytokine that is critical for innate and adaptive immunity against viral and intracellular bacterial infections and for tumor control. IFNγ is an important activator of macrophages. Aberrant IFNγ expression is associated with a number of autoinflammatory and autoimmune diseases. The importance of IFNγ in the immune system stems in part from its ability to inhibit viral replication directly, and most importantly from its immunostimulatory and immunomodulatory effects.

Interleukin 17 is a cytokine that acts as a potent mediator in delayed-type reactions by increasing chemokine production in various tissues to recruit monocytes and neutrophils to the site of inflammation, similar to Interferon gamma. Interleukin 17 as a family functions as a proinflammatory cytokine that responds to the invasion of the immune system by extracellular pathogens and induces destruction of the pathogen's cellular matrix.

Interleukin-1 beta (IL-1β) also known as catabolin, is a cytokine protein, that an important mediator of the inflammatory response, and is involved in a variety of cellular activities, including cell proliferation, differentiation, and apoptosis. The most notable role of IL-17 is its involvement in inducing and mediating proinflammatory responses. IL-17 is commonly associated with allergic responses.

Interleukin-10 (IL-10), also known as human cytokine synthesis inhibitory factor (CSIF), is an anti-inflammatory cytokine IL-10 is a cytokine with pleiotropic effects in immunoregulation and inflammation.

Chemokine (C-X-C motif) ligand 2 (CXCL2), also called macrophage inflammatory protein 2 (MIP-2), plays a major role in mediating the neutrophilic inflammatory response and a mediator in the development of sepsis. KC and macrophage-inflammatory protein-2 (MIP-2) are CXC chemokines that exhibit distinct temporal patterns of expression in the skin following surgical injury. KC and Mip 2 are neutrophil chemoattractant genes. Both chemokines are known to be expressed in a broad spectrum of acute and chronic inflammatory settings and are believed to be critical determinants of the nature and magnitude of the ensuing inflammatory reaction.

Example 37

IDPSCs Isolated from Third Molar (Wisdom) Tooth

FIG. 104 depicts an extracted third molar wisdom tooth. CD 105 is a major marker in MSCs. It was used to verify the distribution of MSCs and identify their niche in the dental pulp. We demonstrate that MSCs expressing this marker is located in perivascular multiple niches, vascular plexus and nerve plexus in the network of vessels or nerves (FIG. 98). Although vascular plexus and nerve plexus are very similar structures, this definition was included in order to distinguish being smaller networks (vascular plexus) as major (nerve plexus). As we observe the CD105+, cells are located in the perivascular niche (FIG. 98B, C, F, black arrow), the vascular plexus (FIG. 98B, C, G, orange arrow), and the nerve plexus (FIG. 98H star).

Another marker of extreme importance for the identification of MSC and their niches is CD73, which is composed of two antibodies: SH-3 and SH-4 that recognize different epitopes on MSCs. We use both antibodies and observed a noticeable difference between them. SH3 showed positive staining distributed throughout the pulp tissue and perivascular location (FIG. 99A). We noted SH3 positive cells in vessels which are located in the layer of endothelial cells (FIG. 99B, C), as well as some SH3+ cells present location of pericytes. Surprisingly, SH3+ cells were found in the neural plexus in the cells that exhibit a distinct, neuronal like (FIG. 99D) morphology, when compared with CD105+ cells located in the same anatomic site (FIG. 98H). As for antibody expression SH4 it showed a very subtle marking (FIG. 99E, F) when compared to SH3 (FIG. 99A-D) and control (FIG. 98A).

Additionally, we tested the expression of the N-cadherin, which is an adhesion molecule of neural cells and considered a key molecule of neural crest cells during embryogenesis. In the dental pulp of the third molar tooth, the expression of N-cadherin was visualized mainly in the perivascular niche, but around the blood vessels of smaller diameter (FIG. 100A-C). Moreover staining was not observed around all vessels (FIG. 100A). In addition, FIG. 100C shows the location of the N-cadherin in the anatomical site of pericytes.

ABCG2 is associated with the cell membrane protein which transports various molecules across internal and external cell membranes. ABCG2 is also considered a marker of stem cells and is abundantly expressed in placenta. We observed cells distributed by pulp connective tissue that showed an intense expression of this marker (FIG. 100D, E) similarly observed for SH-3 (FIG. 99). We also verified the expression of Nanog, which is a transcription factor whose expression was observed in the perivascular region and vascular plexus (FIG. 100F), but it showed no cytoplasmic and nuclear localization.

Comparative analysis of marking two main markers showed that MSC-positive cells and CD105++CD73/SH3 differ in how the location of the pulp tissue niches, both in morphology. The CD105+ cells when found in the pulp tissue, nerve plexus shows the morphology of fibroblast cells—typical for CTM (FIG. 101). CD73/SH3+ cells found in connective tissue are round and are smaller (FIG. 101B) as compared to CD105+. The markup for both CD105+ and +CD73/SH3 antibodies was observed in the perivascular niche, but apparently CD105+ cells are found at the anatomical site of pericytes, CD73/SH3+ cells when endothelial cells (FIG. 101C, D). Turn positive cells N-cadherin are preferentially located in the anatomical site of pericytes (FIG. 101E), and not in endothelial cells niche (FIG. 101C, D). The major difference between CD73/SH3+ and CD105+ was observed in the nerve plexus, where CD73/SH3+ cells facsimile of neuronal morphology (FIG. 102A, B).

This data demonstrate the possibility of isolation stem cells with molecular signature similar to IDPSCs as well as confirm neural commitment of stem cells localized in nerves plexus.

Example 38

Assessment of the Teratogenic Potential of IDPSC

In order to assess the teratogenic potential of IDPSC, $1 \times 10^6$ cells were injected subcutaneously on the back of 15 immunosuppressed mice. After 40 days there was macroscopically observed the formation of cell masses and/or teratomas (FIG. 104).

Example 39

Batch Release Process for Industrial Scale-Up of hIDPSC by LP Method

FIG. 105 depicts an exemplary flow chart for a batch release process for industrial scale-up of hIPDSC by LP method in order to obtain clinically relevant quantities for multiple patient dosing. According to some aspects, dental pulp derived from deciduous teeth is plated on a cell culture flask. Cells from the dental pulp (DP) are passaged by an enzymatic dissociation reagent from passage 1 (P1) to the passage 3 (P3) at each harvest cycle (H). At each harvest (H1-H35), DP is transferred by non-enzymatic method.

At P3, in each harvest cycle, cells from 1-10 dental pulps are pooled and undergo a process of freezing at P4. Thereafter cells are thawed and 50% of the cells are released as a single batch at p %. Afterwards, cells are frozen and ready for therapeutic administration, preferably to induce direct neurogeneration, such as but not limited to intrathecal (IT) or intraspinal cord injection (Product 1-IT).

In order to obtain a high number of cells for intravenous (IV)/systemic or topical/local administration, another 50% of cells are thawed at P4 and can be grown up to passage 15 and released as a single batch at P15. The cells are then pooled and frozen for intravenous administration (Product 2-IV).

Table 9 presents various methods of analysis performed in relation to the batch release process described above and shown in FIG. 105.

TABLE 9

| Method of Analysis | Characteristics | Specifications | Passage |
|---|---|---|---|
| Karyotype analysis | Chromosomal abnormalities | Undetectable | P3, P15 |
| PCR | Mycoplasma test | Undetectable | P3, P5, P15 |
| Morphological test | Morphology | Normal fibroblast like morphology under inverted microscope inspection | P3, P15 |
| XTT | Cell proliferation rate | — | P3, P15 |
| CFU | Clonogenic assay | Number of colonies ___ | P3, P15 |
| FACS analysis | Phenotype analysis | Positive to CD73, CD105, CD44, SOX2 Negative to CD45, HLA-ABC | P3, P15 |

Selected quality control tests were performed at P3 and P15. A certificate analysis was performed and is provided below, in Table 10. The certificate analysis is for a hIDPSC product according to one aspect of this disclosure for intrathecal administration. The batch number for this particular analysis was #001H1-30/P1-5/F.

TABLE 10

| Method of analysis | Characteristics | Specification | Result |
|---|---|---|---|
| Morphological test | Morphology | Normal fibroblast like morphology under inverted microscope inspection | confirms |
| Cell viability via Trypan Blue exclusion | Viability | >95% | confirms |
| PCR Mycoplasma test | Mycoplasma detection | Undetectable | confirms |
| CFU | Cell forming units assay | >5 colonies | confirms |
| LAL | Endotoxin detection | ≤2 Eu/kg body weight/dose | confirms |
| Bacteriostatic and Fungistatic activity | Sterility | Undetectable | confirms |
| Gram stain technique | Microbial contamination | Undetectable | confirms |
| MTT/ or XTT | Cell proliferation rate | At least doubling of cell number in 24 hours | confirms |
| FACS analysis | Phenotype analysis | Positive to CD73, CD105, CD44, SOX2 Negative to CD45, HLA-ABC | confirms |
| Cytokine and growth factors release assay | Cytokine and neuronal factors analysis | Positive to NGF, BDNF, IL8 | confirms |
| FACS analysis | Neuronal markers | Positive to SOX2, or/and Nestin | confirms |

Various related methods are also contemplated as part of this disclosure. Methods may include but are not limited to:

Dental Pulp Isolation. In regards to the teeth preparation just before the sampling, there are different methods. Stem cells isolated from human dental pulp derive from mesenchymal cells produced by neural crests. In order to isolate stem cells from human dental pulp it is necessary that the teeth are healthy and without any communication between pulp and oral cavity.

Cell Culture. Depending on the type of culture system used for the induction of differentiation, the nature of the resulting population may be a priori determined. The common culture system for use comprises a culture matrix comprising extracellular matrix (ECM). In accordance with one embodiment, the ECM is selected from, without being limited thereto, fibronectin, laminin and gelatin. The culture system may be further supplemented by an antibacterial agent. The antibacterial agent may be selected from, without being limited thereto, penicillin and streptomycin, preferably gentamycin (in order to reduce risk of transplantation to penicillin allergic population in traces).

The culture system may be further supplemented by a growth factors, also as described by Stern et al. in U.S. Pat. No. 8,481,308 using sustained release growth factor to maintain cells in homogenous undifferentiated stage.

Another alternative culture system that was developed and used extensively is a serum-free system that includes the knockout (KO) medium supplemented with knockout serum replacement (KOSR) and growth factors such as FGF2. Knockout serum replacement (KOSR) (Gibco) is a chemically defined, serum-free culture medium supplement used as a substitute for animal-based serum in KO-DMEM-based culture systems for propagating stem cells may replace the supplementation with fetal bovine serum (FBS). Another optional culture comprise Neurobasal™ medium is a basal medium especially formulated for growth of neuronal cells, and supplemented with FBS, or B27, or N2 serum replacement and retinoic acid (RA).

The undifferentiated or differentiated cell line is preserved by preservation methods, such as cryopreservation.

According to some aspects, contemplated disclosures are provided an undifferentiated hIDPSC wherein the cell is immunoreactive with markers for human pluripotent stem cells including Oct3/4, Nanog and SOX2, and wherein said cell may differentiate under differentiating conditions to neural cells. Preferably, the cells express the transcription factor SOX1; SOX2 and tubulin as demonstrated by RT-PCR. The said cells maintain a stable diploid karyotype during prolonged cultivation in vitro. Sox and Oct3/4 transcription factors are thought to be central to the transcriptional regulatory hierarchy that specifies ES cell identity. hIDPSC were previously shown to express Oct 4 (Insert ref 2006; and Liezer et al. 2012) approximately in about of 20% of IDPSC throughout the cell culture up to LP. Therefore, the co-existence of both OCT family and SOX family markers, indicate on high stemness and pluripotency of hIDPSC. However enrichment with SOX and beta-tubulin markers indicate on strong affinity towards neuronal fate.

Also disclosed herein is a preparation of undifferentiated hIDPSCs using LP harvesting method where enrichment with SOX1, SOX2, BrdU, beta-3-tubullin molecular markers in LP indicate on the capability of these LP to proliferation in vitro and differentiation (in vivo or ex vivo) into neural progenitor cells, neuron cells and/or glial cells and ganglion cells. Preferably, the undifferentiated hIDPSCs cells have the potential to differentiate into neural progenitor cells, neuron cells and/or glial cells when subjected to differentiating conditions or in vivo micro-environment.

Treatment Methods. The allogeneic nature of aspects of this disclosure substantially mitigate immunotoxicity concerns, as hIDPScs are normally non-HLA typing. A method comprising providing a compositon of hIDPSCS for transplantation to a patient is contemplated. Such hIDPSCs are derived from a LT culture system comprising undifferentiated hIDPSCs in accordance with disclosure, followed by incubating the undifferentiated SCs in a culture system that supports directed differentiation of SCs into the selected somatic cells, preferably maintaining strong neuroectodermal commitment.

In one embodiment, the selected population of somatic cells consists essentially of neural precursor cells. In accordance with another embodiment the selected population of somatic cells consists essentially of dopaminergic neuronal cells. Culture systems which support directed differentiation of SC's into a specifically desirable type of somatic cell, such as neural precursor cells or dopaminergic neuronal cells are well known in the art.

There is provided an undifferentiated cell line capable of differentiation into neural progenitor cells, neuron cells and glial cells and preferably produced by a method of the present invention. There is provided a differentiated committed progenitor cell line that may be cultivated for prolonged periods and give rise to large quantities of progenitor cells. There is provided a differentiated committed progenitor cell line capable of differentiation into mature neurons and/or glial cells. There is also provided a committed neural progenitor cell capable of giving rise to mature neuron cells and glial cells. There is provided a differentiated committed progenitor cell line capable of establishing a graft in a recipient brain, to participate in histogenesis of the nervous system and to constitute the neuronal, astrocyte and oligodendrocyte lineages in vivo.

Also provided is an undifferentiated hIDPSC, a hIDPSC-derived neural progenitor cell-neuroblasts, a neuronal cell and a glial cell that may be used in pharmaceutical composition for cell therapy and gene therapy through cell transplantation systemically, intrathecally, intranasally or locally. The disclosed/anticipated therapeutic neuroprotective action may be activated though protective anti-inflammatory and/or release of nerve growth factors, and/or expression and/or repair of neurogenesis, and/or to improve functional outcomes, such as motor and/or cognitive outcomes.

Such neuroprotective methods offer treatment of CNS and/or PNS diseases by directly replenishing, replacing, and/or supplementing damaged or dysfunctional neural cells (i.e. neurons/glial/oligodendrocytes), and/or by enhancing the growth and/or survival of existing neural cells, and/or slow or reverse the loss of such cells in a neurodegenerative conditions.

Also disclosed herein are compositions comprising hIDPSCs and methods for the prophylaxis and treatment of diseases, conditions and injuries of the central (CNS) and peripheral nervous systems (PNS). Non-limiting additional examples of diseases and conditions treatable by the disclosed hIDPSC transplantation are neurodegenerative disorders and neural disease, such as neurodegenerative disorders (e.g., Alzheimer's, Parkinson's disease, Parkinson's disorders, Huntington's disease (Huntington's Chorea), Lou Gehrig's disease, multiple sclerosis, Pick's disease, Parkinsonism dementia syndrome), progressive subcortical gliosis, progressive supranuclear palsy, thalmic degeneration syndrome, hereditary aphasia, amyotrophic lateral sclerosis, Shy-Drager syndrome, and Lewy body disease; vascular conditions (e.g., infarcts, hemorrhage, cardiac disorders); mixed vascular and Alzheimer's; bacterial meningitis; Creutzfeld-Jacob Disease; and Cushing's disease.

Also contemplated herein is the treatment of neurodegenerative disorders termed acute brain injury. These include but are not limited to: stroke, head trauma, and asphyxia. Stroke refers to a cerebral vascular disease and may also be referred to as a cerebral vascular incident and includes acute thromboembolic stroke. Stroke includes both focal and global ischemia. Other incidents are head trauma, spinal cord trauma, or injury from general anoxia, hypoxia, hypoglycemia, hypotension as well as similar injuries seen during procedures from embole, hyperfusion, and hypoxia. hIDPSCs cells are typically formulated in a unit dosage injectable form, such as a solution, suspension, or emulsion. Dosage forms/pharmaceutical formulations of the aqueous suspension of cells/medium will typically involve adjusting the ionic strength of the suspension to isotonicity to about 0.1 to 0.2 and to physiological pH of about pH 6.8 to 7.5. Said formulation will also typically contain a fluid lubricant.

Pharmaceutical formulations suitable for injection of cells, and/are conditioned medium typically are sterile aqueous solutions and dispersions. Carriers for injectable formulations can be a solvent or dispersing medium containing, for example, water, saline, phosphate buffered saline, or other suitable vehicle, and suitable mixtures thereof. The skilled pharmaceutical expert can determine the amount of cells and optional carrier and additives in compositions to be administered in methods of the invention. Typically, any additives/excipients or active compounds to the hIDPSCs cells are present in an amount of 0.001 to 50 wt % in phosphate buffered saline.

Said compositions can be administered in dosages and by techniques well known to those skilled in the medical and pharmaceutical arts. Doses for humans/mammals can be determined without undue experimentation by the skilled medical practitioner, from this disclosure, the documents cited herein, and the knowledge in the art.

A skilled expert/medical practitioner will be able to determine the appropriate situation in which subjects are susceptible to or at risk of, for example, stroke as well as suffering from stroke for administration of hIDPSC systemically, intrathecally, or locally, as described in the present invention.

Aspects also relate to therapeutic use of the combined therapy where hIDPSC administration is combined with therapeutic chemical or bioactive or/and pharmaceutical compounds agents for neurodegenerative disorders.

The contemplated compositions and methods may be used to moderate, and/or alleviate, and/or to improve medical condition in the patient diagnosed with a neurodegenerative disease as described above. In additional embodiments, methods of use of hIDPSC neuronal precursors neuroblasts with unique biomarkers fingerprint are contemplated, surprisingly expressing C271 and P57. These cells grown in culture are of high interest for future neuroregeneration medicine and drug discovery.

Moreover, disclosed herein for the first time is a unique paracrine characteristics of hIDPSCs, such as (i) immunomodulatory properties, (ii) anti-inflammatory properties and, even, (iii) antimicrobial properties. Such characteristics open new fields of use for IDPSCs. For example, treatment of multiple clinical applications is contemplated: (i) as immunoprotection against immunosuppressive diseases, for example—Graft vs Host; AIDS; cancer chemotherapy side effects; (ii) use of hIDPSCs as anti-inflammatory therapy, for example against arthritis, or IBD—inflammatory bowel disease; and/or (iii) an infectious diseases, such as sepsis and resistant nosocomial infections, etc.

Disclosed herein are methods of treatment that may be used as single therapy or in adjunction, or synergistically, with other treatment modalities, or/and as a preventive therapy (for example in patients at high risk of nosocomial infection or AIDS).

Having herein set forth the various embodiments of the present disclosure, it is anticipated that suitable modifications can be made thereto which will nonetheless remain within the scope of the contemplated disclosures. The invention shall therefore only be construed in accordance with the following claims below.

REFERENCES

Noble M, Mayer-Pröschel M, Davies J E, Davies S J, Pröschel C. Cell therapies for the central nervous system: how do we identify the best candidates? Curr Opin Neurol. 2011 December; 24(6):570-6.

Kempermann G. The pessimist's and optimist's views of adult neurogenesis. Cell. 2011 Jun. 24; 145(7): 1009-11.

Panchision D M. The role of oxygen in regulating neural stem cells in development and disease. J Cell Physiol. 2009 September; 220(3):562-8.

Pevny L H, Sockanathan S, Placzek M, Lovell-Badge R. A role for SOX1 in neural determination. Development. 1998 May; 125(10): 1967-78.

Kempermann G, Gast D, Kronenberg G, Yamaguchi M, Gage F H. Early determination and long-term persistence of adult-generated new neurons in the hippocampus of mice. Development. 2003 January; 130(2):391-9.

Molero A E, Gokhan S, Gonzalez S, Feig J L, Alexandre L C, Mehler M F. Impairment of developmental stem cell-mediated striatal neurogenesis and pluripotency genes in a knock-in model of Huntington's disease. Proc Natl Acad Sci USA. 2009 Dec. 22; 106(51):21900-5.

Kandasamy M, Couillard-Despres S, Raber K A, Stephan M, Lehner B, Winner B, Kohl Z, Rivera F J, Nguyen H P, Riess O, Bogdahn U, Winkler J, von Hörsten S, Aigner L. Stem cell quiescence in the hippocampal neurogenic niche is associated with elevated transforming growth factor-beta signaling in an animal model of Huntington disease. J Neuropathol Exp Neurol. 2010 July; 69(7):717-28.

Cimadamore F, Fishwick K, Giusto E, Gnedeva K, Cattarossi G, Miller A, Pluchino S, Brill L M, Bronner-Fraser M, Terskikh A V. Human ESC-derived neural crest model reveals a key role for SOX2 in sensory neurogenesis. Cell Stem Cell. 2011 May 6; 8(5):538-51.

Zappone, M. V. et al. Sox2 regulatory sequences direct expression of a (beta)-geo transgene to telencephalic neural stem cells and precursors of the mouse embryo, revealing regionalization of gene expression in CNS stem cells. *Development* 127, 2367-2382 (2000).

Komitova M, Eriksson P S. Sox-2 is expressed by neural progenitors and astroglia in the adult rat brain. Neurosci. Lett. 2004; 369(1):24.

Gronthos et al., "Postnatal human dental pulp stem cells (DPSCs) in vitro and in vivo", Proceedings of the National Academy of Sciences of USA, 97:25 (2000), 13625-30.

Handa et al., "Progenitor cells from dental follicle are able to form cemetum matrix in vivo", Connective Tissue Research, 43:2/3 (2002), 406-408.

Harada et al., "Localization of putative stem cells in dental epithelium and their association with Notch and FGF signaling", Journal of Cell Biology, 147:1 (1999), 105-20.

Krebsbach et al., "Dental and skeletal stem cells: potential cellular therapeutics for craniofacial regeneration", Journal of Dental Education, 66:6 (2002), 766-73.

Nakashima et al., Induction of dental pulp stem cell differentiation into odontoblasts by electroporation-mediated gene delivery of growth/differentiation factor 11 (Gdf11), Gene Therapy, 9:12 (2002), 814-18.

Shi et al., "Comparison of human dental pulp and bone marrow stromal stem cells by cDNA microarray analysis", Bone 29:6 (2001), 532-39.

U.S. Pat. No. 5,928,947.
U.S. Pat. No. 5,817,773.
WO 01/176507.

We claim:

1. A method of treating a disease or condition of ectodermal origin, wherein the disease or condition is selected from the group consisting of: a demyelinating disease, wherein the demyelinating disease attacks the central nervous system or the peripheral nervous system, and a spinal cord injury, the method comprising systemically administering to a subject in need thereof a composition comprising a population of migratory immature dental pulp stem cells (IDPSCs) expressing CD73 (ecto-5'-nucleotidase), p53, and p75 in an amount sufficient to treat the disease or condition of ectodermal origin.

2. The method of claim 1, wherein the demyelinating disease is selected from the group consisting of: Multiple sclerosis, idiopathic inflammatory demyelinating diseases, Vitamin B12 deficiency, central pontine myelinolysis, Tabes Dorsalis, transverse myelitis, Devic's disease, Progressive multifocal leukoencephalopathy, Optic neuritis, Leukodystrophies, Guillain-Barré syndrome, chronic inflammatory demyelinating polyneuropathy, Anti-MAG peripheral neuropathy, Charcot-Marie-Tooth Disease, and Copper deficiency.

3. The method of claim 1, wherein the IDPSCs carry mesenchymal stem cell (MSC) markers.

4. The method of claim 3, wherein the IDPSCs express CD105, CD73, and CD90 and lack expression of CD45, CD34, and HLA-DR.

5. The method of claim 4, wherein the IDPSCs are plastic adherent cells.

6. The method of claim 3, wherein the IDPSCs express CD29 (integrin beta 1).

7. The method of claim 6, wherein the IDPSCs are plastic adherent cells.

8. The method of claim 3, wherein the IDPSCs are plastic adherent cells.

9. The method of claim 1, wherein the IDPSCs are plastic adherent cells.

10. The method of any one of claims 1-2, and 3-7, wherein administration of the IDPSCs is parenteral.

11. The method of claim 10, wherein administration of the IDPSCs is intravenous.

* * * * *